US011401328B2

(12) United States Patent
Schebye et al.

(10) Patent No.: US 11,401,328 B2
(45) Date of Patent: Aug. 2, 2022

(54) ANTIBODIES BINDING TO ILT4

(71) Applicants: Five Prime Therapeutics, Inc., South San Francisco, CA (US); Bristol-Myers Squibb Company, Princeton, NJ (US)

(72) Inventors: Xiao Min Schebye, San Carlos, CA (US); Diana Yuhui Chen, San Francisco, CA (US); Andrew Rankin, Redwood City, CA (US); Xiaodi Deng, San Mateo, CA (US); Joseph Toth, Belmont, MA (US); Linda Liang, Mountain View, CA (US); Michelle Minhua Han, Piedmont, CA (US); Christine Bee, San Francisco, CA (US); Hong-An Truong, San Francisco, CA (US); Mark J. Selby, San Francisco, CA (US); Nils Lonberg, Woodside, CA (US); Guodong Chen, East Brunswick, NJ (US); Richard Y. Huang, Bridgewater, NJ (US); Ekaterina G. Deyanova, Lawrenceville, NJ (US); Alan J. Korman, Piedmont, CA (US)

(73) Assignees: Five Prime Therapeutics, Inc., South San Francisco, CA (US); Bristol-Myers Squibb Company, Princeton, NJ (US)

( * ) Notice: Subject to any disclaimer, the term of this patent is extended or adjusted under 35 U.S.C. 154(b) by 218 days.

(21) Appl. No.: 16/506,754

(22) Filed: Jul. 9, 2019

(65) Prior Publication Data

US 2020/0079848 A1 Mar. 12, 2020

Related U.S. Application Data

(63) Continuation of application No. PCT/US2019/040820, filed on Jul. 8, 2019.

(60) Provisional application No. 62/695,600, filed on Jul. 9, 2018, provisional application No. 62/744,611, filed on Oct. 11, 2018.

(51) Int. Cl.

| | |
|---|---|
| ***C07K 16/28*** | (2006.01) |
| ***A61K 39/395*** | (2006.01) |
| ***A61K 45/06*** | (2006.01) |
| ***A61K 47/68*** | (2017.01) |
| ***A61P 35/00*** | (2006.01) |
| ***G01N 33/563*** | (2006.01) |
| ***G01N 33/577*** | (2006.01) |
| *A61K 39/00* | (2006.01) |

(52) U.S. Cl.

CPC ...... *C07K 16/2803* (2013.01); *A61K 39/3955* (2013.01); *A61K 45/06* (2013.01); *A61K 47/6803* (2017.08); *A61P 35/00* (2018.01); *C07K 16/2827* (2013.01); *G01N 33/563* (2013.01); *G01N 33/577* (2013.01); *A61K 2039/505* (2013.01); *C07K 2317/21* (2013.01); *C07K 2317/33* (2013.01); *C07K 2317/34* (2013.01); *C07K 2317/40* (2013.01); *C07K 2317/55* (2013.01); *C07K 2317/565* (2013.01); *C07K 2317/567* (2013.01); *C07K 2317/71* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 5,545,806 | A | 8/1996 | Lonberg et al. |
| 5,545,807 | A | 8/1996 | Surani et al. |
| 5,874,299 | A | 2/1999 | Lonberg et al. |
| 5,877,397 | A | 3/1999 | Lonberg et al. |
| 6,162,963 | A | 12/2000 | Kucherlapati et al. |
| 6,180,370 | B1 | 1/2001 | Queen et al. |
| 6,255,458 | B1 | 7/2001 | Lonberg et al. |
| 6,300,129 | B1 | 10/2001 | Lonberg et al. |
| 6,667,175 | B1 | 12/2003 | Suciu-Foca |
| 6,673,986 | B1 | 1/2004 | Kucherlapati et al. |
| 6,713,610 | B1 | 3/2004 | Kucherlapati et al. |
| 6,759,239 | B2 | 7/2004 | Suciu-Foca et al. |
| 7,144,728 | B1 | 12/2006 | Suciu-Foca et al. |
| 7,943,329 | B2 | 5/2011 | Atwal et al. |
| 8,008,449 | B2 | 8/2011 | Korman et al. |
| 8,110,194 | B2 | 2/2012 | Nichol et al. |
| 8,168,757 | B2 | 5/2012 | Finnefrock et al. |
| 8,217,149 | B2 | 7/2012 | Irving et al. |

(Continued)

FOREIGN PATENT DOCUMENTS

| | | | |
|---|---|---|---|
| EP | 1125584 | A1 | 8/2001 |
| EP | 2503341 | A2 | 9/2012 |

(Continued)

OTHER PUBLICATIONS

Borges et al., "A Family of Human Lymphoid and Myeloid Ig-Like Receptors, Some of Which Bind to MHC Class I Molecules," J. of Immunology, 1997, 159:5192-5196.

(Continued)

*Primary Examiner* — Bridget E Bunner
*Assistant Examiner* — Fozia M Hamud
(74) *Attorney, Agent, or Firm* — McNeill Baur PLLC

(57) ABSTRACT

The present application relates to antibodies specifically binding to immunoglobulin-like transcript 4 (ILT4), which is also known as LILRB2, LIR2, MIR10, and CD85d, and corresponding nucleic acids, host cells, compositions, and uses. In some embodiments, the antibodies bind specifically to human ILT4, but do not significantly bind to ILT2, ILT3, or ILT5, or to other members of the LILRA or LILRB families.

41 Claims, 46 Drawing Sheets

Specification includes a Sequence Listing.

(56) References Cited

U.S. PATENT DOCUMENTS

| | | | |
|---|---|---|---|
| 9,944,685 | B2 | 4/2018 | Hofer et al. |
| 2004/0241167 | A1 | 12/2004 | Suciu-Foca et al. |
| 2005/0238643 | A1 | 10/2005 | Arm et al. |
| 2006/0270045 | A1 | 11/2006 | Cregg et al. |
| 2009/0136500 | A1 | 5/2009 | Staunton et al. |
| 2009/0232794 | A1 | 9/2009 | Tessier-Lavigne et al. |
| 2009/0280109 | A1 | 11/2009 | Suciu-Foca et al. |
| 2009/0285803 | A1 | 11/2009 | Atwal et al. |
| 2010/0047232 | A1 | 2/2010 | Atwal et al. |
| 2011/0117013 | A1 | 5/2011 | Mack et al. |
| 2011/0135672 | A1 | 6/2011 | Horuzsko et al. |
| 2012/0315269 | A1 | 12/2012 | Klechevsky et al. |
| 2015/0004178 | A1 | 1/2015 | Liu et al. |
| 2015/0174203 | A1 | 6/2015 | Chen et al. |
| 2016/0009782 | A1 | 1/2016 | Shatz et al. |
| 2016/0017423 | A1 | 1/2016 | Cazalis et al. |
| 2016/0200815 | A1 | 7/2016 | Feldman et al. |
| 2016/0272724 | A1 | 9/2016 | Loustau et al. |
| 2017/0274003 | A1 | 9/2017 | Shatz et al. |
| 2018/0298096 | A1 | 10/2018 | Joyce-Shaikh et al. |

FOREIGN PATENT DOCUMENTS

| | | | |
|---|---|---|---|
| EP | 2730588 | A1 | 5/2014 |
| WO | 1998024906 | A2 | 6/1998 |
| WO | 1998048017 | A1 | 10/1998 |
| WO | 1999010494 | A2 | 3/1999 |
| WO | 2000068383 | A2 | 11/2000 |
| WO | 2000076320 | A1 | 12/2000 |
| WO | 2003000199 | A2 | 1/2003 |
| WO | 2003041650 | A2 | 5/2003 |
| WO | 2004113304 | A1 | 12/2004 |
| WO | 2006029879 | A2 | 3/2006 |
| WO | 2006033811 | A2 | 3/2006 |
| WO | 2006076288 | A2 | 7/2006 |
| WO | 2006081430 | A2 | 8/2006 |
| WO | 2006105021 | A2 | 10/2006 |
| WO | 2006122150 | A1 | 11/2006 |
| WO | 2006138739 | A2 | 12/2006 |
| WO | 2007005874 | A2 | 1/2007 |
| WO | 2007075598 | A2 | 7/2007 |
| WO | 2007089945 | A2 | 8/2007 |
| WO | 2008036642 | A2 | 3/2008 |
| WO | 2008036653 | A2 | 3/2008 |
| WO | 2008061019 | A2 | 5/2008 |
| WO | 2008079246 | A2 | 7/2008 |
| WO | 2008094176 | A2 | 8/2008 |
| WO | 2008132601 | A1 | 11/2008 |
| WO | 2009009116 | A2 | 1/2009 |
| WO | 2009044273 | A2 | 4/2009 |
| WO | 2009073620 | A2 | 6/2009 |
| WO | 2009076359 | A2 | 6/2009 |
| WO | 2009100135 | A2 | 8/2009 |
| WO | 2009115652 | A2 | 9/2009 |
| WO | 2009140361 | A1 | 11/2009 |
| WO | 2010019570 | A2 | 2/2010 |
| WO | 2010077634 | A1 | 7/2010 |
| WO | 2011028683 | A1 | 3/2011 |
| WO | 2011056652 | A1 | 5/2011 |
| WO | 2011070024 | A1 | 6/2011 |
| WO | 2011091177 | A1 | 7/2011 |
| WO | 2011091181 | A1 | 7/2011 |
| WO | 2011107553 | A1 | 9/2011 |
| WO | 2011109400 | A2 | 9/2011 |
| WO | 2011131407 | A1 | 10/2011 |
| WO | 2011140249 | A2 | 11/2011 |
| WO | 2012032433 | A1 | 3/2012 |
| WO | 2012145493 | A1 | 10/2012 |
| WO | 2012142237 | | 11/2012 |
| WO | 2012151578 | A1 | 11/2012 |
| WO | 2013033734 | A1 | 3/2013 |
| WO | 2013036282 | A2 | 3/2013 |
| WO | 2013052772 | A2 | 4/2013 |
| WO | 2013079174 | A1 | 6/2013 |
| WO | 2013087699 | A1 | 6/2013 |
| WO | 2013132044 | A1 | 9/2013 |
| WO | 2013169264 | A1 | 11/2013 |
| WO | 2013181438 | A2 | 12/2013 |
| WO | 2014006063 | A2 | 1/2014 |
| WO | 2014008218 | A1 | 1/2014 |
| WO | 2014036357 | A1 | 3/2014 |
| WO | 2014072534 | A1 | 5/2014 |
| WO | 2014108646 | A1 | 7/2014 |
| WO | 2013119716 | | 8/2014 |
| WO | 2014164519 | A1 | 10/2014 |
| WO | 2015031667 | A2 | 3/2015 |
| WO | 2015179633 | A1 | 11/2015 |
| WO | 2015189638 | A2 | 12/2015 |
| WO | 2016044022 | A1 | 3/2016 |
| WO | 2016111947 | A2 | 7/2016 |
| WO | 2016127247 | A1 | 8/2016 |
| WO | 2016144728 | A2 | 9/2016 |
| WO | 2017207775 | A1 | 12/2017 |
| WO | 2018013818 | A2 | 1/2018 |
| WO | 2018022881 | A2 | 2/2018 |
| WO | 2018091580 | A1 | 5/2018 |
| WO | 2018187518 | A1 | 10/2018 |
| WO | 2019126514 | A2 | 6/2019 |
| WO | 2019144052 | A1 | 7/2019 |
| WO | 2019202040 | A1 | 10/2019 |
| WO | 2019202041 | A1 | 10/2019 |
| WO | 2020014132 | A2 | 1/2020 |
| WO | 2020023268 | A1 | 1/2020 |
| WO | 2020061059 | A1 | 3/2020 |
| WO | 2020069133 | A1 | 4/2020 |

OTHER PUBLICATIONS

Cella et al, "A Novel Inhibitory Receptor (ILT3) Expressed on Monocytes, Macrophages, and Dendritic Cells Involved in Antigen Processing," J. Exp. Med., 1997, 185(10):1743-1751.

Colonna et al., "A novel family of Ig-like receptors for HLA Class I molecules that modulate function of lymphoid and myeloid cells," J. Leukoc. Biol, 1999, 66:375-381.

Colonna et al., "A family of inhibitory and activating Ig-like receptors that modulate function of lymphoid and myeloid cells," Immunology, 2000, 12:121-127.

Colonna et al., Human Killer Inhibitory Receptors: Specificity for HLA-Class I Molecules and Mechanisms of Signal Transduction, Transplantation Proceedings, 1996, 28(6):3035.

Colonna et al., "Human Myelomonocytic Cells Express an Inhibitory Receptor for Classical and Nonclassical MHC Class I Molecules," Journal of Immunology, 1998, 160:3096-3100.

Dietrich et al., "Ig-Like Transcript 2 (ILT2)/Leukocyte Ig-Like Receptor 1 (LIR1) Inhibits TCR Signaling and Actin Cytoskeleton Reorganization," J. of Immunology, 2001, 166:2514-2521.

Dohring et al., "A Human Killer Inhibitory Receptor Specific for HLA-A 1,2," Journal of Immunology, 1996, 156:3098-3101.

Dohring et al., "Alternatively spliced forms of human killer inhibitory receptors," Immunogenetics, 1996, 44:227-230.

GenBank H26010.1, yl52b10.s1 Soares breast 3NbHBst *Homo sapiens* cDNA clone image sequence, 1995.

Gleissner et al., "IL-10 inhibits endothelium-dependent T cell costimulation by up-regulation of ILT¾ in human vascular endothelial cells," Eur. J. Immunol., 2007, 37:177-192.

Godal et al., "NK cell killing of AML and ALL blasts by Killer-Immunoglobulin Receptor (KIR) negative NK cells after NKG2A and LIR-1 blockade," Biol Blood Marrow Transplant, 2010, 16(5):612-621.

Isnardi et al., "Complement receptor 2/CD21-human naive B cells contain mostly autoreactive unresponsive clones," Blood, 2010, 115(24):5026-5036.

Ju et al., "Immunoglobulin-like transcripts ILT2, ILT3 and ILT7 are expressed by human dendritic cells and down-regulated following activation," Gene, 2004, 331: 159-164.

Liang et al., "Human ILT2 receptor associates with murine MHC class I molecules in vivo and impairs T cell function," Eur. J. Immunol.,2006, 36:2457-2471.

(56) References Cited

OTHER PUBLICATIONS

Ma et al., "Paired Immunoglobin Like Receptor-B regulates the suppressive function and fate of myeloid derived suppressor cells," Immunity, 2011, 34(3): 385-395.
Nakajima et al., "Human Myeloid Cells Express an Activating ILT Receptor (ILT1) That Associates with Fc Receptor y-Chain", Journal of Immunology, 1999, 162:5-8.
Nakajima et al., "Transcriptional Regulation of ILT Family Receptors," J of Immunology, 2003, 171:661-6620.
Rouas-Freiss et al., "The Dual Role of HLA-G in Cancer," J Immunol. Research, 2014, Article 359748, 10 pages.
Samaridis and Colonna, "Cloning of novel immunoglobulin superfamily receptors expressed on human myeloid and lymphoid cells: structural evidence for new stimulatory and inhibitory pathways," Eur. J. Immunol., 1997, 27:660-665.
Saverino et al., "The CD85/LIR-1/ILT2 Inhibitory Receptor is Expressed by All Human T Lymphocytes and Down-Regulates Their Functions," J. of Immunology, 2000, 165:3742-3755.
Suciu-Foca et al., "Molecular characterization of allospecific T suppressor and tolerogenic dendritic cells: review," 2005, International Immunopharmacology, 5:7-11.
Vlad et al., "Immunosuppressive activity of recombinant ILT3," International Immunopharmacology, 2006, 6:1889-1894.
Vlad et al., "Induction of antigen-specific human T suppressor cells by membrane and soluble ILT3," Experimental and Molecular Pathology, 2012, 93:294-301.
Yokoyama, "What Goes Up Must Come Down: The Emerging Spectrum of Inhibitory Receptors," J. Exp. Med., 1997, 186(11):1803-1808.
Zheng et al., "Inhibitory receptors bind ANGPTLs and support blood stem cells and leukaemia development," Nature, 2012, 485:656-660.
Von Bubnoff, D. et al. "Identification of IDO-positive and IDO-negative human dendritic cells after activation by various proinflammatory stimuli." J. Immunol. 186:6701-9 (2011).
Wenink et al "The inhibitory Fc gamma IIb receptor dampens TLR4-mediated immune responses and is selectively up-regulated on dendritic cells from rheumatoid arthritis patients with quiescent disease." J. Immunol. 183:4509-20 (2009).
Wong, J. "Discover of a novel TIM3 binding partner and a key role for TIM3 on macrophages: identification of specific antibodies capable of converting immune-suppressive macrophages to immune-enhancing" AACR Annual Meeting, Apr. 17, 2016, Abstract No. 586, poster1.
Adams et al. "Monoclonal antibody therapy of cancer" Nature Biotechnology, 23(9):1147-1157, 2005.
Anonymous, "Invitrogen Data Sheet: CD85d (ILT4) Monoclonal Antibody (42D1), Functional Grade, eBioscience Catalog No. 16-5149-85," Jan. 1, 2015, XP002788854, https://www.thermofisher.com/order/genome-database/generatePdf?productname=CD85d%20(ILT4)&assayType=PRANT&detailed=true&productId=16-5149-85, 4 pages.
Banchereau et al. "Immunoglobulin-like transcript receptors on human dermal CD14+ dendritic cells act as a CD8-antagonist to control cytotoxic T cell priming" PNAS 109(46):18885-18890 (2012).
Beinhauer, et al. "Interleukin 10 regulates cell surface and soluble LIR-2 (CD85d) expression on dendritic cells resulting in T cell hyporesponsiveness in vitro" Eur. J. Immunol. 34: 74-80 (2004).
Brenk et al. "Tryptophan Deprivation Induces Inhibitory Receptors ILT3 and ILT4 on Dendritic Cells Favoring the Induction of Human CD4+ CD25+ Foxp3+ T Regulatory Cells" J Immunol 183:145-154 (2009).
Chang et al. "Tolerization of dendritic cells by Ts cells: the crucial role in inhibitory receptors ILT3 and ILT4" Nature Immunology 3(3): 237-243 (2002).
Chen and Mellman "Oncology Meets Immunology: The Cancer-Immunity Cycle" Immunity 39, 1-10 (2013).
Chen et al., "Blocking Immunoinhibitory receptor LILRB2 reprograms tumor-associated myeloid cells and promotes antitumor immunity," J Clin Invest, 2018, 128(12):5647-5662.
Chiba et al, "Tumor-infiltrating DCs suppress nucleic acid-mediated innate immune responses through interactions between the receptor TIM-3 and the alarmin HMGB1" Nat Immunol 13:832-843 (2012).
Choo et al., "SPdb—a signal peptide database" BMC Bioinformatics, 6: 249 (2005).
Colonna and Samaridis "Cloning of immunoglobulin-superfamily members associated with HLA-C and HLA-B recognition by human natural killer cells" Science 268:405 (1995).
Crill, W. D., et al "Monoclonal Antibodies That Bind to Domain III of Dengue Virus E Glycoprotein Are the Most Efficient Blockers of Virus Adsorption in Vero Cells" Journal of Virology, 75(16):7769-7773 (2001).
Dekruyff et al, "T Cell/Transmembrane, Ig, and Mucin-3 Allelic Variants Differentially Recognize Phosphatidylserine and Mediate Phagocytosis of Apoptotic Cells" J Immunol, 184:1918-1930 (2010).
Deng et al., "A motif in LILRB2 critical for Angpt12 binding and activation," Blood, 2014, 124(6):924-935.
File History of U.S. Appl. No. 14/921,096, filed Oct. 23, 2015.
File History of U.S. Appl. No. 14/921,100, filed Oct. 23, 2015.
File History of U.S. Appl. No. 16/159,586, filed Oct. 12, 2018.
File History of U.S. Appl. No. 16/159,592, filed Oct. 12, 2018.
File History of U.S. Appl. No. 16/857,810, filed Apr. 24, 2020.
File History of U.S. Appl. No. 16/857,878, filed Apr. 24, 2020.
Gabrilovich et al. "Coordinated regulation of myeloid cells by tumours" Nat. Rev. Immun. 12:253-268 (2012).
Gregori, et al. "Differentiation of type 1 T regulatory cells (Tr1) by tolerogenic DC-10 requires the IL-10-dependent ILT4/HLA-G pathway" Blood 116(6): 935-944 (2010).
Giles, J et al. "HLA-B27 homodimers and free H chains are stronger ligands for leukocyte Ig-like receptor B2 than classical HLA class I." J. Immunol. 188:6184-93 (2012).
Human ILT2, precursor, with signal peptide, UniProtKB Ref. Q8NHL6.1, Jul. 24, 2013.
Human ILT3, precursor, with signal peptide, UniProtKB Ref. Q8NHJ6.3, Sep. 18, 2013.
Human ILT4 precursor, with signal peptide, isoform 2, NCBI Ref. NP_001074447.1, Mar. 30, 2014.
Human ILT4 precursor, with signal peptide, UniProtKB Ref. Q8N423.4, Jul. 24, 2013.
Human ILT5, precursor, with signal peptide, UniProtKB Ref. O75022.3, Jul. 24, 2013.
Human TIM3 precursor, with signal peptide, UniProtKB Ref. Q8TDQ0.3, Sep. 18, 2013.
International Search Report and Written Opinion in PCT/US/2019/040820 dated Jan. 23, 2020, 28 pages.
Jayaraman et al. "Tim3 binding to galectin-9 stimulates antimicrobial immunity" J. Exp. Med. 207(11): 2343-2354 (2010).
Jounce Therapeutics, "Jounce Therapeutics to Present Program Updates at AACR Annual Meeting 2016" Press Release, Mar. 16, 2016.
Katz "Inhibition of Inflammatory Responses by LeukocyteIg-Like Receptors" Advances in Immunology, 91:251-272 (2006).
Liang, et al. "Modulation of dendritic cell differentiation by HLA-G and ILT4 requires the IL-6—STAT3 signaling pathway" Proc Natl Acad Sci U S A. Jun. 17, 2008;105(24):8357-62.
Lichterfeld et al. "A viral CTL escape mutation leading to immunoglobulin-like transcript 4-mediated functional inhibition of myelomonocytic cells" JEM vol. 204 No. 12 2813, (2007).
Liu et al. "Specific suppression of allo-MHC" International immunology 10:775 (1998).
Liu et al., "ANGPTL2/LILRB2 Signaling Promotes the Propagation of Lung Cancer Cells," Oncotarget, 6(25): 21004-21015.
Maldonado and Von Andrian "How Tolerogenic Dendritic Cells Induce Regulatory T Cells" Advances in Immunology, vol. 108, Chapter 4, 111-165 (2010).
Manavalan, et al. "High expression of ILT3 and ILT4 is a general feature of tolerogenic dendritic cells" Transplant Immunology 11: 245-258 (2003).
Masuda, T. et al. "Cis binding between inhibitory receptors and MHC class I can regulate mast cell activation." J. Exp. Med. 204:907-20 (2007).
Mouse TIM3 precursor, with signal peptide, UniProtKB Ref. Q8VIM0.1, Sep. 18, 2013.

(56) References Cited

OTHER PUBLICATIONS

Ngiow, et al. "Prospects for TIM3-Targeted Antitumor Immunotherapy" Cancer Res; 71(21): 6567-6571 (2011).
Rabinovich, et al. "Immunosuppressive Strategies that are Mediated by Tumor Cells" Annu. Rev. Immunol. 25: 267-296 (2007).
Ristich, V. et al. "Mechanisms of prolongation of allograft survival by HLA-G/ILT4-modified dendritic cells." Hum. Immunol. 68 (4): 264-271, (2007).
Saito et al. "Defective IL-10 signaling in hyper-IgE syndrome results in impaired generation of tolerogenic dendritic cells and induced regulatory T cells" J. Exp. Med, 208(2): 235-249 (2011).
Shiroishi, M. et al. "Human inhibitory receptors Ig-like transcript 2 (ILT2) and ILT4 compete with CD8 for MHC class I binding and bind preferentially to HLA-G" Proc. Natl. Acad. Sci. U.S.A 100:(15):8856-61 (2003).
Shiroishi, M. et al. "Structural basis for recognition of the nonclassical MHC molecule HLA-G by the leukocyte Ig-like receptor B2 (LILRB2/LIR2/ILT4/CD85d)." Proc. Natl. Acad. Sci. U.S.A 103: 16412-16417, (2006).
Su et al. "TIM-1 and TIM-3 Proteins in Immune Regulation" Cytokine, 44(1): 9-13 (2008).
Sun et al. "Expression of Ig-Like Transcript 4 Inhibitory Receptor in Human Non-small Cell Lung Cancer" Chest, 134:783-788, 2008.
Vlad et al. "License to heal: bidirectional interaction of antigen-specific regulatory T cells and tolerogenic APC" J Immunol 174, 5907-14 (2005).

| | FAMILY | LOCUS | RF | TGL | VBASEENTRY |
|---|---|---|---|---|---|
| V-SEGMENT | VH4 | 4-59 | | | DP-71/3d197d...+ |
| D-SEGMENT | D3 | 3-16 | 2 | | D3-16 |
| J-SEGMENT | JH4 | 4 | | | JH4b |
| INPUT | 9G4.E10.B3-VH1 | | | | |

```
        Q   V   Q   L   Q   E   S   G   P   G   L   V   K   P   S   E   T
1       CAG GTG CAG CTG CAG GAG TCG GGC CCA GGA CTG GTG AAG CCT TCG GAG ACC

                                                           _CDR1__________
        L   S   L   T   C   T   V   S   G   G   S   I   S   S   Y   Y   W
52      CTG TCC CTC ACC TGC ACT GTC TCT GGT GGC TCC ATC AGT AGT TAC TAC TGG

        ___                                                    _CDR2___
        N   W   I   R   Q   P   P   G   K   G   L   E   W   L   G   Y   I
103     AAC TGG ATC CGG CAG CCC CCA GGG AAG GGA CTG GAG TGG CTT GGG TAC ATC

        ______________________________________________________
        Y   Y   S   G   S   T   K   Y   N   P   S   L   K   S   R   V   T
154     TAT TAC AGT GGG AGT ACC AAG TAC AAC CCC TCC CTC AAG AGT CGA GTC ACC

        I   S   V   D   T   S   K   N   Q   F   S   L   K   L   S   S   V
205     ATA TCA GTA GAC ACG TCC AAG AAC CAG TTC TCC CTG AAG CTG AGC TCT GTG

                                                       _CDR3____________
        T   A   A   D   T   A   V   Y   Y   C   A   S   S   G   W   Y   Y
256     ACC GCT GCG GAC ACG GCC GTG TAT TAT TGT GCC AGC AGT GGC TGG TAC TAC

        __________
        F   D   Y   W   G   Q   G   T   L   V   T   V   S   S
307     TTT GAC TAT TGG GGC CAG GGA ACC CTG GTC ACC GTC TCC TCA
```

*FIGURE 1*

| | FAMILY | LOCUS | TGL | VBASEENTRY |
|---|---|---|---|---|
| V-SEGMENT | VK3 | L6 | | Vg/38K...+ |
| J-SEGMENT | JK1 | 1 | | JK1 |
| INPUT | 9G4.E10.B3-VK1 | | | |

```
         E   I   V   L   T   Q   S   P   A   T   L   S   L   S   P   G   E
1        GAA ATT GTG TTG ACA CAG TCT CCA GCC ACC CTG TCT TTG TCT CCA GGG GAA

                                _CDR1_____________________________________
         R   A   T   L   S   C   R   A   S   Q   S   V   S   S   Y   L   A
52       AGA GCC ACC CTC TCC TGC AGG GCC AGT CAG AGT GTT AGC AGC TAC TTA GCC

                                                                 _CDR2___
         W   Y   Q   Q   K   P   G   Q   A   P   R   L   L   I   Y   D   A
103      TGG TAC CAA CAG AAA CCT GGC CAG GCT CCC AGG CTC CTC ATC TAT GAT GCG

         ___________________
         S   N   R   A   T   G   I   P   A   R   F   S   G   S   G   S   G
154      TCC AAC AGG GCC ACT GGC ATC CCA GCC AGG TTC AGT GGC AGT GGG TCT GGG

         T   D   F   T   L   T   I   S   S   L   E   P   E   D   F   A   G
205      ACA GAC TTC ACT CTC ACC ATC AGC AGC CTA GAG CCT GAA GAT TTT GCA GGT

                     _CDR3______________________________
         Y   Y   C   Q   Q   R   S   Y   W   P   W   T   F   G   Q   G   T
256      TAT TAC TGT CAG CAG CGT AGC TAC TGG CCG TGG ACG TTC GGC CAA GGG ACC

         K   V   E   I   K
307      AAG GTG GAA ATC AAA
```

*FIGURE 2*

| | FAMILY | LOCUS | RF | TGL | VBASEENTRY |
|---|---|---|---|---|---|
| V-SEGMENT | VH1 | 1-08 | | | DP-15/V1-8+ |
| D-SEGMENT | UNDETERMINED | | | | . |
| J-SEGMENT | JH6 | 6 | | | JH6b |
| INPUT | 9C8.A6_NT | | | | |

```
         Q   V   Q   L   V   Q   S   G   A   E   V   K   K   P   G   A   S
1        CAG GTG CAA CTG GTG CAG TCT GGG GCT GAG GTA AAG AAG CCT GGG GCC TCA

                                                             _CDR1________
         V   K   V   S   C   K   A   S   G   Y   T   F   T   S   S   D   I
52       GTG AAG GTC TCC TGC AAG GCT TCT GGA TAC ACC TTC ACC AGC TCT GAT ATC

         ___                                                     _CDR2___
         N   W   V   R   Q   A   T   G   Q   G   L   E   W   M   G   W   M
103      AAC TGG GTG CGA CAG GCC ACT GGA CAA GGG CTT GAG TGG ATG GGA TGG ATG

         ___________________________________________________________
         N   P   N   S   G   H   T   G   Y   A   Q   K   F   Q   D   R   V
154      AAC CCT AAC AGT GGT CAC ACA GGC TAT GCA CAG AAG TTC CAG GAC AGA GTC

         T   L   T   R   D   T   S   I   S   T   A   Y   M   E   L   S   S
205      ACC TTG ACC CGG GAC ACC TCC ATA AGC ACA GCC TAC ATG GAG CTG AGC AGC

                                                             _CDR3________
         L   R   S   E   D   S   A   V   Y   Y   C   A   R   G   G   N   S
256      CTG AGA TCT GAG GAC TCG GCC GTG TAT TAC TGT GCG AGA GGT GGG AAT AGC

         _______________________________________________
         I   D   W   G   F   S   Y   Y   G   L   D   V   W   G   Q   G   T
307      ATT GAC TGG GGG TTC TCC TAC TAC GGT CTG GAC GTC TGG GGC CAA GGG ACC

         T   V   T   V   S   S
358      ACG GTC ACC GTC TCC TCA
```

*FIGURE 3*

| | FAMILY | LOCUS | TGL | VBASEENTRY |
|---|---|---|---|---|
| V-SEGMENT | VK1 | L4 | | Va'+ |
| J-SEGMENT | JK3 | 3 | | JK3 |
| INPUT | 9C8.A6_NT | | | |

```
         A   I   Q   L   T   Q   S   P   S   S   L   S   A   S   V   G   D
1        GCC ATC CAG TTG ACC CAG TCT CCA TCC TCC CTG TCT GCA TCT GTA GGA GAC

                                _CDR1______________________________________
         R   V   T   I   T   C   R   A   S   Q   G   I   S   S   A   L   A
52       AGA GTC ACC ATC ACT TGC CGG GCA AGT CAG GGC ATT AGC AGT GCT TTA GCC

                                                                    _CDR2___
         W   Y   Q   Q   K   P   G   K   A   P   K   L   L   I   Y   D   A
103      TGG TAT CAG CAG AAA CCA GGG AAA GCT CCT AAG CTC CTG ATC TAT GAT GCC

         ___________________
         S   S   L   E   S   G   V   P   S   R   F   S   G   S   G   S   G
154      TCC AGT TTG GAA AGT GGG GTC CCA TCA AGG TTC AGC GGC AGT GGA TCT GGG

         T   D   F   T   L   T   I   S   S   L   Q   P   E   D   F   A   T
205      ACA GAT TTC ACT CTC ACC ATC AGC AGC CTG CAG CCT GAA GAT TTT GCA ACT

                     _CDR3______________________________
         Y   Y   C   Q   Q   F   N   S   Y   P   F   T   F   G   P   G   T
256      TAT TAC TGT CAA CAG TTT AAT AGT TAC CCA TTC ACT TTC GGC CCT GGG ACC

         K   V   D   I   K
307      AAA GTG GAT ATC AAA
```

FIGURE 4

| | FAMILY | LOCUS | RF | TGL | VBASEENTRY |
|---|---|---|---|---|---|
| V-SEGMENT | VH1 | - | | | 2M27/11M27... |
| D-SEGMENT | D3 | 3-10 | 3 | | D3-10/DXP'1 |
| J-SEGMENT | JH6 | 6 | | | JH6b |
| INPUT | 2H2.H3_NT | | | | |

```
        Q   V   Q   L   V   Q   S   G   A   E   V   K   K   P   G   S   S
1       CAG GTC CAG TTG GTG CAG TCT GGG GCT GAG GTG AAG AAG CCT GGG TCC TCG

                                                            _CDR1___________
        V   E   V   S   C   K   A   S   G   G   T   F   S   N   Y   A   I
52      GTG GAG GTC TCC TGC AAG GCT TCT GGG GGC ACC TTC AGC AAC TAT GCT ATC

        ___                                                         _CDR2___
        S   W   V   R   Q   A   P   G   Q   G   L   E   W   M   G   G   I
103     AGC TGG GTG CGA CAG GCC CCT GGA CAA GGG CTT GAG TGG ATG GGA GGG ATC

        ____________________________________________________________
        I   P   I   L   A   T   A   N   Y   A   P   K   F   Q   G   R   V
154     ATC CCC ATC TTG GCT ACA GCA AAC TAC GCA CCG AAG TTC CAG GGC AGA GTC

        T   I   T   A   D   E   F   T   S   S   A   Y   M   E   L   S   S
205     ACG ATT ACC GCG GAC GAA TTC ACG AGC TCA GCT TAC ATG GAG CTG AGC AGC

                                                            _CDR3___________
        L   R   S   E   D   T   A   V   Y   Y   C   A   K   S   S   I   T
256     CTG AGA TCT GAG GAC ACG GCC GTG TAT TAC TGT GCG AAG TCT AGT ATT ACT

        ____________________________________________________________
        M   I   R   G   A   Y   L   Y   Y   Y   D   G   M   D   V   W   G
307     ATG ATT CGG GGA GCC TAT CTT TAC TAC TAC GAC GGT ATG GAC GTC TGG GGC

        Q   G   T   T   V   T   V   S   S
358     CAA GGG ACC ACG GTC ACC GTC TCC TCA
```

*FIGURE 5*

| | FAMILY | LOCUS | TGL | VBASEENTRY |
|---|---|---|---|---|
| V-SEGMENT | VK3 | A27 | | DPK22/A27...+ |
| J-SEGMENT | JK2 | 2 | | JK2 |
| INPUT | 2H2.H3_NT | | | |

```
         E   I   V   L   T   Q   S   P   G   T   L   S   L   S   P   G   E
1        GAA ATT GTG TTG ACG CAG TCT CCA GGC ACC CTG TCT TTG TCT CCA GGG GAA

                                 _CDR1____________________________________
         R   A   T   L   S   C   R   A   S   Q   S   V   S   S   S   Y   L
52       AGA GCC ACC CTC TCC TGC AGG GCC AGT CAG AGT GTT AGC AGC AGC TAC TTA

         ___                                                             _CDR2
         A   W   Y   Q   Q   K   P   G   Q   A   P   R   L   L   I   Y   G
103      GCC TGG TAC CAG CAG AAA CCT GGC CAG GCT CCC AGG CTC CTC ATC TAT GGT

         _______________________
         A   S   S   R   A   T   G   I   P   D   R   F   S   G   S   G   S
154      GCA TCC AGC AGG GCC ACT GGC ATC CCA GAC AGG TTC AGT GGC AGT GGG TCT

         G   T   D   F   T   L   T   I   S   R   L   E   P   E   D   F   A
205      GGG ACA GAC TTC ACT CTC ACC ATC AGC AGA CTG GAG CCT GAA GAT TTT GCA

                         _CDR3_______________________
         V   Y   Y   C   Q   Q   Y   G   S   S   Y   T   F   G   Q   G   T
256      GTG TAT TAC TGT CAG CAG TAT GGT AGC TCG TAC ACT TTT GGC CAG GGG ACC

         K   L   E   I   K
307      AAG CTG GAG ATC AAA
```

*FIGURE 6*

| | FAMILY | LOCUS | RF | TGL | VBASEENTRY |
|---|---|---|---|---|---|
| V-SEGMENT | VH3 | 3-33 | | pH3v4D | DP-50/hv3019b9...+ |
| D-SEGMENT | D3 | 3-10 | 2 | | D3-10/DXP'1 |
| J-SEGMENT | JH4 | 4 | | | JH4b |
| INPUT | 2E5.A11_NT | | | | |

```
        Q   V   Q   L   V   E   S   G   G   G   V   V   Q   P   G   R   S
1       CAG GTG CAG CTG GTG GAG TCT GGG GGA GGC GTG GTC CAG CCT GGG AGG TCC

                                                         _CDR1___________
        L   R   L   S   C   T   A   S   G   F   T   F   S   N   Y   G   M
52      CTG AGA CTC TCC TGT ACA GCG TCT GGA TTC ACC TTC AGT AAC TAT GGC ATG

        ___                                                      _CDR2___
        H   W   V   R   Q   A   P   G   K   G   L   E   W   V   A   V   I
103     CAC TGG GTC CGC CAG GCT CCA GGC AAG GGA CTG GAG TGG GTG GCA GTT ATC

        ___________________________________________________________
        W   Y   D   G   S   N   E   Y   Y   A   E   S   V   K   G   R   L
154     TGG TAT GAT GGA AGT AAT GAA TAC TAT GCA GAA TCC GTG AAG GGC CGA CTC

        T   I   S   R   D   N   S   K   N   T   L   Y   L   Q   V   N   S
205     ACC ATC TCC AGA GAC AAT TCC AAG AAC ACG CTG TAT CTG CAA GTG AAC AGC

                                                         _CDR3___________
        L   R   A   E   D   T   A   V   Y   Y   C   A   R   D   P   F   Y
256     CTG AGA GCC GAG GAC ACG GCT GTG TAT TAT TGT GCG AGA GAT CCT TTC TAT

        _______________________________
        G   S   G   N   Y   F   D   Y   W   G   Q   G   T   L   V   T   V
307     GGT TCG GGG AAT TAC TTT GAC TAC TGG GGC CAG GGA ACC CTG GTC ACC GTC

        S   S
358     TCC TCA
```

*FIGURE 7*

| | FAMILY | LOCUS | TGL | VBASEENTRY |
|---|---|---|---|---|
| V-SEGMENT | VK3 | L6 | | Vg/38K...+ |
| J-SEGMENT | JK1 | 1 | | JK1 |
| INPUT | 2E5.A11_NT | | | |

```
        E   I   V   L   T   Q   S   P   A   T   L   S   L   S   P   G   E
1       GAA ATT GTG TTG ACA CAG TCT CCA GCC ACC CTG TCT TTG TCT CCA GGG GAA

                                _CDR1_____________________________________
        R   A   T   L   S   C   R   A   S   Q   S   V   S   S   Y   L   A
52      AGA GCC ACC CTC TCC TGC AGG GCC AGT CAG AGT GTT AGC AGC TAC TTA GCC

                                                                    _CDR2___
        W   Y   Q   Q   K   P   G   Q   A   P   R   L   L   I   Y   D   A
103     TGG TAC CAA CAG AAA CCT GGC CAG GCT CCC AGG CTC CTC ATC TAT GAT GCA

        ___________________
        S   N   R   A   T   G   I   P   A   R   F   S   G   S   G   S   G
154     TCC AAC AGG GCC ACT GGC ATC CCA GCC AGG TTC AGT GGC AGT GGG TCT GGG

        T   D   F   T   L   T   I   S   S   L   E   P   E   D   F   A   V
205     ACA GAC TTC ACT CTC ACC ATC AGC AGC CTA GAG CCT GAA GAT TTT GCA GTT

                    _CDR3_________________________________________
        Y   Y   C   Q   Q   R   S   N   W   P   P   W   T   F   G   Q   G
256     TAT TAC TGT CAG CAG CGT AGC AAC TGG CCT CCG TGG ACG TTC GGC CAA GGG

        T   K   V   E   I   K
307     ACC AAG GTG GAA ATC AAA
```

*FIGURE 8*

| | FAMILY | LOCUS | RF | TGL | VBASEENTRY |
|---|---|---|---|---|---|
| V-SEGMENT | VH3 | 3-23 | | pVx6 | DP-47/V3-23...+ |
| D-SEGMENT | D2 | 2-2 | 3 | | D2-2 |
| J-SEGMENT | JH4 | 4 | | | JH4b |
| INPUT | 24E5.A7_NT | | | | |

```
         E   V   Q   L   L   E   S   G   G   G   L   V   Q   P   G   G   S
1       GAG GTG CAG CTG TTG GAG TCT GGG GGA GGC TTG GTA CAG CCT GGG GGG TCC

                                                             _CDR1__________
         L   R   L   S   C   A   A   S   G   F   T   F   S   S   Y   V   M
52      CTG AGA CTC TCC TGT GCA GCC TCT GGA TTC ACC TTT AGC AGC TAT GTC ATG

        ___                                                          _CDR2___
         S   W   V   R   Q   A   P   G   K   G   L   E   W   V   S   G   I
103     AGC TGG GTC CGC CAG GCT CCA GGG AAG GGG CTG GAG TGG GTC TCA GGT ATT

        ___________________________________________________________
         S   G   S   G   G   S   T   Y   Y   A   D   S   V   K   G   R   F
154     AGT GGT AGT GGT GGT AGC ACA TAC TAC GCA GAC TCC GTG AAG GGC CGG TTC

         T   I   S   R   D   N   S   K   N   T   L   Y   L   Q   M   N   S
205     ACC ATC TCC AGA GAC AAT TCC AAG AAC ACG CTG TAT CTG CAA ATG AAC AGC

                                                             _CDR3__________
         L   R   A   E   D   T   A   V   Y   Y   C   A   K   D   Q   D   I
256     CTG AGA GCC GAG GAC ACG GCC GTA TAT TAC TGT GCG AAA GAT CAG GAT ATT

        _______________________________
         I   A   A   Y   Y   F   V   Y   W   G   Q   G   T   L   V   T   V
307     ATA GCA GCA TAC TAC TTT GTC TAC TGG GGC CAG GGA ACC CTG GTC ACC GTC

         S   S
358     TCC TCA
```

*FIGURE 9*

```
              FAMILY      LOCUS    TGL      VBASEENTRY

V-SEGMENT     VK1         L15               DPK7/HK134...+

J-SEGMENT     JK4         4                 JK4

INPUT         24E5.A7_NT


         D   I   Q   M   T   Q   S   P   S   S   L   S   A   S   V   G   D
1        GAC ATC CAG ATG ACC CAG TCT CCA TCC TCA CTG TCT GCA TCT GTA GGA GAC

                                _CDR1______________________________________
         R   V   T   I   T   C   R   A   S   Q   G   I   S   S   W   L   A
52       AGA GTC ACC ATC ACT TGT CGG GCG AGT CAG GGT ATT AGC AGC TGG TTA GCC

                                                                    _CDR2___
         W   Y   Q   Q   K   P   E   K   A   P   K   S   L   I   Y   A   A
103      TGG TAT CAG CAG AAA CCA GAG AAA GCC CCT AAG TCC CTG ATC TAT GCT GCA

         ____________________
         S   S   L   Q   S   G   V   P   S   R   F   S   G   S   G   S   G
154      TCC AGT TTG CAA AGT GGG GTC CCA TCA AGG TTC AGC GGC AGT GGA TCT GGG

         T   D   F   T   L   T   I   S   S   L   Q   P   E   D   F   A   T
205      ACA GAT TTC ACT CTC ACC ATC AGC AGC CTG CAG CCT GAA GAT TTT GCA ACT

                     _CDR3______________________________
         Y   Y   C   Q   Q   Y   N   S   Y   P   L   T   F   G   G   G   T
256      TAT TAC TGC CAA CAG TAT AAT AGT TAC CCT CTC ACT TTC GGC GGA GGG ACC

         K   V   E   I   K
307      AAG GTG GAG ATC AAA
```

*FIGURE 10*

| | FAMILY | LOCUS | RF | TGL | VBASEENTRY |
|---|---|---|---|---|---|
| V-SEGMENT | VH3 | 3-23 | | pVx6 | DP-47/V3-23...+ |
| D-SEGMENT | D3 | 3-10 | 2 | | D3-10/DXP'1 |
| J-SEGMENT | JH4 | 4 | | | JH4b |
| INPUT | 21D9.H11_NT | | | | |

```
        E   G   Q   L   L   E   S   G   G   D   L   V   Q   P   G   G   S
1       GAG GGA CAG CTG TTG GAG TCT GGG GGA GAC TTG GTA CAG CCT GGG GGG TCC

                                                    _CDR1__________
        L   R   L   S   C   A   T   S   G   F   T   F   S   N   Y   A   M
52      CTG AGA CTC TCC TGT GCA ACC TCT GGA TTC ACC TTT AGC AAC TAT GCC ATG

        ___                                                     _CDR2___
        N   W   V   R   Q   A   P   G   K   G   L   E   W   I   S   V   I
103     AAC TGG GTC CGC CAG GCT CCA GGG AAG GGG CTG GAG TGG ATC TCA GTT ATT

        ____________________________________________________________
        S   V   S   G   G   S   T   Y   Y   A   D   S   V   K   G   R   F
154     AGT GTT AGT GGT GGT AGC ACA TAC TAC GCA GAC TCC GTG AAG GGC CGG TTC

        T   I   S   R   D   N   S   K   N   T   L   Y   L   Q   M   N   S
205     ACC ATC TCC AGA GAC AAT TCC AAG AAC ACG CTG TAT CTG CAA ATG AAT AGC

                                                    _CDR3__________
        L   R   A   E   D   T   A   V   Y   Y   C   A   K   D   Y   Y   Y
256     CTG AGA GCC GAG GAC ACG GCC GTA TAT TAC TGT GCG AAA GAT TAT TAC TAT

        ________________________________________________
        D   S   G   S   Y   Y   D   S   F   F   D   Y   W   G   Q   G   T
307     GAT TCG GGG AGT TAT TAT GAC TCT TTC TTT GAC TAC TGG GGC CAG GGA ACC

        L   V   T   V   S   S
358     CTG GTC ACC GTC TCC TCA
```

*FIGURE 11*

| | FAMILY | LOCUS | TGL | VBASEENTRY |
|---|---|---|---|---|
| V-SEGMENT | VK3 | A27 | | DPK22/A27...+ |
| J-SEGMENT | JK4 | 4 | | JK4 |
| INPUT | 21D9.H11_NT | | | |

```
          E   I   V   L   T   Q   S   P   G   T   L   S   L   S   P   G   E
1        GAA ATT GTG TTG ACG CAG TCT CCA GGC ACC CTG TCT TTG TCT CCA GGG GAA

                                _CDR1_______________________________________
          R   A   T   L   S   C   R   A   S   Q   S   V   S   S   S   Y   L
52       AGA GCC ACC CTC TCC TGC AGG GCC AGT CAG AGT GTT AGC AGC AGC TAC TTA

         ___                                                           _CDR2
          A   W   Y   Q   Q   K   P   G   Q   A   P   R   L   L   I   Y   G
103      GCC TGG TAC CAG CAG AAA CCT GGC CAG GCT CCC AGG CTC CTC ATC TAT GGT

         _______________________
          A   S   S   R   A   T   G   I   P   D   R   F   S   G   S   G   S
154      GCA TCC AGC AGG GCC ACT GGC ATC CCA GAC AGG TTC AGT GGC AGT GGG TCT

          G   T   D   F   T   L   T   I   S   R   L   E   P   E   D   F   A
205      GGG ACA GAC TTC ACT CTC ACC ATC AGC AGA CTG GAG CCT GAA GAT TTT GCA

                        _CDR3_________________________________
          V   Y   Y   C   Q   Q   Y   G   S   S   P   L   T   F   G   G   G
256      GTG TAT TAC TGT CAG CAG TAT GGT AGC TCA CCT CTC ACT TTC GGC GGA GGG

          T   K   V   E   I   K
307      ACC AAG GTG GAG ATC AAA
```

*FIGURE 12*

Framework sequence || <u>*CDR sequences*</u> || *Liabilities* || Framework mutations || Framework mutations not in any germline (7mers)

>Query: Heavy
EGQLLESGGDLVQPGGSLRLSCATS*GFTFSNYAMN*WVRQAPGKGLEWIS*VISVSGGSTYYADSVKG*RFTISRDNSKNTLYLQMNSLRAEDTAVYYCAK*DYYYDSGSYYDSFFDY*WGQGTLVTVSS >Germline: hIGHV3-23*01
EVQLLESGGGLVQPGGSLRLSCAAS*GFTFSSYAMS*WVRQAPGKGLEWVS*AISVSGGSTYYADSVKG*RFTISRDNSKNTLYLQMNSLRAEDTAVYYCAK >Germline J-Gene: IGHJ4
WGQGTLVTVSS

FIGURE 13A

| | |
|---|---|
| 21D9.b | EvqllesggGlvqpggslrlscatsgftfsnyamnwvrqapgkglewisvisvsggstyyadsvkgrftisrdns |
| hIgG1.3 | kntlylqmnslraedtavyycakdyyydsgsyydsffdywgqgtlvtvss |
| 21D9.c | EvqllesggdlvqpggslrlscaAsgftfsnyamnwvrqapgkglewisvisvsggstyyadsvkgrftisrdns |
| hIgG1.3 | kntlylqmnslraedtavyycakdyyydsgsyydsffdywgqgtlvtvss |
| 21D9.d | EvqllesggdlvqpggslrlscatsgftfsnyamnwvrqapgkglewVsvisvsggstyyadsvkgrftisrdns |
| hIgG1.3 | kntlylqmnslraedtavyycakdyyydsgsyydsffdywgqgtlvtvss |
| 21D9.e | EvqllesggGlvqpggslrlscaAsgftfsnyamnwvrqapgkglewVsvisvsggstyyadsvkgrftisrdns |
| hIgG1.3 | kntlylqmnslraedtavyycakdyyydsgsyydsffdywgqgtlvtvss |

FIGURE 13B

>Query: Light
EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPLTFGGGTKVEIK >Germline: hIGKV3-20*01
EIVLTQSPGTLSLSPGERATLSCRASQSVSSSYLAWYQQKPGQAPRLLIYGASSRATGIPDRFSGSGSGTDFTLTISRLEPEDFAVYYCQQYGSSP >Germline: J-Gene: IGKJ4
FGGGTKVEIK

FIGURE 13C

Framework sequence || CDR sequences || Liabilities || Framework mutations || Framework mutations not in any germline (7mers)

>Query: Heavy
QVQLVQSGAEVKKPGASVKVSCKASGYTFTDYYLHWVRQAPGQGLEWMGIFHPSGDITSSAQNFQGRVTMIRDTSTSTVYMELSSLRSEDTAVYYCARGGVLRYLDWSHAFDIWGQGTMVTVSS >Germline: hIGHV1-46*01
QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCAR >Germline J-Gene: IGHJ3
WGQGTMVTVSS

FIGURE 14A

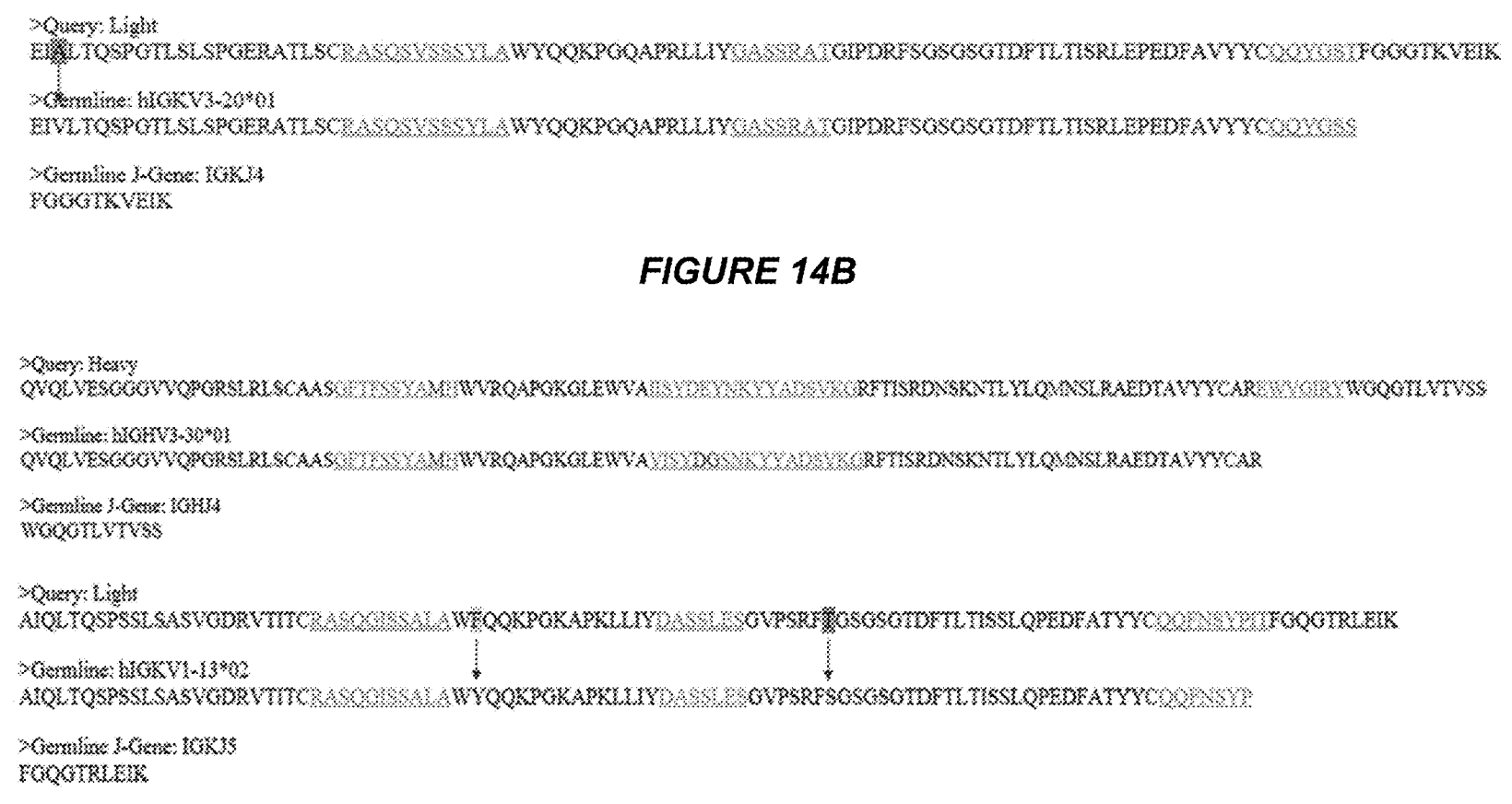

>Query: Light
EI[illegible]LTQSPGTLSLSPGERATLSCRASQSVSSSYLAWYQQKPGQAPRLLIYGASSRATGIPDRFSGSGSGTDFTLTISRLEPEDFAVYYCQQYGSTFGGGTKVEIK >Germline: hIGKV3-20*01
EIVLTQSPGTLSLSPGERATLSCRASQSVSSSYLAWYQQKPGQAPRLLIYGASSRATGIPDRFSGSGSGTDFTLTISRLEPEDFAVYYCQQYGSS >Germline J-Gene: IGKJ4
FGGGTKVEIK

*FIGURE 14B*

>Query: Heavy
QVQLVESGGGVVQPGRSLRLSCAASGFTFSSYAMHWVRQAPGKGLEWVAISYDEYNKYYADSVKGRFTISRDNSKNTLYLQMNSLRAEDTAVYYCAREWYGIRYWGQGTLVTVSS >Germline: hIGHV3-30*01
QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCAR >Germline J-Gene: IGHJ4
WGQGTLVTVSS >Query: Light
AIQLTQSPSSLSASVGDRVTITCRASQGISSALAWFQQKPGKAPKLLIYDASSLESGVPSRF[illegible]GSGSGTDFTLTISSLQPEDFATYYCQQFNSYPITFGQGTRLEIK >Germline: hIGKV1-13*02
AIQLTQSPSSLSASVGDRVTITCRASQGISSALAWYQQKPGKAPKLLIYDASSLESGVPSRFSGSGSGTDFTLTISSLQPEDFATYYCQQFNSYP >Germline J-Gene: IGKJ5
FGQGTRLEIK

*FIGURE 15*

| | 2H2 | 10F10 WT | 21A5 WT | 21A5.a | 21D9 WT | 21D9.e |
|---|---|---|---|---|---|---|
| EC50 | 0.2485 | 0.01499 | 0.05179 | 0.06271 | 0.01274 | 0.004157 |

| | EC50 |
|---|---|
| 2E5 | 0.09861 |
| 2H2 | 0.2614 |
| 3B3 | 0.4860 |
| 6E10 | 6.415 |
| 7A2 | 1.547 |
| 7B1 | 15.38 |
| 8H8 | 0.5348 |
| 9C8 | 0.1893 |
| 9G4 | 2.843 |
| 11E4 | 0.5080 |
| 13D4 | 0.3673 |
| 15B11 | 0.3159 |
| 17D6 | 0.3875 |
| 21D9 | 0.01741 |
| 24E5 | 0.2684 |
| 287219 | 0.03224 |
| 42D6 | 0.2520 |

| | EC50 |
|---|---|
| 10F10 | 0.1311 |
| 21A5.a | 0.3951 |
| 21D9.e | 0.03406 |

| | hIgG1.3 | 21D9 WT | 21D9.e | 21A5 WT | 21A5.a | 10F10 WT |
|---|---|---|---|---|---|---|
| EC50 | | ~ 0.4321 | ~ 0.3385 | ~ 0.1932 | 0.2638 | ~ 0.2892 |

| | hIgG1.3 | 21D9 WT | 21D9.e | 21A5 WT | 21A5.a | 10F10 WT |
|---|---|---|---|---|---|---|
| EC50 | | 0.3733 | ~ 0.2107 | ~ 0.1943 | 0.6183 | 0.3874 |

22 60
QTGTIPKPTLWAEPDSVITQGSPVTLSCQGSLEAQEYRL
61 120
REKKSASWITRIRPELVKNGQFHIPSITWEHTGRYGCQYYSRARWSELSDPLVLVMTGA
121 180
YPKPTLSAQPSPVVTSGGRVTLQCESQVAFGGFILCKEGEEEHPQCLNSQPHARGSSRAI
181 240
FSVGPVSPNRRWSHRCYGYDLNSPYVWSSPSDLLELLVPGVSKKPSLSVQPGPVVAPGES
241 300
LTLQCVSDVGYDRFVLYKEGERDLRQLPGRQPQAGLSQANFTLGPVSRSYGGQYRCYGAH
301 360
NLSSESSAPSDPLDILITGQIRGTPFISVQPGPTVASGENVTLLCQSWRQFHTFLLTKAG
361 420
AADAPLRLRSIHEYPKYQAEFPMSPVTSAHAGTYRCYGSLNSDPYLLSHPSEPLELVVSG
421 480
PSMGSSPPPTGPISTPAGPEDQPLTPTGSDPQSGLGRHLGSPGGGSGGGSEQKLISEEDL
481 500
GHHHHHHGLNDIFEAQKIEWHE

*FIGURE 27C*

| | HLA-A | HLA-B |
|---|---|---|
| IC50 | 2.882 | 0.9179 |

| | HLA-A | HLA-B |
|---|---|---|
| IC50 | 3.372 | 0.7475 |

| | HLA-A | HLA-B |
|---|---|---|
| IC50 | 3.602 | 1.551 |

| | HLA-A | HLA-B |
|---|---|---|
| IC50 | 3.826 | 1.613 |

| 21D9.e hIgG1.3 | 21D9.e hIgG4 | 21D9.e hIgG1 |
|---|---|---|
| 0.001916 | 0.002948 | 0.003728 |

| | 10F10 | 21A5 | KLH-g1.1f | 21D9 | 2H2 |
|---|---|---|---|---|---|
| EC50 | 0.02786 | 0.0738 | | | |

| | 10F10 | 21A5 | KLH-g1.1f | 21D9 | 2H2 |
|---|---|---|---|---|---|
| EC50 | 0.04919 | 0.08977 | | | |

ANTIBODIES BINDING TO ILT4

PRIORITY INFORMATION

The present application claims priority to US Provisional Patent Application Nos. 62/695,600, filed Jul. 9, 2018, and 62/744,611, filed Oct. 11, 2018, and is also a continuation of International Patent Application PCT/US2019/40820, filed Jul. 8, 2019. All of these applications are incorporated in their entirety by reference herein.

SEQUENCE LISTING

The present application is filed with a Sequence Listing in electronic format. The Sequence Listing is provided as a file entitled "01134-0060-00PCT_ST25.txt" created on Aug. 2, 2019, which is 258,058 bytes in size. The information in the electronic format of the sequence listing is incorporated herein by reference in its entirety.

FIELD

The present application relates to antibodies specifically binding to and inhibiting ILT4, and their use in cancer treatment.

BACKGROUND

ILT4 (immunoglobulin-like transcript 4; also known as LILRB2, LIR2, MIR10, and CD85d) is expressed on myeloid cells, such as monocytes, macrophages, and dendritic cells. ILT4 is part of a family of structurally-related receptors that also includes the proteins LILRA1, LILRA2, LILRA3, LILRA4, LILRA5, LILRA6, ILT2, ILT3, ILT5, and LIR8.

The extracellular domains of proteins in this family contain several immunoglobulin-like repeats, while their cytoplasmic tails contain several tyrosine-based inhibitory motifs (ITIMs), which recruit tyrosine phosphatases.

BRIEF DESCRIPTION OF THE FIGURES

The present application claims priority to US provisional patent applications that contain at least one drawing from the list below executed in color. Once this international application publishes and its priority provisional applications become available to the public, it is assumed that the color drawings will be provided by the US Patent and Trademark Office upon request and payment of the necessary fee.

FIG. 1 shows the nucleotide and amino acid sequences of the heavy chain variable region ("VH") of anti-hILT4 antibody 9G4, indicating the location of the VH CDRs. The 9G4 VH amino acid sequence depicted in the figure is that of SEQ ID NO: 180, and the 9G4 VH DNA sequence depicted in the figure is that of SEQ ID NO: 181.

FIG. 2 shows the nucleotide and amino acid sequences of the light chain variable region ("VL") of anti-hILT4 antibody 9G4, indicating the location of the VL CDRs. The 9G4 VL amino acid sequence depicted in the figure is that of SEQ ID NO: 182, and the 9G4 VL DNA sequence depicted in the figure is that of SEQ ID NO: 183.

FIG. 3 shows the nucleotide and amino acid sequences of the VH of anti-hILT4 antibody 9C8, indicating the location of the VH CDRs. The 9C8 VH amino acid sequence depicted in the figure is that of SEQ ID NO: 55, and the 9C8 VH DNA sequence depicted in the figure is that of SEQ ID NO: 57.

FIG. 4 shows the nucleotide and amino acid sequences of the VL of anti-hILT4 antibody 9C8, indicating the location of the VL CDRs. The 9C8 VL amino acid sequence depicted in the figure is that of SEQ ID NO: 54, and the 9C8 VL DNA sequence depicted in the figure is that of SEQ ID NO: 56.

FIG. 5 shows the nucleotide and amino acid sequences of the VH of anti-hILT4 antibody 2H2, indicating the location of the VH CDRs. The 2H2 VH amino acid sequence depicted in the figure is that of SEQ ID NO: 58, and the 2H2 VH DNA sequence depicted in the figure is that of SEQ ID NO: 60.

FIG. 6 shows the nucleotide and amino acid sequences of the VL of anti-hILT4 antibody 2H2, indicating the location of the VL CDRs. The 2H2 VL amino acid sequence depicted in the figure is that of SEQ ID NO: 59, and the 2H2 VL DNA sequence depicted in the figure is that of SEQ ID NO: 61.

FIG. 7 shows the nucleotide and amino acid sequences of the VH of anti-hILT4 antibody 2E5, indicating the location of the VH CDRs. The 2E5 VH amino acid sequence depicted in the figure is that of SEQ ID NO: 63, and the 2E5 VH DNA sequence depicted in the figure is that of SEQ ID NO: 65.

FIG. 8 shows the nucleotide and amino acid sequences of the VL of anti-hILT4 antibody 2E5, indicating the location of the VL CDRs. The 2E5 VL amino acid sequence depicted in the figure is that of SEQ ID NO: 62, and the 2E5 VL DNA sequence depicted in the figure is that of SEQ ID NO: 64.

FIG. 9 shows the nucleotide and amino acid sequences of the VH of anti-hILT4 antibody 24E5, indicating the location of the VH CDRs. The 24E5 VH amino acid sequence depicted in the figure is that of SEQ ID NO: 67, and the 24E5 VH DNA sequence depicted in the figure is that of SEQ ID NO: 69.

FIG. 10 shows the nucleotide and amino acid sequences of the VL of anti-hILT4 antibody 24E5, indicating the location of the VL CDRs. The 24E5 VL amino acid sequence depicted in the figure is that of SEQ ID NO: 66, and the 24E5 VL DNA sequence depicted in the figure is that of SEQ ID NO: 68.

FIG. 11 shows the nucleotide and amino acid sequences of the VH of anti-hILT4 antibody 21D9, indicating the location of the VH CDRs. The 21D9 VH amino acid sequence depicted in the figure is that of SEQ ID NO: 71, and the 21D9 VH DNA sequence depicted in the figure is that of SEQ ID NO: 73.

FIG. 12 shows the nucleotide and amino acid sequences of the VL of anti-hILT4 antibody 21D9, indicating the location of the VL CDRs. The 21D9 VL amino acid sequence depicted in the figure is that of SEQ ID NO: 70, and the 21D9 VL DNA sequence depicted in the figure is that of SEQ ID NO: 72.

FIGS. 13A and 13C show alignments of the amino acid sequences of the variable domains of the heavy (VH) (FIG. 13A) and (VL) (FIG. 13C) chains of ILT4 antibody 21D9 (SEQ ID NO: 71) with germline immunoglobulin sequences hIGHV3-23*01 (SEQ ID NO: 184) and IGHJ4 (SEQ ID NO: 185) and hIGKV3-20*01 (SEQ ID NO: 186) and IGKJ4 (SEQ ID NO: 187), respectively. Arrows point to germline mutations. AbM VH CDR1 and Kabat VH CDR2, VH CDR3, and VL CDR1-3 sequences are shown in light text. FIG. 13B shows the VH amino acid sequences of the four germline reversion mutants 21D9.b, 21D9.c, 21D9.d and 21D9.e (SEQ ID Nos: 74, 75, 78, and 80, respectively), with an IgG1.3 heavy chain constant region (i.e. 21D9.b-.e hIgG1.3). Amino acid residues represented in upper case in FIG. 13B are germline reversion substitutions.

FIGS. 14A and 14B show alignments of the amino acid sequences of the variable domains of the heavy and light chains of ILT4 antibody 21A5 (SEQ ID NO: 83) with germline immunoglobulin sequences hIGHV1-46*01 (SEQ ID NO: 188) and IGHJ3 (SEQ ID NO: 189) (FIG. 14A) and hIGKV3-20*01 (SEQ ID NO: 186) and IGKJ4 (SEQ ID NO: 187) (FIG. 14B), respectively. AbM VH CDR1 and Kabat VH CDR2, VH CDR3, and VL CDR1-3 sequences are shown in light text. Arrows point to germline reversion mutations.

FIG. 15 shows alignments of the amino acid sequences of variable domains of the heavy and light chains of ILT4 antibody 10F10 (SEQ ID NO: 91 and 90, respectively) with germline immunoglobulin sequences hIGHV3-30*01 (SEQ ID NO: 190) and IGHJ4 (SEQ ID NO: 191) (top 3 lines) and hIGKV1-13*02 (SEQ ID NO: 192) and IGKJ5 (SEQ ID NO: 193) (bottom 3 lines), respectively. AbM VH CDR1 and Kabat VH CDR2, VH CDR3, and VL CDR1-3 sequences are shown in light text. Arrows point to germline reversion mutations.

FIG. 21A is a histogram of $^3$H thymidine incorporation of T co-cells cultured with CHO cells transfected with hILT4 and OKT3 incubated with (from left to right on x-axis) no antibody, isotype control hIgG1.3 antibody, and antibodies 21D9 ("21D9 WT"), 21D9.e, 21A5 ("21A5 WT"), 21A5.a and 10F10 ("10F10 WT") as a function of antibody concentration (20, 4, 0.8, 0.16, 0.032, and 0.0064 μg/ml). FIG. 21B provides the associated EC50 values. FIG. 21C shows T cell activity of anti-hILT4 antibodies. FIG. 21C is a histogram of IFNγ production of T cells co-cultured with CHO cells transfected with hILT4 and OKT3 incubated with (from left to right on x-axis) no antibody, isotype control hIgG1.3 antibody, and antibodies 21D9 ("21D9 WT"), 21D9.e, 21A5 ("21A5 WT"), 21A5.a and 10F10 ("10F10 WT") as a function of antibody concentration (20, 4, 0.8, 0.16, 0.032, and 0.0064 μg/ml). FIG. 21D provides the associated EC50 values.

FIG. 25A shows the percentage of CD4 T cell proliferation by FACS analysis based on CFSE dilution.

FIG. 26A shows one experiment from one macrophage: CD4 T allogenic pair.

FIG. 27A shows the hILT4 sequence (SEQ ID NO: 119) coverage by Pepsin. FIG. 27C shows the HDX epitopes of the two Fabs mapped to the linear sequence of hILT4 (SEQ ID NO: 119). The epitope of antibody 21D9 is shown by a single underline. The epitope of antibody 2H2 is shown in the double underline and shaded/hatched underline portions of the sequence.

FIG. 29A shows IFN-γ secretion in CD4+ T cells; FIG. 29B shows TNF-α secretion in CD4+ T cells; FIG. 29C shows IFN-γ secretion in CD8+ T cells; and FIG. 29D shows TNF-α secretion in CD8+ T cells.

FIG. 34 shows that the level of TNF-alpha secreted by in vitro differentiated macrophages incubated with 21D9.e in the context of IgG1, IgG4 or IgG1.3 is similar.

FIGS. 37A and B show competition (or cross-blocking) assay results of 2H2 (FIG. 37A) and 21D9 (FIG. 37B) by 10F10 and 21A5 antibodies of hILT4 expressed on the surface of CHO cells. FIG. 37C is a diagram showing a three-dimensional representation of hILT4 with the location of Ig-like domains 1 and 2, and indicating the areas of hILT4 to which antibodies 21D9, 29A5, 2H2 and 10F10 bind.

FIG. 37D shows a further three-dimensional representation of hILT4 with the location of Ig-like domains 1 and 2, and indicating the areas of hILT4 to which antibodies 21D9, 21A5, and 10F10 bind.

SUMMARY OF THE DISCLOSURE

Figure 16:
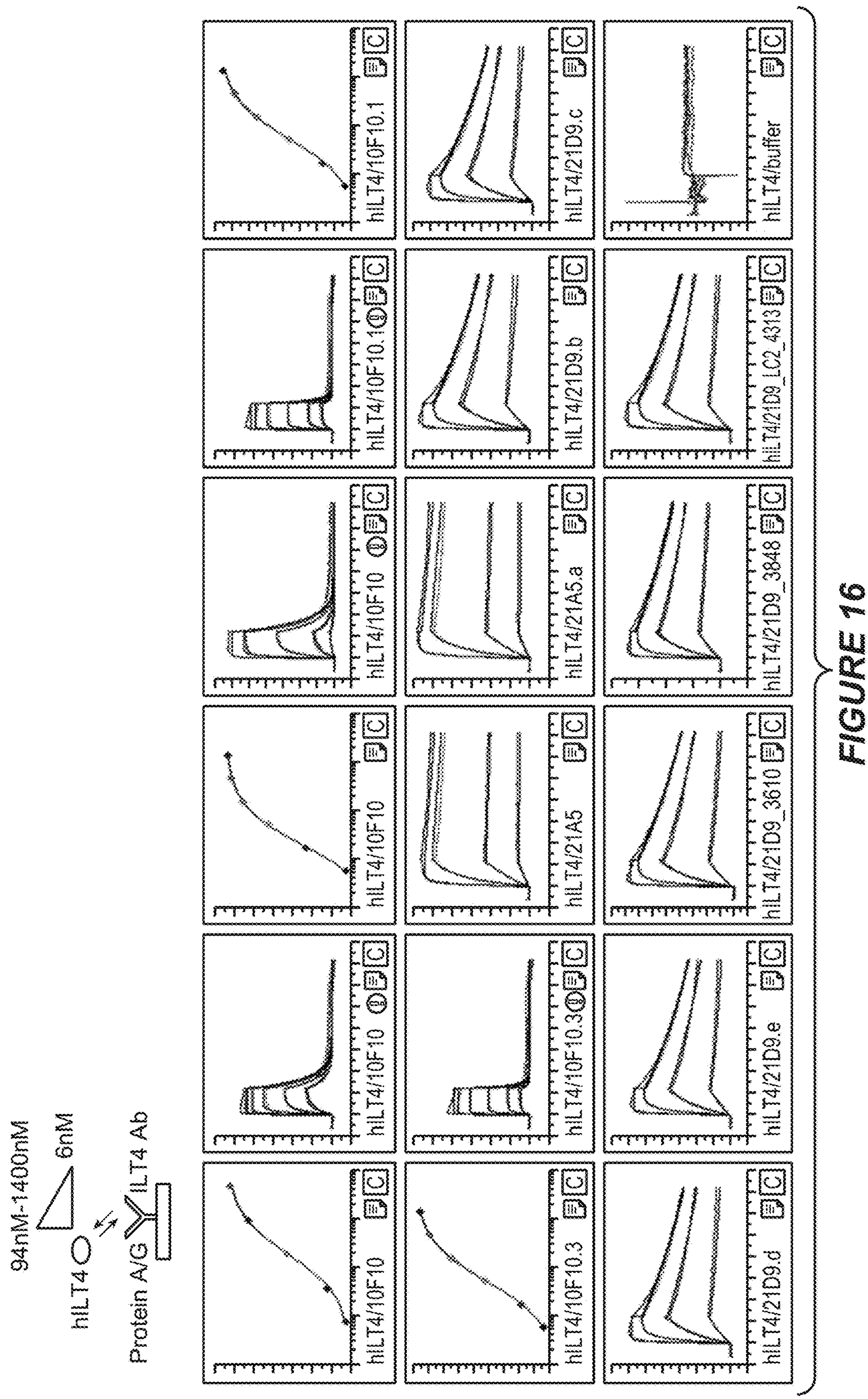
FIG. 16 shows sensorgrams of binding of the indicated anti-hILT4 antibodies to hILT4. A schematic of the method used is shown above the sensorgram panels.

Certain embodiments of this disclosure are summarized in the claims are the end of the disclosure. For example, the present disclosure includes the following embodiments, as well as other embodiments described in further sections of the text and in the figures and sequences herein.

Embodiment 1

An isolated antibody that binds specifically to human ILT4 (hILT4 or ILT4), the antibody comprising a heavy chain and a light chain, and further comprising one or more of the following characteristics:

- specific binding to hILT4 (e.g. comprising the amino acid sequence of SEQ ID NO: 108, 109, 111, 112, or 119), e.g., with a $K_D$ of $10^{-8}$M or less, or of $10^{-9}$ M or less;
- lack of specific binding to hILT2, hILT3, and/or hILT5;
- lack of specific binding to one or more members of the LILRA and/or LILRB families;
- stimulates T cell activation, e.g., in a mixed lymphocyte reaction (MLR) assay, as measured by increased T cell proliferation or IFN-gamma secretion, e.g., as shown in an assay described in the Examples;
- stimulates differentiation or activation of monocytes into macrophages, e.g., stimulates differentiation of monocytes into pro-inflammatory macrophages, e.g., as shown in an assay described in the Examples;
- promotes expression of CD83 and CD86 on human monocyte derived immature dendritic cells (Mo-iDC), e.g., as shown in an assay described in the Examples;
- enhances IFN-γ secretion upon antigen stimulation in a cytomegalovirus (CMV) lysate assay, e.g., as shown in an assay described in the Examples;
- enhances IFN-γ and TNF-α secretion by CD4+ and CD8+ T cells in an allo-mixed lymphocyte reaction (MLR) assay upon CD3 stimulation, e.g., as shown in an assay described in the Examples;
- inhibits binding of HLA-A and/or HLA-B to ILT4;
- binds to $^{70}$ITRIRPELVKNGQFHIPSITWEHTGRYGCQY$^{100}$ (SEQ ID NO: 122) as determined by hydrogen deuterium exchange (HDX), e.g., as shown in an HDX assay described in the Examples;
- competes for binding to hILT4 with an antibody described herein;
- binds specifically to a cyno ILT4 comprising SEQ ID NO: 118, e.g., as shown in a binding assay described in the Examples;
- inhibits binding of human ILT4 (hILT4) to an ILT4 binding partner, such as an MEW class I molecule, such as HLA-A and HLA-B (for example, inhibits binding of hILT4 to both HLA-A and HLA-B);
- has an HLA-A and HLA-B binding profile shown in FIG. 28;
- promotes pro-inflammatory polarization of macrophages towards M1 macrophages;
- has a binding profile as shown in FIG. 27;
- does not induce (or trigger) basophil activation;
- binds to the following regions of hILT4: (i) $^{70}$ITRIRPEL$^{77}$ (SEQ ID NO: 120) and/or $^{78}$VKNGQFHIPSITWEHTGRYGCQY$^{100}$ (SEQ ID NO: 121); (ii) $^{70}$ITRIRPELVKNGQFHIPSITWEHT- GRYGCQY$^{100}$ (SEQ ID NO: 122); or (iii) $^{154}$ILCKEGEEEHPQCLNSQPHARGSSRAIF$^{181}$ (SEQ ID NO: 123) and/or $^{425}$SSPPPTGPIS$^{434}$ (SEQ ID NO: 124), and, if binding to (i) or (ii), then optionally, not binding significantly to other regions of the extracellular domain of ILT4, such as regions or residues located N-terminal to amino acid 170, wherein the amino acid numbering of hILT4 is that of immature hILT4 (i.e., ILT4 comprising its native signal sequence); and interacts with one or more (or all of) amino acid residues Lys43, Ile49, Thr50 and Arg51 of mature hILT4 or interacts with one or more (or all of) amino acid residues Gly117, Val119, Try120, Leu134, Lys136, Gln149, Pro150, Ile159, Ser161, Val162, Gly163, Pro164, Pro167, His173, Try178, Pro183 and Tyr184 of mature hILT4 or interacts with one or more (or all of) amino acid residues Glu42, Lys43, Gly76, Cys77, Leu88, Pro91, Pro183 and Tyr184 of mature hILT4, as determined by carbene foot-printing, e.g., as described in the Examples.

Embodiment 2

The isolated antibody of embodiment 1, comprising a heavy chain and a light chain, wherein the heavy chain comprises VH CDR1, CDR2 and CDR3 of anti-ILT4 antibody 9G4 (SEQ ID Nos: 125-127), 9C8 (SEQ ID Nos: 131-133), 2H2 (SEQ ID Nos: 137-139), 2E5 (SEQ ID Nos: 143-145), 24E5 (SEQ ID Nos: 149-151), 21D9 (SEQ ID Nos: 155-157), 21A5 (SEQ ID Nos: 161-163), or 10F10 (SEQ ID Nos: 167-169).

Embodiment 3

The isolated antibody of embodiment 1 or 2, comprising a heavy chain and a light chain, wherein the light chain comprises VL CDR1, CDR2 and CDR3 of anti-ILT4 antibody 9G4 (SEQ ID Nos: 128-130), 9C8 (SEQ ID Nos: 134-136), 2H2 (SEQ ID Nos: 140-142), 2E5 (SEQ ID Nos: 146-148), 24E5 (SEQ ID Nos: 152-154), 21D9 (SEQ ID Nos: 158-160), 21A5 (SEQ ID Nos: 164-166), or 10F10 (SEQ ID Nos: 170-172).

Embodiment 4

The isolated antibody of embodiment 2, wherein the heavy chain comprises VH CDR1, CDR2 and CDR3 and VL CDR1, CDR2 and CDR3 of anti-ILT4 antibody 9G4 (SEQ ID Nos: 143-148), 24E5 (SEQ ID Nos: 149-154), 21D9 (SEQ ID Nos: 155-160), 21A5 (SEQ ID Nos: 161-166), or 10F10 (SEQ ID Nos: 167-172).

Embodiment 5

The isolated antibody of any one of embodiments 1-4, which comprises:

a VH comprising the amino acid sequence of the VH CDR1, CDR2 and CDR3 of 9G4 (SEQ ID Nos: 125-127) and a VL comprising the amino acid sequence of the VL CDR1, CDR2 and CDR3 of 9G4 (SEQ ID Nos: 128-130);

a VH comprising the amino acid sequence of the VH CDR1, CDR2 and CDR3 of 9C8 (SEQ ID Nos: 131-133) and a VL comprising the amino acid sequence of the VL CDR1, CDR2 and CDR3 of 9C8 (SEQ ID Nos: 134-136);

a VH comprising the amino acid sequence of the VH CDR1, CDR2 and CDR3 of 2H2 (SEQ ID Nos: 137-139) and a VL comprising the VL CDR1, CDR2 and CDR3 of 2H2 (SEQ ID Nos: 140-142);

a VH comprising the amino acid sequence of the VH CDR1, CDR2 and CDR3 of 2E5 (SEQ ID Nos: 143-145) and a VL comprising the amino acid sequence of the VL CDR1, CDR2 and CDR3 of 2E5 (SEQ ID Nos: 146-148);

a VH comprising the amino acid sequence of the VH CDR1, CDR2 and CDR3 of 24E5 (SEQ ID Nos: 149-151) and a VL comprising the amino acid sequence of the VL CDR1, CDR2 and CDR3 of 24E5 (SEQ ID Nos: 152-154);

a VH comprising the amino acid sequence of the VH CDR1, CDR2 and CDR3 of 21D9 (SEQ ID Nos: 155-157) and a VL comprising the amino acid sequence of the VL CDR1, CDR2 and CDR3 of 21D9 (SEQ ID Nos: 158-160);

a VH comprising the amino acid sequence of the VH CDR1, CDR2 and CDR3 of 21D9.b (SEQ ID Nos: 155-157) and a VL comprising the amino acid sequence of the VL CDR1, CDR2 and CDR3 of 21D9.b (SEQ ID Nos: 158-160);

a VH comprising the amino acid sequence of the VH CDR1, CDR2 and CDR3 of 21D9.c (SEQ ID Nos: 155-157) and a VL comprising the amino acid sequence of the VL CDR1, CDR2 and CDR3 of 21D9.c (SEQ ID Nos: 158-160);

a VH comprising the amino acid sequence of the VH CDR1, CDR2 and CDR3 of 21D9.d (SEQ ID Nos: 155-157) and a VL comprising the amino acid sequence of the VL CDR1, CDR2 and CDR3 of 21D9.d (SEQ ID Nos: 158-160);

a VH comprising the amino acid sequence of the VH CDR1, CDR2 and CDR3 of 21D9.e (SEQ ID Nos: 155-157) and a VL comprising the amino acid sequence of the VL CDR1, CDR2 and CDR3 of 21D9.e (SEQ ID Nos: 158-160);

a VH comprising the amino acid sequence of the VH CDR1, CDR2 and CDR3 of 21A5 (SEQ ID Nos: 161-163) and a VL comprising the amino acid sequence of the VL CDR1, CDR2 and CDR3 of 21A5 (SEQ ID Nos: 164-166);

a VH comprising the amino acid sequence of the VH CDR1, CDR2 and CDR3 of 21A5.a (SEQ ID Nos: 161-163) and a VL comprising the amino acid sequence of the VL CDR1, CDR2 and CDR3 of 21A5.a (SEQ ID Nos: 164-166);

a VH comprising the amino acid sequence of the VH CDR1, CDR2 and CDR3 of 10F10 (SEQ ID Nos: 167-169) and a VL comprising the amino acid sequence of the VL CDR1, CDR2 and CDR3 of 10F10 (SEQ ID Nos: 170-172);

a VH comprising the amino acid sequence of the VH CDR1, CDR2 and CDR3 of 10F10.1 (SEQ ID Nos: 167-169) and a VL comprising the amino acid sequence of VL CDR1, CDR2 and CDR3 of 10F10.1 (SEQ ID Nos: 170-172);

a VH comprising the amino acid sequence of the VH CDR1, CDR2 and CDR3 of 10F10.3 (SEQ ID Nos: 167-169) and a VL comprising the amino acid sequence of the VL CDR1, CDR2 and CDR3 of 10F10.3 (SEQ ID Nos: 170-172); or a VH comprising the amino acid sequence of the VH CDR1, CDR2 and CDR3 of 10F10.4 (SEQ ID Nos:

167-169) and a VL comprising the amino acid sequence of the VL CDR1, CDR2 and CDR3 of 10F10.4 (SEQ ID Nos: 170-172).

Embodiment 6

The isolated antibody of any one of embodiments 1-5, wherein the antibody heavy chain comprises a VH with an amino acid sequence at least 95%, at least 96%, at least 97%, at least 98%, or at least 99% identical to the amino acid sequence of the VH of 9G4 (SEQ ID NO: 51, amino acids 20-135), 9C8 (SEQ ID NO: 55), 2H2 (SEQ ID NO: 58), 2E5 (SEQ ID NO: 63), 24E5 (SEQ ID NO: 67), 21D9 (SEQ ID NO: 71), 21D9.b (SEQ ID NO: 74), 21D9.c (SEQ ID NO: 75), 21D9.d (SEQ ID NO: 78), 21D9.e (SEQ ID NO: 80), 21A5 (SEQ ID NO: 83), 21A5.a (SEQ ID NO: 87), 10F10 (SEQ ID NO: 91), 10F10.1 (SEQ ID NO: 91), 10F10.3 (SEQ ID NO: 91), or 10F10.4 (SEQ ID NO: 91).

Embodiment 7

The isolated antibody of any one of embodiments 1-6, wherein the antibody light chain comprises a VL with an amino acid sequence at least 95%, at least 96%, at least 97%, at least 98%, or at least 99% identical to the amino acid sequence of the VL of 9G4 (SEQ ID NO: 50, amino acids 19-125), 9C8 (SEQ ID NO: 54), 2H2 (SEQ ID NO: 59), 2E5 (SEQ ID NO: 62), 24E5 (SEQ ID NO: 66), 21D9 (SEQ ID NO: 70), 21D9.b (SEQ ID NO: 70), 21D9.c (SEQ ID NO: 70), 21D9.d (SEQ ID NO: 70), 21D9.e (SEQ ID NO: 70), 21A5 (SEQ ID NO: 82), 21A5.a (SEQ ID NO: 86), 10F10 (SEQ ID NO: 90), 10F10.1 (SEQ ID NO: 94), 10F10.3 (SEQ ID NO: 96), or 10F10.4 (SEQ ID NO: 114).

Embodiment 8

The isolated antibody of any one of embodiments 1-7, wherein the antibody heavy chain comprises a VH with an amino acid sequence comprising 1, 2, 3, 4, or 5 amino acid substitutions, conservative substitutions, or reversion substitutions compared to the amino acid sequence of the VH of 9G4 (SEQ ID NO: 51, amino acids 20-135), 9C8 (SEQ ID NO: 55), 2H2 (SEQ ID NO: 58), 2E5 (SEQ ID NO: 63), 24E5 (SEQ ID NO: 67), 21D9 (SEQ ID NO: 71), 21D9.b (SEQ ID NO: 74), 21D9.c (SEQ ID NO: 75), 21D9.d (SEQ ID NO: 78), 21D9.e (SEQ ID NO: 80), 21A5 (SEQ ID NO: 83), 21A5.a (SEQ ID NO: 87), 10F10 (SEQ ID NO: 91), 10F10.1 (SEQ ID NO: 91), 10F10.3 (SEQ ID NO: 91), or 10F10.4 (SEQ ID NO: 91).

Embodiment 9

The isolated antibody of any one of embodiments 1-8, wherein the antibody light chain comprises a VL with an amino acid sequence comprising 1, 2, 3, 4, or 5 amino acid substitutions, conservative substitutions, or reversion substitutions compared to the amino acid sequence of the VL of 9G4 (SEQ ID NO: 50, amino acids 19-125), 9C8 (SEQ ID NO: 54), 2H2 (SEQ ID NO: 59), 2E5 (SEQ ID NO: 62), 24E5 (SEQ ID NO: 66), 21D9 (SEQ ID NO: 70), 21D9.b (SEQ ID NO: 70), 21D9.c (SEQ ID NO: 70), 21D9.d (SEQ ID NO: 70), 21D9.e (SEQ ID NO: 70), 21A5 (SEQ ID NO: 82), 21A5.a (SEQ ID NO: 86), 10F10 (SEQ ID NO: 90), 10F10.1 (SEQ ID NO: 94), 10F10.3 (SEQ ID NO: 96), or 10F10.4 (SEQ ID NO: 114).

Embodiment 10

The isolated antibody of any one of embodiments 1-9, wherein the heavy chain comprises the VH of anti-ILT4 antibody 9G4 (SEQ ID NO: 51, amino acids 20-135), 9C8 (SEQ ID NO: 55), 2H2 (SEQ ID NO: 58), 2E5 (SEQ ID NO: 63), 24E5 (SEQ ID NO: 67), 21D9 (SEQ ID NO: 71), 21D9.b (SEQ ID NO: 74), 21D9.c (SEQ ID NO: 75), 21D9.d (SEQ ID NO: 78), 21D9.e (SEQ ID NO: 80), 21A5 (SEQ ID NO: 83), 21A5.a (SEQ ID NO: 87), 10F10 (SEQ ID NO: 91), 10F10.1 (SEQ ID NO: 91), 10F10.3 (SEQ ID NO: 91), or 10F10.4 (SEQ ID NO: 91).

Embodiment 11

The isolated antibody of any one of embodiments 1-10, wherein the light chain comprises the VL of anti-ILT4 antibody 9G4 (SEQ ID NO: 50, amino acids 19-125), 9C8 (SEQ ID NO: 54), 2H2 (SEQ ID NO: 59), 2E5 (SEQ ID NO: 62), 24E5 (SEQ ID NO: 66), 21D9 (SEQ ID NO: 70), 21D9.b (SEQ ID NO: 70), 21D9.c (SEQ ID NO: 70), 21D9.d (SEQ ID NO: 70), 21D9.e (SEQ ID NO: 70), 21A5 (SEQ ID NO: 82), 21A5.a (SEQ ID NO: 86), 10F10 (SEQ ID NO: 90), 10F10.1 (SEQ ID NO: 94), 10F10.3 (SEQ ID NO: 96), or 10F10.4 (SEQ ID NO: 114).

Embodiment 12

The isolated antibody of any one of embodiments 1-11, which comprises VH and VL of anti-ILT4 antibody 9G4 (SEQ ID NO: 51, amino acids 20-135 and SEQ ID NO: 50, amino acids 19-125), 9C8 (SEQ ID NO: 55 and SEQ ID NO: 54), 2H2 (SEQ ID NO: 58 and SEQ ID NO: 59), 2E5 (SEQ ID NO: 63 and SEQ ID NO: 62), 24E5 (SEQ ID NO: 67 and SEQ ID NO: 66), 21D9 (SEQ ID NO: 71 and SEQ ID NO: 70), 21D9.b (SEQ ID NO: 74 and SEQ ID NO: 70), 21D9.c (SEQ ID NO: 75 and SEQ ID NO: 70), 21D9.d (SEQ ID NO: 78 and SEQ ID NO: 70), 21D9.e (SEQ ID NO: 80 and SEQ ID NO: 70), 21A5 (SEQ ID NO: 83 and SEQ ID NO: 82), 21A5.a (SEQ ID NO: 87 and SEQ ID NO: 86), 10F10 (SEQ ID NO: 91 and SEQ ID NO: 90), 10F10.1 (SEQ ID NO: 91 and SEQ ID NO: 94), 10F10.3 (SEQ ID NO: 91 and SEQ ID NO: 96), or 10F10.4 (SEQ ID NO: 91 and SEQ ID NO: 114).

Embodiment 13

The isolated antibody of any one of embodiments 1-11, which comprises:

a VH comprising the VH CDRs of the VH of 9G4 (SEQ ID Nos: 125-127), and a VL comprising the VL CDRs of 9G4 (SEQ ID Nos: 128-130), and VH and VL amino acid sequences that are at least 90%, at least 91%, at least 92%, at least 93%, at least 94%, at least 95%, at least 96%, at least 97%, at least 98%, or at least 99% identical to the VH and VL of 9G4 (SEQ ID NO: 51, amino acids 20-135 and SEQ ID NO: 50, amino acids 19-125);

a VH comprising the VH CDRs of the VH of 9C8 (SEQ ID Nos: 131-133), and a VL comprising the VL CDRs of 9C8 (SEQ ID Nos: 134-136), and VH and VL amino acid sequences that are at least 90%, at least 91%, at least 92%, at least 93%, at least 94%, at least 95%, at least 96%, at least 97%, at least 98%, or at least 99% identical to the VH and VL of 9C8 (SEQ ID NO: 55 and SEQ ID NO: 54);

a VH comprising the VH CDRs of the VH of 2H2 (SEQ ID Nos: 137-139), and a VL comprising the VL CDRs of 2H2 (SEQ ID Nos: 140-142), and VH and VL amino acid sequences that are at least 90%, at least 91%, at least 92%, at least 93%, at least 94%, at least 95%, at least 96%, at least 97%, at least 98%, or at least 99% identical to the VH and VL of 2H2 (SEQ ID NO: 58 and SEQ ID NO: 59);

a VH comprising the VH CDRs of the VH of 2E5 (SEQ ID Nos: 143-145), and a VL comprising the VL CDRs of 2E5 (SEQ ID Nos: 146-148), and VH and VL amino acid sequences that are at least 90%, at least 91%, at least 92%, at least 93%, at least 94%, at least 95%, at least 96%, at least 97%, at least 98%, or at least 99% identical to the VH and VL of 2E5 (SEQ ID NO: 63 and SEQ ID NO: 62);

a VH comprising the VH CDRs of the VH of 24E5 (SEQ ID Nos: 149-151), and a VL comprising the VL CDRs of 24E5 (SEQ ID Nos: 152-154), and VH and VL amino acid sequences that are at least 90%, at least 91%, at least 92%, at least 93%, at least 94%, at least 95%, at least 96%, at least 97%, at least 98%, or at least 99% identical to the VH and VL of 24E5 (SEQ ID NO: 67 and SEQ ID NO: 66);

a VH comprising the VH CDRs of the VH of 21D9 (SEQ ID Nos: 155-157), and a VL comprising the VL CDRs of 21D9 (SEQ ID Nos: 158-160), and VH and VL amino acid sequences that are at least 90%, at least 91%, at least 92%, at least 93%, at least 94%, at least 95%, at least 96%, at least 97%, at least 98%, or at least 99% identical to the VH and VL of 21D9 (SEQ ID NO: 71 and SEQ ID NO: 70);

a VH comprising the VH CDRs of the VH of 21D9.b (SEQ ID Nos: 155-157), and a VL comprising the VL CDRs of 21D9.b (SEQ ID Nos: 158-160), and VH and VL amino acid sequences that are at least 90%, at least 91%, at least 92%, at least 93%, at least 94%, at least 95%, at least 96%, at least 97%, at least 98%, or at least 99% identical to the VH and VL of 21D9.b (SEQ ID NO: 74 and SEQ ID NO: 70);

a VH comprising the VH CDRs of the VH of 21D9.c (SEQ ID Nos: 155-157), and a VL comprising the VL CDRs of 21D9.c (SEQ ID Nos: 158-160), and VH and VL amino acid sequences that are at least 90%, at least 91%, at least 92%, at least 93%, at least 94%, at least 95%, at least 96%, at least 97%, at least 98%, or at least 99% identical to the VH and VL of 21D9.c (SEQ ID NO: 75 and SEQ ID NO: 70);

a VH comprising the VH CDRs of the VH of 21D9.d (SEQ ID Nos: 155-157), and a VL comprising the VL CDRs of 21D9.d (SEQ ID Nos: 158-160), and VH and VL amino acid sequences that are at least 90%, at least 91%, at least 92%, at least 93%, at least 94%, at least 95%, at least 96%, at least 97%, at least 98%, or at least 99% identical to the VH and VL of 21D9.d (SEQ ID NO: 78 and SEQ ID NO: 70);

a VH comprising the VH CDRs of the VH of 21D9.e (SEQ ID Nos: 155-157), and a VL comprising the VL CDRs of 21D9.e (SEQ ID Nos: 158-160), and VH and VL amino acid sequences that are at least 90%, at least 91%, at least 92%, at least 93%, at least 94%, at least 95%, at least 96%, at least 97%, at least 98%, or at least 99% identical to the VH and VL of 21D9.e (SEQ ID NO: 80 and SEQ ID NO: 70);

a VH comprising the VH CDRs of the VH of 21A5 (SEQ ID Nos: 161-163), and a VL comprising the VL CDRs of 21A5 (SEQ ID Nos: 164-166), and VH and VL amino acid sequences that are at least 90%, at least 91%, at least 92%, at least 93%, at least 94%, at least 95%, at least 96%, at least 97%, at least 98%, or at least 99% identical to the VH and VL of 21A5 (SEQ ID NO: 83 and SEQ ID NO: 82);

a VH comprising the VH CDRs of the VH of 21A5.a (SEQ ID Nos: 161-163), and a VL comprising the VL CDRs of 21A5.a (SEQ ID Nos: 164-166), and VH and VL amino acid sequences that are at least 90%, at least 91%, at least 92%, at least 93%, at least 94%, at least 95%, at least 96%, at least 97%, at least 98%, or at least 99% identical to the VH and VL of 21A5.a (SEQ ID NO: 87 and SEQ ID NO: 86);

a VH comprising the VH CDRs of the VH of 10F10 (SEQ ID Nos: 167-169), and a VL comprising the VL CDRs of 10F10 (SEQ ID Nos: 170-172), and VH and VL amino acid sequences that are at least 90%, at least 91%, at least 92%, at least 93%, at least 94%, at least 95%, at least 96%, at least 97%, at least 98%, or at least 99% identical to the VH and VL of 10F10 (SEQ ID NO: 91 and SEQ ID NO: 90);

a VH comprising the VH CDRs of the VH of 10F10.1 (SEQ ID Nos: 167-169), and a VL comprising the VL CDRs of 10F10.1 (SEQ ID Nos: 170-172), and VH and VL amino acid sequences that are at least 90%, at least 91%, at least 92%, at least 93%, at least 94%, at least 95%, at least 96%, at least 97%, at least 98%, or at least 99% identical to the VH and VL of 10F10.1 (SEQ ID NO: 91 and SEQ ID NO: 94);

a VH comprising the VH CDRs of the VH of 10F10.3 (SEQ ID Nos: 167-169), and a VL comprising the VL CDRs of 10F10.3 (SEQ ID Nos: 170-172), and VH and VL amino acid sequences that are at least 90%, at least 91%, at least 92%, at least 93%, at least 94%, at least 95%, at least 96%, at least 97%, at least 98%, or at least 99% identical to the VH and VL of 10F10.3 (SEQ ID NO: 91 and SEQ ID NO: 96); or a VH comprising the VH CDRs of the VH of 10F10.4 (SEQ ID Nos: 167-169), and a VL comprising the VL CDRs of 10F10.4 (SEQ ID Nos: 170-172), and VH and VL amino acid sequences that are at least 90%, at least 91%, at least 92%, at least 93%, at least 94%, at least 95%, at least 96%, at least 97%, at least 98%, or at least 99% identical to the VH and VL of 10F10.4 (SEQ ID NO: 91 and SEQ ID NO: 114).

Embodiment 14

The isolated antibody of any one of embodiments 1-13, which comprises:

a VH comprising the amino acid sequence of the VH of 9G4 (SEQ ID NO: 51 residues 20-135) and a VL comprising the amino acid sequence of the VL of 9G4 (SEQ ID NO: 50 residues 19-125);

a VH comprising the amino acid sequence of the VH of 9C8 and a VL comprising the amino acid sequence of the VL of 9C8 (SEQ ID NO: 55 and SEQ ID NO: 54);

a VH comprising the amino acid sequence of the VH of 2H2 and a VL comprising the amino acid sequence of the VL of 2H2 (SEQ ID NO: 58 and SEQ ID NO: 59);

a VH comprising the amino acid sequence of the VH of 2E5 and a VL comprising the amino acid sequence of the VL of 2E5 (SEQ ID NO: 63 and SEQ ID NO: 62);

a VH comprising the amino acid sequence of the VH of 24E5 and a VL comprising the amino acid sequence of the VL of 24E5 (SEQ ID NO: 67 and SEQ ID NO: 66);

a VH comprising the amino acid sequence of the VH of 21D9 and a VL comprising the amino acid sequence of the VL of 21D9 (SEQ ID NO: 71 and SEQ ID NO: 70);

- a VH comprising the amino acid sequence of the VH of 21D9.b and a VL comprising the amino acid sequence of the VL of 21D9.b (SEQ ID NO: 74 and SEQ ID NO: 70);
- a VH comprising the amino acid sequence of the VH of 21D9.c and a VL comprising the amino acid sequence of the VL of 21D9.c (SEQ ID NO: 75 and SEQ ID NO: 70);
- a VH comprising the amino acid sequence of the VH of 21D9.d and a VL comprising the amino acid sequence of the VL of 21D9.d (SEQ ID NO: 78 and SEQ ID NO: 70);
- a VH comprising the amino acid sequence of the VH of 21D9.e and a VL comprising the amino acid sequence of the VL of 21D9.e (SEQ ID NO: 80 and SEQ ID NO: 70);
- a VH comprising the amino acid sequence of the VH of 21A5 and a VL comprising the amino acid sequence of the VL of 21A5 (SEQ ID NO: 83 and SEQ ID NO: 82);
- a VH comprising the amino acid sequence of the VH of 21A5.a and a VL comprising the amino acid sequence of the VL of 21A5.a (SEQ ID NO: 87 and SEQ ID NO: 86);
- a VH comprising the amino acid sequence of the VH of 10F10 and a VL comprising the amino acid sequence of the VL of 10F10 (SEQ ID NO: 91 and SEQ ID NO: 90);
- a VH comprising the amino acid sequence of the VH of 10F10.1 and a VL comprising the amino acid sequence of the VL of 10F10.1 (SEQ ID NO: 91 and SEQ ID NO: 94);
- a VH comprising the amino acid sequence of the VH of 10F10.3 and a VL comprising the amino acid sequence of the VL of 10F10.3 (SEQ ID NO: 91 and SEQ ID NO: 96); or
- a VH comprising the amino acid sequence of the VH of 10F10.4 and a VL comprising the amino acid sequence of the VL of 10F10.4 (SEQ ID NO: 91 and SEQ ID NO: 114).

Embodiment 15

The isolated antibody of any one of embodiments 1-14, which is an IgG antibody.

Embodiment 16

The isolated antibody of embodiment 15, which is an IgG1, IgG2 or IgG4 antibody, wherein the IgG4 optionally comprises an S228P substitution (EU numbering).

Embodiment 17

The isolated antibody of any one of embodiments 1-16, wherein the antibody is an effectorless antibody.

Embodiment 18

The isolated antibody of embodiment 17, wherein the heavy chain constant region comprises 1, 2, 3, 4, or 5 mutations in an otherwise wild type human heavy chain constant region that reduce the effector function of the antibody compared to an antibody without the 1, 2, 3, 4, or 5 mutations but otherwise with the same amino acid sequence.

Embodiment 19

The isolated antibody of any one of embodiments 1-18, wherein the heavy chain constant region of the antibody comprises an IgG1.3 heavy chain constant region, an IgG1.1 heavy chain constant region, or an IgG1 heavy chain constant region with a P238K (EU numbering) substitution, or an IgG1 heavy chain constant region comprising the amino acid sequence of any one of SEQ ID Nos: 98, 100, 102, 103, or 104.

Embodiment 20

The isolated antibody of any one of embodiments 1-16 or 19, wherein the antibody has effector function.

Embodiment 21

The isolated antibody of embodiment 20, wherein the antibody is afucosylated (e.g., an afucosylated IgG1 antibody).

Embodiment 22

The isolated antibody of embodiment 20 or 21, wherein the heavy chain constant region comprises 1, 2, 3, 4, or 5 mutations in an otherwise wild type human heavy chain constant region that enhance the effector function of the antibody compared to an antibody without the 1, 2, 3, 4, or 5 mutations but otherwise with the same amino acid sequence.

Embodiment 23

The isolated antibody of any one of embodiments 1-22, which comprises the HC of anti-ILT4 antibody 9G4, 9C8, 2H2, 2E5, 24E5, 21D9, 21D9.b, 21D9.c, 21D9.d, 21D9.e, 21A5, 21A5.a, 10F10, 10F10.1 or 10F10.3, wherein the constant region of the HC is IgG1 (e.g. 9G4.IgG1, etc.), IgG1.3 (e.g. 9G4.IgG1.3, etc.), IgG1.1f (e.g. 9G4.IgG1.1f, etc.), IgG4 (e.g., 9G4.IgG4, etc.), or IgG4 S228P (EU numbering) (e.g., 9G4.IgG4_S228P).

Embodiment 24

The isolated antibody of embodiment 23, wherein the antibody comprises a HC amino acid sequence as follows:

- IgG1, e.g. 9G4.IgG1, 9G4 (SEQ ID NO: 2), 9C8 (SEQ ID NO: 4), 2H2 (SEQ ID NO: 6), 2E5 (SEQ ID NO: 8), 24E5 (SEQ ID NO: 10), 21D9 (SEQ ID NO: 12), 21D9.b (SEQ ID NO: 74 and SEQ ID NO: 98), 21D9.c (SEQ ID NO: 75 and SEQ ID NO: 98), 21D9.d (SEQ ID NO: 78 and SEQ ID NO: 98), 21D9.e (SEQ ID NO: 80 and SEQ ID NO: 98), 21A5 (SEQ ID NO: 83 and SEQ ID NO: 98), 21A5.a (SEQ ID NO: 87 and SEQ ID NO: 98), 10F10 (SEQ ID NO: 91 and SEQ ID NO: 98), 10F10.1 (SEQ ID NO: 91 and SEQ ID NO: 98), 10F10.3 (SEQ ID NO: 91 and SEQ ID NO: 98), or 10F10.4 (SEQ ID NO: 91 and SEQ ID NO: 98),
- IgG1, e.g. 9G4.IgG1, 9G4 (SEQ ID NO: 51, amino acids 20-135, and SEQ ID NO: 102), 9C8 (SEQ ID NO: 55 and SEQ ID NO: 102), 2H2 (SEQ ID NO: 58 and SEQ ID NO: 102), 2E5 (SEQ ID NO: 63 and SEQ ID NO: 102), 24E5 (SEQ ID NO: 67 and SEQ ID NO: 102), 21D9 (SEQ ID NO: 71 and SEQ ID NO: 102), 21D9.b (SEQ ID NO: 74 and SEQ ID NO: 102), 21D9.c (SEQ ID NO: 75 and SEQ ID NO: 102), 21D9.d (SEQ ID NO: 78 and SEQ ID NO: 102), 21D9.e (SEQ ID NO: 80 and SEQ ID NO: 102), 21A5 (SEQ ID NO: 83 and SEQ ID NO: 102), 21A5.a (SEQ ID NO: 87 and SEQ ID NO: 102), 10F10 (SEQ ID NO: 91 and SEQ ID NO:

102), 10F10.1 (SEQ ID NO: 91 and SEQ ID NO: 102), 10F10.3 (SEQ ID NO: 91 and SEQ ID NO: 102), or 10F10.4 (SEQ ID NO: 91 and SEQ ID NO: 102), IgG1.3 (e.g. 9G4.IgG1.3, etc.), 9G4 (SEQ ID NO: 51, amino acids 20-135, and SEQ ID NO: 100), 9C8 (SEQ ID NO: 55 and SEQ ID NO: 100), 2H2 (SEQ ID NO: 58 and SEQ ID NO: 100), 2E5 (SEQ ID NO: 63 and SEQ ID NO: 100), 24E5 (SEQ ID NO: 67 and SEQ ID NO: 100), 21D9 ((i) SEQ ID NO: 113, or (ii) SEQ ID NO: 71 and SEQ ID NO: 100), 21D9.b (SEQ ID NO: 36), 21D9.c (SEQ ID NO: 38), 21D9.d (SEQ ID NO: 40), 21D9.e (SEQ ID NO: 13), 21A5 (SEQ ID NO: 15), 21A5.a (SEQ ID NO: 17), 10F10 (SEQ ID NO: 19), 10F10.1 (SEQ ID NO: 91 and SEQ ID NO: 100), 10F10.3 (SEQ ID NO: 91 and SEQ ID NO: 100), or 10F10.4 (SEQ ID NO: 91 and SEQ ID NO: 100);

IgG1.1f (e.g. 9G4.IgG1.1f, etc.), 9G4 (SEQ ID NO: 51, amino acids 20-135, and SEQ ID NO: 103), 9C8 (SEQ ID NO: 55 and SEQ ID NO: 103), 2H2 (SEQ ID NO: 58 and SEQ ID NO: 103), 2E5 (SEQ ID NO: 63 and SEQ ID NO: 103), 24E5 (SEQ ID NO: 67 and SEQ ID NO: 103), 21D9 (SEQ ID NO: 71 and SEQ ID NO: 103), 21D9.b (SEQ ID NO: 74 and SEQ ID NO: 103), 21D9.c (SEQ ID NO: 75 and SEQ ID NO: 103), 21D9.d (SEQ ID NO: 78 and SEQ ID NO: 103), 21D9.e (SEQ ID NO: 80 and SEQ ID NO: 103), 21A5 (SEQ ID NO: 83 and SEQ ID NO: 103), 21A5.a (SEQ ID NO: 87 and SEQ ID NO: 103), 10F10 (SEQ ID NO: 91 and SEQ ID NO: 103), 10F10.1 (SEQ ID NO: 91 and SEQ ID NO: 103), 10F10.3 (SEQ ID NO: 91 and SEQ ID NO: 103), or 10F10.4 (SEQ ID NO: 91 and SEQ ID NO: 103), IgG1fa.P238K (e.g., 9G4.IgG1fa.P238K, etc.) 9G4 (SEQ ID NO: 51, amino acids 20-135, and SEQ ID NO: 104), 9C8 (SEQ ID NO: 55 and SEQ ID NO: 104), 2H2 (SEQ ID NO: 58 and SEQ ID NO: 104), 2E5 (SEQ ID NO: 63 and SEQ ID NO: 104), 24E5 (SEQ ID NO: 67 and SEQ ID NO: 104), 21D9 (SEQ ID NO: 71 and SEQ ID NO: 104), 21D9.b (SEQ ID NO: 74 and SEQ ID NO: 104), 21D9.c (SEQ ID NO: 75 and SEQ ID NO: 104), 21D9.d (SEQ ID NO: 78 and SEQ ID NO: 104), 21D9.e (SEQ ID NO: 80 and SEQ ID NO: 104), 21A5 (SEQ ID NO: 83 and SEQ ID NO: 104), 21A5.a (SEQ ID NO: 87 and SEQ ID NO: 104), 10F10 (SEQ ID NO: 91 and SEQ ID NO: 104), 10F10.1 (SEQ ID NO: 91 and SEQ ID NO: 104), 10F10.3 (SEQ ID NO: 91 and SEQ ID NO: 104), or 10F10.4 (SEQ ID NO: 91 and SEQ ID NO: 104), or IgG4 S228P (e.g. 9G4.IgG4 S228P, etc.), 9G4 (SEQ ID NO: 51, amino acids 20-135, and SEQ ID NO: 179), 9C8 (SEQ ID NO: 55 and SEQ ID NO: 179), 2H2 (SEQ ID NO: 58 and SEQ ID NO: 179), 2E5 (SEQ ID NO: 63 and SEQ ID NO: 179), 24E5 (SEQ ID NO: 67 and SEQ ID NO: 179), 21D9 (SEQ ID NO: 71 and SEQ ID NO: 179), 21D9.b (SEQ ID NO: 74 and SEQ ID NO: 179), 21D9.c (SEQ ID NO: 75 and SEQ ID NO: 179), 21D9.d (SEQ ID NO: 78 and SEQ ID NO: 179), 21D9.e (SEQ ID NO: 80 and SEQ ID NO: 179), 21A5 (SEQ ID NO: 83 and SEQ ID NO: 179), 21A5.a (SEQ ID NO: 87 and SEQ ID NO: 179), 10F10 (SEQ ID NO: 91 and SEQ ID NO: 179), 10F10.1 (SEQ ID NO: 91 and SEQ ID NO: 179), 10F10.3 (SEQ ID NO: 91 and SEQ ID NO: 179), or 10F10.4 (SEQ ID NO: 91 and SEQ ID NO: 179).

Embodiment 25

The isolated antibody of embodiment 23, wherein the HC of the antibody lacks a C-terminal lysine residue.

Embodiment 26

The isolated antibody of embodiment 23, wherein the HC of the antibody comprises the heavy chain constant region amino acid sequence of any one of SEQ ID Nos: 98, 100, 102, 103, 104, or 179.

Embodiment 27

The isolated antibody of any one of embodiments 1-26, which comprises the LC of anti-ILT4 antibody 9G4, 9C8, 2H2, 2E5, 24E5, 21D9, 21D9.b, 21D9.c, 21D9.d, 21D9.e, 21A5, 21A5.a, 10F10, 10F10.1, 10F10.3, or 10F10.4.

Embodiment 28

The isolated antibody of embodiment 27, wherein the light chain constant region is a human Kappa light chain constant region.

Embodiment 29

The isolated antibody of embodiment 27, wherein the LC comprises the sequence of: 9G4 (SEQ ID NO: 1), 9C8 (SEQ ID NO: 3), 2H2 (SEQ ID NO: 5), 2E5 (SEQ ID NO: 7), 24E5 (SEQ ID NO: 9), 21D9 (SEQ ID NO: 11), 21D9.b, 21D9.c, 21D9.d, 21D9.e, 21A5 (SEQ ID NO: 14), 21A5.a (SEQ ID NO: 16), 10F10 (SEQ ID NO: 18), 10F10.1 (SEQ ID NO: 20), 10F10.3 (SEQ ID NO: 21), or 10F10.4 (SEQ ID NO: 116).

Embodiment 30

The isolated antibody of any one of embodiments 1-29, which comprises HC and LC of anti-ILT4 antibody 9G4, 9C8, 2H2, 2E5, 24E5, 21D9, 21D9.b, 21D9.c, 21D9.d, 21D9.e, 21A5, 21A5.a, 10F10, 10F10.1, 10F10.3, or 10F10.4, wherein the constant region of the HC is IgG1 (e.g. 9G4.IgG1, etc.), IgG1.3 (e.g. 9G4.IgG1.3, etc.), IgG1.1f (e.g. 9G4.IgG1.1f, etc.), IgG4 (e.g., 9G4.IgG4, etc.), or IgG4 S228P (EU numbering) (e.g., 9G4.IgG4_S228P).

Embodiment 31

The isolated antibody of embodiment 30, which comprises:

a heavy chain (HC) comprising the amino acid sequence of the heavy chain of 9G4 ((i) SEQ ID NO: 2, or (ii) SEQ ID NO: 51, amino acids 20-135, and one of SEQ ID NO: 98, 100, 102, 103, 104, or 179) and a light chain (LC) comprising the light chain amino acid sequence of 9G4 (SEQ ID NO: 1);

a heavy chain comprising the amino acid sequence of the heavy chain of 9C8 ((i) SEQ ID NO: 4 or (ii) SEQ ID NOs: 55 and one of SEQ ID NO: 98, 100, 102, 103, 104, or 179) and a light chain comprising the light chain amino acid sequence of 9C8 (SEQ ID NO: 3);

a heavy chain comprising the amino acid sequence of the heavy chain of 2H2 ((i) SEQ ID NO: 6 or (ii) SEQ ID NOs: 58 and one of SEQ ID NO: 98, 100, 102, 103, 104, or 179) and a light chain comprising the light chain amino acid sequence of 2H2 (SEQ ID NO: 5);

a heavy chain comprising the amino acid sequence of the heavy chain of 2E5 ((i) SEQ ID NO: 8 or (ii) SEQ ID NOs: 63 and one of SEQ ID NO: 98, 100, 102, 103, 104, or 179) and a light chain comprising the light chain amino acid sequence of 2E5 (SEQ ID NO: 7);
a heavy chain comprising the amino acid sequence of the heavy chain of 24E5 ((i) SEQ ID NO: 10 or (ii) SEQ ID NOs: 67 and one of SEQ ID NO: 98, 100, 102, 103, 104, or 179) and a light chain comprising the light chain amino acid sequence of 24E5 (SEQ ID NO: 9);
a heavy chain comprising the amino acid sequence of the heavy chain of 21D9 ((i) SEQ ID NO: 12 or 113, or (ii) SEQ ID NOs: 71 and one of SEQ ID NO: 98, 100, 102, 103, 104, or 179) and a light chain comprising the light chain amino acid sequence of 21D9 (SEQ ID NO: 11);
a heavy chain comprising the amino acid sequence of the heavy chain of 21D9.b (SEQ ID NOs: 74 and one of SEQ ID NO: 98, 100, 102, 103, 104, or 179) and a light chain comprising the light chain amino acid sequence of 21D9.b (SEQ ID NO: 11);
a heavy chain comprising the amino acid sequence of the heavy chain of 21D9.c (SEQ ID NOs: 75 and one of SEQ ID NO: 98, 100, 102, 103, 104, or 179) and a light chain comprising the light chain amino acid sequence of 21D9.c (SEQ ID NO: 11);
a heavy chain comprising the amino acid sequence of the heavy chain of 21D9.d (SEQ ID NOs: 78 and one of SEQ ID NO: 98, 100, 102, 103, 104, or 179) and a light chain comprising the light chain amino acid sequence of 21D9.d (SEQ ID NO: 11);
a heavy chain comprising the amino acid sequence of the heavy chain of 21D9.e ((i) SEQ ID NO: 13, 176, 177, or 178; or (ii) SEQ ID NOs: 80 and one of SEQ ID NO: 98, 100, 102, 103, 104, or 179) and a light chain comprising the light chain amino acid sequence of 21D9.e (SEQ ID NO: 11);
a heavy chain comprising the amino acid sequence of the heavy chain of 21A5 ((i) SEQ ID NO: 15 or (ii) SEQ ID NOs: 83 and one of SEQ ID NO: 98, 100, 102, 103, 104, or 179) and a light chain comprising the light chain amino acid sequence of 21A5 (SEQ ID NO: 14);
a heavy chain comprising the amino acid sequence of the heavy chain of 21A5.a (i) SEQ ID NO: 17 or (ii) SEQ ID NOs: 87 and one of SEQ ID NO: 98, 100, 102, 103, 104, or 179) and a light chain comprising the light chain amino acid sequence of 21A5.a (SEQ ID NO: 16);
a heavy chain comprising the amino acid sequence of the heavy chain of 10F10 ((i) SEQ ID NO: 19 or (ii) SEQ ID NOs: 91 and one of SEQ ID NO: 98, 100, 102, 103, 104, or 179) and a light chain comprising the light chain amino acid sequence of 10F10 (SEQ ID NO: 18);
a heavy chain comprising the amino acid sequence of the heavy chain of 10F10.1 (i) SEQ ID NO: 19 or (ii) SEQ ID NOs: 91 and one of SEQ ID NO: 98, 100, 102, 103, 104, or 179) and a light chain comprising the light chain amino acid sequence of 10F10.1 (SEQ ID NO: 20);
a heavy chain comprising the amino acid sequence of the heavy chain of 10F10.3 ((i) SEQ ID NO: 19 or (ii) SEQ ID NOs: 91 and one of SEQ ID NO: 98, 100, 102, 103, 104, or 179) and a light chain comprising the light chain amino acid sequence of 10F10.3 (SEQ ID NO: 21); or
a heavy chain comprising the amino acid sequence of the heavy chain of 10F10.4 ((i) SEQ ID NO: 19 or (ii) SEQ ID NOs: 91 and one of SEQ ID NO: 98, 100, 102, 103, 104, or 179) and a light chain comprising the light chain amino acid sequence of 10F10.4 (SEQ ID NO: 116).

Embodiment 32

An isolated antibody that binds specifically to human ILT4, comprising a heavy chain comprising the amino acid sequence of SEQ ID NO: 13 and a light chain comprising the light chain amino acid sequence of SEQ ID NO: 11.

Embodiment 33

An isolated antibody that binds specifically to human ILT4, comprising a heavy chain comprising the amino acid sequence of SEQ ID NO: 176 and a light chain comprising the light chain amino acid sequence of SEQ ID NO: 11.

Embodiment 34

An isolated antibody that binds specifically to human ILT4, comprising a heavy chain comprising the amino acid sequence of SEQ ID NO: 177 and a light chain comprising the light chain amino acid sequence of SEQ ID NO: 11.

Embodiment 35

An isolated antibody that binds specifically to human ILT4, comprising a heavy chain comprising the amino acid sequence of SEQ ID NO: 178 and a light chain comprising the light chain amino acid sequence of SEQ ID NO: 11.

Embodiment 36

The isolated antibody of any one of embodiments 32-35, wherein the antibody has one or more of the properties of the antibodies of embodiment 1.

Embodiment 37

The isolated antibody of any one of embodiments 1-36, which is a full length antibody.

Embodiment 38

The isolated antibody of any one of embodiments 1-14, which is an antibody fragment.

Embodiment 39

The isolated antibody of any one of embodiments 1-38, which is a multimeric (e.g., dimeric or trimeric) antibody.

Embodiment 40

The isolated antibody of any one of embodiments 1-39, which is linked (e.g., covalently) to another molecule.

Embodiment 41

The isolated antibody of embodiment 40, wherein the other molecule is a label.

Embodiment 42

The isolated antibody of embodiment 40, wherein the other molecule is a peptide.

Embodiment 43

The isolated antibody of embodiment 40, which is an antibody drug conjugate (ADC).

Embodiment 44

An isolated nucleic acid encoding an antibody of any one of embodiments 1-43.

Embodiment 45

An isolated nucleic acid encoding the heavy chain and/or the light chain of an antibody of any one of embodiments 1-43.

Embodiment 46

A set of at least two isolated nucleic acids encoding the heavy chain and the light chain of an antibody of any one of embodiments 1-43.

Embodiment 47

A composition comprising a nucleic acid encoding the heavy chain of an antibody of any one of embodiments 1-43 and a nucleic acid encoding the light chain of the antibody of any one of embodiments 1-43.

Embodiment 48

A cell comprising the isolated nucleic acid of any one of embodiments 44-46 or the composition of embodiment 47.

Embodiment 49

A method of preparing an antibody, comprising culturing the cell of embodiment 48 in conditions under which the antibody is expressed.

Embodiment 50

A composition comprising an isolated antibody, nucleic acid, composition or cell of any one of embodiments 1-49 and a pharmaceutically acceptable carrier.

Embodiment 51

The composition of embodiment 50, comprising a second therapeutic agent.

Embodiment 52

The composition of embodiment 51, wherein the second therapeutic agent is an immunostimulatory agent.

Embodiment 53

The composition of embodiment 52, wherein the immunostimulating agent is an antagonist of an immunosuppressive molecule, e.g., the PD-1/PD-L1, a CTLA-4 and LAG-3, or an agonist of an immunostimulating molecule, e.g., GITR and OX40.

Embodiment 54

A method of treating a subject having cancer, comprising administering to the subject a therapeutically effective amount of a composition of any one of embodiments 50-53 or isolated antibody of any one of embodiments 1-43 that stimulates an immune response and/or is an ILT-4 antagonist.

Embodiment 55

The method of embodiment 54, wherein the method further comprises administering a second therapy.

Embodiment 56

The method of embodiment 55, wherein the second therapy is radiotherapy, surgery or administration of a second agent.

Embodiment 57

The method of embodiment 55, wherein the second therapy is a second agent and the second agent is an immunostimulatory agent.

Embodiment 58

The method of embodiment 57, wherein the immunostimulatory agent is an antagonist of an immunosuppressive molecule, e.g., the PD-1/PD-L1, an CTLA-4 and LAG-3, or an agonist of an immunostimulating molecule, e.g., GITR and OX40.

Embodiment 60

A method of treating an infectious disease (e.g., viral disease) in a subject, comprising administering to the subject a therapeutically effective amount of a composition of any one of embodiments 50-53 or isolated antibody of any one of embodiments 1-43 that stimulates an immune response and/or is an ILT4 antagonist.

Embodiment 61

A method of detecting ILT4 in a sample, comprising contacting the sample with an ILT4 antibody of any one of embodiments 1-43.

Embodiment 62

The isolated antibody of any one of embodiments 1-43, having the following characteristics:

a. specific binding to hILT4 (e.g. comprising the amino acid sequence of SEQ ID NO: 108, 109, 111, 112, or 119), e.g., with a $K_D$ of $10^{-8}$M or less, or of $10^{-9}$M or less;
b. stimulates differentiation or activation of monocytes into macrophages, e.g., stimulates differentiation of monocytes into pro-inflammatory macrophages, e.g., as shown in an assay described in the Examples;
c. has a binding profile as shown in FIG. 27; and
d. binds to the Ig-like domains 1, 2 or 1 and 2 of hILT4, such as comprising the following regions of hILT4: (i) $^{70}$ITRIRPEL$^{77}$ (SEQ ID NO: 120) and/or $^{78}$VKNGQFHIPSITWEHTGRYGCQY$^{100}$ (SEQ ID NO: 121); (ii) $^{70}$ITRIRPELVKNGQFHIPSITWEHTGRYGCQY$^{100}$ (SEQ ID NO: 122); or (iii) $^{154}$ILCKEGEEEHPQCLNSQPHARGSSRAIF$^{181}$ (SEQ ID NO: 123) and/or $^{425}$SSPPPTGPIS$^{434}$ (SEQ ID NO: 124), and does not bind significantly to other regions of the extracellular domain of ILT4, such as regions or residues that located N-terminal to amino acid 170, wherein the amino acid numbering of hILT4 is that of immature hILT4 (i.e., ILT4 comprising its native signal sequence).

Embodiment 63

The isolated antibody of any one of embodiments 1-43, having the following characteristics:

a. specific binding to hILT4 (e.g. comprising the amino acid sequence of SEQ ID NO: 108, 109, 111, 112, or 119), e.g., with a $K_D$ of $10^{-8}$ M or less, or of $10^{-9}$ M or less;
b. lack of specific binding to hILT2, hILT3, and/or hILT5;
c. lack of specific binding to one or more members of the LILRA and/or LILRB families;
d. stimulates T cell activation, e.g., in a mixed lymphocyte reaction (MLR) assay, as measured by increased T cell proliferation or IFN-gamma secretion, e.g., as shown in an assay described in the Examples;
e. stimulates differentiation or activation of monocytes into macrophages, e.g., stimulates differentiation of monocytes into pro-inflammatory macrophages, e.g., as shown in an assay described in the Examples;
f. inhibits binding of hILT4 to HLA-A and HLA-B;
g. has a binding profile as shown in FIG. 27;
h. binds to the Ig-like domains 1, 2 or 1 and 2 of hILT4, such as comprising the following regions of hILT4: (i) $^{70}$ITRIRPEL$^{77}$ (SEQ ID NO: 120) and/or $^{78}$VKNGQFHIPSITWEHTGRYGCQY$^{100}$ (SEQ ID NO: 121); (ii) $^{70}$ITRIRPELVKNGQFHIPSITWEHTGRYGCQY$^{100}$ (SEQ ID NO: 122), and does not bind significantly to other regions of the extracellular domain of ILT4, such as regions or residues that located N-terminal to amino acid 170; wherein the amino acid numbering of hILT4 is that of immature hILT4 (i.e., ILT4 with its signal sequence).
i. promotes pro-inflammatory polarization of macrophages towards M1 macrophages;
j. does not induce (or trigger) basophil activation; and
k. comprises less than 5% of high and low molecular weight species after 3 months incubation at 25° C. and/or less than 10% of high and low molecular weight species after 3 months incubation at 40° C.

Embodiment 64

The isolated antibody of any one of embodiments 1-43, having the following characteristics:

a. promotes expression of CD83 and CD86 on human monocyte derived immature dendritic cells (Mo-iDC), e.g., as shown in an assay described in the Examples;
b. enhances IFN-γ secretion upon antigen stimulation in a cytomegalovirus (CMV) lysate assay, e.g., as shown in an assay described in the Examples;
c. enhances IFN-γ and TNF-α secretion by CD4+ and CD8+ T cells in an allo-mixed lymphocyte reaction (MLR) assay upon CD3 stimulation, e.g., as shown in an assay described in the Examples;
d. inhibits binding of HLA-A and/or HLA-B to ILT4;
e. binds to Ig-like domains 1, 2 or 1 and 2 of hILT4, such as to a region comprising (i) $^{70}$ITRIRPEL$^{77}$ (SEQ ID NO: 120) and/or $^{78}$VKNGQFHIPSITWEHTGRYGCQY$^{100}$ (SEQ ID NO: 121); (ii) $^{70}$ITRIRPELVKNGQFHIPSITWEHTGRYGCQY$^{100}$ (SEQ ID NO: 122); or (iii) $^{154}$ILCKEGEEEHPQCLNSQPHARGSSRAIF$^{181}$ (SEQ ID NO: 123) and/or $^{425}$SSPPPTGPIS$^{434}$ (SEQ ID NO: 124), as determined by hydrogen deuterium exchange (HDX), e.g., as shown in an HDX assay described in the Examples;
f. interacts with one or more (or all of) amino acid residues Lys43, Ile49, Thr50 and Arg51 of mature hILT4 or interacts with one or more (or all of) amino acid residues Gly117, Val119, Try120, Leu134, Lys136, Gln149, Pro150, Ile159, Ser161, Val162, Gly163, Pro164, Pro167, His173, Try178, Pro183 and Tyr184 of mature hILT4 or interacts with one or more (or all of) amino acid residues Glu42, Lys43, Gly76, Cys77, Leu88, Pro91, Pro183 and Tyr184 of mature hILT4, as determined by carbene foot-printing, e.g., as described in the Examples;
g. competes for binding to hILT4 with an antibody described herein; and
h. binds specifically to a cyno ILT4 comprising SEQ ID NO: 118, e.g., as shown in a binding assay described in the Examples.

DETAILED DESCRIPTION OF CERTAIN EMBODIMENTS

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

In this application, the use of "or" means "and/or" unless stated otherwise. In the context of a multiple dependent claim, the use of "or" refers back to more than one preceding independent or dependent claim in the alternative only. The terms "comprising," "including," and "having" can be used interchangeably herein. According to the present invention, an "isolated" molecule is a molecule that has been removed from its natural milieu. As such, the term "isolated" does not necessarily reflect the extent to which the molecule has been purified.

The term "polypeptide" refers to a polymer of amino acid residues, and is not limited to a minimum length. A "protein" may comprise one or more polypeptides. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" or "protein" refers to a polypeptide or protein, respectively, which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts that produce the proteins or errors due to PCR amplification. A protein may comprise two or more polypeptides. The letter "h" in front of a protein name denotes a native, human protein herein, e.g. "hILT4."

The terms "ILT4," "human ILT4," "hILT4," "immunoglobulin-like transcript 4," "Ig-like transcript 4," "leukocyte immunoglobulin-like receptor B2," "LIR2," "LILRB2," "MIR10," and "CD85d" are all used interchangeably and refer to a native, human ILT4, unless otherwise specifically indicated (e.g. mouse ILT4, cynomolgus ILT4, etc.). The term includes full-length, unprocessed ILT4 as well as any form of ILT4 that results from processing in the cell. The term encompasses naturally occurring variants of human ILT4, e.g., splice variants or allelic variants. In some embodiments, ILT4 comprises or consists of an amino acid sequence of SEQ ID NO: 107 (precursor, with signal peptide) or SEQ ID NO: 108 (mature, without signal peptide). In some embodiments, ILT4 comprises an amino acid sequence of SEQ ID NO: 110 (precursor, with signal peptide) or SEQ ID NO: 111 (mature, without signal peptide).

As used herein, the term "ILT4 fragment" refers to ILT4 having one or more residues deleted from the N- and/or C-terminus of the full-length ILT4. The ILT4 fragment may or may not include an N-terminal signal peptide but that retains the ability to bind to T cells. As used herein, the term "ILT4 variant" refers to ILT4 that contains naturally occurring amino acid additions, deletions, and substitutions but that retains the ability to bind to T cells.

The term "antagonist" is used in the broadest sense, and includes any molecule that partially or fully inhibits or neutralizes a biological activity of a polypeptide, such as ILT4. Exemplary antagonist molecules include antagonist antibodies. The term "ILT4 antagonist" refers to a molecule that inhibits or blocks the biological activity of ILT4, by, e.g., blocking or inhibiting the interaction between ILT4 and a target cell, e.g., a T cell, and/or a target molecule. Exemplary ILT4 antagonists include antibodies that block binding of ILT4 to a target cell, e.g., a T cell, and/or a target molecule. An ILT4 antagonist is considered to "block binding of ILT4 to target cells or target molecules" when it reduces the amount of detectable binding to at least one of ILT4 to a target cell, e.g., a T cell, and/or a target molecule by at least 50% in a cell binding assay. In some embodiments, an ILT4 antagonist reduces the amount of detectable binding by at least 60%, at least 70%, at least 80%, or at least 90%. In some such embodiments, the antagonist is said to block ligand binding by at least 50%, at least 60%, at least 70%, etc. Blocking of binding of ILT4 to target cells, e.g., T cells, may be demonstrated, e.g., by binding of cells transfected with ILT4, e.g., ILT4 ECD and transmembrane domain, or recombinant ILT4 Fc fusion protein e.g., recombinant ILT4 ECD Fc fusion proteins on cells, such as T cells, in the presence or absence of the antagonist.

The terms "inhibition" or "inhibit" refer to a decrease, reduction, or cessation of any phenotypic characteristic or to the decrease, reduction, or cessation in the incidence, degree, or likelihood of that characteristic. In some embodiments, by "reduce" or "inhibit" is meant the ability to cause a decrease of 20% or greater. In another embodiment, by "reduce" or "inhibit" is meant the ability to cause a decrease of 50% or greater. In yet another embodiment, by "reduce" or "inhibit" is meant the ability to cause an overall decrease of 75%, 85%, 90%, 95%, or greater.

The terms "enhancing T cell activity" or "enhancement of T cell activity" refer to an enhancement or increase of at least one of T cell activation, cytokine secretion, such as interferon-gamma (IFN-γ) secretion, or T cell proliferation in a subject. "Enhancing T cell activity" can be by using an agent that is an agonist of T cell activity, and/or an agent that is an antagonist of (i.e., inhibits or blocks) a mechanism that inhibits T cell activity. Changes in T cell activity may be measured by, e.g., T cell proliferation assay or an IFN-γ ELISA, e.g., as described in the Examples.

The terms "ILT4 antibody" or "hILT4 antibody" or "anti-ILT4 antibody" or "anti-hILT4 antibody" or "antibody that binds ILT4," as used herein, refer to an antibody that binds to ILT4 and that optionally inhibits the biological activity of ILT4, such as by blocking or inhibiting the binding of ILT4 to target cells, such as T cells, or target molecule. In some embodiments, the extent of binding of an ILT4 antibody to an unrelated, non-ILT4 protein is less than 10% of the binding of the antibody to ILT4 as measured, e.g., by SPR (Biacore®) or in a radioimmunoassay (MA). In some embodiments, the extent of binding of an ILT4 antibody to other ILT family proteins, such as LILRA is less than 20%, less than 10%, less than 5% of the binding of the antibody to ILT4 as measured, e.g., by SPR or in a radioimmunoassay (RIA). In some embodiments, an ILT4 antibody binds ILT4 but does not bind at least one protein selected from ILT2, ILT3, and ILT5.

The term "leader peptide" or "leader sequence" or "signal peptide" or "signal sequence" refers to a peptide or sequence of amino acid residues located at the N terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached.

The term "antibody" or "Ab" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. As used herein, the term refers to a molecule comprising at least complementarity-determining region (CDR) 1, CDR2, and CDR3 of a heavy chain and at least CDR1, CDR2, and CDR3 of a light chain, wherein the molecule is capable of binding to antigen. The term antibody also includes, but is not limited to, chimeric antibodies, humanized antibodies, human antibodies, and antibodies of various species such as mouse, cynomolgus monkey, etc. The term "antibody fragment" includes, but is not limited to, fragments that are capable of binding antigen, such as Fv, single-chain Fv (scFv), Fab, Fab', and $(Fab')_2$.

The term "heavy chain" or "HC" refers to a polypeptide comprising at least a heavy chain variable region, with or without a leader sequence. In some embodiments, a heavy chain comprises at least a portion of a heavy chain constant region. The term "full-length heavy chain" refers to a polypeptide comprising a heavy chain variable region and a heavy chain constant region, with or without a leader sequence, and with or without a C-terminal lysine (K). The term "mature full-length heavy chain" refers to a polypeptide comprising a heavy chain variable region and a heavy chain constant region, without a leader sequence, and with or without a C-terminal lysine (K).

The term "heavy chain variable region" or "VII" refers to a region comprising a heavy chain complementary determining region (CDR) 1, framework region (FR) 2, CDR2, FR3, and CDR3 of the heavy chain. In some embodiments, a heavy chain variable region also comprises at least a portion of an FR1 and/or at least a portion of an FR4. In some embodiments the heavy chain CDRs are as specified herein, such as in the sequence table below or in FIGS. 1-12. As used herein, the VH CDR1, CDR2, and CDR3 are Kabat CDRs as provided in FIGS. 1-12, for example.

The term "light chain" or "LC" refers to a polypeptide comprising at least a light chain variable region, with or without a leader sequence. In some embodiments, a light chain comprises at least a portion of a light chain constant region. The term "full-length light chain" refers to a polypeptide comprising a light chain variable region and a light chain constant region, with or without a leader sequence. The term "mature full-length light chain" refers to a polypeptide comprising a light chain variable region and a light chain constant region, without a leader sequence.

The term "light chain variable region" or "VL" refers to a region comprising a light chain CDR1, FR2, HVR2, FR3, and HVR3. In some embodiments, a light chain variable region also comprises an FR1 and/or an FR4. In some embodiments, the light chain CDRs are as specified herein such as in the sequence table or in FIGS. 1-12. As used herein, the VL CDR1, CDR2, and CDR3 are Kabat CDRs as provided in FIGS. 1-12, for example.

A "chimeric antibody" refers to an antibody in which a portion of the heavy and/or light chain is derived from a particular source or species, while the remainder of the heavy and/or light chain is derived from a different source or species. In some embodiments, a chimeric antibody refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species.

A "humanized antibody" refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is an Fab, an scFv, a $(Fab')_2$, etc.

A "human antibody" as used herein refers to antibodies produced in humans, antibodies produced in non-human animals that comprise human immunoglobulin genes, such as XenoMouse®, and antibodies selected using in vitro methods, such as phage display, wherein the antibody repertoire is based on a human immunoglobulin sequences.

In some embodiments, an antibody herein may contain one or more "conservative substitutions" compared to a particular, specified sequence. "Conservative amino acid substitutions" herein refer to substitutions of an amino acid residue with an amino acid residue having a similar side chain. Families of amino acid residues having similar side chains include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, a predicted nonessential amino acid residue in an antibody herein is replaced with another amino acid residue from the same side chain family (e.g., basic, acidic, beta-branched, aromatic, uncharged polar). Methods of identifying nucleotide and amino acid conservative substitutions which do not eliminate antigen binding have been described, for example, in Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)).

In some embodiments, an antibody herein may contain one or more "reversion substitutions." Examples are depicted in FIGS. 13-15 herein. Reversion substitutions are mutations back to a germ line amino acid sequence from which an antibody heavy chain or light chain was derived.

A "$K_D$" or "dissociation constant" for binding of an antibody to a protein, e.g., ILT4, is a measure of the affinity or specific binding of the antibody to the protein, e.g., ILT4. A lower $K_D$ indicates improved binding or affinity over a higher $K_D$. A $K_D$ is composed of a ratio between an "off-rate" or $k_{off}$ or $k_d$ and an "on-rate" or $k_{on}$ or $k_a$ for the antibody and polypeptide.

The terms "specific binding" or "specifically binds" or like terms signify that the $K_D$ for the binding of two polypeptides, such as an antibody and its polypeptide target, is less than would be the case between two random polypeptides existing under the same conditions. In other words, the $K_D$ is less than that due to nonspecific aggregation of polypeptides in the system.

A "tumor model," as used herein, refers to an in vivo preclinical assay, which may be used for studying the biological activity of an ILT4 antibody, and includes xenograft or native mouse tumor assay systems. In some cases, a tumor model may allow for tracking of tumor size or growth upon treatment with the antibody, and/or tracking of the presence of immune cells in the tumor, such as specific types of T-cells or NK cells, in order to determine whether an antibody has triggered or enhanced an immune response.

The term "immune stimulating agent" as used herein refers to a molecule that stimulates the immune system by either acting as an agonist of an immune-stimulatory molecule, including a co-stimulatory molecule, or acting as an antagonist of an immune inhibitory molecule, including a co-inhibitory molecule. The immune-stimulatory molecule or immune inhibitory molecule may be an immune checkpoint regulator, such as a checkpoint inhibitor or checkpoint stimulator. An immune stimulating agent may be a biologic, such as an antibody or antibody fragment, other protein, or vaccine, or may be a small molecule drug. An "immune stimulatory molecule" includes a receptor or ligand that acts to enhance, stimulate, induce, or otherwise "turn-on" an immune response. Immune stimulatory molecules as defined herein include co-stimulatory molecules. An "immune inhibitory molecule" includes a receptor or ligand that acts to reduce, inhibit, suppress, or otherwise "turn-off" an immune response. Immune inhibitory molecules as defined herein include co-inhibitory molecules. Such immune stimulatory and immune inhibitory molecules may be, for example, receptors or ligands found on immune cells such as a T cells, or found on cells involved in innate immunity such as NK cells.

"Percent (%) amino acid sequence identity," % identity," "percent amino acid sequence homology," and "% homology" with respect to a peptide, polypeptide or antibody sequence mean the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGNTM (DNASTAR) software. Those skilled in the art can determine appropriate parameters for measuring alignment, including any algorithms needed to achieve maximal alignment over the full length of the sequences being compared.

"Treatment" as used herein, covers any administration or application of a therapeutic for disease in a human, and includes inhibiting disease progression of the disease or one or more disease symptoms, slowing the disease or its progression or one or more of its symptoms, arresting its development, partially or fully relieving the disease or one or more of its symptoms, or preventing a recurrence of one or more symptoms of the disease.

The terms "subject" and "patient" are used interchangeably herein to refer to a human unless specifically stated otherwise.

The term "effective amount" or "therapeutically effective amount" refers to an amount of a drug effective for treatment of a disease or disorder in a subject, such as to partially or fully relieve one or more symptoms. In some embodiments, an effective amount refers to an amount effective, at dosages and for periods of time necessary, to achieve the desired therapeutic or prophylactic result.

The term "cancer" is used herein to refer to a group of cells that exhibit abnormally high levels of proliferation and growth. A cancer may be benign (also referred to as a benign tumor), pre-malignant, or malignant. Cancer cells may be solid cancer cells or leukemic cancer cells. The term "tumor growth" is used herein to refer to proliferation or growth by a cell or cells that comprise a cancer that leads to a corresponding increase in the size or extent of the cancer.

Examples of cancers applicable to methods of treatment herein include but are not limited to, carcinoma, lymphoma, blastoma, sarcoma, and leukemia. More particular nonlimiting examples of such cancers include squamous cell cancer, small-cell lung cancer, pituitary cancer, esophageal cancer, astrocytoma, soft tissue sarcoma, non-small cell lung cancer (including squamous cell non-small cell lung cancer), adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cell carcinoma, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer (including squamous cell carcinoma of the head and neck).

Administration "in combination with" one or more further therapeutic agents includes simultaneous (concurrent) and consecutive (sequential) administration in any order.

A "pharmaceutically acceptable carrier" refers to a nontoxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

A "chemotherapeutic agent" is a chemical compound useful in the treatment of cancer. Examples of chemotherapeutic agents that can be administered in methods herein include, but are not limited to, alkylating agents such as thiotepa and Cytoxan® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegaIl (see, e.g., Agnew, *Chem Intl. Ed. Engl.*, 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, Adriamycin® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), Abraxane® Cremophor-free, albumin-engineered nanoparticle formulation of paclitaxel (American Pharmaceutical Partners, Schaumberg, Ill.), and Taxotere® doxetaxel (Rhone-Poulenc Rorer, Antony, France); chloranbucil; Gemzar® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

Further nonlimiting exemplary chemotherapeutic agents that can be administered in methods herein include anti-hormonal agents that act to regulate or inhibit hormone action on cancers such as anti-estrogens and selective estrogen receptor modulators (SERMs), including, for example, tamoxifen (including Nolvadex® tamoxifen), raloxifene, droloxifene, 4-hydroxytamoxifen, trioxifene, keoxifene, LY117018, onapristone, and Fareston® toremifene; aromatase inhibitors that inhibit the enzyme aromatase, which regulates estrogen production in the adrenal glands, such as, for example, 4(5)-imidazoles, aminoglutethimide, Megase® megestrol acetate, Aromasin® exemestane, formestanie, fadrozole, Rivisor® vorozole, Femara® letrozole, and Arimidex® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., Angiozyme® ribozyme) and a HER2 expression inhibitor; vaccines such as gene therapy vaccines, for example, Allovectin® vaccine, Leuvectin® vaccine, and Vaxid® vaccine; Proleukin® rIL-2; Lurtotecan® topoisomerase 1 inhibitor; Abarelix® rmRH; and pharmaceutically acceptable salts, acids or derivatives of any of the above.

An "anti-angiogenesis agent" or "angiogenesis inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent that can be administered in methods herein can include an antibody or other antagonist to an angiogenic agent, e.g., antibodies to VEGF-A (e.g., bevacizumab (Avastin)) or to the VEGF-A receptor (e.g., KDR receptor or Flt-1 receptor), anti-PDGFR inhibitors such as Gleevec® (Imatinib Mesylate), small molecules that block VEGF receptor signaling (e.g., PTK787/ZK2284, SU6668, Sutent®/SU11248 (sunitinib malate), AMG706, or those described in, e.g., international patent application WO 2004/113304). Anti-angiogensis agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12): 1359-1364; Tonini et al. (2003) *Oncogene* 22:6549-6556 (e.g., Table 2 listing known anti-angiogenic factors); and, Sato (2003) *Int. J. Clin. Oncol.* 8:200-206 (e.g., Table 1 listing anti-angiogenic agents used in clinical trials).

A "growth inhibitory agent" as used herein refers to a compound or composition that inhibits growth of a cell (such as a cell expressing VEGF) either in vitro or in vivo. Thus, the growth inhibitory agent that can be administered in methods herein may be one that significantly reduces the percentage of cells (such as a cell expressing VEGF) in S phase. Examples of growth inhibitory agents include, but are not limited to, agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (Taxotere®, Rhone-Poulenc Rorer), derived from the European yew, is a semisynthetic analogue of paclitaxel (Taxol®, Bristol-Myers Squibb). Paclitaxel and docetaxel promote the assembly of microtubules from tubulin dimers and stabilize microtubules by preventing depolymerization, which results in the inhibition of mitosis in cells.

The term "anti-neoplastic composition" refers to a composition useful in treating cancer comprising at least one active therapeutic agent. Examples of therapeutic agents include, but are not limited to, e.g., chemotherapeutic agents, growth inhibitory agents, cytotoxic agents, agents used in radiation therapy, anti-angiogenesis agents, cancer immunotherapeutic agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva®), platelet derived growth factor inhibitors (e.g., Gleevec® (Imatinib Mesylate)), a COX-2 inhibitor (e.g., celecoxib), interferons, CTLA4 inhibitors (e.g., anti-CTLA antibody ipilimumab (YERVOY®)), PD-1 ore PD-L1 inhibitors (e.g., OPDIVO®, KEYTRUDA®, TECENTRIQ®, BAVENCIO®, IMFINZI®), TIM3 inhibitors (e.g., anti-TIM3 antibodies), LAG-3 inhibitors, cytokines, antagonists (e.g., neutralizing antibodies) that bind to one or more of the following targets ErbB2, ErbB3, ErbB4, PDGFR-beta, BlyS, APRIL, BCMA, CTLA4, TIM3, or VEGF receptor(s), TRAIL/Apo2, and other bioactive and organic chemical agents, etc. Combinations thereof are also included in this disclosure.

Antibodies Specifically Binding to ILT4

The Sequence Table below provides the amino acid sequence of human ILT4 with or without signal peptide, respectively (see SEQ ID Nos: 107-108 and 110-111). The extracellular domain (ECD) comprises the amino acid residues shown in SEQ ID Nos: 109 and 112. An exemplary ECD coupled to a His-Avi tag comprises the amino acid sequence of SEQ ID NO: 119.

Anti-ITL4 antibodies (Abs) may specifically bind to the ILT4-ECD or fragments thereof (see SEQ ID Nos: 109 and 112, as well as 119).

Provided herein are Abs that bind to ILT4 with a $K_D$ of $10^{-6}$ M or less, $10^{-7}$ M or less, $10^{-8}$ M or less, $10^{-9}$ M or less or $10^{-10}$ M or less, as measured, e.g., at 25° C. or at 37° C.

Determining how well an Ab binds to an ILT4 protein can be conducted using several different methods. For example, by surface plasmon resonance (SPR), such as by BIACORE® assays. An exemplary SPR assay comprises capturing one or several antibodies on a CM4 sensor chip with immobilized capture reagent (e.g., using Biacore® anti-human Fc capture kit, GE Healthcare catalog #BR-1008-39, or Biacore® anti-mouse capture kit, GE Healthcare catalog #BR-1008-39), and flowing ILT4 antigen (e.g. ILT4 ECD) as analyte in a concentration series to determine binding kinetics and affinities in a running buffer. In one embodiment, ILT4 is injected at two to five concentrations in the range of 0.1 nM to 500 nM (e.g., 0.1 nM, 1 nM, 10 nM, 100 nM, 500 nM) with a flow rate of 30 uL/min, up to four minutes association time and up to ten minutes dissociation time. Between binding cycles, the capture surface is regenerated following the manufacturer's instructions for the respective capture kit. All data are double-referenced using a reference flow cell and a blank injection. Data with simple 1:1 kinetics are fitted to a Langmuir binding model with mass transfer using the Biacore® T200 evaluation software. The SPR methods described in the Examples may also be used.

The affinity of an Ab for an ILT4 ECD polypeptide may be determined using cells expressing an ILT4 polypeptide on their surface, which method comprises flow cytometry. An exemplary flow cytometry assay comprises the following: T cells or other cells ectopically expressing ILT4 are re-suspended in a buffer in which the Ab has been serially diluted from approximately 20 μg/mL and incubated with the re-suspended cells for 30 minutes at 4° C. Cells are then washed twice with the same buffers, maintaining the desired buffer conditions, and incubated with a fluorophore-conjugated secondary antibody that recognizes the primary antibody (e.g., human IgG). Cells are then washed as before and acquired immediately, without fixation, on a BD Fortessa® or other flow cytometer. The affinity of an Ab for an ILT4 polypeptide may be determined as described in the Examples.

In certain embodiments, Abs that bind to ILT4 block binding of ILT4 to target cells, such as T cells. Inhibition or blocking may be 100% or at least 99%, 95%, 90%, 85%, 80%, 75%, or 50%.

Inhibition of binding between ILT4 and ILT4-binding cells such as T cells can be determined by measuring the inhibition of binding of cells to which ILT4 binds in the presence and absence of the antibody. An exemplary experiment that can be used to determine if an antibody inhibits the binding of ILT4 to ILT4-binding cells is a flow cytometry assay, e.g., an assay that comprises the following: human peripheral blood mononuclear cells from donor blood, buffy coat, or leukopak are re-suspended in a buffer consisting of HBSS+1% BSA. The cells are then incubated for 30 minutes at 4° C. with 20 μg/mL of, for example, ILT4 ECD or an ILT4 ECD fusion protein fused to human IgG1 Fc and with varying concentrations of candidate ILT4 blocking antibodies or control antibodies. Cells are then washed twice in the same buffers and incubated for another 30 minutes at 4° C. with a fluorophore-conjugated secondary antibody that recognizes ILT4, but not the candidate blocking antibodies or control antibodies. Cells are then washed as before and acquired immediately, without fixation, on a BD Fortessa® or other flow cytometer. Inhibition of binding can also be determined, e.g., as described in the Examples.

Exemplary ILT4 Binding Abs

Provided herein are Abs that bind specifically to ILT4, e.g., to ILT4 ECD.

In certain embodiments, an ILT4 Ab comprises a heavy chain variable region ("VH") comprising VH CDR1, CDR2 and/or CDR3 of any of the ILT4 Abs provided herein. VH CDRs herein are Kabat CDRs as shown in FIGS. 1, 3, 5, 7, 9, and 11 herein, unless specified otherwise (e.g. an AbM CDR1, etc.) In certain embodiments, an ILT4 Ab comprises a VH comprising the VH CDR1, CDR2 and CDR3 of any of the ILT4 Abs provided herein. In certain embodiments, an ILT4 Ab comprises a VH comprising VH CDR1, CDR2 and/or CDR3 of any one of 9G4, 9C8, 2H2, 2E5, 24E5, 21D9, 21D9.b, 21D9.c, 21D9.d, 21D9.e, 21A5, 21A5.a, 10F10, 10F10.1, 10F10.3, or 10F10.4, (i.e., any one of 9G4 (SEQ ID Nos: 125-127), 9C8 (SEQ ID Nos: 131-133), 2H2 (SEQ ID Nos: 137-139), 2E5 (SEQ ID Nos: 143-145), 24E5 (SEQ ID Nos: 149-151), 21D9 (SEQ ID Nos: 155-157), 21D9.b (SEQ ID Nos: 155-157), 21D9.c (SEQ ID Nos: 155-157), 21D9.d (SEQ ID Nos: 155-157), 21D9.e (SEQ ID Nos: 155-157), 21A5 (SEQ ID Nos: 161-163), 10F10 (SEQ ID Nos: 167-169), 10F10.1 (SEQ ID Nos: 167-169), 10F10.3 (SEQ ID Nos: 167-169), or 10F10.4 (SEQ ID Nos: 167-169)).

In certain embodiments, an ILT4 Ab comprises a VH comprising VH CDR1, CDR2 and CDR3 of any of the ILT4 Abs provided herein. In certain embodiments, an ILT4 Ab comprises a VH comprising VH CDR1, CDR2 and CDR3 of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4.

In certain embodiments, an ILT4 Ab comprises a VH comprising VH CDR1, CDR2 and/or CDR3 of any of the ILT4 Abs provided herein and a VL comprising CDR1, CDR2 and/or CDR3 of any of the ILT4 Abs provided herein. VL CDRs herein are Kabat CDRs as shown in FIGS. 2, 4, 6, 8, 10, and 12 herein, unless specified otherwise (e.g. an AbM CDR1, etc.) In certain embodiments, an ILT4 Ab comprises a VH comprising VH CDR1, CDR2 and CDR3 of any of the ILT4 Abs provided herein and a VL comprising CDR1, CDR2 and CDR3 of any of the ILT4 Abs provided herein. In certain embodiments, an ILT4 Ab comprises a VH comprising VH CDR1, CDR2 and/or CDR3 of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4 and a VL comprising VL CDR1, CDR2, and/or CDR3 of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4 (i.e., any one of 9G4 (SEQ ID Nos: 128-130), 9C8 (SEQ ID Nos: 134-136), 2H2 (SEQ ID Nos: 140-142), 2E5 (SEQ ID Nos: 146-148), 24E5 (SEQ ID Nos: 152-154), 21D9 (SEQ ID Nos: 158-160), 21D9.b (SEQ ID Nos: 158-160), 21D9.c (SEQ ID Nos: 158-160), 21D9.d (SEQ ID Nos: 158-160), 21D9.e (SEQ ID Nos: 158-160), 21A5 (SEQ ID Nos: 164-166), 10F10 (SEQ ID Nos: 170-172), 10F10.1 (SEQ ID Nos: 170-172), 10F10.3 (SEQ ID Nos: 170-172), or 10F10.4 (SEQ ID Nos: 170-172)).

In some embodiments, an ILT4 Ab may comprise:

(a) a VH comprising the amino acid sequence of the VH CDR1, CDR2 and CDR3 of 9G4 and a VL comprising the VL CDR1, CDR2 and CDR3 of 9G4;

(b) a VH comprising the amino acid sequence of the VH CDR1, CDR2 and CDR3 of 9C8 and a VL comprising the VL CDR1, CDR2 and CDR3 of 9C8;

(c) a VH comprising the amino acid sequence of the VH CDR1, CDR2 and CDR3 of 2H2 and a VL comprising the VL CDR1, CDR2 and CDR3 of 2H2;

(d) a VH comprising the amino acid sequence of the VH CDR1, CDR2 and CDR3 of 25E5 and a VL comprising the VL CDR1, CDR2 and CDR3 of 25E5;

(e) a VH comprising the amino acid sequence of the VH CDR1, CDR2 and CDR3 of 24E5 and a VL comprising the VL CDR1, CDR2 and CDR3 of 24E5;

(f) a VH comprising the amino acid sequence of the VH CDR1, CDR2 and CDR3 of 21D9 and a VL comprising the VL CDR1, CDR2 and CDR3 of 21D9;

(g) a VH comprising the amino acid sequence of the VH CDR1, CDR2 and CDR3 of 21D9.b and a VL comprising the VL CDR1, CDR2 and CDR3 of 21D9.b;

(h) a VH comprising the amino acid sequence of the VH CDR1, CDR2 and CDR3 of 21D9.c and a VL comprising the VL CDR1, CDR2 and CDR3 of 21D9.c;

(i) a VH comprising the amino acid sequence of the VH CDR1, CDR2 and CDR3 of 21D9.d and a VL comprising the VL CDR1, CDR2 and CDR3 of 21D9.d;

(j) a VH comprising the amino acid sequence of the VH CDR1, CDR2 and CDR3 of 21D9.e and a VL comprising the VL CDR1, CDR2 and CDR3 of 21D9.e;

(k) a VH comprising the amino acid sequence of the VH CDR1, CDR2 and CDR3 of 21A5 and a VL comprising the VL CDR1, CDR2 and CDR3 of 21A5;

(l) a VH comprising the amino acid sequence of the VH CDR1, CDR2 and CDR3 of 21A5.a and a VL comprising the VL CDR1, CDR2 and CDR3 of 21A5.a;

(m) a VH comprising the amino acid sequence of the VH CDR1, CDR2 and CDR3 of 10F10 and a VL comprising the VL CDR1, CDR2 and CDR3 of 10F10;

(n) a VH comprising the amino acid sequence of the VH CDR1, CDR2 and CDR3 of 10F10.1 and a VL comprising the VL CDR1, CDR2 and CDR3 of 10F10.1;

(o) a VH comprising the amino acid sequence of the VH CDR1, CDR2 and CDR3 of 10F10.3 and a VL comprising the VL CDR1, CDR2 and CDR3 of 10F10.3; or (p) a VH comprising the amino acid sequence of the VH CDR1, CDR2 and CDR3 of 10F10.4 and a VL comprising the VL CDR1, CDR2 and CDR3 of 10F10.4.

Again, the Sequence Table below provides the heavy and light chain variable region sequences and full length heavy and light chain sequences of the antibodies listed above.

In certain embodiments, an ILT4 Ab comprises a VH comprising the amino acid sequence of the VH of any of the ILT4 Abs provided herein. The individual VH sequences for particular antibody species provided herein are listed in the Sequence Table. In certain embodiments, an ILT4 Ab comprises a VH comprising the amino acid sequence of the VH of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4, (i.e., any one of 9G4 (SEQ ID NO: 51, amino acids 20-135), 9C8 (SEQ ID NO: 55), 2H2 (SEQ ID NO: 58), 2E5 (SEQ ID NO: 63), 24E5 (SEQ ID NO: 67), 21D9 (SEQ ID NO: 71), 21D9.b (SEQ ID NO: 74), 21D9.c (SEQ ID NO: 75), 21D9.d (SEQ ID NO: 78), 21D9.e (SEQ ID NO: 80), 21A5 (SEQ ID NO: 83), 21A5.a (SEQ ID NO: 87), 10F10 (SEQ ID NO: 91), 10F10.1 (SEQ ID NO: 91), 10F10.3 (SEQ ID NO: 91), or 10F10.4 (SEQ ID NO: 91)).

In some embodiments, an ILT4 Ab comprises the VH of any of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4, but with 1, 2, 3, 4, or 5 amino acid substitutions in the framework regions of the VH sequence, such as 1, 2, 3, 4, or 5 conservative substitutions. In some embodiments, an ILT4 Ab comprises the VH of any of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4, but with 1, 2, 3, 4, or 5 reversion substitutions in the framework regions of the VH sequence.

In some embodiments, an ILT4 Ab comprises the VH and VL CDRs of any of the ILT4 Abs described herein, wherein the CDRs comprise 1, 2 or 3 amino acid additions, substitutions (e.g., conservative substitutions), or deletion among all of the CDRs.

In certain embodiments, an ILT4 Ab comprises a VH CDR1, CDR2, and CDR3 comprising the amino acid sequences of the VH CDRs of any of the ILT4 Abs provided herein and comprises a VH that is at least 90%, at least 91%, at least 92%, at least 93%, at least 94%, at least 95%, at least 96%, at least 97%, at least 98%, or at least 99% identical to the VH of any of the ILT4 Abs provided herein. In certain embodiments, an ILT4 Ab comprises a VH comprising an amino acid sequence that is at least 90%, at least 91%, at least 92%, at least 93%, at least 94%, at least 95%, at least 96%, at least 97%, at least 98%, or at least 99% identical to the amino acid sequence of the VH of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4. In certain embodiments, the VH of the antibody differs from that of the VH sequences shown in the Sequence Table due to 1, 2, 3, 4, or 5 amino acid substitutions in the framework regions of the VH sequence, such as 1, 2, 3, 4, or 5 conservative substitutions. In certain embodiments, the VH of the antibody differs from that of the VH sequences shown in the Sequence Table due to 1, 2, 3, 4, or 5 reversion substitutions in the framework regions of the VH sequence.

In certain embodiments, an ILT4 Ab comprises a VH consisting of the amino acid sequence of the VH of any of the ILT4 Abs provided herein. In certain embodiments, an ILT4 Ab comprises a VH that consists of the amino acid sequence of the VH of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4.

In certain embodiments, an ILT4 Ab comprises a VL comprising the amino acid sequence of the VL of any of the ILT4 Abs provided herein. In certain embodiments, an ILT4 Ab comprises a VL comprising the amino acid sequence of the VL of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4, (i.e., 9G4 (SEQ ID NO: 50, amino acids 19-125), 9C8 (SEQ ID NO: 54), 2H2 (SEQ ID NO: 59), 2E5 (SEQ ID NO: 62), 24E5 (SEQ ID NO: 66), 21D9 (SEQ ID NO: 70), 21D9.b (SEQ ID NO: 70), 21D9.c (SEQ ID NO: 70), 21D9.d (SEQ ID NO: 70), 21D9.e (SEQ ID NO: 70), 21A5 (SEQ ID NO: 82), 21A5.a (SEQ ID NO: 86), 10F10 (SEQ ID NO: 90), 10F10.1 (SEQ ID NO: 94), 10F10.3 (SEQ ID NO: 96), or 10F10.4 (SEQ ID NO: 114)). In certain embodiments, an ILT4 Ab comprises a VL CDR1, CDR2, and CDR3 comprising the amino acid sequences of the VL CDRs of any of the ILT4 Abs provided herein and comprises a VL that is at least 90%, at least 91%, at least 92%, at least 93%, at least 94%, at least 95%, at least 96%, at least 97%, at least 98%, or at least 99% identical to the VL of any of the ILT4 Abs provided herein. In certain embodiments, an ILT4 Ab comprises a VL comprising an amino acid sequence that is at least 90%, at least 91%, at least 92%, at least 93%, at least 94%, at least 95%, at least 96%, at least 97%, at least 98%, or at least 99% identical to the amino acid sequence of the VL of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4. In certain embodiments, the VL of the antibody differs from that of the VL sequences shown in the Sequence Table due to 1, 2, 3, 4, or 5 amino acid substitutions in the framework regions of the VL sequence, such as 1, 2, 3, 4, or 5 conservative substitutions. In certain embodiments, the VL of the antibody differs from that of the VL sequences shown in the Sequence Table due to 1, 2, 3, 4, or 5 reversion substitutions.

In certain embodiments, an ILT4 Ab comprises a VL consisting of the amino acid sequence of the VL of any of the ILT4 Abs provided herein. In certain embodiments, an ILT4 Ab comprises a VL that consists of the amino acid sequence of the VL of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4.

In certain embodiments, an ILT4 Ab comprises a VH comprising the amino acid sequence of the VH of any of the ILT4 Abs provided herein and comprises a VL comprising the amino acid sequence of the VL of any of the ILT4 Abs provided herein. In certain of these embodiments, an ILT4 Ab comprises a VH comprising the amino acid sequence of the VH of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4 and a VL comprising the amino acid sequence of the VL of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4.

In certain embodiments, however, the VH of the antibody is that of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4, but with 1, 2, 3, 4, or 5 amino acid substitutions in the framework regions of the VH sequence, such as 1, 2, 3, 4, or 5 conservative substitutions, and the VL is that of any one of the same species from the list above. In certain embodiments, however, the VH of the antibody is that of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4, but with 1, 2, 3, 4, or 5 reversion substitutions in the framework regions of the VH sequence.

In certain embodiments, an ILT4 Ab comprises a VH and a VL comprising the amino acid sequences of the VH and VL of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4.

In certain embodiments, an ILT4 Ab comprises a VH CDR1, CDR2, and CDR3 comprising the amino acid sequences of the VH CDRs of any of the ILT4 Abs provided herein as well as a VL CDR1, CDR2, and CDR3 comprising the amino acid sequences of the VL CDRs of any of the ILT4 Abs provided herein, and also comprises a VH and a VL that are each at least 90%, at least 91%, at least 92%, at least 93%, at least 94%, at least 95%, at least 96%, at least 97%, at least 98%, or at least 99% identical to the corresponding VH and VL of any of the ILT4 Abs provided herein. In certain embodiments, the VH and the VL of the antibody differ from the VH and VL sequences shown in the Sequence Table due to 1, 2, 3, 4, or 5 amino acid substitutions in the framework regions of the sequences, such as 1, 2, 3, 4, or 5 conservative substitutions, or such as 1, 2, 3, 4 or 5 reversion substitutions.

In certain embodiments, an ILT4 Ab comprises a VH and a VL consisting of the amino acid sequence of the VH and VL of any of the ILT4 Abs provided herein. In certain embodiments, an ILT4 Ab comprises a VH and a VL that each consist of the amino acid sequences of the VH and VL of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4.

An ILT4 Ab may comprise:

(a) a VH comprising the amino acid sequence of the VH of 9G4 and a VL comprising the amino acid sequence of the VL of 9G4;

(b) a VH comprising the amino acid sequence of the VH of 9C8 and a VL comprising the amino acid sequence of the VL of 9C8;

(c) a VH comprising the amino acid sequence of the VH of 2H2 and a VL comprising the amino acid sequence of the VL of 2H2;

(d) a VH comprising the amino acid sequence of the VH of 25E5 and a VL comprising the amino acid sequence of the VL of 25E5;

(e) a VH comprising the amino acid sequence of the VH of 24E5 and a VL comprising the amino acid sequence of the VL of 24E5;

(f) a VH comprising the amino acid sequence of the VH of 21D9 and a VL comprising the amino acid sequence of the VL of 21D9;

(g) a VH comprising the amino acid sequence of the VH of 21D9.b and a VL comprising the amino acid sequence of the VL of 21D9.b;

(h) a VH comprising the amino acid sequence of the VH of 21D9.c and a VL comprising the amino acid sequence of the VL of 21D9.c;

(i) a VH comprising the amino acid sequence of the VH of 21D9.d and a VL comprising the amino acid sequence of the VL of 21D9.d;

(j) a VH comprising the amino acid sequence of the VH of 21D9.e and a VL comprising the amino acid sequence of the VL of 21D9.e;

(k) a VH comprising the amino acid sequence of the VH of 21A5 and a VL comprising the amino acid sequence of the VL of 21A5;

(l) a VH comprising the amino acid sequence of the VH of 21A5.a and a VL comprising the amino acid sequence of the VL of 21A5.a;

(m) a VH comprising the amino acid sequence of the VH of 10F10 and a VL comprising the amino acid sequence of the VL of 10F10;

(n) a VH comprising the amino acid sequence of the VH of 10F10.1 and a VL comprising the amino acid sequence of the VL of 10F10.1;

(o) a VH comprising the amino acid sequence of the VH of 10F10.3 and a VL comprising the amino acid sequence of the VL of 10F10.3; or (p) a VH comprising the amino acid sequence of the VH of 10F10.4 and a VL comprising the amino acid sequence of the VL of 10F10.4.

An ILT4 Ab may comprise:

(a) a VH comprising the VH CDRs of the VH of 9G4, and a VL comprising the VL CDRs of 9G4, and VH and VL amino acid sequences that are at least 90%, at least 91%, at least 92%, at least 93%, at least 94%, at least 95%, at least 96%, at least 97%, at least 98%, or at least 99% identical to the VH and VL of 9G4;

(b) a VH comprising the VH CDRs of the VH of 9C8, and a VL comprising the VL CDRs of 9C8, and VH and VL amino acid sequences that are at least 90%, at least 91%, at least 92%, at least 93%, at least 94%, at least 95%, at least 96%, at least 97%, at least 98%, or at least 99% identical to the VH and VL of 9C8;

(c) a VH comprising the VH CDRs of the VH of 2H2, and a VL comprising the VL CDRs of 2H2, and VH and VL amino acid sequences that are at least 90%, at least 91%, at least 92%, at least 93%, at least 94%, at least 95%, at least 96%, at least 97%, at least 98%, or at least 99% identical to the VH and VL of 2H2;

(d) a VH comprising the VH CDRs of the VH of 25E5, and a VL comprising the VL CDRs of 25E5, and VH and VL amino acid sequences that are at least 90%, at least 91%, at least 92%, at least 93%, at least 94%, at least 95%, at least 96%, at least 97%, at least 98%, or at least 99% identical to the VH and VL of 25E5;

(e) a VH comprising the VH CDRs of the VH of 24E5, and a VL comprising the VL CDRs of 24E5, and VH and VL amino acid sequences that are at least 90%, at least 91%, at least 92%, at least 93%, at least 94%, at least 95%, at least 96%, at least 97%, at least 98%, or at least 99% identical to the VH and VL of 24E5;

(f) a VH comprising the VH CDRs of the VH of 21D9, and a VL comprising the VL CDRs of 21D9, and VH and VL amino acid sequences that are at least 90%, at least 91%, at least 92%, at least 93%, at least 94%, at least 95%, at least 96%, at least 97%, at least 98%, or at least 99% identical to the VH and VL of 21D9;

(g) a VH comprising the VH CDRs of the VH of 21D9.b, and a VL comprising the VL CDRs of 21D9.b, and VH and VL amino acid sequences that are at least 90%, at least 91%, at least 92%, at least 93%, at least 94%, at least 95%, at least 96%, at least 97%, at least 98%, or at least 99% identical to the VH and VL of 21D9.b;

(h) a VH comprising the VH CDRs of the VH of 21D9.c, and a VL comprising the VL CDRs of 21D9.c, and VH and VL amino acid sequences that are at least 90%, at least 91%, at least 92%, at least 93%, at least 94%, at least 95%, at least 96%, at least 97%, at least 98%, or at least 99% identical to the VH and VL of 21D9.c;

(i) a VH comprising the VH CDRs of the VH of 21D9.d, and a VL comprising the VL CDRs of 21D9.d, and VH and VL amino acid sequences that are at least 90%, at least 91%, at least 92%, at least 93%, at least 94%, at least 95%, at least 96%, at least 97%, at least 98%, or at least 99% identical to the VH and VL of 21D9.d;

(j) a VH comprising the VH CDRs of the VH of 21D9.e, and a VL comprising the VL CDRs of 21D9.e, and VH and VL amino acid sequences that are at least 90%, at least 91%, at least 92%, at least 93%, at least 94%, at least 95%, at least 96%, at least 97%, at least 98%, or at least 99% identical to the VH and VL of 21D9.e;

(k) a VH comprising the VH CDRs of the VH of 21A5, and a VL comprising the VL CDRs of 21A5, and VH and VL amino acid sequences that are at least 90%, at least 91%, at least 92%, at least 93%, at least 94%, at least 95%, at least 96%, at least 97%, at least 98%, or at least 99% identical to the VH and VL of 21A5;

(l) a VH comprising the VH CDRs of the VH of 21A5.a, and a VL comprising the VL CDRs of 21A5.a, and VH and VL amino acid sequences that are at least 90%, at least 91%, at least 92%, at least 93%, at least 94%, at least 95%, at least 96%, at least 97%, at least 98%, or at least 99% identical to the VH and VL of 21A5.a;

(m) a VH comprising the VH CDRs of the VH of 10F10, and a VL comprising the VL CDRs of 10F10, and VH and VL amino acid sequences that are at least 90%, at least 91%, at least 92%, at least 93%, at least 94%, at least 95%, at least 96%, at least 97%, at least 98%, or at least 99% identical to the VH and VL of 10F10;

(n) a VH comprising the VH CDRs of the VH of 10F10.1, and a VL comprising the VL CDRs of 10F10.1, and VH and VL amino acid sequences that are at least 90%, at least 91%, at least 92%, at least 93%, at least 94%, at least 95%, at least 96%, at least 97%, at least 98%, or at least 99% identical to the VH and VL of 10F10.1;

(o) a VH comprising the VH CDRs of the VH of 10F10.3, and a VL comprising the VL CDRs of 10F10.3, and VH and VL amino acid sequences that are at least 90%, at least 91%, at least 92%, at least 93%, at least 94%, at least 95%, at least 96%, at least 97%, at least 98%, or at least 99% identical to the VH and VL of 10F10.3; or (p) a VH comprising the VH CDRs of the VH of 10F10.3, and a VL comprising the VL CDRs of 10F10.4, and VH and VL amino acid sequences that are at least 90%, at least 91%, at least 92%, at least 93%, at least 94%, at least 95%, at least 96%, at least 97%, at least 98%, or at least 99% identical to the VH and VL of 10F10.4.

In some of the above embodiments, the VH and/or VL may differ from the sequence of each of the species (a) to (p) by the presence of 1, 2, 3, 4, or 5 amino acid substitutions, such as 1, 2, 3, 4, or 5 conservative substitutions. In some embodiments, the VH may comprise 1, 2, 3, 4, or 5 reversion substitutions.

An ILT4 Ab may comprise:

(a) a VH consisting of the amino acid sequence of the VH of 9G4 and a VL consisting of the VL of 9G4;

(b) a VH consisting of the amino acid sequence of the VH of 9C8 and a VL consisting of the VL of 9C8;

(c) a VH consisting of the amino acid sequence of the VH of 2H2 and a VL consisting of the VL of 2H2;

(d) a VH consisting of the amino acid sequence of the VH of 25E5 and a VL consisting of the VL of 25E5;

(e) a VH consisting of the amino acid sequence of the VH of 24E5 and a VL consisting of the VL of 24E5;

(f) a VH consisting of the amino acid sequence of the VH of 21D9 and a VL consisting of the VL of 21D9;

(g) a VH consisting of the amino acid sequence of the VH of 21D9.b and a VL consisting of the VL of 21D9.b;

(h) a VH consisting of the amino acid sequence of the VH of 21D9.c and a VL consisting of the VL of 21D9.c;

(i) a VH consisting of the amino acid sequence of the VH of 21D9.d and a VL consisting of the VL of 21D9.d;

(j) a VH consisting of the amino acid sequence of the VH of 21D9.e and a VL consisting of the VL of 21D9.e;

(k) a VH consisting of the amino acid sequence of the VH of 21A5 and a VL consisting of the VL of 21A5;

(l) a VH consisting of the amino acid sequence of the VH of 21A5.a and a VL consisting of the VL of 21A5.a;

(m) a VH consisting of the amino acid sequence of the VH of 10F10 and a VL consisting of the VL of 10F10;

(n) a VH consisting of the amino acid sequence of the VH of 10F10.1 and a VL consisting of the VL of 10F10.1;

(o) a VH consisting of the amino acid sequence of the VH of 10F10.3 and a VL consisting of the VL of 10F10.3; or (p) a VH consisting of the amino acid sequence of the VH of 10F10.4 and a VL consisting of the VL of 10F10.4.

In certain embodiments, an ILT4 Ab comprises any of the variable regions and/or variable region CDRs 1-3 of the antibodies described above and elsewhere herein, such as:

(1) one or more of VH CDR1, CDR2 and CDR3 of: 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4;

(2) the VH CDR1, CDR2 and CDR3 of: 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4;

(3) the VH of: 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4;

(4) one or more of VH CDR1, CDR2 and CDR3 and one or more of VL CDR1, CDR2 and CDR3 of: 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4;

(5) the VH CDR1, CDR2 and CDR3 and VL CDR1, CDR2 and CDR3 of: 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4;

(6) the VH and the VLs of: 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4;

or (7) the VL and the VH, with the exception of 1, 2, 3, 4, or 5 reversion or conservative substitutions in the VH and/or VL of: 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4; and the ILT4 Ab is also an IgG antibody, such as IgG1, IgG2, IgG3 or IgG4 antibody or a modified form thereof as described in the section below. In some embodiments, the constant region has effector function, and in some embodiments, the constant region is effectorless. In certain embodiments, the constant region is that of IgG1.3 or IgG1.1f or another constant region described herein, e.g., IgG1 and IgG1.238K.

Figure 37A:
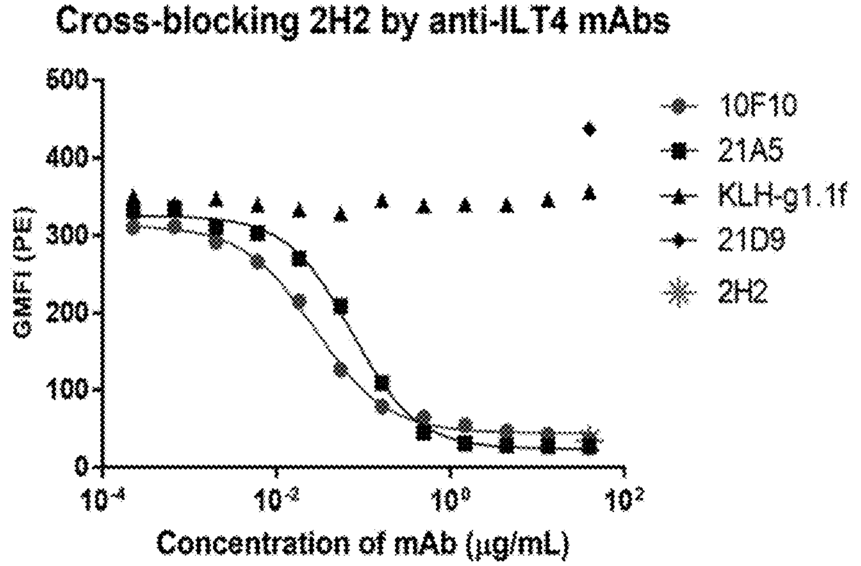
FIGS. 37A-D show results from experiments to determine the epitopes of certain antibodies.
Figure 37B:
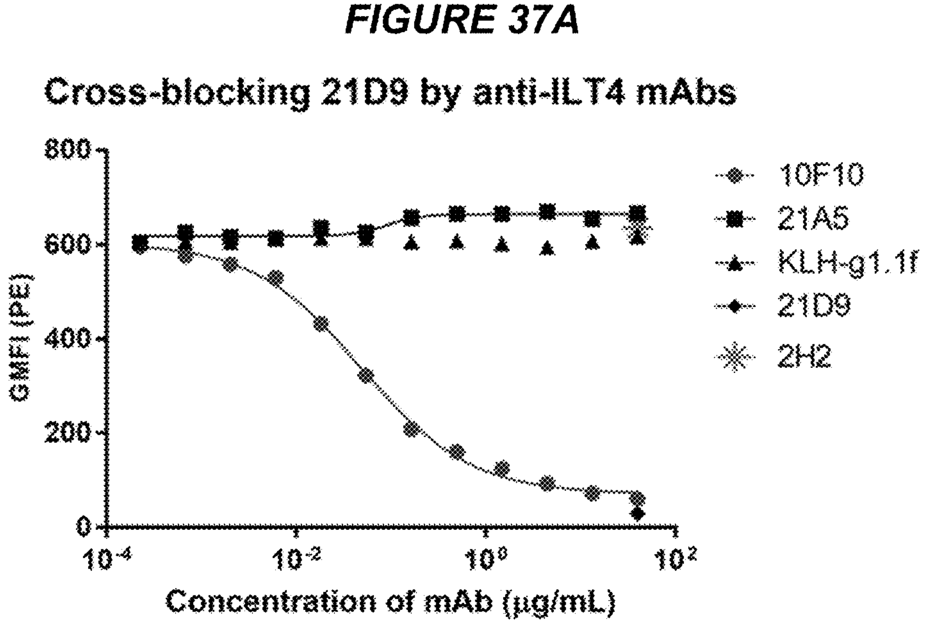
Figure 37C:
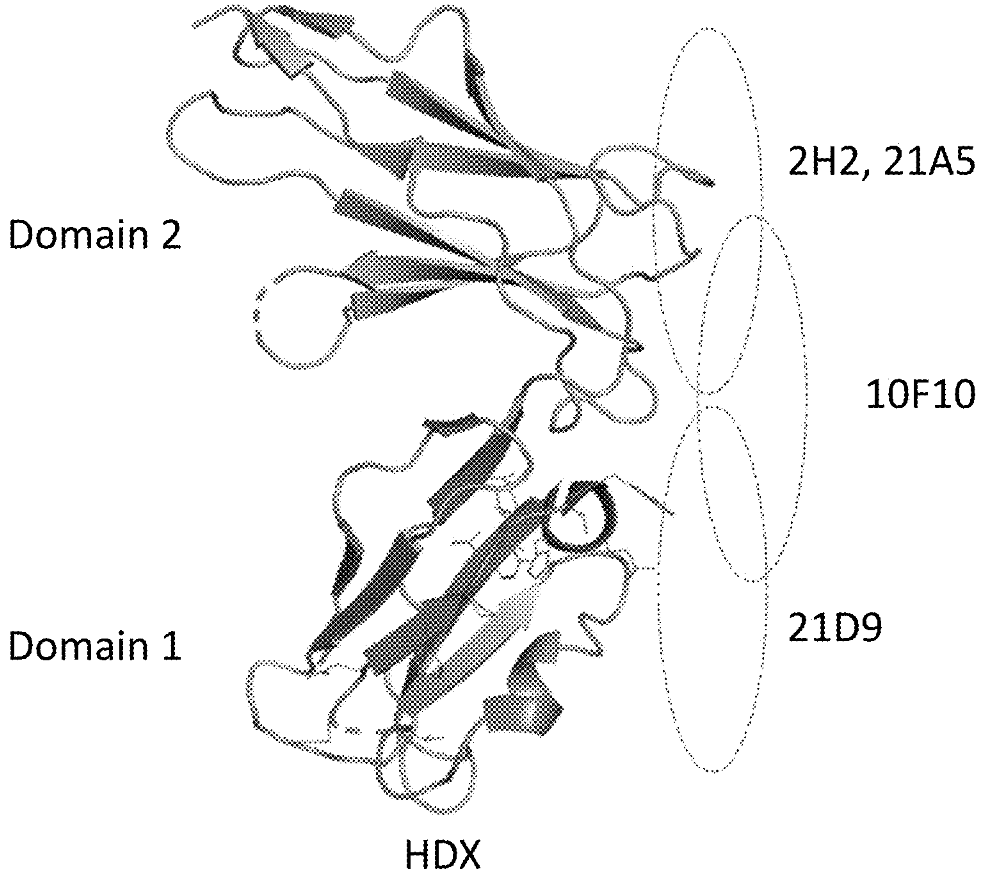

In certain embodiments, an ILT4 Ab comprises any of the variable regions and/or variable region CDRs 1-3 of the antibodies described above and elsewhere herein, such as:

(1) one or more of VH CDR1, CDR2 and CDR3 of: 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4;

(2) the VH CDR1, CDR2 and CDR3 of: 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4;

(3) the VH of: 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4;

(4) one or more of VH CDR1, CDR2 and CDR3 and one or more of VL CDR1, CDR2 and CDR3 of: 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4;

(5) the VH CDR1, CDR2 and CDR3 and VL CDR1, CDR2 and CDR3 of: 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4;

(6) the VH and the VLs of: 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4;

or (7) the VL and the VH of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4, with the exception of 1, 2, 3, 4, or 5 reversion or conservative substitutions in the VH and/or VL;

and the antibody further comprises one or more of the following characteristics:

- specific binding to hILT4, e.g., with a $K_D$ of $10^{-8}$ M, $10^{-9}$ M or less;
- lack of specific binding to hILT2, hILT3, hILT5;
- lack of specific binding to one or more members of the LILRA and/or LILRB families;
- stimulates T cell activation, e.g., in an MLR, as measured by increased T cell proliferation or IFN-g secretion, e.g., as shown in an assay described in the Examples;
- stimulates differentiation or activation of monocytes into macrophages, e.g., stimulates differentiation of monocytes into pro-inflammatory macrophages, e.g., as shown in an assay described in the Examples;
- promotes expression of CD83 and CD86 on human monocyte derived immature dendritic cells (Mo-iDC), e.g., as shown in an assay described in the Examples;
- enhances IFN-γ secretion upon antigen stimulation in a CMV lysate assay, e.g., as shown in an assay described in the Examples;
- enhances IFN-γ and TNF-α secretion by CD4+ and CD8+ T cells in an allo-mixed lymphocyte reaction (allo-MLR) assay upon CD3 stimulation, e.g., as shown in an assay described in the Examples;
- does not induce (or trigger) basophil activation;
- inhibits binding of HLA-A and/or HLA-B to ILT4;
- has a binding profile to hILT4 as shown in FIG. 27 or FIG. 37C;
- binds to Ig-like domains 1, 2 or 1 and 2 of hILT4 (which correspond to amino acids 27-110 and 111-229 of SEQ ID NO: 107, respectively), such as to a region comprising (i) $^{70}$ITRIRPEL$^{77}$ (SEQ ID NO: 120) and/or $^{78}$VKNGQFHIPSITWEHTGRYGCQY$^{100}$ (SEQ ID NO: 121); (ii) $^{70}$ITRIRPELVKNGQFHIPSITWEHTGRYGCQY$^{100}$ (SEQ ID NO: 122); or (iii) $^{154}$ILCKEGEEEHPQCLNSQPHARGSSRAIF$^{181}$ (SEQ ID NO: 123) and/or $^{425}$SSPPPTGPIS$^{434}$ (SEQ ID NO: 124), as determined by hydrogen deuterium exchange (HDX), e.g., as shown in an HDX assay described in the Examples;
- does not bind significantly to other regions of the extracellular domain of ILT4, such as regions or residues that located N-terminal to amino acid 170; wherein the amino acid numbering of hILT4 is that of immature hILT4 (i.e., ILT4 with its signal sequence);
- competes for binding to hILT4 with an antibody described herein;
- binds specifically to cyno ILT4 comprising SEQ ID NO: 118, e.g., as shown in a binding assay described in the Examples;
- promotes pro-inflammatory polarization of macrophages towards M1 macrophages;
- does not induce (or trigger) basophil activation; and
- comprises less than 5% of high and low molecular weight species after 3 months incubation at 25° C. and/or less than 10% of high and low molecular weight species after 3 months incubation at 40° C.

In certain embodiments, an ILT4 Ab comprises a heavy chain (HC) comprising the amino acid sequence of the heavy chain of any of the ILT4 Abs provided herein. In certain embodiments, an ILT4 Ab comprises a heavy chain comprising the amino acid sequence of the heavy chain of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4, as shown below in the Sequence Table (i.e., a complete HC sequence as provided in the Table, or a composite of a VH sequence for the antibody with an HC constant region sequence such as SEQ ID NO: 98, 100, 102, 103, 104, or 179, as provided in the Table).

Thus, for example, in some embodiments, the antibody may comprise a HC amino acid sequence of one of the types below, comprising an amino acid sequence as follows:

a. IgG1, e.g. 9G4.IgG1, 9G4 (SEQ ID NO: 2), 9C8 (SEQ ID NO: 4), 2H2 (SEQ ID NO: 6), 2E5 (SEQ ID NO: 8), 24E5 (SEQ ID NO: 10), 21D9 (SEQ ID NO: 12), 21D9.b (SEQ ID NO: 74 and SEQ ID NO: 98), 21D9.c (SEQ ID NO: 75 and SEQ ID NO: 98), 21D9.d (SEQ ID NO: 78 and SEQ ID NO: 98), 21D9.e (SEQ ID NO: 80 and SEQ ID NO: 98), 21A5 (SEQ ID NO: 83 and SEQ ID NO: 98), 21A5.a (SEQ ID NO: 87 and SEQ ID NO: 98), 10F10 (SEQ ID NO: 91 and SEQ ID NO: 98), 10F10.1 (SEQ ID NO: 91 and SEQ ID NO: 98), 10F10.3 (SEQ ID NO: 91 and SEQ ID NO: 98), or 10F10.4 (SEQ ID NO: 91 and SEQ ID NO: 98),
b. IgG1, e.g. 9G4.IgG1, 9G4 (SEQ ID NO: 51, amino acids 20-135, and SEQ ID NO: 102), 9C8 (SEQ ID NO: 55 and SEQ ID NO: 102), 2H2 (SEQ ID NO: 58 and SEQ ID NO: 102), 2E5 (SEQ ID NO: 63 and SEQ ID NO: 102), 24E5 (SEQ ID NO: 67 and SEQ ID NO: 102), 21D9 (SEQ ID NO: 71 and SEQ ID NO: 102), 21D9.b (SEQ ID NO: 74 and SEQ ID NO: 102), 21D9.c (SEQ ID NO: 75 and SEQ ID NO: 102), 21D9.d (SEQ ID NO: 78 and SEQ ID NO: 102), 21D9.e (SEQ ID NO: 80 and SEQ ID NO: 102), 21A5 (SEQ ID NO: 83 and SEQ ID NO: 102), 21A5.a (SEQ ID NO: 87 and SEQ ID NO: 102), 10F10 (SEQ ID NO: 91 and SEQ ID NO: 102), 10F10.1 (SEQ ID NO: 91 and SEQ ID NO: 102), 10F10.3 (SEQ ID NO: 91 and SEQ ID NO: 102), or 10F10.4 (SEQ ID NO: 91 and SEQ ID NO: 102),
c. IgG1.3 (e.g. 9G4.IgG1.3, etc.), 9G4 (SEQ ID NO: 51, amino acids 20-135, and SEQ ID NO: 100), 9C8 (SEQ ID NO: 55 and SEQ ID NO: 100), 2H2 (SEQ ID NO: 58 and SEQ ID NO: 100), 2E5 (SEQ ID NO: 63 and SEQ ID NO: 100), 24E5 (SEQ ID NO: 67 and SEQ ID NO: 100), 21D9 ((i) SEQ ID NO: 113, or (ii) SEQ ID NO: 71 and SEQ ID NO: 100), 21D9.b (SEQ ID NO: 36), 21D9.c (SEQ ID NO: 38), 21D9.d (SEQ ID NO: 40), 21D9.e (SEQ ID NO: 13), 21A5 (SEQ ID NO: 15), 21A5.a (SEQ ID NO: 17), 10F10 (SEQ ID NO: 19), 10F10.1 (SEQ ID NO: 91 and SEQ ID NO: 100), 10F10.3 (SEQ ID NO: 91 and SEQ ID NO: 100), or 10F10.4 (SEQ ID NO: 91 and SEQ ID NO: 100);
d. IgG1.1f (e.g. 9G4.IgG1.1f, etc.), 9G4 (SEQ ID NO: 51, amino acids 20-135, and SEQ ID NO: 103), 9C8 (SEQ ID NO: 55 and SEQ ID NO: 103), 2H2 (SEQ ID NO: 58 and SEQ ID NO: 103), 2E5 (SEQ ID NO: 63 and SEQ ID NO: 103), 24E5 (SEQ ID NO: 67 and SEQ ID NO: 103), 21D9 (SEQ ID NO: 71 and SEQ ID NO: 103), 21D9.b (SEQ ID NO: 74 and SEQ ID NO: 103), 21D9.c (SEQ ID NO: 75 and SEQ ID NO: 103), 21D9.d (SEQ ID NO: 78 and SEQ ID NO: 103), 21D9.e (SEQ ID NO: 80 and SEQ ID NO: 103), 21A5 (SEQ ID NO: 83 and SEQ ID NO: 103), 21A5.a (SEQ ID NO: 87 and SEQ ID NO: 103), 10F10 (SEQ ID NO: 91 and SEQ ID NO: 103), 10F10.1 (SEQ ID NO: 91 and SEQ ID NO: 103), 10F10.3 (SEQ ID NO: 91 and SEQ ID NO: 103), or 10F10.4 (SEQ ID NO: 91 and SEQ ID NO: 103),
e. IgG1fa.P238K (e.g., 9G4.IgG1fa.P238K, etc.) 9G4 (SEQ ID NO: 51, amino acids 20-135, and SEQ ID NO: 104), 9C8 (SEQ ID NO: 55 and SEQ ID NO: 104), 2H2 (SEQ ID NO: 58 and SEQ ID NO: 104), 2E5 (SEQ ID NO: 63 and SEQ ID NO: 104), 24E5 (SEQ ID NO: 67 and SEQ ID NO: 104), 21D9 (SEQ ID NO: 71 and SEQ ID NO: 104), 21D9.b (SEQ ID NO: 74 and SEQ ID NO: 104), 21D9.c (SEQ ID NO: 75 and SEQ ID NO: 104), 21D9.d (SEQ ID NO: 78 and SEQ ID NO: 104), 21D9.e (SEQ ID NO: 80 and SEQ ID NO: 104), 21A5 (SEQ ID NO: 83 and SEQ ID NO: 104), 21A5.a (SEQ ID NO: 87 and SEQ ID NO: 104), 10F10 (SEQ ID NO: 91 and SEQ ID NO: 104), 10F10.1 (SEQ ID NO: 91 and SEQ ID NO: 104), 10F10.3 (SEQ ID NO: 91 and SEQ ID NO: 104), or 10F10.4 (SEQ ID NO: 91 and SEQ ID NO: 104), or
f. IgG4 S228P (e.g. 9G4.IgG4 S228P, etc.), 9G4 (SEQ ID NO: 51, amino acids 20-135, and SEQ ID NO: 179), 9C8 (SEQ ID NO: 55 and SEQ ID NO: 179), 2H2 (SEQ ID NO: 58 and SEQ ID NO: 179), 2E5 (SEQ ID NO: 63 and SEQ ID NO: 179), 24E5 (SEQ ID NO: 67 and SEQ ID NO: 179), 21D9 (SEQ ID NO: 71 and SEQ ID NO: 179), 21D9.b (SEQ ID NO: 74 and SEQ ID NO: 179), 21D9.c (SEQ ID NO: 75 and SEQ ID NO: 179), 21D9.d (SEQ ID NO: 78 and SEQ ID NO: 179), 21D9.e (SEQ ID NO: 80 and SEQ ID NO: 179), 21A5 (SEQ ID NO: 83 and SEQ ID NO: 179), 21A5.a (SEQ ID NO: 87 and SEQ ID NO: 179), 10F10 (SEQ ID NO: 91 and SEQ ID NO: 179), 10F10.1 (SEQ ID NO: 91 and SEQ ID NO: 179), 10F10.3 (SEQ ID NO: 91 and SEQ ID NO: 179), or 10F10.4 (SEQ ID NO: 91 and SEQ ID NO: 179).

In certain embodiments, an ILT4 Ab comprises a heavy chain comprising the amino acid sequence of the heavy chain of any of the ILT4 Abs provided herein, which comprise an IgG1.3 heavy chain constant region, and the amino acid sequence of the light chain of any of the ILT4 Abs provided herein. In certain embodiments, an ILT4 Ab comprises a heavy chain comprising the amino acid sequence of the VH any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4, which comprise an IgG1.3 HC constant region (which is denoted by the nomenclature 9G4.IgG1.3, etc.); and a light chain comprising the amino acid sequence of the light chain of any one of 9G4, 9C8, 2H2, 25E5, 24E5, 21D9, 21D9.b, 21D9.c, 21D9.d, 21D9.e, 21A5, 21A5.a, 10F10, 10F10.1, 10F10.3, or 10F10.4. In some embodiments, the light chain is a Kappa light chain comprising an amino acid sequence as follows: 9G4 (SEQ ID NO: 1), 9C8 (SEQ ID NO: 3), 2H2 (SEQ ID NO: 5), 2E5 (SEQ ID NO: 7), 24E5 (SEQ ID NO: 9), 21D9 (SEQ ID NO: 11), 21D9.b, 21D9.c, 21D9.d, 21D9.e, 21A5 (SEQ ID NO: 14), 21A5.a (SEQ ID NO: 16), 10F10 (SEQ ID NO: 18), 10F10.1 (SEQ ID NO: 20), 10F10.3 (SEQ ID NO: 21), or 10F10.4 (SEQ ID NO: 116).

An ILT4 Ab may comprise:

(a) a heavy chain comprising the amino acid sequence of the heavy chain of 9G4 and a light chain comprising the light chain amino acid sequence of 9G4;
(b) a heavy chain comprising the amino acid sequence of the heavy chain of 9C8 and a light chain comprising the light chain amino acid sequence of 9C8;
(c) a heavy chain comprising the amino acid sequence of the heavy chain of 2H2 and a light chain comprising the light chain amino acid sequence of 2H2;
(d) a heavy chain comprising the amino acid sequence of the heavy chain of 25E5 and a light chain comprising the light chain amino acid sequence of 25E5;
(e) a heavy chain comprising the amino acid sequence of the heavy chain of 24E5 and a light chain comprising the light chain amino acid sequence of 24E5;
(f) a heavy chain comprising the amino acid sequence of the heavy chain of 9G4 and a light chain comprising the light chain amino acid sequence of 21D9;

(g) a heavy chain comprising the amino acid sequence of the heavy chain of 21D9.b and a light chain comprising the light chain amino acid sequence of 21D9.b;

(h) a heavy chain comprising the amino acid sequence of the heavy chain of 21D9.c and a light chain comprising the light chain amino acid sequence of 21D9.c;

(i) a heavy chain comprising the amino acid sequence of the heavy chain of 21D9.d and a light chain comprising the light chain amino acid sequence of 21D9.d;

(j) a heavy chain comprising the amino acid sequence of the heavy chain of 21D9.e and a light chain comprising the light chain amino acid sequence of 21D9.e;

(k) a heavy chain comprising the amino acid sequence of the heavy chain of 21A5 and a light chain comprising the light chain amino acid sequence of 21A5;

(l) a heavy chain comprising the amino acid sequence of the heavy chain of 21A5.a and a light chain comprising the light chain amino acid sequence of 21A5.a;

(m) a heavy chain comprising the amino acid sequence of the heavy chain of 10F10 and a light chain comprising the light chain amino acid sequence of 10F10;

(n) a heavy chain comprising the amino acid sequence of the heavy chain of 10F10.1 and a light chain comprising the light chain amino acid sequence of 10F10.1;

(o) a heavy chain comprising the amino acid sequence of the heavy chain of 10F10.3 and a light chain comprising the light chain amino acid sequence of 10F10.3; or (p) a heavy chain comprising the amino acid sequence of the heavy chain of 10F10.4 and a light chain comprising the light chain amino acid sequence of 10F10.4.

An ILT4 Ab may comprise:

(a) a heavy chain (HC) comprising the HC CDRs of the HC of 9G4 and a light chain (LC) comprising the LC CDRs of 9G4 and HC and LC amino acid sequences that are at least 90%, at least 91%, at least 92%, at least 93%, at least 94%, at least 95%, at least 96%, at least 97%, at least 98%, or at least 99% identical to the HC and LC of 9G4, respectively;

(b) a HC comprising the HC CDRs of the HC of 9C8, and a light chain (LC) comprising the LC CDRs of 9C8 and HC and LC amino acid sequences that are at least 90%, at least 91%, at least 92%, at least 93%, at least 94%, at least 95%, at least 96%, at least 97%, at least 98%, or at least 99% identical to the HC and LC of 9C8, respectively;

(c) a HC comprising the HC CDRs of the HC of 2H2, and a light chain (LC) comprising the LC CDRs of 2H2 and HC and LC amino acid sequences that are at least 90%, at least 91%, at least 92%, at least 93%, at least 94%, at least 95%, at least 96%, at least 97%, at least 98%, or at least 99% identical to the HC and LC of 2H2, respectively;

(d) a HC comprising the HC CDRs of the HC of 25E5, and a light chain (LC) comprising the LC CDRs of 25E5 and HC and LC amino acid sequences that are at least 90%, at least 91%, at least 92%, at least 93%, at least 94%, at least 95%, at least 96%, at least 97%, at least 98%, or at least 99% identical to the HC and LC of 25E5, respectively;

(e) a HC comprising the HC CDRs of the HC of 24E5, and a light chain (LC) comprising the LC CDRs of 24E5 and HC and LC amino acid sequences that are at least 90%, at least 91%, at least 92%, at least 93%, at least 94%, at least 95%, at least 96%, at least 97%, at least 98%, or at least 99% identical to the HC and LC of 24E5, respectively;

(f) a HC comprising the HC CDRs of the HC of 21D9, and a light chain (LC) comprising the LC CDRs of 21D9 and HC and LC amino acid sequences that are at least 90%, at least 91%, at least 92%, at least 93%, at least 94%, at least 95%, at least 96%, at least 97%, at least 98%, or at least 99% identical to the HC and LC of 21D9, respectively;

(g) a HC comprising the HC CDRs of the HC of 21D9.b, and a light chain (LC) comprising the LC CDRs of 21D9.b and HC and LC amino acid sequences that are at least 90%, at least 91%, at least 92%, at least 93%, at least 94%, at least 95%, at least 96%, at least 97%, at least 98%, or at least 99% identical to the HC and LC of 21D9.b, respectively;

(h) a HC comprising the HC CDRs of the HC of 21D9.c, and a light chain (LC) comprising the LC CDRs of 21D9.c and HC and LC amino acid sequences that are at least 90%, at least 91%, at least 92%, at least 93%, at least 94%, at least 95%, at least 96%, at least 97%, at least 98%, or at least 99% identical to the HC and LC of 21D9.c, respectively;

(i) a HC comprising the HC CDRs of the HC of 21D9.d, and a light chain (LC) comprising the LC CDRs of 21D9.d and HC and LC amino acid sequences that are at least 90%, at least 91%, at least 92%, at least 93%, at least 94%, at least 95%, at least 96%, at least 97%, at least 98%, or at least 99% identical to the HC and LC of 21D9.d, respectively;

(j) a HC comprising the HC CDRs of the HC of 21D9.e, and a light chain (LC) comprising the LC CDRs of 21D9.e and HC and LC amino acid sequences that are at least 90%, at least 91%, at least 92%, at least 93%, at least 94%, at least 95%, at least 96%, at least 97%, at least 98%, or at least 99% identical to the HC and LC of 21D9.e, respectively;

(k) a HC comprising the HC CDRs of the HC of 21A5, and a light chain (LC) comprising the LC CDRs of 21A5 and HC and LC amino acid sequences that are at least 90%, at least 91%, at least 92%, at least 93%, at least 94%, at least 95%, at least 96%, at least 97%, at least 98%, or at least 99% identical to the HC and LC of 21A5, respectively;

(l) a HC comprising the HC CDRs of the HC of 21A5.a, and a light chain (LC) comprising the LC CDRs of 21A5.a and HC and LC amino acid sequences that are at least 90%, at least 91%, at least 92%, at least 93%, at least 94%, at least 95%, at least 96%, at least 97%, at least 98%, or at least 99% identical to the HC and LC of 21A5.a, respectively;

(m) a HC comprising the HC CDRs of the HC of 10F10, and a light chain (LC) comprising the LC CDRs of 10F10 and HC and LC amino acid sequences that are at least 90%, at least 91%, at least 92%, at least 93%, at least 94%, at least 95%, at least 96%, at least 97%, at least 98%, or at least 99% identical to the HC and LC of 10F10, respectively;

(n) a HC comprising the HC CDRs of the HC of 10F10.1, and a light chain (LC) comprising the LC CDRs of 10F10.1 and HC and LC amino acid sequences that are at least 90%, at least 91%, at least 92%, at least 93%, at least 94%, at least 95%, at least 96%, at least 97%, at least 98%, or at least 99% identical to the HC and LC of 10F10.1, respectively;

(o) a HC comprising the HC CDRs of the HC of 10F10.3, and a light chain (LC) comprising the LC CDRs of 10F10.3 and HC and LC amino acid sequences that are at least 90%, at least 91%, at least 92%, at least 93%, at least 94%, at least 95%, at least 96%, at least 97%, at least 98%, or at least 99% identical to the HC and LC of 10F10.3, respectively; or (p) a HC comprising the HC CDRs of the HC of 10F10.3, and a light chain (LC) comprising the LC CDRs of 10F10.4 and HC and LC amino acid sequences that are at least 90%, at least 91%, at least 92%, at least 93%, at least 94%, at least 95%, at least 96%, at least 97%, at least 98%, or at least 99% identical to the HC and LC of 10F10.4, respectively.

In some of the above embodiments, the HC and/or LC may differ from the sequence of each of the species (a) to (p) by the presence of 1, 2, 3, 4, or 5 amino acid substitutions, such as 1, 2, 3, 4, or 5 conservative substitutions. In some of the above embodiments, the HC and/or LC may differ from the sequence of each of the species (a) to (p) by the presence of 1, 2, 3, 4, or 5 amino acid substitutions, such as 1, 2, 3, 4, or 5 reversion substitutions.

In some embodiments, an ILT4 Ab may comprise:

(a) a heavy chain consisting of the amino acid sequence of the heavy chain of 9G4 and a light chain consisting of the amino acid sequence of the light chain of 9G4;

(b) a heavy chain consisting of the amino acid sequence of the heavy chain of 9C8 and a light chain consisting of the amino acid sequence of the light chain of 9C8;

(c) a heavy chain consisting of the amino acid sequence of the heavy chain of 2H2 and a light chain consisting of the amino acid sequence of the light chain of 2H2;

(d) a heavy chain consisting of the amino acid sequence of the heavy chain of 25E5 and a light chain consisting of the amino acid sequence of the light chain of 25E5;

(e) a heavy chain consisting of the amino acid sequence of the heavy chain of 24E5 and a light chain consisting of the amino acid sequence of the light chain of 24E5;

(f) a heavy chain consisting of the amino acid sequence of the heavy chain of 21D9 and a light chain consisting of the amino acid sequence of the light chain of 21D9;

(g) a heavy chain consisting of the amino acid sequence of the heavy chain of 21D9.b and a light chain consisting of the amino acid sequence of the light chain of 21D9.b;

(h) a heavy chain consisting of the amino acid sequence of the heavy chain of 21D9.c and a light chain consisting of the amino acid sequence of the light chain of 21D9.c;

(i) a heavy chain consisting of the amino acid sequence of the heavy chain of 21D9.d and a light chain consisting of the amino acid sequence of the light chain of 21D9.d;

(j) a heavy chain consisting of the amino acid sequence of the heavy chain of 21D9.e and a light chain consisting of the amino acid sequence of the light chain of 21D9.e;

(k) a heavy chain consisting of the amino acid sequence of the heavy chain of 21A5 and a light chain consisting of the amino acid sequence of the light chain of 21A5;

(l) a heavy chain consisting of the amino acid sequence of the heavy chain of 21A5.a and a light chain consisting of the amino acid sequence of the light chain of 21A5.a;

(m) a heavy chain consisting of the amino acid sequence of the heavy chain of 10F10 and a light chain consisting of the amino acid sequence of the light chain of 10F10;

(n) a heavy chain consisting of the amino acid sequence of the heavy chain of 10F10.1 and a light chain consisting of the amino acid sequence of the light chain of 10F10.1;

(o) a heavy chain consisting of the amino acid sequence of the heavy chain of 10F10.3 and a light chain consisting of the amino acid sequence of the light chain of 10F10.3; or (p) a heavy chain consisting of the amino acid sequence of the heavy chain of 10F10.4 and a light chain consisting of the amino acid sequence of the light chain of 10F10.4.

In some embodiments, an ILT4 Ab may comprise a heavy chain amino acid sequence comprising the VH amino acid sequence of the antibody species herein, but rather than an IgG1.3 heavy chain constant region, as provided in the HC sequences in the Sequence Table herein (and see SEQ ID NO: 100), the antibody may comprise a different heavy chain constant region sequence, such as a human wild-type IgG1 constant region such as those provided in SEQ ID Nos: 98 and 102-104, or an IgG4 heavy chain constant region, or an IgG4 constant region with an S228P substitution (EU numbering), or any of the other heavy chain constant regions described in the section on constant regions that follows below.

In some embodiments, such modified ILT4 Abs possess one or more of the following characteristics:

specific binding to hILT4, e.g., with a $K_D$ of $10^{-8}$ M or less, or of $10^{-9}$ M or less;

lack of specific binding to one, two, or all three of hILT2, hILT3, hILT5;

lack of specific binding to one or more members of the LILRA and/or LILRB families;

stimulates T cell activation, e.g., in an MLR assay, as measured by increased T cell proliferation or IFN-gamma secretion; and stimulates differentiation or activation of monocytes into macrophages.

In some embodiments, the antibody binds to Ig-like domains 1, 2 or 1 and 2 of hILT4, which correspond to amino acids 27-110 on the sequence of SEQ ID NO: 107 (domain 1) and 111-229 on that sequence (domain 2), at the locations comprising $^{70}$ITRIRPEL$^{77}$ (SEQ ID NO: 120) and/or $^{78}$VKNGQFHIPSITWEHTGRYGCQY$^{100}$ (SEQ ID NO: 121); (ii) $^{70}$ITRIRPELVKNGQFHIPSITWEHTGRYGCQY$^{100}$ (SEQ ID NO: 122); or (iii) $^{154}$ILCKEGEEEHPQCLNSQPHARGSSRAIF$^{181}$(SEQ ID NO: 123) and/or $^{425}$SSPPPTGPIS$^{434}$ (SEQ ID NO: 124), as determined by hydrogen deuterium exchange (HDX), e.g., as shown in an HDX assay described in the Examples. (See FIG. 27.)

Exemplary Antibody Constant Regions

In some embodiments, an antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, an antibody described herein comprises a human IgG constant region, such as an IgG1, IgG2, IgG3, or IgG4. In some embodiments, an antibody described herein comprises a human IgG4 heavy chain constant region. In some such embodiments, an antibody described herein comprises an S241P mutation in the human IgG4 constant region. In some embodiments, an antibody described herein comprises a human IgG4 constant region and a human κ light chain.

The choice of heavy chain constant region can determine whether or not an antibody will have effector function in vivo. Such effector function, in some embodiments, includes antibody-dependent cell-mediated cytotoxicity (ADCC) and/or complement-dependent cytotoxicity (CDC), and can result in killing of the cell to which the antibody is bound.

In some methods of treatment, including methods of treating some cancers, cell killing may be desirable, for example, when the antibody binds to a cell that supports the maintenance or growth of the tumor. Exemplary cells that may support the maintenance or growth of a tumor include, but are not limited to, tumor cells themselves, cells that aid in the recruitment of vasculature to the tumor, and cells that provide ligands, growth factors, or counter-receptors that support or promote tumor growth or tumor survival. In some embodiments, when effector function is desirable, an antibody comprising a human IgG1 heavy chain or a human IgG3 heavy chain is selected.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibodies with certain improved properties. For example, in some embodiments an antibody may be afucosylated, for example, by mutating residues such as Asn297 that are normally glycosylated with fucose-containing glycosylations, or through other means. In some embodiments, antibodies herein may comprise an afucosylated human IgG1 constant region.

Antibodies are further provided with bisected oligosaccharides, e.g., in which a biantennary oligosaccharide attached to the Fc region of the antibody is bisected by GlcNAc. Such antibodies may have reduced fucosylation and/or improved ADCC function. Examples of such antibodies are described, e.g., in WO 2003/011878 (Jean-Mairet et al.); U.S. Pat. No. 6,602,684 (Umana et al.); and US 2005/0123546 (Umana et al.). Antibodies with at least one galactose residue in the oligosaccharide attached to the Fc region are also provided. Such antibodies may have improved CDC function. Such antibodies are described, e.g., in WO 1997/30087 (Patel et al.); WO 1998/58964 (Raju, S.); and WO 1999/22764 (Raju, S.).

Antibodies are also provided with amino-terminal leader extensions. For example, one or more amino acid residues of the amino-terminal leader sequence are present at the amino-terminus of any one or more heavy or light chains of an antibody. An exemplary amino-terminal leader extension comprises or consists of three amino acid residues, VHS, present on one or both light chains of an antibody.

The in vivo or serum half-life of human FcRn high affinity binding polypeptides can be assayed, e.g., in transgenic mice, in humans, or in non-human primates to which the polypeptides with a variant Fc region are administered. See also, e.g., Petkova et al. *International Immunology* 18(12): 1759-1769 (2006).

In some embodiments of the invention, an afucosylated antibody mediates ADCC in the presence of human effector cells more effectively than a parent antibody that comprises fucose, Generally, ADCC activity may be determined using the in vitro ADCC assay as herein disclosed, but other assays or methods for determining ADCC activity, e.g. in an animal model etc., are contemplated.

In certain embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320, 322, 330, and/or 331 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In some examples, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In some examples, one or more amino acid residues within amino acid positions 231 and 239 are altered to thereby alter the ability of the antibody to fix complement. This approach is described further in PCT Publication WO 94/29351 by Bodmer et al. In some examples, the Fc region can be modified to decrease antibody dependent cellular cytotoxicity (ADCC) and/or to decrease the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F/324T. Other Fc modifications that can be made to Fcs are those for reducing or ablating binding to FcγR and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, 328, 330, and/or 331 (e.g., 330 and 331), wherein numbering is according to the EU index. Exemplary substitutions include but are not limited to 234A, 235E, 236R, 237A, 267R, 269R, 325L, 328R, 330S, and 331S (e.g., 330S, and 331S), wherein numbering is according to the EU index. An Fc variant can comprise 236R/328R. Other modifications for reducing FcγR and complement interactions include substitutions 297A, 234A, 235A, 237A, 318A, 228P, 236E, 268Q, 309L, 330S, 331 S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, *Current Opinion in Biotechnology* 20:685-691. For example, the human IgG1.3 Fc constant region contains L234A, L235E, and G237A substitutions. The IgG1fa.P238K (or IgG1.P238K) contains a P238K substitution. The IgG1.1f comprises L234A, L235E, G237A, A330S, and P331S substitutions.

Fc variants that enhance affinity for an inhibitory receptor FcγRIIb can also be used. Such variants can provide an Fc fusion protein with immunomodulatory activities related to FcγRIIb cells, including for example B cells and monocytes. In one embodiment, the Fc variants provide selectively enhanced affinity to FcγRIIb relative to one or more activating receptors. Modifications for altering binding to FcγRIIb include one or more modifications at a position selected from the group consisting of 234, 235, 236, 237, 239, 266, 267, 268, 325, 326, 327, 328, 330, 331, and 332, according to the EU index. Exemplary substitutions for enhancing FcγRIIb affinity include but are not limited to 234A, 234D, 234E, 234F, 234W, 235D, 235E, 235F, 235R, 235Y, 236D, 236N, 237A, 237D, 237N, 239D, 239E, 266M, 267D, 267E, 268D, 268E, 327D, 327E, 328F, 328W, 328Y, 330S, 331S, and 332E. Exemplary substitutions include 235Y, 236D, 239D, 266M, 267E, 268D, 268E, 328F, 328W, and 328Y. Other Fc variants for enhancing binding to FcγRIIb include 235Y/267E, 236D/267E, 239D/268D, 239D/267E, 267E/268D, 267E/268E, and 267E/328F.

Other modifications for enhancing FcγR and complement interactions include but are not limited to substitutions 298 A, 333A, 334A, 326A, 2471, 339D, 339Q, 280H, 290S, 298D, 298V, 243L, 292P, 300L, 396L, 3051, and 396L. These and other modifications are reviewed in Strohl, 2009, Current Opinion in Biotechnology 20:685-691. Fc modifications that increase binding to an Fcγ receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 338, 340, 360, 373, 376, 379, 382, 388, 389, 398, 414, 416, 419, 430, 434, 435, 437, 438 or 439 of the Fc region, wherein the numbering of the residues in the Fc region is that of the EU index as in Patent Publication No. WO 00/42072.

Optionally, the Fc region can comprise a non-naturally occurring amino acid residue at additional and/or alternative positions known to one skilled in the art (see, e.g., U.S. Pat. Nos. 5,624,821; 6,277,375; 6,737,056; 6,194,551; 7,317,091; 8,101,720; PCX Patent Publications WO 00/42072; WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114).

The affinities and binding properties of an Fc region for its ligand can be determined by a variety of in vitro assay methods (biochemical or immunological based assays) known in the art including but not limited to, equilibrium methods (e.g., enzyme-linked immunoabsorbent assay (ELISA), or radioimmunoassay (RIA)), or kinetics (e.g., BIACORE analysis), and other methods such as indirect binding assays, competitive inhibition assays, fluorescence resonance energy transfer (FRET), gel electrophoresis and chromatography (e.g., gel filtration). These and other methods can utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental immunology, 4th Ed., Lippincott-Raven, Philadelphia (1999), which focuses on antibody-immunogen interactions.

In certain embodiments, the antibody is modified to increase its biological half-life. Various approaches are possible. For example, this can be done by increasing the binding affinity of the Fc region for FcRn, For example, one or more of more of following residues can be mutated: 252, 254, 256, 433, 435, 436, as described in U.S. Pat. No. 6,277,375. Specific exemplary substitutions include one or more of the following: T252L, T254S, and/or T256F. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary variants that increase binding to FcRn and/or improve pharmacokinetic properties include substitutions at positions 259, 308, 428, and 434, including for example 2591, 308F, 428L, 428M, 434S, 4341 1. 434F, 434Y, and 434X1. Other variants that increase Fc binding to FcRn include: 250E, 250Q, 428 L, 428F, 250Q/428L (Hinton et al. 2004, *J. Biol. Chem.* 279(8): 6213-6216, Hinton et al. 2006 *Journal of Immunology* 176:346-356), 256A, 272A, 286A, 305A, 307A, 307Q, 31 1A, 312A, 376A, 378Q, 380A, 382A, 434A (Shields et al., *Journal of Biological Chemistry,* 2001, 276(9):6591-6604), 252F, 252T, 252Y, 252W, 254T, 256S, 256R, 256Q, 256E, 256D, 256T, 309P, 31 1 S, 433R, 433S, 4331, 433P, 433Q, 434H, 434F, 434Y, 252Y/254T/256E, 433K/434F/436H, 308T/309P/311S (Dall Acqua et al. *Journal of Immunology,* 2002, 169:5171-5180, Dall'Acqua et al., 2006, *Journal of Biological Chemistry* 281:23514-23524). Other modifications for modulating FcRn binding are described in Yeung et al., 2010, *J Immunol,* 182:7663-7671.

In certain embodiments, hybrid IgG isotypes with particular biological characteristics can be used. For example, an IgG1/IgG3 hybrid variant can be constructed by substituting IgG1 positions in the CH2 and/or CH3 region with the amino acids from IgG3 at positions where the two isotypes differ. Thus a hybrid variant IgG antibody can be constructed that comprises one or more substitutions, e.g., 274Q, 276K, 300F, 339T, 356E, 358M, 384S, 392N, 397M, 4221, 435R, and 436F. In some embodiments described herein, an IgG1/IgG2 hybrid variant can be constructed by substituting IgG2 positions in the CH2 and/or CH3 region with amino acids from IgG1 at positions where the two isotypes differ. Thus a hybrid variant IgG antibody can be constructed that comprises one or more substitutions, e.g., one or more of the following amino acid substitutions: 233E, 234L, 235L, −236G (referring to an insertion of a glycine at position 236), and 327A.

Moreover, the binding sites on human IgG1 for FcγRI, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A, which has been shown to exhibit enhanced FcγRIIIa binding and ADCC activity (Shields et al., 2001). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys (Lazar et al., 2006). Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys (Lazar et al., 2006). In addition, IgG1 mutants containing L235V, F243L, R292P, Y300L and P396L mutations which exhibited enhanced binding to FcγRIIIa and concomitantly enhanced ADCC activity in transgenic mice expressing human FcγRIIIa in models of B cell malignancies and breast cancer have been identified (Stavenhagen et al., 2007; Nordstrom et al., 2011). Other Fc mutants that can be used include: S298A/E333A/L334A, S239D/I332E, S239D/I332E/A330L, L235V/F243L/R292P/Y300L/P396L, and M428L/N434S.

In certain embodiments, an Fc is chosen that has reduced binding to FcγRs. An exemplary Fc, e.g., IgG1 Fc, with reduced FcγR binding comprises the following three amino acid substitutions: L234A, L235E and G237A.

In certain embodiments, an Fc is chosen that has reduced complement fixation. An exemplary Fc, e.g., IgG1 Fc, with reduced complement fixation has the following two amino acid substitutions: A330S and P331S.

In certain embodiments, an Fc is chosen that has essentially no effector function, i.e., it has reduced binding to FcγRs and reduced complement fixation. An exemplary Fc, e.g., IgG1 Fc, that is effectorless comprises the following five mutations: L234A, L235E, G237A, A330S and P331S.

When using an IgG4 constant domain, it can include the substitution S228P, which mimics the hinge sequence in IgG1 and thereby stabilizes IgG4 molecules.

Fc modifications described in WO 2017/087678 or WO2016081746 may also be used.

In certain embodiments, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation can increase the affinity of the antibody for antigen. Such an approach is described in further detail in U.S. Pat. Nos. 5,714,350 and 6,350,861 by Co et al.

Glycosylation of the constant region on N297 can be prevented by mutating the N297 residue to another residue, e.g., N297A, and/or by mutating an adjacent amino acid, e.g., 298 to thereby reduce glycosylation on N297.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies described herein to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Led 3 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases {e.g., beta(1, 4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17: 176-180).

Another modification of the antibodies described herein is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. In some embodiments, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-CIO) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. See for example, EP 0 154 316 by Nishimura et al. and EP 0 401 384 by Ishikawa et al.

Specific exemplary antibody embodiments herein are further listed in the following sections.

Embodiments Relating to Antibody 21D9.e:

Embodiment 1

An isolated antibody ("Ab") that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70.

Embodiment 2

An isolated antibody that binds to human ILT4, wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein the antibody stimulates T cell activation (or potentiates a T cell response), e.g., (i) in a mixed lymphocyte reaction (MLR) assay, as evidenced, e.g., by enhanced T cell proliferation or IFN-gamma secretion or TNF-alpha production, or (ii) in a T cell: CHO-OKT3-ILT4 assay (e.g., as described in Example 5).

Embodiment 3

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein the Ab enhances T cell activation in a monocyte: T cell allo-MLR.

Embodiment 4

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein the Ab enhances IFN-gamma secretion from PBMCs upon antigen stimulation in a cytomegalovirus (CMV) lysate assay.

Embodiment 5

An isolated antibody that binds to human ILT4, wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein the antibody potentiates TNF-alpha secretion from macrophages, e.g., differentiated macrophages.

Embodiment 6

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein the antibody increases expression of CD83 and/or CD86 on monocyte-derived dendritic cells (MoDCs).

Embodiment 7

An isolated antibody that binds to human ILT4, wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein the antibody inhibits binding of hILT4 to a T cell and/or to a binding partner, e.g., HLA-A and/or HLA-B.

Embodiment 8

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein the Ab (a) binds to the Ig-like domain 1 of hILT4 and/or the region of hILT4 comprising $^{70}$ITRIRPEL$^{77}$ (SEQ ID NO: 120) and/or $^{78}$VKNGQFHIPSITWEHTGRYGCQY$^{100}$ (SEQ ID NO: 121) and/or $^{70}$ITRIRPELVKNGQFHIPSITWEHTGRYGCQY$^{100}$ (SEQ ID NO: 122), as determined by HDX; and/or (b) interacts with one or more (or all of) amino acid residues Lys43, Ile49, Thr50 and Arg51 of mature hILT4, as determined by carbene foot-printing.

Embodiment 9

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein the Ab inhibits binding of (or competes with) an antibody comprising a HC comprising SEQ ID NO: 12 or 13 and a light chain comprising SEQ ID NO: 11 and/or inhibits binding of an antibody comprising VH and VL of 21D9.IgG1.1f and/or 21D9.e.IgG1.3, to hILT4.

Embodiment 10

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein the Ab binds to hILT4 with a $K_D$ of $10^{-8}$ M or $10^{-9}$ M or less.

Embodiment 11

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein the Ab binds to cyno ILT4 with a $K_D$ of $10^{-7}$ M or $10^{-8}$ M or less and/or promote expression of CD80, CD83 and/or CD86 on cyno monocyte derived dendritic cells.

Embodiment 12

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein the Ab does not significantly bind to the human proteins LILRA1, LILRA2, LILRA3, LILRA4, LILRA6, ILT2, ILT3, ILT5 or LIRE.

Embodiment 13

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein the Ab promotes pro-inflammatory polarization of macrophages towards M1 macrophages.

Embodiment 14

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein the Ab does not induce (or trigger) basophil activation.

Embodiment 15

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein a composition comprising the Ab comprises less than 5% of high and low molecular weight species after 3 months incubation at 25° C. and/or less than 10% of high and low molecular weight species after 3 months incubation at 40° C.

Embodiment 16

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively, and/or (ii) the heavy chain comprises VH comprising SEQ ID NO: 80 and the light chain comprises VL comprising SEQ ID NO: 70, wherein the Ab comprises an IgG heavy chain constant region, e.g., an IgG1 (e.g., SEQ ID NO: 98 or 102), IgG1.1f (SEQ ID NO: 103), IgG1.3 (SEQ ID NO: 100), IgGP238K (SEQ ID NO: 104), IgG4 or IgG4.S228P (SEQ ID NO: 179).

Embodiment 17

An isolated antibody that binds to hILT4, wherein the Ab comprises a heavy chain comprising SEQ ID NO: 13 and a light chain comprising SEQ ID NO: 11, wherein, optionally, the heavy chain comprises a C-terminal lysine.

Embodiment 18

An isolated antibody that binds to hILT4, wherein the Ab comprises two heavy chains, each heavy chain comprising SEQ ID NO: 13, and two light chains, each light chain comprising SEQ ID NO: 11, wherein, optionally one or both of the heavy chains comprise a C-terminal lysine.

Embodiment 19

Isolated antibody that binds to hILT4, wherein the Ab comprises a heavy chain comprising SEQ ID NO: 13 and a light chain comprising SEQ ID NO: 11, wherein, optionally the heavy chain comprises a C-terminal lysine, and wherein the Ab comprises at least one disulfide bond linking the heavy chains.

Embodiment 20

An isolated antibody that binds to hILT4, wherein the Ab comprises a heavy chain comprising SEQ ID NO: 176 and a light chain comprising SEQ ID NO: 11, wherein, optionally the heavy chain comprises a C-terminal lysine.

Embodiment 21

An isolated antibody that binds to hILT4, wherein the Ab comprises a heavy chain comprising SEQ ID NO: 177 and a light chain comprising SEQ ID NO: 11, wherein, optionally the heavy chain comprises a C-terminal lysine.

Embodiment 22

An isolated antibody that binds to hILT4, wherein the Ab comprises a heavy chain comprising SEQ ID NO: 178 and a light chain comprising SEQ ID NO: 11, wherein, optionally the heavy chain comprises a C-terminal lysine.

Embodiment 23

An isolated nucleic acid or set of nucleic acids encoding the antibody of any one of Embodiments 1-22.

Embodiment 24

A host cell for producing any one of the antibodies of Embodiments 1-22, for example comprising the isolated nucleic acid or set of nucleic acids of Embodiment 23.

Embodiment 25

A method of treating cancer in a subject, comprising administering to the subject a therapeutically effective dose of the antibody of any one of Embodiments 1-22, or of an antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively; (ii) the heavy chain comprises VH comprising SEQ ID NO: 80 and the light chain comprises VL comprising SEQ ID NO: 70 and/or (iii) the heavy chain comprises SEQ ID NO: 13 and the light chain comprises SEQ ID NO: 11.

Embodiment 26

A method of treating cancer in a subject, comprising administering to the subject a therapeutically effective dose of:

(A) (1) the antibody of any one of Embodiments 1-19, or (2) an antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively; (ii) the heavy chain comprises VH comprising SEQ ID NO: 80 and the light chain comprises VL comprising SEQ ID NO: 70 and/or (iii) the heavy chain comprises SEQ ID NO: 13 and the light chain comprises SEQ ID NO: 11, and (B) an antagonist of PD-1 or PD-L1, such as an antagonist antibody binding to human PD-1 or human PD-L1, e.g., nivolumab, pembrolizumab, cemiplimab, toripalimab, sintilimab, atezolizumab, durvalumab or avelumab.

Embodiment 27

A composition comprising:

(A) (1) the antibody of any one of Embodiments 1-19, or (2) an antibody that binds to human ILT4 (hILT4), wherein the Ab comprises a heavy chain and a light chain, wherein (i) the heavy chain comprises VH CDR1, CDR2 and CDR3 comprising SEQ ID Nos: 155, 156, and 157, respectively, and the light chain comprises VL CDR1, CDR2 and CDR3 comprising SEQ ID Nos: 158, 159 and 160, respectively; (ii) the heavy chain comprises VH comprising SEQ ID NO: 80 and the light chain comprises VL comprising SEQ ID NO: 70 and/or (iii) the heavy chain comprises SEQ ID NO: 13 and the light chain comprises SEQ ID NO: 11 and (B) an antagonist of PD-1 or PD-L1, such as an antagonist antibody binding to human PD-1 or human PD-L1, e.g., nivolumab, pembrolizumab, cemiplimab, toripalimab, sintilimab, atezolizumab, durvalumab or avelumab.

Embodiments Relating to Antibody 21D5.a:

Embodiment 1

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86.

Embodiment 2

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein the antibody stimulates T cell activation (or potentiates a T cell response), e.g., (i) in a mixed lymphocyte reaction (MLR) assay, as evidenced, e.g., by enhanced T cell proliferation or IFN-gamma secretion or TNF-alpha production, or (ii) in a T cell: CHO-OKT3-ILT4 assay (e.g., as described in Example 5).

Embodiment 3

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein the Ab enhances T cell activation in a monocyte: T cell allo-MLR.

Embodiment 4

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein the Ab enhances IFN-gamma secretion from PBMCs upon antigen stimulation in a CMV lysate assay.

Embodiment 5

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein the antibody potentiates TNF-alpha secretion from macrophages, e.g., differentiated macrophages.

Embodiment 6

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein the antibody increases expression of CD83 and/or CD86 on monocyte-derived dendritic cells (Mo-DCs).

Embodiment 7

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein the antibody inhibits binding of hILT4 to a T cell and/or to a binding partner, e.g., HLA-A and/or HLA-B.

Embodiment 8

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein the Ab (a) binds to the Ig-like 2 domain of hILT4 and/or the region of hILT4 comprising: $^{154}$ILCKEG-EEEHPQCLNSQPHARGSSRAIF$^{181}$ (SEQ ID NO: 123) and/or $^{425}$SSPPPTGPIS$^{434}$ (SEQ ID NO: 124), as determined by HDX; and/or (b) interacts with one or more (or all of) amino acid residues Gly117, Val119, Try120, Leu134, Lys136, Gln149, Pro150, Ile159, Ser161, Val162, Gly163, Pro164, Pro167, His173, Try178, Pro183 and Tyr184 of mature hILT4, determined by carbene foot-printing.

Embodiment 9

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein the Ab inhibits binding of (or competes with) an antibody comprising a HC comprising SEQ ID NO: 15 or 17 and a light chain comprising SEQ ID NO: 14 or 16, respectively, and/or inhibits binding of an antibody comprising VH and VL of 21D5 or 21D5.a, to hILT4.

Embodiment 10

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein the Ab binds to hILT4 with a $K_D$ of $10^{-8}$ M or $10^{-9}$ M or less.

Embodiment 11

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein the Ab binds to cyno ILT4 with a $K_D$ of $10^{-7}$ M or $10^{-8}$ M or less and/or promote expression of CD80, CD83 and/or CD86 on cyno monocyte derived dendritic cells.

Embodiment 12

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein the Ab does not significantly bind to the human proteins LILRA1, LILRA2, LILRA4, LILRA5, LILRA6, ILT2, ILT3, ILT5 or LIRE.

Embodiment 13

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein the Ab promotes pro-inflammatory polarization of macrophages towards M1 macrophages.

Embodiment 14

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein the Ab does not induce (or trigger) basophil activation.

Embodiment 15

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein a composition comprising the Ab comprises less than 5% of high and low molecular weight species after 3 months incubation at 25° C. and/or less than 10% of high and low molecular weight species after 3 months incubation at 40° C.

Embodiment 16

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86, wherein the Ab comprises an IgG heavy chain constant region, e.g., an IgG1 (e.g., SEQ ID NO: 98 or 102), IgG1.1f (SEQ ID NO: 103), IgG1.3 (SEQ ID NO: 100), IgGP238K (SEQ ID NO: 104), IgG4 or IgG4.S228P (SEQ ID NO: 179).

Embodiment 17

An isolated antibody that binds to hILT4, wherein the Ab comprises a heavy chain comprising SEQ ID NO: 17 and a light chain comprising SEQ ID NO: 16, wherein, optionally the heavy chain comprises a C-terminal lysine.

Embodiment 18

An isolated antibody that binds to hILT4, wherein the Ab comprises two heavy chains, each heavy chain comprising SEQ ID NO: 17, and two light chains, each light chain comprising SEQ ID NO: 16, wherein, optionally one or both of the heavy chains comprise a C-terminal lysine.

Embodiment 19

An isolated antibody that binds to hILT4, wherein the Ab comprises a heavy chain comprising SEQ ID NO: 17 and a light chain comprising SEQ ID NO: 16, wherein, optionally the heavy chain comprises a C-terminal lysine, and wherein the Ab comprises at least one disulfide bond linking the heavy chains.

Embodiment 20

An isolated antibody that binds to hILT4, wherein the Ab comprises a heavy chain comprising SEQ ID NO: 15 and a light chain comprising SEQ ID NO: 14, wherein, optionally the heavy chain comprises a C-terminal lysine.

Embodiment 21

An isolated antibody that binds to hILT4, wherein the Ab comprises a heavy chain comprising SEQ ID NO: 17 and a light chain comprising SEQ ID NO: 16, wherein, optionally the heavy chain comprises a C-terminal lysine.

Embodiment 22

An isolated antibody that binds to hILT4, wherein the Ab comprises a heavy chain comprising SEQ ID NO: 15 or 17 and a light chain comprising SEQ ID NO: 14 or 16, wherein, optionally the heavy chain comprises a C-terminal lysine.

Embodiment 23

An isolated nucleic acid or set of nucleic acids encoding the antibody of any one of Embodiments 1-22.

Embodiment 24

A host cell for producing any one of the antibodies of Embodiments 1-22, for example comprising the isolated nucleic acid or set of nucleic acids of Embodiment 23.

Embodiment 25

A method of treating cancer in a subject, comprising administering to the subject a therapeutically effective dose of an antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86 and/or (iii) the heavy chain comprises SEQ ID NO: 17 and the light chain comprises SEQ ID NO: 16.

Embodiment 26

A method of treating cancer in a subject, comprising administering to the subject a therapeutically effective dose of (A) an antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86 and/or (iii) the heavy chain comprises SEQ ID NO: 17 and the light chain comprises SEQ ID NO: 16, and (B) an antagonist of PD-1 or PD-L1, such as an antagonist antibody binding to human PD-1 or human PD-L1, e.g., nivolumab, pembrolizumab, cemiplimab, toripalimab, sintilimab, atezolizumab, durvalumab or avelumab.

Embodiment 27

A composition comprising (A) an antibody that binds to human ILT4 (hILT4), wherein the Ab comprises a heavy chain and a light chain, wherein (i) the heavy chain comprises VH CDR1, CDR2 and CDR3 comprising SEQ ID Nos: 161, 162 and 163, respectively, and the light chain comprises VL CDR1, CDR2 and CDR3 comprising SEQ ID Nos: 164, 165 and 166, respectively, and/or (ii) the heavy chain comprises VH comprising SEQ ID NO: 87 and the light chain comprises VL comprising SEQ ID NO: 86 and/or (iii) the heavy chain comprises SEQ ID NO: 17 and the light chain comprises SEQ ID NO: 16, and (B) an antagonist of PD-1 or PD-L1, such as an antagonist antibody binding to human PD-1 or human PD-L1, e.g., nivolumab, pembrolizumab, cemiplimab, toripalimab, sintilimab, atezolizumab, durvalumab or avelumab.

Embodiments Related to Antibodies 10F10, 10F10.1, 10F10.3 and 10F10.4:

Embodiment 1

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114.

Embodiment 2

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein the antibody stimulates T cell activation (or potentiates a T cell response), e.g., (i) in a mixed lymphocyte reaction (MLR) assay, as evidenced, e.g., by enhanced T cell proliferation or IFN-gamma secretion or TNF-alpha production, or (ii) in a T cell: CHO-OKT3-ILT4 assay (e.g., as described in Example 5).

Embodiment 3

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein the Ab enhances T cell activation in a monocyte: T cell allo-MLR.

Embodiment 4

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein the Ab enhances IFN-gamma secretion from PBMCs upon antigen stimulation in a CMV lysate assay.

Embodiment 5

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein the Ab inhibits binding of hILT4 to a T cell and/or to a binding partner, e.g., HLA-A and/or HLA-B.

Embodiment 6

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein the antibody potentiates TNF-alpha secretion from macrophages, e.g., differentiated macrophages.

Embodiment 7

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein the antibody increases expression of CD83 and/or CD86 on monocyte-derived dendritic cells (MoDCs).

Embodiment 8

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein the Ab (i) binds to the Ig-like domain 2 of hILT4, close to the Ig-like domain 1, and/or (ii) interacts with one or more (or all of) amino acid residues Glu42, Lys43, Gly76, Cys77, Leu88, Pro91, Pro183 and Tyr184 of mature hILT4, as determined by carbene foot-printing.

Embodiment 9

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein the Ab inhibits binding of (or competes with) an antibody comprising a HC comprising SEQ ID NO: 19 and a light chain comprising SEQ ID NO: 18, 20, 21, or 116, respectively, and/or inhibits binding of an antibody comprising VH and VL of 10F10, 10F10.1, 10F10.3 and/or 10F10.4, to hILT4.

Embodiment 10

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein the Ab binds to hILT4 with a $K_D$ of $10^{-8}$ M or $10^{-9}$ M or less.

Embodiment 11

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein the Ab binds to cyno ILT4 with a $K_D$ of $10^{-7}$ M or $10^{-8}$ M or less and/or promote expression of CD80, CD83 and/or CD86 on cyno monocyte derived dendritic cells.

Embodiment 12

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein the Ab promotes pro-inflammatory polarization of macrophages towards M1 macrophages.

Embodiment 13

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein the Ab does not induce (or trigger) basophil activation.

Embodiment 14

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein a composition comprising the Ab comprises less than 5% of high and low molecular weight species after 3 months incubation at 25° C. and/or less than 10% of high and low molecular weight species after 3 months incubation at 40° C.

Embodiment 15

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein the Ab does not significantly bind to the human proteins LILRA1, LILRA2, LILRA3, LILRA4, LILRA5, LILRA6, ILT2, ILT3, ILT5 or LIRE.

Embodiment 16

An isolated antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, wherein the Ab comprises an IgG heavy chain constant region, e.g., an IgG1 (e.g., SEQ ID NO: 98 or 102), IgG1.1f (SEQ ID NO: 103), IgG1.3 (SEQ ID NO: 100), IgGP238K (SEQ ID NO: 104), IgG4 or IgG4.S228P (SEQ ID NO: 179).

Embodiment 17

An isolated antibody that binds to hILT4, wherein the Ab comprises a heavy chain comprising SEQ ID NO: 19 and a light chain comprising SEQ ID NO: 18, 20, 21 or 116, wherein, optionally the heavy chain comprises a C-terminal lysine.

Embodiment 18

An isolated antibody that binds to hILT4, wherein the Ab comprises a heavy chain comprising SEQ ID NO: 19 and a light chain comprising SEQ ID NO: 18, 20, 21 or 116, wherein, optionally one or both of the heavy chains comprise a C-terminal lysine.

Embodiment 19

An isolated antibody that binds to hILT4, wherein the Ab comprises a heavy chain comprising SEQ ID NO: 19 and a light chain comprising SEQ ID NO: 18, 20, 21 or 116, wherein, optionally the heavy chain comprises a C-terminal lysine, and wherein the Ab comprises at least one disulfide bond linking the heavy chains.

Embodiment 20

An isolated antibody that binds to hILT4, wherein the Ab comprises a heavy chain comprising SEQ ID NO: 19 and a light chain comprising SEQ ID NO: 18, wherein, optionally the heavy chain comprises a C-terminal lysine.

Embodiment 21

An isolated antibody that binds to hILT4, wherein the Ab comprises a heavy chain comprising SEQ ID NO: 19 and a light chain comprising SEQ ID NO: 20, wherein, optionally the heavy chain comprises a C-terminal lysine.

Embodiment 22

An isolated antibody that binds to hILT4, wherein the Ab comprises a heavy chain comprising SEQ ID NO: 19 and a light chain comprising SEQ ID NO: 21, wherein, optionally the heavy chain comprises a C-terminal lysine.

Embodiment 23

An isolated antibody that binds to hILT4, wherein the Ab comprises a heavy chain comprising SEQ ID NO: 19 and a light chain comprising SEQ ID NO: 116, wherein, optionally the heavy chain comprises a C-terminal lysine.

Embodiment 24

An isolated nucleic acid or set of nucleic acids encoding the antibody of any one of Embodiments 1-23.

Embodiment 25

A host cell for producing any one of the antibodies of Embodiments 1-23, for example comprising the isolated nucleic acid or set of nucleic acids of Embodiment 24.

Embodiment 26

A method of treating cancer in a subject, comprising administering to the subject a therapeutically effective dose of an an antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, and/or (iii) the heavy chain comprises SEQ ID NO: 19 and the light chain comprises SEQ ID NO: 18, 20, 21 or 116.

Embodiment 27

A method of treating cancer in a subject, comprising administering to the subject a therapeutically effective dose of an antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, and/or (iii) the heavy chain comprises SEQ ID NO: 19 and the light chain comprises SEQ ID NO: 18, 20, 21 or 116, and (B) an antagonist of PD-1 or PD-L1, such as an antagonist antibody binding to human PD-1 or human PD-L1, e.g., nivolumab, pembrolizumab, cemiplimab, toripalimab, sintilimab, atezolizumab, durvalumab or avelumab.

Embodiment 28

A composition comprising (A) an antibody that binds to human ILT4 (hILT4), wherein the Ab comprises a heavy chain and a light chain, wherein (i) the heavy chain comprises VH CDR1, CDR2 and CDR3 comprising SEQ ID Nos: 167, 168 and 169, respectively, and the light chain comprises VL CDR1, CDR2 and CDR3 comprising SEQ ID Nos: 170, 171 and 172, respectively, and/or (ii) the heavy chain comprises VH comprising SEQ ID NO: 91 and the light chain comprises VL comprising SEQ ID NO: 90, 94, 96 or 114, and/or (iii) the heavy chain comprises SEQ ID NO: 19 and the light chain comprises SEQ ID NO: 18, 20, 21 or 116, and (B) an antagonist of PD-1 or PD-L1, such as an antagonist antibody binding to human PD-1 or human PD-L1, e.g., nivolumab, pembrolizumab, cemiplimab, toripalimab, sintilimab, atezolizumab, durvalumab or avelumab.

Nucleic Acids and Host Cells

Also provided are nucleic acids encoding an antibody or a heavy or light chain thereof or a portion thereof. Exemplary nucleic acids are provided in the Sequence Table. Any nucleic acid that is at least 80%, 85%, 90%, 95%, 97%, 98% or 99% to a nucleic acid in the Sequence Table is encompassed herein. Compositions comprising nucleic acids encoding an antibody provided herein are also encompassed, as are cells comprising these and methods for preparing antibodies, comprising culturing a cell transformed with a nucleic acid encoding an ILT4 antibody, and isolating the antibody from the medium or the cell.

Methods of Treatment Using ILT4 Binding Abs and Related Pharmaceutical Compositions The antibodies described herein may be used, for example, for treating cancer. In some embodiments, methods for treating cancer are provided, comprising administering an effective amount of an antibody described herein to a patient. In some embodiments, the Abs may trigger or enhance an immune response in the patient, such as an antigen-specific immune response. In some embodiments, the Abs may stimulate T cell activity. In some embodiments, the Abs may inhibit the growth of at least one tumor in the patient.

Provided herein are methods for treating a subject having cancer, comprising administering to the subject a therapeutically effective amount of an ILT4 antibody described herein, such that the subject is treated. An ILT4 antibody can be used alone. Alternatively, an ILT4 antibody can be used in conjunction with another agent, as described further below.

Cancers can be cancers with solid tumors or blood malignancies (liquid tumors).

Non-limiting examples of cancers for treatment include squamous cell carcinoma, small-cell lung cancer, non-small cell lung cancer, squamous non-small cell lung cancer (NSCLC), nonsquamous NSCLC, glioma, gastrointestinal cancer, renal cancer (e.g., clear cell carcinoma), ovarian cancer, liver cancer, colorectal cancer, endometrial cancer, kidney cancer (e.g., renal cell carcinoma (RCC)), prostate cancer (e.g., hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, T-cell lymphoma, environmentally-induced cancers including those induced by asbestos, virus-related cancers or cancers of viral origin (e.g., human papilloma virus (HPV-related or -originating tumors)), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B cell hematologic malignancy, e.g., B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, B cell lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein can also be used for treatment of metastatic cancers, unresectable, refractory cancers (e.g., cancers refractory to previous immunotherapy, e.g., with a blocking CTLA-4 or PD-1 antibody), and/or recurrent cancers.

In certain embodiments, an antibody described herein is administered to patients having a cancer that has exhibited an inadequate response to, or progressed on, a prior treatment, e.g., a prior treatment with an immuno-oncology or immunotherapy drug. In some embodiments, the cancer is refractory or resistant to a prior treatment, either intrinsically refractory or resistant (e.g., refractory to a PD-1 pathway antagonist), or a resistance or refractory state is acquired. For example, an antibody described herein may be administered to subjects who are not responsive or not sufficiently responsive to a first therapy or who have disease progression following treatment, e.g., anti-PD-1 pathway antagonist treatment, either alone or in combination with another therapy (e.g., with an anti-PD-1 pathway antagonist therapy). In other embodiments, an antibody described herein is administered to patients who have not previously received (i.e., been treated with) an immuno-oncology agent, e.g., a PD-1 pathway antagonist.

Combinations with Immune Stimulating Agents

In some embodiments, an antibody as described herein, e.g., an ILT4 antibody described herein, is administered in combination with and at least one immune stimulating agent. For example, the therapeutics may be infused together or injected at roughly the same time. In some embodiments, the antibody and the at least one immune stimulating agent are administered sequentially. For example, in some embodiments the antibody is administered sequentially before or after at least one immune stimulating agent such that the two therapeutics are administered 30 minutes, 60 minutes, 90 minutes, 120 minutes, 3 hours, 6 hours, 12 hours, 24 hours, 36 hours, 48 hours, 3 days, 5 days, 7 days, or two weeks apart.

In some embodiments, at least one, at least two, at least three doses, at least five doses, or at least ten doses of the antibody are administered prior to administration of at least one immune stimulating agent. In some embodiments, at least one, at least two, at least three doses, at least five doses, or at least ten doses of at least one immune stimulating agent is administered prior to administration of the antibody. In some embodiments, the last dose of immune stimulating agent is administered at least one, two, three, five, days or ten, or one, two, three, five, twelve, or twenty four weeks prior to the first dose of the antibody. In some embodiments, the last dose of the antibody is administered at least one, two, three, five, days or ten, or one, two, three, five, twelve, or twenty four weeks prior to the first dose of at least one immune stimulating agent. In some embodiments, a subject has received, or is receiving, therapy with at least one immune stimulating agent and an ILT4 antibody is added to the therapeutic regimen.

In some embodiments, the at least one immune stimulating agent comprises an antagonist of an inhibitor of the activation of immune cells, such as T cells, while in some embodiments, the at least one immune stimulating agent comprises an agonist of a stimulator of the activation of an immune cell, such as a T cell. In some embodiments, the at least one immune stimulating agent comprises an antagonist of CTLA4, LAG-3, PD-1, PD-L1, Galectin 1, Galectin 9, CEACAM-1, BTLA, CD25, CD69, TIGIT, CD113, GPR56, VISTA, B7-H3, B7-H4, 2B4, CD48, GARP, PD1H, LAIR1, TIM1, TIM3, TIM4, IL-6, IL-10, TGFβ, VEGF, KIR, adenosine A2A receptor, PI3Kdelta, or IDO. In some embodiments, the at least one immune stimulating agent comprises an agonist of B7-1, B7-2, CD28, 4-1BB (CD137), 4-1BBL, ICOS, ICOS-L, OX40, OX40L, GITR, GITRL, CD27, CD40, CD40L, DR3, CD28H, IL-2, IL-7, IL-12, IL-15, IL-21, IFNα, STING, or a Toll-like receptor agonist such as a TLR2/4 agonist. In some embodiments, the at least one immune stimulating agent comprises an agent that binds to another member of the B7 family of membrane-bound proteins such as B7-1, B7-2, B7-H2 (ICOS-L), B7-H3, B7-H4, and B7-H6. In some embodiments, the at least one immune stimulating agent comprises an agent that binds to a member of the TNF receptor family or a co-stimulatory or co-inhibitory molecule binding to a member of the TNF receptor family such as CD40, CD40L, OX40, OX40L, GITR, GITRL, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, EDA1, EDA2, TACI, APRIL, BCMA, LTβR, LIGHT, DeR3, HVEM, VEGL/TL1A, TRAMP/DR3, TNFR1, TNFβ, TNFR2, TNFα, 1β2, FAS, FASL, RELT, DR6, TROY, or NGFβ. In some embodiments, the at least one immune stimulating agent comprises an agent that antagonizes or inhibits a cytokine that inhibits T cell activation such as IL-6, IL-10, TGFβ, VEGF. In some embodiments, the at least one immune stimulating agent comprises an agonist of a cytokine that stimulates T cell activation such as IL-2, IL-7, IL-12, IL-15, IL-21, and IFNα. In some embodiments, the at least one immune stimulating agent comprises an antagonist of a chemokine, such as CXCR2, CXCR4, CCR2, or CCR4. In some embodiments, the at least one immune stimulating agent comprises an antibody. In some embodiments, the at least one immune stimulating agent may comprise a vaccine, such as a mesothelin-targeting vaccine or attenuated listeria cancer vaccine such as CRS-207.

For example, an ILT4 antibody described herein could be administered with one or more of the following agents:

(1) An antagonist (inhibitor or blocking agent) of a protein that inhibits T cell activation (e.g., immune checkpoint inhibitors), such as CTLA-4, PD-1, PD-L1, PD-L2, and LAG-3, Galectin 9, CEACAM-1, BTLA, CD69, Galectin-1, TIGIT, CD113, GPR56, B7-H3, B7-H4, 2B4, CD48, GARP, PD1H, LAIR1, TIM-1,TIM-3 and TIM-4; and/or (2) An agonist of a protein that stimulates T cell activation, such as B7-1, B7-2, CD28, 4-1BB (CD137), 4-1BBL, GITR, ICOS, ICOS-L, OX40, OX40L, CD70, CD27, CD40, DR3 and CD28H.

Exemplary agents that can be combined with ILT4 antibodies described herein for treating cancer include: YERVOY® (ipilimumab) or Tremelimumab (to CTLA-4), galiximab (to B7.1), BMS-936558 (to PD-1), MK-3475 (to PD-1), atezolizumab (TECENTRIQ®), Avelumab, Durvalumab, AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-0X40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3); anti-GITR antibodies MK4166, TRX518, Medi1873, INBRX-110, LK2-145, GWN-323, GITRL-Fc, or any combination thereof.

Other molecules that can be combined with ILT4 antibodies for the treatment of cancer include antagonists of inhibitory receptors on NK cells or agonists of activating receptors on NK cells, for example, antagonists of KIR (e.g., lirilumab).

T cell activation may also be regulated by soluble cytokines. In some embodiments, ILT4 antibodies can be administered in combination with antagonists of cytokines that are intended to inhibit T cell activation or agonists of cytokines that stimulate T cell activation. For example, ILT4 antibodies can be used in combination with (i) antagonists (or inhibitors or blocking agents) of proteins of the IgSF family or B7 family or the TNF family that inhibit T cell activation or antagonists of cytokines that inhibit T cell activation (e.g., IL-6, IL-10, TGF-β, VEGF; “immunosuppressive cytokines”) and/or (ii) agonists of stimulatory receptors of the IgSF family, B7 family or the TNF family or of cytokines that stimulate T cell activation.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

ILT4 antibodies can also be administered with agents that inhibit TGF-β signaling.

Additional agents that can be combined with an ILT4 antibody include agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Yet other therapies that can be combined with an ILT4 antibody include therapies that deplete or block Treg cells, e.g., an agent that specifically binds to CD25.

Another therapy that can be combined with an ILT4 antibody is a therapy that inhibits a metabolic enzyme such as indoleamine dioxigenase (IDO), dioxigenase, arginase, or nitric oxide synthetase.

Another class of agents that can be used with an ILT4 antibody includes agents that inhibit the formation of adenosine, e.g., CD73 inhibitors, or inhibit the adenosine A2A receptor.

Other therapies that can be combined with an ILT4 antibody for treating cancer include therapies that reverse/prevent T cell anergy or exhaustion and therapies that trigger an innate immune activation and/or inflammation at a tumor site.

Other therapies that can be combined with an ILT4 antibody for treating cancer include therapies that block IL-8, e.g., with HuMax®-IL8.

An ILT4 antibody can be combined with more than one immuno-oncology agent, and can be, e.g., combined with a combinatorial approach that is intended to target multiple elements of the immune pathway, such as one or more of the following: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Tregs or other immune suppressing cells; a therapy that stimulates positive immune regulation, e.g., with agonists that stimulate the CD-137, OX-40, and/or CD40 or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; or blocking of immuno repressive cytokines.

ILT4 antibodies described herein can be used together with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In certain embodiments, an ILT4 antibody is administered to a subject together with a BRAF inhibitor if the subject is BRAF V600 mutation positive.

Suitable PD-1 antagonists for use in the combination therapy described herein, include, without limitation, ligands, antibodies (e.g., monoclonal antibodies and bispecific antibodies), and multivalent agents. In one embodiment, the PD-1 antagonist is a fusion protein, e.g., an Fc fusion protein, such as AMP-244. In one embodiment, the PD-1 antagonist is an anti-PD-1 or anti-PD-L1 antibody.

An exemplary anti-PD-1 antibody is nivolumab (BMS-936558) or an antibody that comprises the CDRs or variable regions of one of antibodies 17D8, 2D3, 4H1, 5C4, 7D3, 5F4 and 4A11 described in WO 2006/121168. In certain embodiments, an anti-PD-1 antibody is MK-3475 (Lambrolizumab) described in WO2012/145493; AMP-514 described in WO 2012/145493; or PDR001. Further known PD-1 antibodies and other PD-1 inhibitors include those described in WO 2009/014708, WO 03/099196, WO 2009/114335, WO 2011/066389, WO 2011/161699, WO 2012/145493, U.S. Pat. Nos. 7,635,757 and 8,217,149, and U.S. Patent Publication No. 2009/0317368. Any of the anti-PD-1 antibodies disclosed in WO2013/173223 can also be used. An anti-PD-1 antibody that competes for binding with, and/or binds to the same epitope on PD-1 as, as one of these antibodies can also be used in combination treatments.

In some embodiments, the anti-PD-L1 antibody useful for the combination therapy is BMS-936559 (referred to as 12A4 in WO 2007/005874 and U.S. Pat. No. 7,943,743), or an antibody that comprises the CDRs or variable regions of 3G10, 12A4, 10A5, 5F8, 10H10, 1B12, 7H1, 11E6, 12B7 and 13G4, which are described in PCT Publication WO 07/005874 and U.S. Pat. No. 7,943,743. In certain embodiment an anti-PD-L1 antibody is MEDI4736 (also known as durvalumab and Anti-B7-H1), MPDL3280A (also known as atezolizumab and RG7446), MSB0010718C (also known as avelumab; WO2013/79174), or rHigM12B7. Any of the anti-PD-L1 antibodies disclosed in WO2013/173223, WO2011/066389, WO2012/145493, U.S. Pat. Nos. 7,635,757 and 8,217,149 and U.S. Publication No. 2009/145493 can also be used. Anti-PD-L1 antibodies that compete with and/or bind to the same epitope as that of any of these antibodies can also be used in combination treatments.

In certain embodiments, the ILT4 antibody of the disclosure can be used with a CTLA-4 antagonist, e.g., an anti-CTLA-4 antibody. In one embodiment, an anti-CTLA-4 antibody is an antibody selected from the group of: YERVOY (ipilimumab or antibody 10D1, described in PCT Publication WO 01/14424), tremelimumab (formerly ticilimumab, CP-675,206), monoclonal or an anti-CTLA-4 antibody described in any of the following publications: WO 98/42752; WO 00/37504; U.S. Pat. No. 6,207,156; Hurwitz et al. (1998) *Pro. Natl. Acad. Sci. USA* 95(17): 10067-10071; Camacho et al. (2004) *J. Clin. Oncology* 22(145): Abstract No. 2505 (antibody CP-675206); and Mokyr et al. (1998) *Cancer Res.* 58:5301-5304. Any of the anti-CTLA-4 antibodies disclosed in WO2013/173223 can also be used.

In some embodiments, an ILT4 antibody of the disclosure is used in combination with a LAG3 antagonist. Examples of anti-LAG3 antibodies include antibodies comprising the CDRs or variable regions of antibodies 25F7, 26H10, 25E3, 8B7, 11F2 or 17E5, which are described in U.S. Patent Publication No. US2011/0150892, WO10/19570 and WO2014/008218. In one embodiment, an anti-LAG-3 antibody is BMS-986016. Other art recognized anti-LAG-3 antibodies that can be used include IMP731 and IMP-321, described in US 2011/007023, WO08/132601, and WO09/44273. Anti-LAG-3 antibodies that compete with and/or bind to the same epitope as that of any of these antibodies can also be used in combination treatments.

In some embodiments, an ILT4 antibody of the disclosure can be administered in combination with a CD137 (4-1BB) agonist, such as an agonistic CD137 antibody. Suitable CD137 antibodies include, for example, urelumab or PF-05082566 (WO12/32433).

In some embodiments, an ILT4 antibody can be administered in combination with an OX40 agonist, such as an agonistic OX40 antibody. Suitable OX40 antibodies include, for example, MEDI-6383, MEDI-6469 or MOXR0916 (RG7888; WO06/029879).

In one embodiment, an ILT4 antibody is administered in combination with a CD40 agonist, such as an agonistic CD40 antibody. In certain embodiments, the immuno-oncology agent is a CD40 antagonist, such as an antagonistic CD40 antibody. Suitable CD40 antibodies include, for example, lucatumumab (HCD122), dacetuzumab (SGN-40), CP-870,893 or Chi Lob 7/4.

In one embodiment, an ILT4 antibody is administered in combination with a CD27 agonist, such as an agonistic CD27 antibody. Suitable CD27 antibodies include, for example, varlilumab (CDX-1127).

In certain embodiments, the ILT4 antibody is administered together with an anti-GITR antibody, e.g., an antibody having the CDR sequences of 6C8, e.g., a humanized antibody having the CDRs of 6C8, as described, e.g., in WO2006/105021; an antibody comprising the CDRs of an anti-GITR antibody described in WO2011/028683; an antibody comprising the CDRs of an anti-GITR antibody described in JP2008278814, an antibody comprising the CDRs of an anti-GITR antibody described in WO2015/031667, WO2015/187835, WO2015/184099, WO2016/054638, WO2016/057841 or WO2016/057846 or other anti-GITR antibody described or referred to herein.

In some embodiments, an ILT4 antibody is administered in combination with MGA271 (to B7H3) (WO11/109400).

In some embodiments, an ILT4 antibody is administered in combination with a KIR antagonist, such as lirilumab.

In some embodiments, an ILT4 antibody is administered in combination with an IDO antagonist. Suitable IDO antagonists include, for example, INCB-024360 (WO2006/122150, WO07/75598, WO08/36653, WO08/36642), indoximod, NLG-919 (WO09/73620, WO09/1156652, WO11/56652, WO12/142237) or F001287.

In some embodiments, an ILT4 antibody is administered in combination with a Toll-like receptor agonist, e.g., a TLR2/4 agonist (e.g., Bacillus Calmette-Guerin); a TLR7 agonist (e.g., Hiltonol or Imiquimod); a TLR7/8 agonist (e.g., Resiquimod); or a TLR9 agonist (e.g., CpG7909).

In one embodiment, an ILT4 is administered in combination with a TGF-β inhibitor, e.g., GC1008, LY2157299, TEW7197, or IMC-TR1.

Additional Combination Therapy

The Abs herein may also be provided before, substantially contemporaneous with, or after other modes of treatment, for example, surgery, chemotherapy, radiation therapy, or the administration of a biologic, such as another therapeutic antibody. In some embodiments, the cancer has recurred or progressed following a therapy selected from surgery, chemotherapy, and radiation therapy, or a combination thereof. For example, an ILT4 antibody as described herein could be administered as adjunctive therapy when there is a risk that micrometastases can be present and/or in order to reduce the risk of a relapse.

For treatment of cancer, the combinations may be administered in conjunction with one or more additional anti-cancer agents, such as a chemotherapeutic agent, growth inhibitory agent, anti-cancer vaccine such as a gene therapy vaccine, anti-angiogenesis agent and/or anti-neoplastic composition. Nonlimiting examples of chemotherapeutic agent, growth inhibitory agent, anti-cancer vaccine, anti-angiogenesis agent and anti-neoplastic composition that can be used in combination with the antibodies of the present invention are provided herein under "Definitions."

In some embodiments, an anti-inflammatory drug may be administered with the combination, such as a steroid or a non-steroidal anti-inflammatory drug (NSAID). In cases where it is desirable to render aberrantly proliferative cells quiescent in conjunction with or prior to treatment with ILT4 antibodies described herein, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX®, can also be administered to the patient. When employing the methods or compositions described herein, other agents used in the modulation of tumor growth or metastasis in a clinical setting, such as antimimetics, can also be administered as desired.

Antibodies described herein can also be combined with an immunogenic agent, such as cancerous cells, purified tumor antigens (including recombinant proteins, peptides, and carbohydrate molecules), cells, and cells transfected with genes encoding immune stimulating cytokines (He et al., (2004) *J Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

An ILT4 antibody described herein, can also be combined with a vaccination protocol. Many experimental strategies for vaccination against tumors have been devised (see Rosenberg, S., 2000, Development of Cancer Vaccines, ASCO Educational Book Spring: 60-62; Logothetis, C, 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

The study of gene expression and large scale gene expression patterns in various tumors has led to the definition of so called tumor specific antigens (Rosenberg, S A (1999) *Immunity* 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. ILT4 inhibition can be used in conjunction with a collection of recombinant proteins and/or peptides expressed in a tumor in order to generate an immune response to these proteins. These proteins are normally viewed by the immune system as self antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) *Science* 266: 2011-2013). Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with ILT4 Abs is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269: 1585-1588; Tamura et al. (1997) *Science* 278: 117-120).

Dendritic cells (DC) are potent antigen presenting cells that can be used to prime antigen-specific responses. DCs can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be combined with ILT4 inhibition to activate more potent anti-tumor responses.

Infectious Disease Treatments

Methods described herein can also be used to treat patients that have been exposed to particular toxins or pathogens. Accordingly, this disclosure also contemplates methods of treating an infectious disease in a subject comprising administering to the subject an antibody as described herein, e.g., an ILT4 antibody, such that the subject is treated for the infectious disease. Similar to its application to tumors as discussed above, antibody-mediated ILT4 inhibition can be used alone, or as an adjuvant, in combination with vaccines, to stimulate the immune response to pathogens, toxins, and self-antigens. Examples of pathogens for which this therapeutic approach might be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, *Leishmania, Staphylococcus aureus, Pseudomonas aeruginosa*. ILT4 inhibition can be useful against established infections by agents such as HIV that present altered antigens over the course of the infections.

Some examples of pathogenic viruses causing infections that may be treatable by methods described herein include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections that may be treatable by methods described herein include chlamydia, rickettsial bacteria, mycobacteria, staphylococci, streptococci, pneumonococci, meningococci and gonococci, klebsiella, proteus, serratia, pseudomonas, legionella, diphtheria, salmonella, bacilli, cholera, tetanus, botulism, anthrax, plague, leptospirosis, and Lymes disease bacteria.

Some examples of pathogenic fungi causing infections that may be treatable by methods described herein include Candida (albicans, krusei, glabrata, tropicalis, etc.), Cryptococcus neoformans, Aspergillus (fumigatus, niger, etc.), Genus Mucorales (mucor, absidia, rhizopus), *Sporothrix schenkii, Blastomyces dermatitidis, Paracoccidioides brasiliensis, Coccidioides immitis* and *Histoplasma capsulatum.*

Some examples of pathogenic parasites causing infections that may be treatable by methods described herein include *Entamoeba histolytica, Balantidium coli, Naegleriafowleri, Acanthamoeba* sp., *Giardia lambia, Cryptosporidium* sp *Pneumocystis carinii, Plasmodium vivax, Babesia microti, Trypanosoma brucei, Trypanosoma cruzi, Leishmania donovani, Toxoplasma gondii*, and *Nippostrongylus brasiliensis.*

In all of the above methods, ILT4 inhibition can be combined with other forms of immunotherapy, e.g., those described herein, such as cytokine treatment (e.g., interferons, GM-CSF, G-CSF, IL-2), or bispecific antibody therapy, which may provide for enhanced presentation of tumor antigens (see, e.g., Holliger (1993) *Proc. Natl. Acad. Sci. USA* 90:6444-6448; Poljak (1994) *Structure* 2: 1121-1123).

Routes of Administration and Carriers

In various embodiments, antibodies may be administered in vivo by various routes, including, but not limited to, intra-venous (i.v.), subcutaneous, oral, intra-arterial, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. A nucleic acid molecule encoding an antibody may be coated onto gold microparticles and delivered intradermally by a particle bombardment device, or "gene gun," as described in the literature (see, e.g., Tang et al., *Nature* 356:152-154 (1992)). The appropriate formulation and route of administration may be selected according to the intended application.

In various embodiments, compositions comprising antibodies are provided in formulations with a wide variety of pharmaceutically acceptable carriers (see, e.g., Gennaro, *Remington: The Science and Practice of Pharmacy with Facts and Comparisons: Drugfacts Plus,* $20^{th}$ ed. (2003); Ansel et al., *Pharmaceutical Dosage Forms and Drug Delivery Systems,* $7^{th}$ ed., Lippencott Williams and Wilkins (2004); Kibbe et al., *Handbook of Pharmaceutical Excipients,* $3^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In various embodiments, compositions comprising antibodies may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical packs and kits comprising one or more containers, each containing one or more doses of an antibody or combination of antibodies are also provided. In some embodiments, a unit dosage is provided wherein the unit dosage contains a predetermined amount of a composition comprising an antibody or combination of antibodies, with or without one or more additional agents. In some embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective Ph range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In general, antibodies may be administered in an amount in the range of about 10 μg/kg body weight to about 100 mg/kg body weight per dose. In some embodiments, antibodies may be administered in an amount in the range of about 50 μg/kg body weight to about 5 mg/kg body weight per dose. In some embodiments, antibodies may be administered in an amount in the range of about 100 μg/kg body weight to about 10 mg/kg body weight per dose. In some embodiments, antibodies may be administered in an amount in the range of about 100 μg/kg body weight to about 20 mg/kg body weight per dose. In some embodiments, antibodies may be administered in an amount in the range of about 0.5 mg/kg body weight to about 20 mg/kg body weight per dose.

The antibody compositions may be administered as needed to subjects. Determination of the frequency of administration may be made by persons skilled in the art, such as an attending physician based on considerations of the condition being treated, age of the subject being treated, severity of the condition being treated, general state of health of the subject being treated and the like. In some embodiments, an effective dose of an antibody is administered to a subject one or more times. In various embodiments, an effective dose of an antibody is administered to the subject once a month, less than once a month, such as, for example, every two months or every three months. In other embodiments, an effective dose of an antibody is administered more than once a month, such as, for example, every three weeks, every two weeks or every week. In some embodiments, an effective dose of an antibody is administered once per 1, 2, 3, 4, or 5 weeks. In some embodiments, an effective dose of an antibody is administered twice or three times per week. An effective dose of an antibody is administered to the subject at least once. In some embodiments, the effective dose of an antibody may be administered multiple times, including for periods of at least a month, at least six months, or at least a year.

In certain embodiments, the combination of the ILT4 antibody and a second agent discussed herein can be administered concurrently as a single composition in a pharmaceutically acceptable carrier, or concurrently as separate compositions with the ILT4 antibody and the second agent in a pharmaceutically acceptable carrier. In one embodiment, the combination of the ILT4 antibody and the second agent can be administered sequentially. The administration of the two agents can start at times that are, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks apart, or administration of the second agent can start, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks after the first agent has been administered.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Antibodies Binding to Human ILT4

Anti-human ILT4 monoclonal antibodies (ILT4 antibodies or hILT4 antibodies) were generated using transgenic mice that express human antibody genes. Fully human monoclonal antibodies to human ILT4 were generated by immunizing 2 types of human immunoglobulin transgenic animals. KM [M/K] mice were immunized with hILT4-mFc recombinant protein, which was composed of the extracellular portion of hILT4 with a C-terminal mouse Fc tag. The antigen was mixed 1:1 with Ribi adjuvant and mice were immunized at weekly intervals intraperitoneally and subcutaneously. The HCo42:01 [J/K] strain was immunized with hILT4-his tagged recombinant protein, which was composed of the extracellular portion of hILT4 with a his-tag at the C-terminus. The antigen was mixed 1:1 with Ribi adjuvant and mice were immunized at weekly intervals in the footpad. The serum titers in both types of mice were monitored following four and six injections. Mice received final boosts prior to the final harvest. Depending on the immunization route, draining lymph nodes and the spleen were harvested for subsequent fusions.

Mouse lymphocytes were isolated from immunized mice. Hybridomas were generated by fusions with a mouse myeloma fusion partner by electric field based electrofusion using a Cyto Pulse Hybrimmune large chamber cell fusion electroporator (BTX/Harvard Apparatus). Single cell suspensions of lymphocytes from immunized mice were fused to an equal number of P3X63 Ag8.6.53 (ATCC) non secreting mouse myeloma cells (fusion numbers 4865 and 6951). Resulting cells were plated in flat bottom microtiter plates in Medium E (StemCell Technologies) supplemented with aminopterin for selection of hybridomas (Sigma).

Individual wells were screened for the presence of human IgG/human kappa light chain (hIgG/hK) antibodies using a homogenous HTRF assay after 10-12 days of culture. Hybridoma supernatants from wells positive for hIgG/hK were tested by FACS or by FMAT for binding to cells transfected with hILT4 or control CHO cells. The following antibodies that interacted specifically with hILT4 were further characterized: 9C8.A6, 24E5.A7, 2H2.H3, 21D9.H11, 2E5.A11 and 9G4. Antibodies 21A5 and 10F10 were isolated from a later immunization.

Antibodies from the hybridomas were sequenced using an NGS high throughput sequencing method. Briefly, for each hybridoma clone in a well of a 96 well plate, PCR amplification of the VH and VL regions was done using unique DNA barcodes to identify each well. The 5' PCR primer hybridizes to the leader region so that the entire variable region sequence is obtained. A particular hybridoma antibody sequence is identified by matching the barcode and the location of the clone on the plate.

Anti-ILT4 antibodies 9G4, 9C8, 2H2, 2E5, 24E5, 21D9, 21A5 and 10F10 were recombinantly expressed in the context of an IgG1, IgG1.1 or IgG1.3 heavy chain constant region, and are also referred to as provided in Table 1. The amino acid sequence of, and nucleotide sequences encoding, the HCs, LCs, VHs, and VLs are provided in FIGS. 1-12 and the Sequence Table below. The location of each of the CDRs is provided in the Figures as well as indicated by underlining in the variable region sequences of the Sequence Table, and the CDRs are included also as separate SEQ ID Nos toward the end of the Sequence Table.

An analysis of the amino acid sequences of the variable domains of antibodies 21D9, 21A5, 2H2 and 10F10 indicated that certain framework amino acid residues were not present in any human germline. To reduce potential immunogenicity issues when these antibodies are administered to humans, germline reversion mutants of these ILT4 antibodies were generated.

For the antibody 21D9, four framework mutations in the heavy chain variable region relative to germline sequences were identified (V2G, G10D, A24T and V481), and are shown in FIG. 13. Among the various combinations of these 4 reverse mutations, four reversion mutants (21D9.b, 21D9.c, 21D9.d and 21D9.e) were generated (see FIG. 13) and tested for binding to hILT4. All 4 reversion mutants comprise the N-terminal EGQ to EVQ (or G2V) mutation, which is unlikely to affect binding to ILT4. In addition to this substitution, mutants 21D9.b, 21D9.c, and 21D9.d each comprise one of the additional substitutions shown in FIG. 13 (D10G; I24A; and/or I48V), and 21D9.e comprises substitutions of all three (see FIG. 13). The four mutants were generated in the context of an IgG1.3 heavy chain constant region, which is an IgG1 constant region comprising amino acid substitutions L234A, L235E and G237A, to reduce effector function. The mutants are referred to as 21D9.b.hIgG1.3 ("21D9.VH-G2V/D10G8V.IgG1.3"), 21D9.c.hIgG1.3 ("21D9.VH-G2V/T24A.IgG1.3"), 21D9.d.hIgG1.3 ("21D9.VH-G2V/I48V") and 21D9.e.hIgG1.3 ("21D9.VH-G2V/D10G/T24A/I48V.IgG1.3"), and comprise the light chain of 21D9. No germline reversions were made to the light chain.

For the antibody 21A5, one framework mutation was identified in the each of the heavy chain (T701) and light chain (V3A) variable regions, as shown in FIG. 14. As the N-terminal reversion in the kappa light chain, shown at A3V, is unlikely to affect binding, one mutant comprising both heavy (I70T) and light (A3V) chain reversion mutations (21A5.a with a 21A5.1 light chain) was generated and tested in the context of IgG1.3 (21A5.a.IgG1.3, also referred to as "21A5.VH-170T.VK-A3V.IgG1.3").

For the antibody 10F10, two framework mutations were identified in the light chain variable region (Y36F and S63T), and are shown in FIG. 15. No framework mutation was found in the heavy chain variable region. As the F to Y reversion at position 36 is a minor difference, a double mutant (10F10.3) comprising both light chain reversion mutations F36Y and T63S was generated and tested in the context of IgG1.3 (10F10.3.IgG1.3, also referred to as "10F10.VK-F36Y/T63S.IgG1.3"). A mutant having only the reversion mutation F36Y was also generated and tested in the context of IgG1.3 (10F10.1.IgG1.3, also referred to as "10F10.VK-F36Y.IgG1.3"). Both reversion mutant Abs comprise the heavy chain of 10F10. Table 1 sets forth the alternative names of recombinant antibodies described herein.

TABLE 1

| Alternative names of recombinant anti-hILT4 antibodies | |
|---|---|
| 9G4.IgG1.1 | ILT4.1.IgG1.1 |
| 9C8.IgG1.1 | ILT4.2.IgG1.1 |
| 2H2.IgG1.1 | ILT4.3.IgG1.1 |
| 2E5.IgG1.1 | ILT4.4.IgG1.1 |
| 24E5.IgG1.1 | ILT4.5.IgG1.1 |

TABLE 1-continued

| Alternative names of recombinant anti-hILT4 antibodies | |
|---|---|
| 21D9.IgG1.1 | ILT4.6.IgG1.1 |
| 21D9.IgG1.3 | ILT4.6.IgG1.3 |
| 21D9.e.IgG1.3 | ILT4.8.IgG1.3 |
| 21A5.a.IgG1.3 | ILT4.9.IgG1.3 |
| 10F10.IgG1.3 | ILT4.10.IgG1.3 |
| 10F10.3.IgG1.3 | ILT4.11.IgG1.3 |

Example 2: Binding of Anti-hILT4 Antibodies to Soluble hILT4

The binding kinetics of the parent and germline reversion mutant anti-hILT4 antibodies (in the context of IgG1.3) were measured via Surface Plasmon Resonance (SPR) using a Biacore® T200 instrument. The assay temperature was 37° C. and the running buffer was PBS pH 7.4 supplemented with 0.05% Tween-20. Allanti-hILT4 antibodies were captured on a CM4 chip with pre-immobilized protein A/G (Pierce Thermo Scientific catalog number 21186). Three different lots of 21D9 were used as controls. Monomeric human ILT4 was injected as analyte. Appropriate concentrations were used for analysis: For 10F10.1 and 10F10.3 a, 3-fold dilution series with a hILT4 top concentration of 1.4 μM was analyzed. For 10F10, two independent hILT4 dilution series were analyzed: 1.4 μM top concentration, 5-fold dilutions and 470 nM, 3-fold dilutions. For all other antibodies, a hILT4 top concentration of 94 nM and a 5-fold dilution series were used. The hILT4 used in this experiment, comprising the extracellular region of hILT4 linked to a His-Avi tag, consists of the following amino acid sequence:

```
(hILT4-His-Avi tag; SEQ ID NO: 119)
QTGTIPKPTLWAEPDSVITQGSPVTLSCQGSLEAQEYRLYREKKSASWIT

RIRPELVKNGQFHIPSITWEHTGRYGCQYYSRARWSELSDPLVLVMTGAY

PKPTLSAQPSPVVTSGGRVTLQCESQVAFGGFILCKEGEEEHPQCLNSQP

HARGSSRAIFSVGPVSPNRRWSHRCYGYDLNSPYVWSSPSDLLELLVPGV

SKKPSLSVQPGPVVAPGESLTLQCVSDVGYDRFVLYKEGERDLRQLPGRQ

PQAGLSQANFTLGPVSRSYGGQYRCYGAHNLSSESSAPSDPLDILITGQI

RGTPFISVQPGPTVASGENVTLLCQSWRQFHTFLLTKAGAADAPLRLRSI

HEYPKYQAEFPMSPVTSAHAGTYRCYGSLNSDPYLLSHPSEPLELVVSGP

SMGSSPPPTGPISTPAGPEDQPLTPTGSDPQSGLGRHLGSPGGGSGGGSE

QKLISEEDLGHHHHHHGLNDIFEAQKIEWHE.
```

The results are shown in Table 2 and FIG. 16.

TABLE 2

Binding kinetics of anti-hILT4 antibodies to hILT4

| Ligand | Sample | ka (1/Ms) | kd (1/s) | KD (M) | Rmax (RU) | Ligand Level (RU) | app. act. |
|---|---|---|---|---|---|---|---|
| 10F10 | hILT4 | steady state | | 1.8E−08 | 31.2 | 39.4 | 114% |
| 10F10 | hILT4 | 1.6E+06 | 2.3E−02 | 1.4E−08 | 22.3 | 24.7 | 130% |
| 10F10 | hILT4 | steady state | | 1.9E−08 | 20.5 | 24.7 | 120% |
| 10F10 | hILT4 | 1.3E+06 | 2.0E−02 | 1.5E−08 | 30.7 | 39.4 | 112% |
| 10F10.1 | hILT4 | 1.5E+06 | ~7E−02 | 4.6E−08 | 21.3 | 32.8 | 94% |
| 10F10.1 | hILT4 | steady state | | 5.6E−08 | 20 | 32.8 | 88% |
| 10F10.3 | hILT4 | steady state | | 5.2E−08 | 18.8 | 23.5 | 115% |
| 10F10.3 | hILT4 | 1.7E+06 | ~8E−02 | 4.7E−08 | 20.1 | 23.5 | 123% |
| 21A5 | hILT4 | 1.2E+06 | 1.7E−04 | 1.4E−10 | 27.1 | 31 | 126% |
| 21A5.a | hILT4 | 1.1E+06 | 1.9E−04 | 1.7E−10 | 27.9 | 41 | 98% |
| 21D9.b | hILT4 | 3.1E+06 | 1.1E−03 | 3.4E−10 | 24.9 | 39.8 | 90% |
| 21D9.c | hILT4 | 3.0E+06 | 1.2E−03 | 4.2E−10 | 27.4 | 40.7 | 97% |
| 21D9.d | hILT4 | 3.1E+06 | 1.1E−03 | 3.5E−10 | 26.3 | 45.3 | 84% |
| 21D9.e | hILT4 | 3.1E+06 | 1.2E−03 | 3.9E−10 | 25.4 | 39.3 | 93% |
| 21D9_3610 | hILT4 | 3.3E+06 | 1.0E−03 | 3.1E−10 | 14.3 | 27.5 | 75% |
| 21D9_3848 | hILT4 | 3.2E+06 | 1.0E−03 | 3.2E−10 | 15.8 | 44.1 | 52% |
| 21D9_LC2_4313 | hILT4 | 3.0E+06 | 1.1E−03 | 3.7E−10 | 27.8 | 40.8 | 98% |

The results show that the 4 reversion mutants of 21D9 have similar kinetics and affinities. 21A5 and its reversion mutant 21A5.a also have similar kinetics and affinities. However, the two 10F10 reversion mutants, 10F10.1 and 10F10.3, have slightly faster dissociation rates than their parent 10F10, driving an about 3 fold loss in overall affinity. Dissociation rates of 10F10.1 and 10F10.3 are too fast to be determined with high confidence.

Example 3: Binding of Anti-hILT4 Antibodies to hILT4-Expressing Cells

This Example describes the binding characteristics of anti-hILT4 antibodies to CHO cells transfected with hILT4 and to human monocytes expressing hILT4.

CHO cells were transfected with hILT4 and were stained with individual anti-hILT4 antibodies 2H2, 10F10 (“10F10 WT”), 21A5 (“21A5 WT”), 21A5.a, 21D9 (“21D9 WT”) and 21D9e (all in the context of IgG1.3) that were titrated from 20 μg/ml by 3-fold serial dilution and then subjected to a PE-conjugated secondary anti-human IgG. FACS analysis for geometric mean fluorescence intensity (GMFI) was used to determine the $EC_{50}$.

Figure 17:
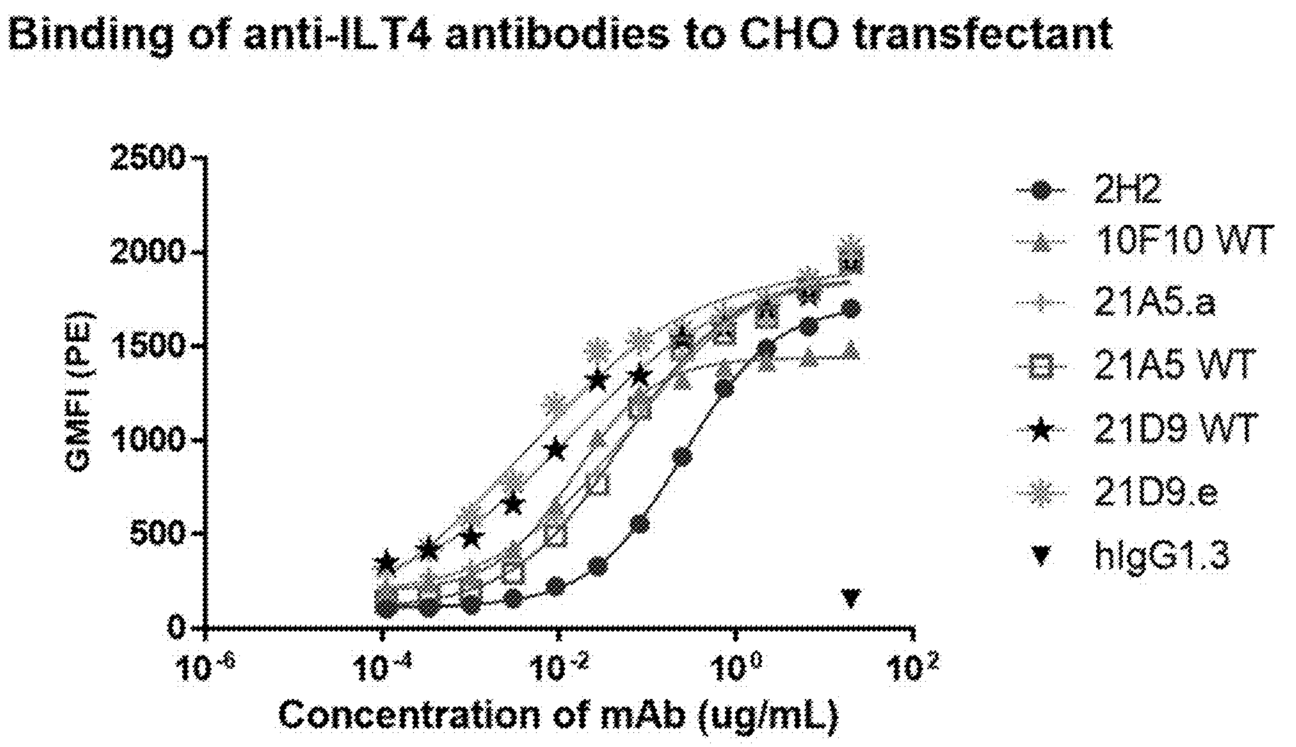
FIG. 17 shows binding of anti-hILT4 antibodies 2H2, 10F10 wildtype (WT, i.e., parent antibody), 21A5.a, 21A5 WT, 21D9 WT, 21D9e and isotype control hIgG1.3 to hILT4 transfected CHO cells, as a function of antibody concentration, and as determined by flow cytometry. $EC_{50}$ values are provided below a graph of the binding data.
Figure 18A:
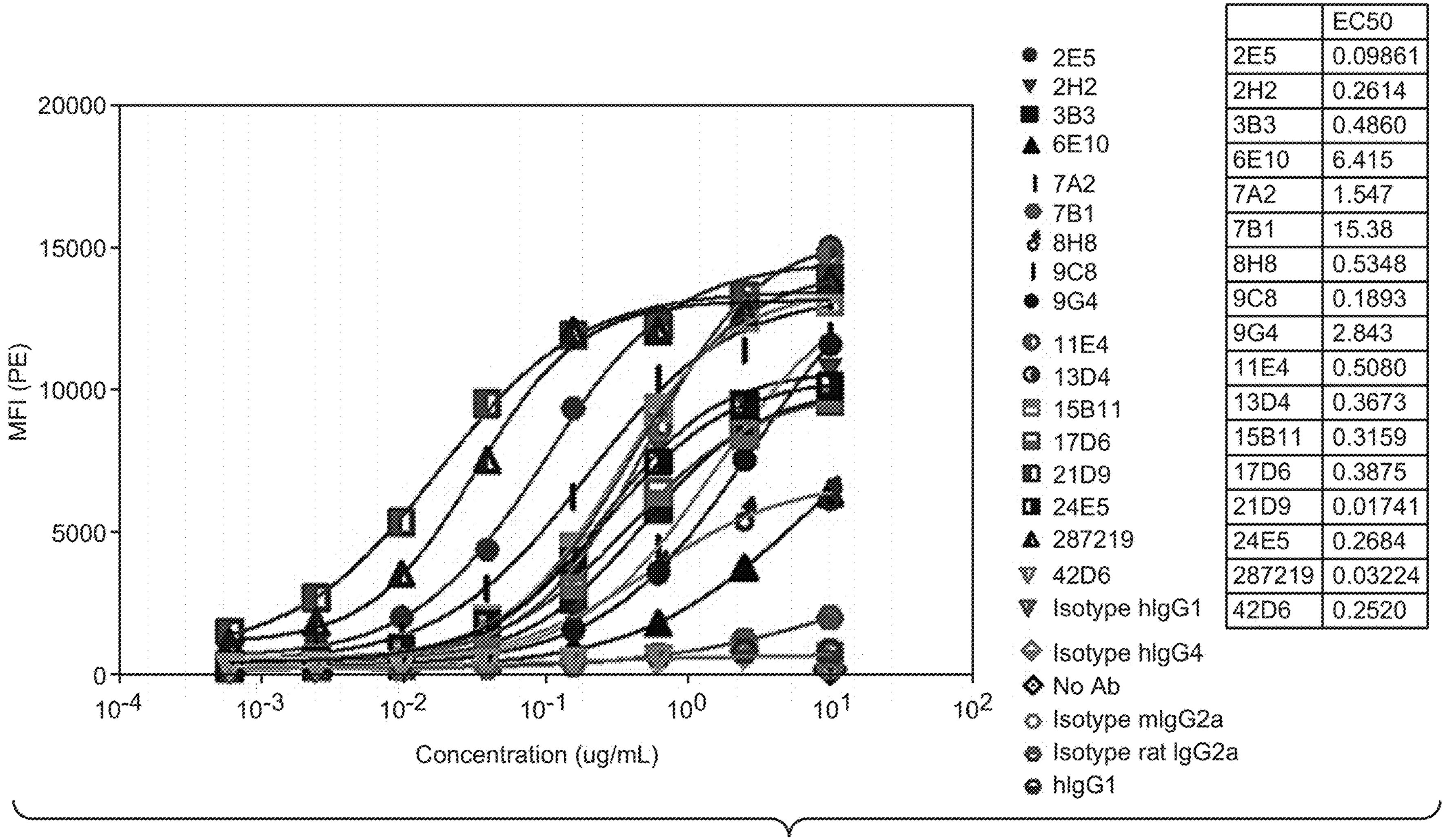
FIG. 18A shows binding of the specified anti-hILT4 antibodies and isotype controls to hILT4 transfected CHO cells, as a function of antibody concentration, and as determined by flow cytometry. $EC_{50}$ values are provided to the right of the binding data graph.

The binding curves and EC values are shown in FIGS. 17 and 18A.

Figure 18B:
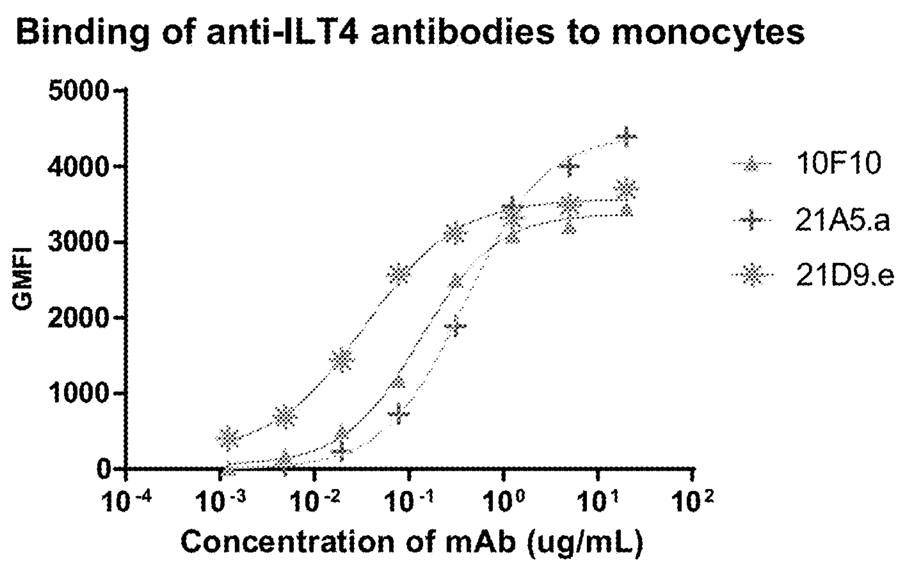
FIG. 18B shows binding of anti-hILT4 antibodies to human monocytes isolated from a normal healthy donor's peripheral blood. The antibody species are listed next to the graph and the EC50 values are provided in the tables just below the graph.

In FIG. 18B, monocytes selected from a normal healthy donor’s peripheral blood were stained with individual anti-ILT4 antibodies conjugated to Alexa67. Antibodies were titrated from 20 ug/mL by 3-fold serial dilution, and GMFI was determined by FACS analysis for calculating EC50 (shown in the table below the graph).

Example 4: Selectivity of Anti-ILT4 Antibodies Against Members of LILRA/B Family ILT4 is a member of a family of related receptors, also referred to as the LILRA and LILRB family. In this Example, the binding of hILT4 antibodies to various members of the LILRA/LILRB family was measured.

Individual ILT family members were overexpressed in 293T cells. Each transfectant was stained with 20 μg/ml of anti-ILT4 antibodies followed by 1 μg/ml of anti-human IgG secondary mAb. Binding of the antibodies to each transfectant was measured by flow cytometry. In a second experiment, LILRA1, LILRA3 and ILT4 transfectants were incubated with various concentrations of 21A5 and 21A5.a.

Figure 19A:
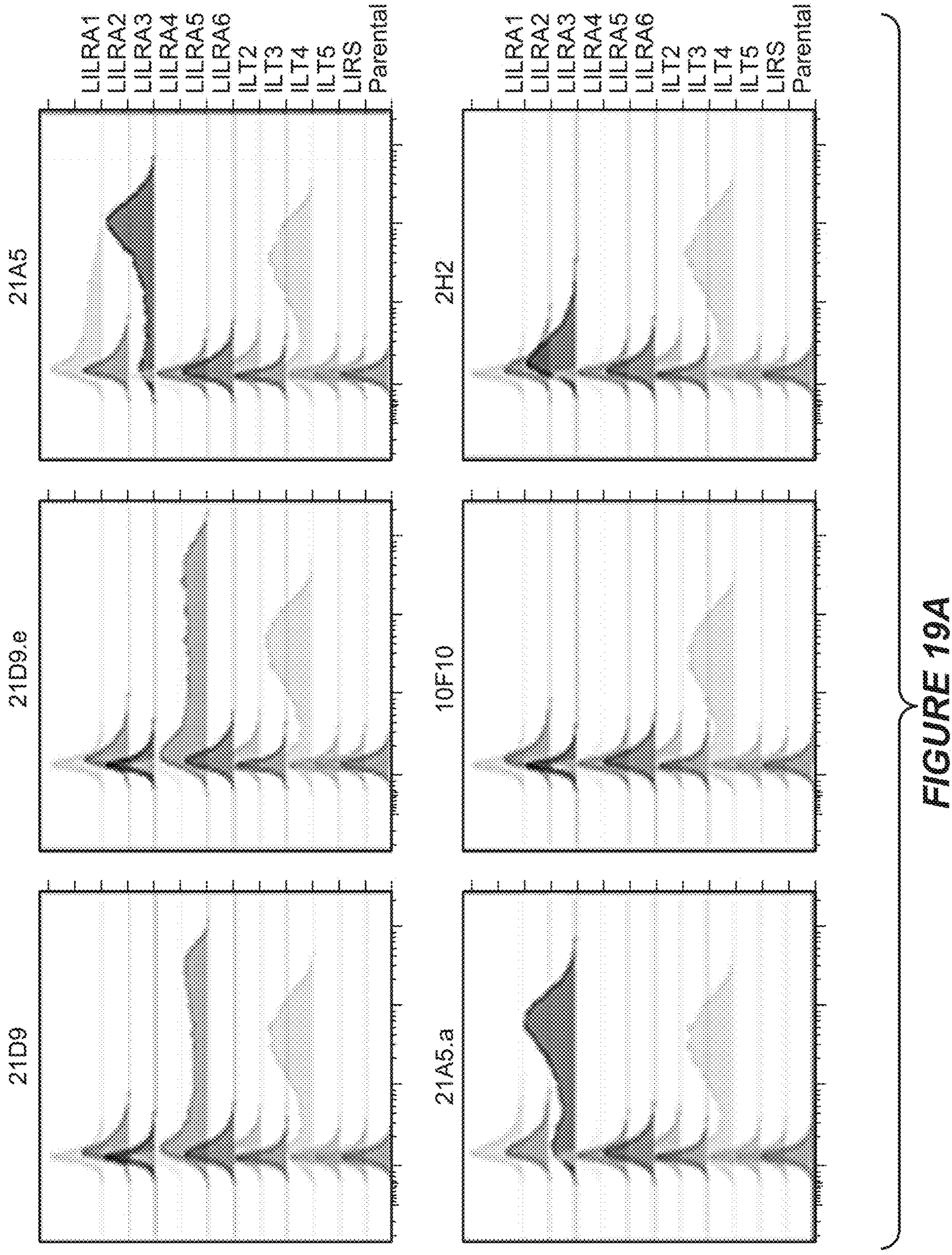
FIG. 19A shows flow cytometry diagrams of binding of anti-hILT4 antibodies 21D9, 21D9.e, 21A5, 21A5.a, 10F10 and 2H2 (left to right) to human LILRA1, human LILRA2, human LILRA3, human LILRA4, human LILRA5, human LILRA6, human ILT2, human ILT3, human ILT4, human ILT5 and human LIR8 (top to bottom).
Figure 19B:
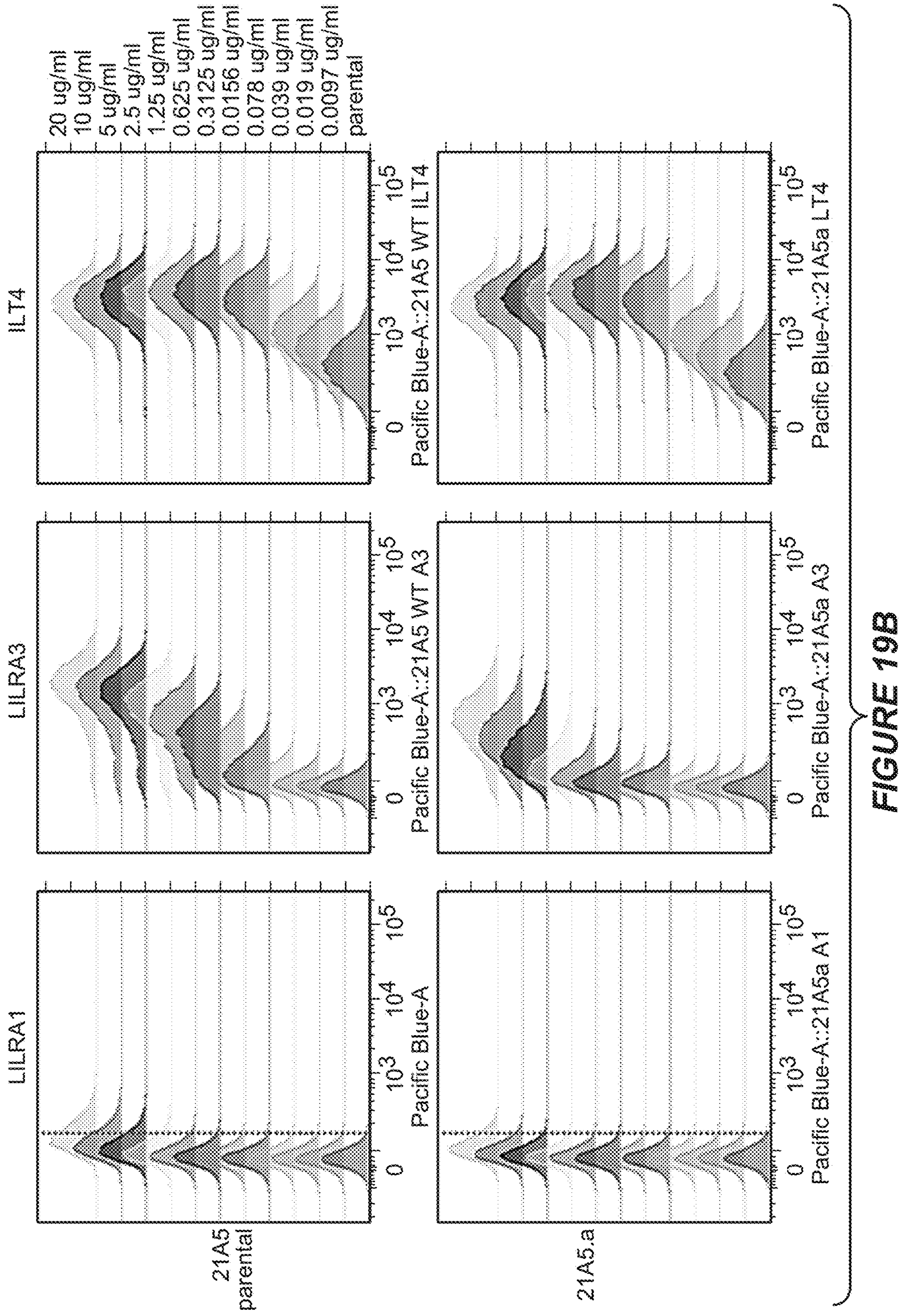
FIG. 19B shows flow cytometry diagrams of binding of anti-hILT4 antibodies 21A5 and germline reversion mutant 21A5.a to human LIRA1, LIRA3 and ILT4.

The results, which are shown in FIGS. 19A and B and in Table 3, indicate that anti-hILT4 antibodies bind mostly selectively to hILT4, relative to other LILRA and LILRB family members. LILRA3 is the only secreted protein in the LILRA/B family. More specifically, 21D9 and 21D9.e do not bind significantly to LILRA1, LILRA2, LILRA3, LILRA4, LILRA6, ILT2, ILT3, ILT5 and LIRE, and only weak binding to LILRA5.

TABLE 3

Selectivity profile of anti-ILT4 antibodies at 20 μg/ml

| | LILRA1 | LILRA2 | LILRA3 | LILRA4 | LILRA5 | LILRA6 | ILT2 | ILT3 | ILT4 | ILT5 | LIR8 | Parental |
|---|---|---|---|---|---|---|---|---|---|---|---|---|
| 21D9 | | | | | + | | | | +++ | | | |
| 21D9.e | | | | | + | | | | +++ | | | |
| 21A5 | | | +++ | | | | | | +++ | | | |
| 21A5.a | | | ++ | | | | | | +++ | | | |
| 2H2 | | | | | | | | | +++ | | | |
| 10F10 | | | | | | | | | +++ | | | |

“Parenteral” in Table 3 refers to the parental cell line in which the LILRA or LILRB molecules were expressed.

Cross-reactivity towards other family members of LILRA was further tested as follows. An antibody titration flow cytometry binding assay was performed to determine the binding potency of 21D9, 21D9.e, 21A5 and 21A5.a to hILT4 and their respective cross-reacting ILT molecules.

$EC_{50}$ was determined using the nonlinear regression formula from the GraphPad Prism® software.

Figure 20A:
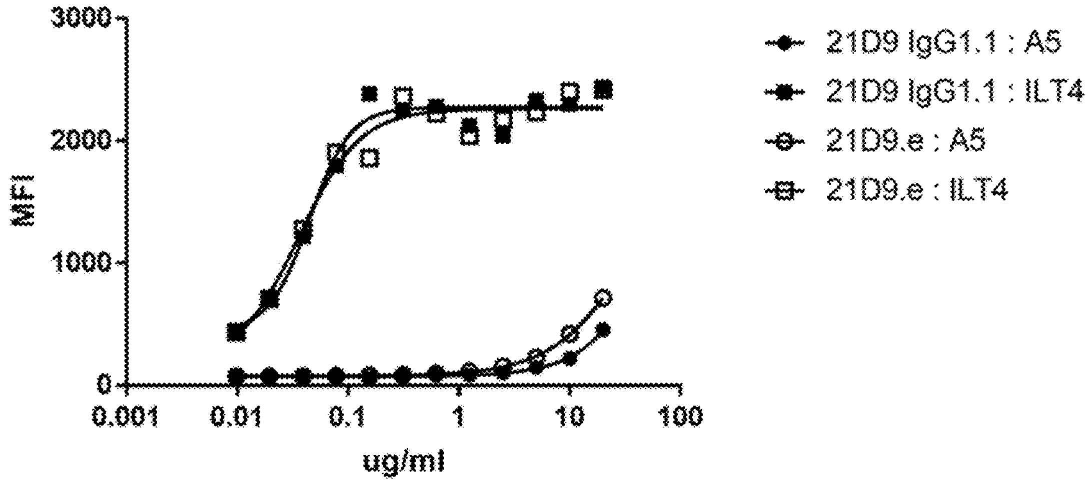
FIGS. 20A and B show the percentage of maximum binding of the specified antibodies 21D9 ("21D9 IgG1.1") and 21D9.e (FIG. 20A) and 21A5 ("21A5WT") and 21A5.a (FIG. 20B) to the specified human LILRA/LILRB family members, LILRA5, ILT4 in FIG. 20A and LILRA1, LILRA3, and ILT4 in FIG. 20B, as a function of antibody concentration, indicating that the anti-ILT4 antibodies 21D9, 21D9.e, 21A5 and 21A5.a show weak cross-reactivity to other LILRA family members.
Figure 20B:
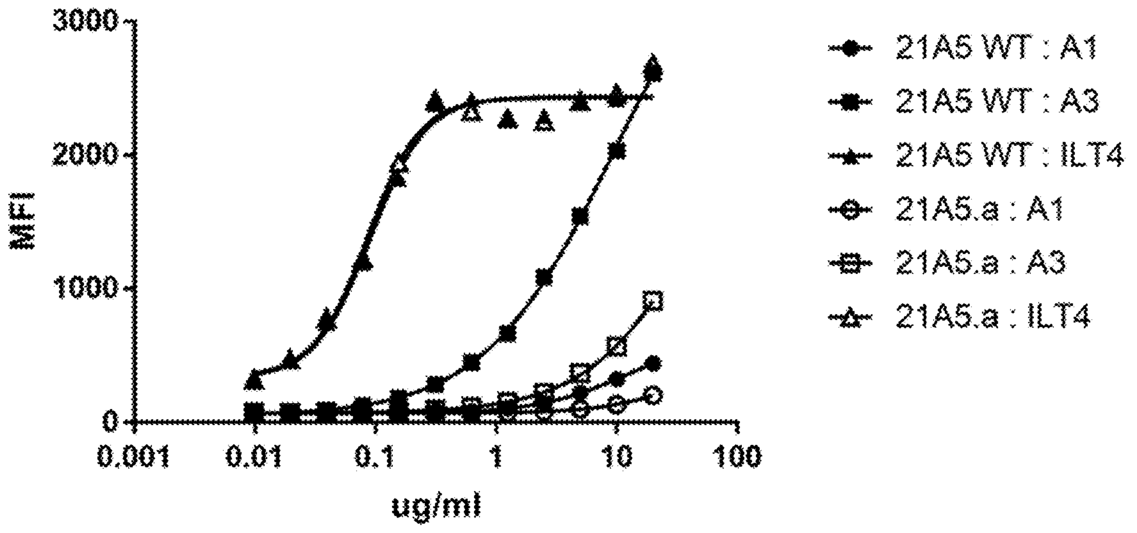
Figures 21A, 21B:
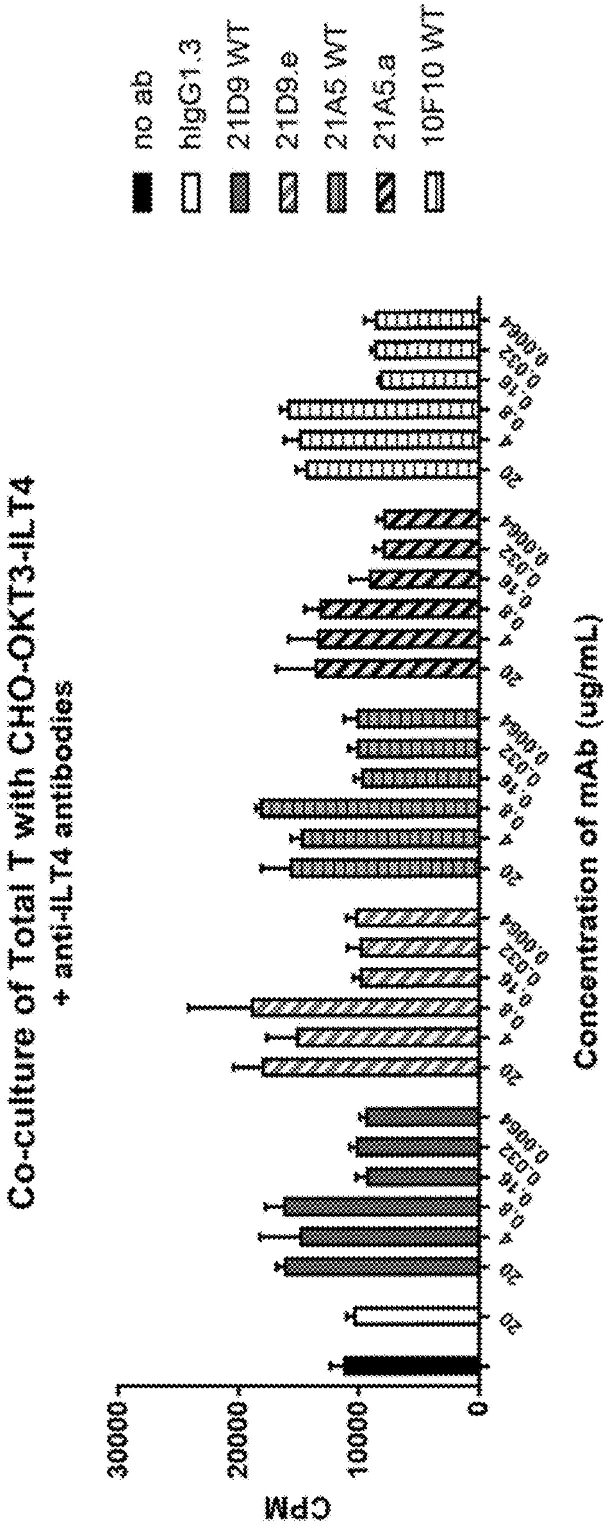
FIGS. 21A-D show T cell activity of anti-hILT4 antibodies.
Figures 21C, 21D:
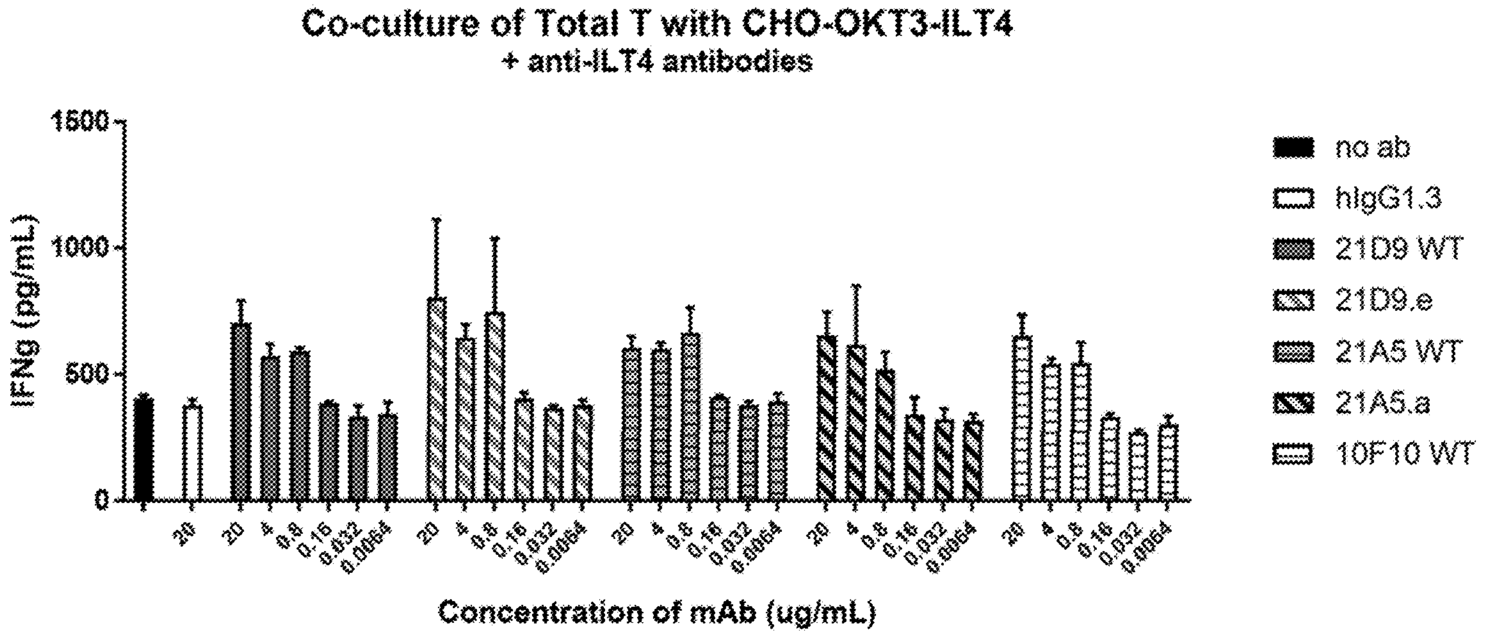
Figure 22A:
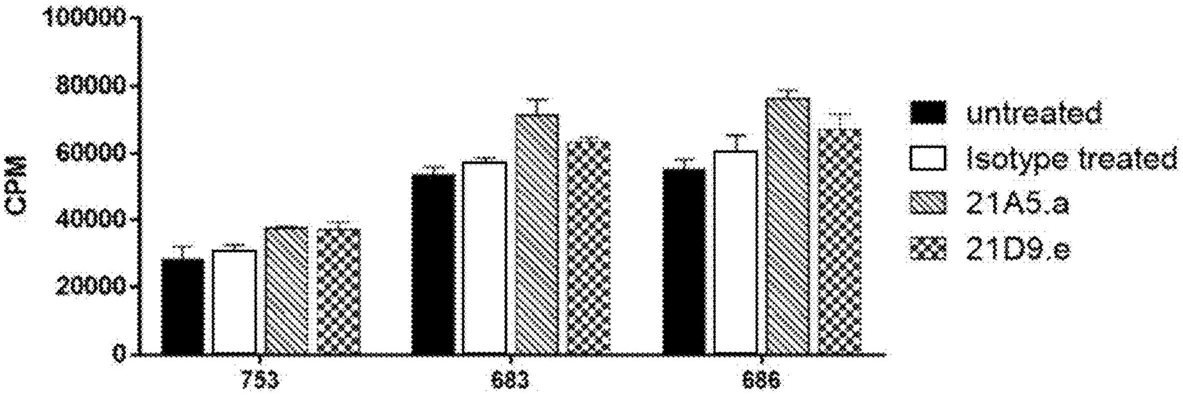
FIGS. 22A-D show proliferation (FIGS. 22A and 22C) and IFNγ production (FIGS. 22B and 22D) of T cells in an allo-MLR (mixed lymphocyte reaction) of monocyte-derived dendritic cells (MoDC) co-cultured with T cells. Anti-hILT4 antibody 21A5.a or 21D9.e (FIGS. 22A and 22B) or 2H2 or 21D9 (FIGS. 22C and 22D), or isotype control or no antibody ("untreated") were added during monocyte differentiation to MoDC and each antibody was not added during the allo-MLR assay.
Figure 22B:
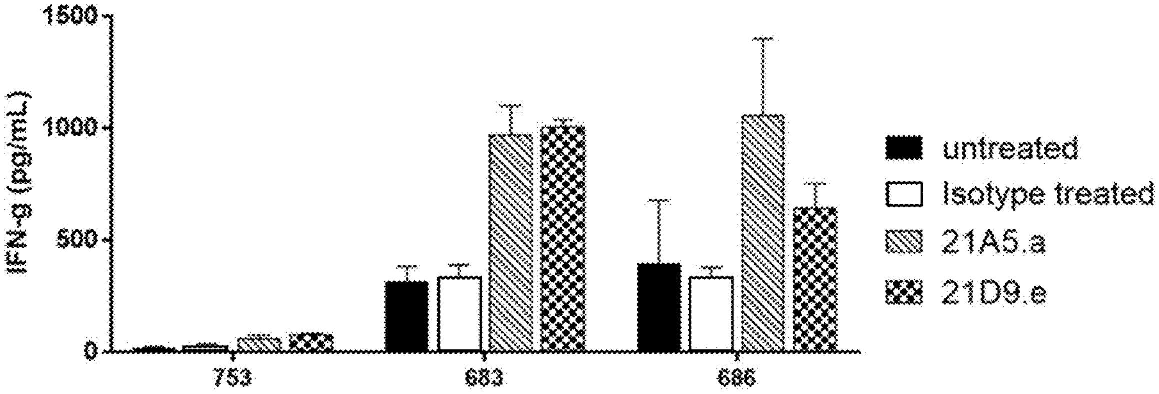
Figure 22C:
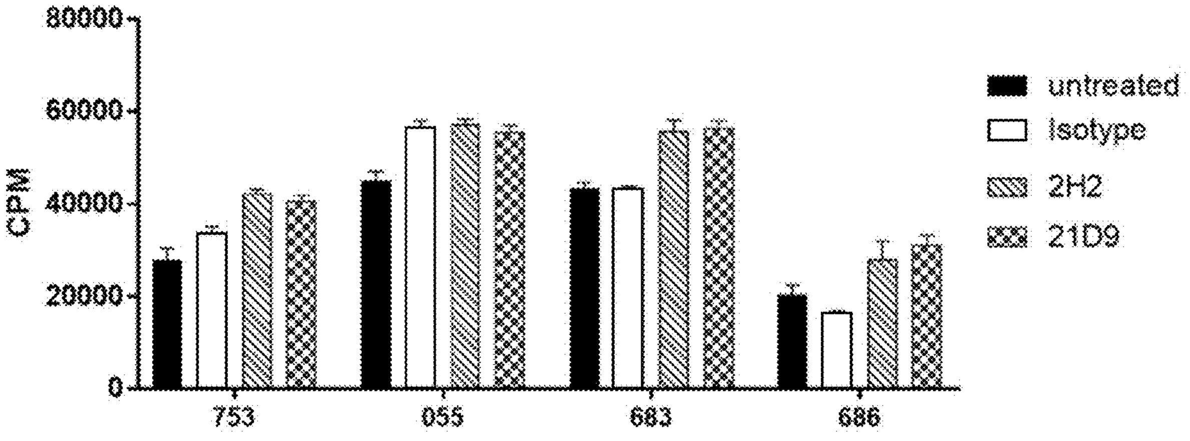
Figure 22D:
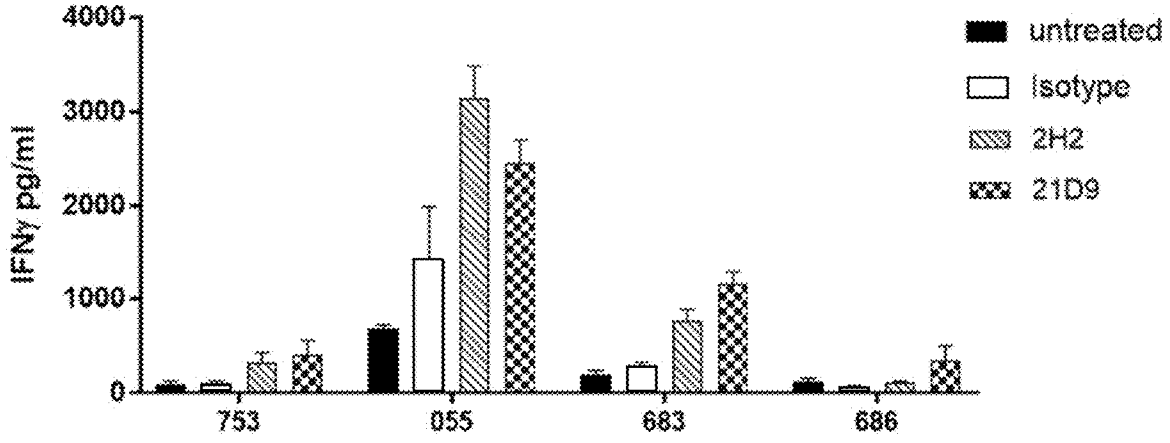
Figure 23A:
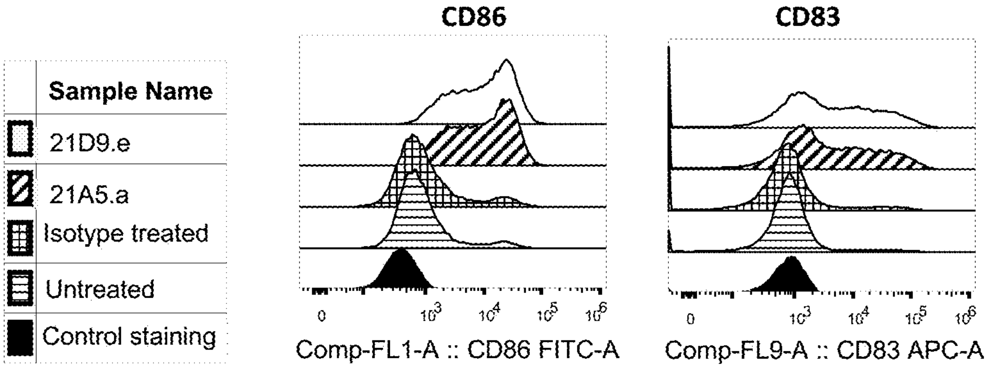
FIGS. 23A-D show expression levels of CD83 and CD86 on monocyte-derived dendritic cells (MoDC). Anti-hILT4 antibodies 21D9.e, 21A5.a (FIG. 23A), 21A5, 10F10, 21D9 (FIG. 23B) or 2H2 (FIGS. 23C and 23D) or isotype control were incubated during the monocyte differentiation to MoDC or left untreated (no antibody).
Figure 23B:
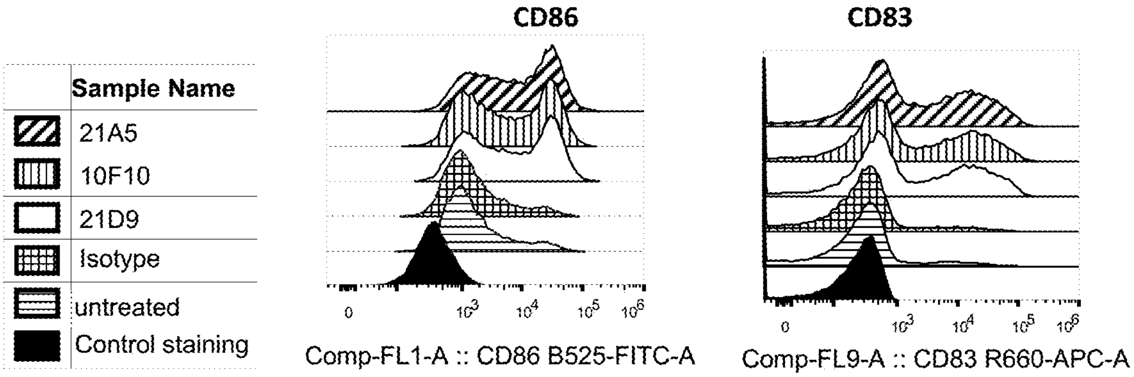
Figure 23C:
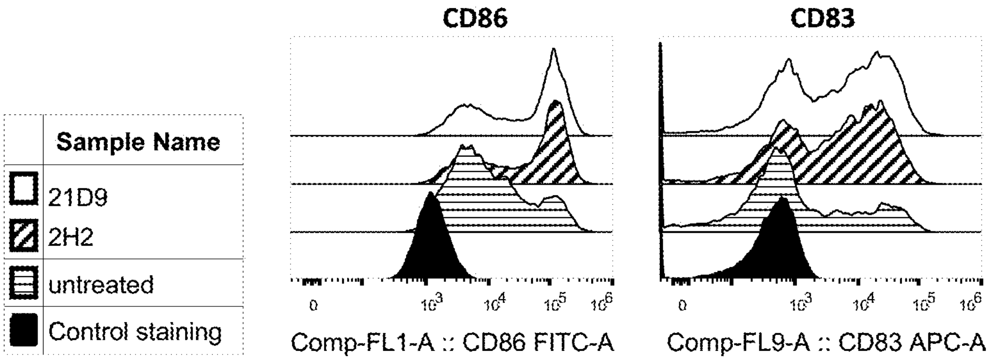
Figure 23D:
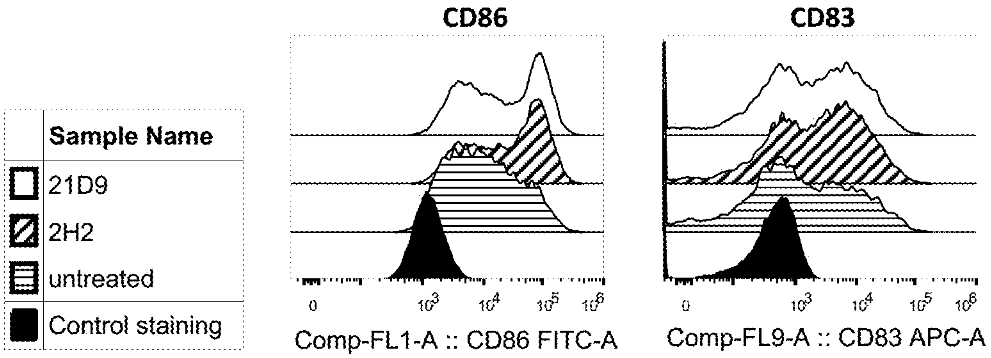

The results, which are shown in Table 4 and FIG. 20, show that anti-ILT4 antibodies 21D9, 21D9.e, 21A5 and 21A5.a show weak cross-reactivity to other family members of LILRA: 21D9 and 21D9.e to LILRA5 and 21A5 and 21A5.a to LILRA1 and LILRA3.

TABLE 4

Summary of $EC_{50}$ binding potency of anti-ILT4 antibodies to cross-reacting ILTs (μg/ml)

| | 21D9 | 21D9.e | 21A5 | 21A5.a |
|---|---|---|---|---|
| LLT4 | 0.0460 | 0.039 | 0.091 | 0.085 |
| LILRA5 | ~29964 | ~312.6 | No binding | No binding |
| LILRA1 | No binding | No binding | 12.53 | 49.82 |
| LILRA3 | No binding | No binding | 9.18 | 52.94 |

21D9 and 21D9.e bind to hILT4 with high affinity, but do not bind significantly to hLILRA1, hLILRA2, hLILRA3, hLILRA4, hLILRA6, hILT2, hILT3, hILT5 and hLIR8, and only weakly to hLILRA5. Thus, 21D9 and 21D9.e are much more specific in binding to hILT4 relative to other hLILRA and hLIRB family members than other anti-ILT4 antibodies, such as clone 287219 from R&D Systems, which is cross-reactive with ILT5 (LILRB3) and LILRA6.

Example 5: Anti-hILT4 Antibodies Potentiate T Cell Responses

The effect of the anti-hILT4 antibodies on T cell responses, particularly T cell proliferation and interferon-gamma (IFNγ) T cell secretion, was determined as follows. The cytoplasmic truncated hILT4 was transfected into a CHO cells expressing a low level of single-chain variable fragment of anti-CD3 antibody (CHO-OKT3 cells). The transfected cell line was designated as CHO-OKT3-ILT4. Total T cells isolated from human PBMCs were co-cultured with irradiated (growth arrested) CHO-OKT3-ILT4 cells at a 4:1 ratio. Anti-ILT4 antibodies 21D9 ("21D9 WT"), 21D9.e, 21A5 ("21A5 WT"), 21A5.a and 10F10 ("10F10 WT") were titrated from 20 μg/mL by 5-fold serial dilution, and incubated for 3 days at 37C. Supernatant was harvested to assess IFNγ levels by ELISA, and the plates were pulsed overnight with $^3$H thymidine to assess proliferation by thymidine incorporation.

The results, which are shown in FIGS. 21A-D, indicate that anti-ILT4 antibodies 21D9, 21D9.e, 21A5, 21A5.a and 10F10 stimulate T cell proliferation and IFNγ secretion in a dose dependent manner. No significant differences in activity were found between these antibodies in this assay.

Example 6: Pre-Treatment of Monocytes with Anti-ILT4 Antibodies During Differentiation Results in Monocyte-Derived Dendritic Cells (MoDC) that are More Stimulatory to Allogeneic T Cells CD14+ monocytes were isolated from human PBMC using StemCell EasySep® Human Monocyte Isolation Kit, plated at 1 million cells per mL, and differentiated into monocyte-derived immature DC (Mo-iDC) in RPMI culture medium supplemented with 50 ng/mL GM-CSF and 100 ng/mL IL-4 for six or seven days. During the differentiation, the cells were incubated with anti-ILT4 or isotype antibody or left untreated. After the cells were differentiated to Mo-iDC, they were washed to remove anti-ILT4 antibodies, GM-CSF and IL-4, and were further activated to matured dendritic cells (DC (Mo-mDC) in the presence of 50 ng/mL of CD40 agonistic antibody. The matured DC (Mo-mDC) were set up for an allogeneic mixed leukocyte reaction assay (allo-MLR) by co-culturing them with T cells at 1:10 ratio (Mo-mDC:T) for 5 days. The cell supernatant was harvested at the end of the allo-MLR for measuring IFNγ by ELISA, and T cell proliferation was assessed by $^3$H-thymidine incorporation of the final 16 hours.

The results of separate assays, which are shown in FIG. 22, indicate that CD4+ T cell proliferation (FIGS. 22A and C) and IFNγ secretion (FIGS. 22B and D) in an allo-MLR with MoDC assay are enhanced when the MoDC are differentiated from monocytes in the presence of anti-ILT4 antibodies 21A5.a or 21D9.e. Monocytes from two different donors were used in the separate assays.

Example 7: Monocyte-Derived Dendritic Cells (MoDC) Differentiated from Anti-ILT4 Antibody Primed Monocytes have Increased Expression of Costimulatory or Maturation Molecules CD14+ monocytes were isolated from human PBMC using StemCell EasySep® Human Monocyte Isolation Kit, plated at 1 million cells per mL, and differentiated into monocyte-derived immature dendritic cells (Mo-iDC) in RPMI culture medium supplemented with 50 ng/mL GM-CSF and 100 ng/mL IL-4 for six or seven days in presence of anti-ILT4 antibodies 21D9.e, 21A5.a, 21A5, 10F10, 21D9, 2H2 or isotype antibody or left untreated. The Mo-iDC were then harvested for staining of cell surface markers CD86 and CD83.

The results, which are shown in FIG. 23, indicate increased expression of CD86 and CD83, a costimulatory and a maturation molecule, respectively, on Mo-iDC when anti-ILT4 antibodies were present during monocyte differentiation to Mo-iDC. Taken together with the results of Example 6, these results show that treating monocytes with anti-hILT4 antibody during monocyte differentiation to MoDC promotes proinflammation of MoDC as shown by upregulation of CD83 and CD86 (FIGS. 23A-D), which consequently triggers enhanced T cell proliferation and IFNγ production from allogeneic T cells in the allo-MLR assay (FIG. 22). By enhancing T cell functions, treatment with anti-hILT4 antibodies may provide for an enhanced anti-cancer immune response.

Figure 24A:
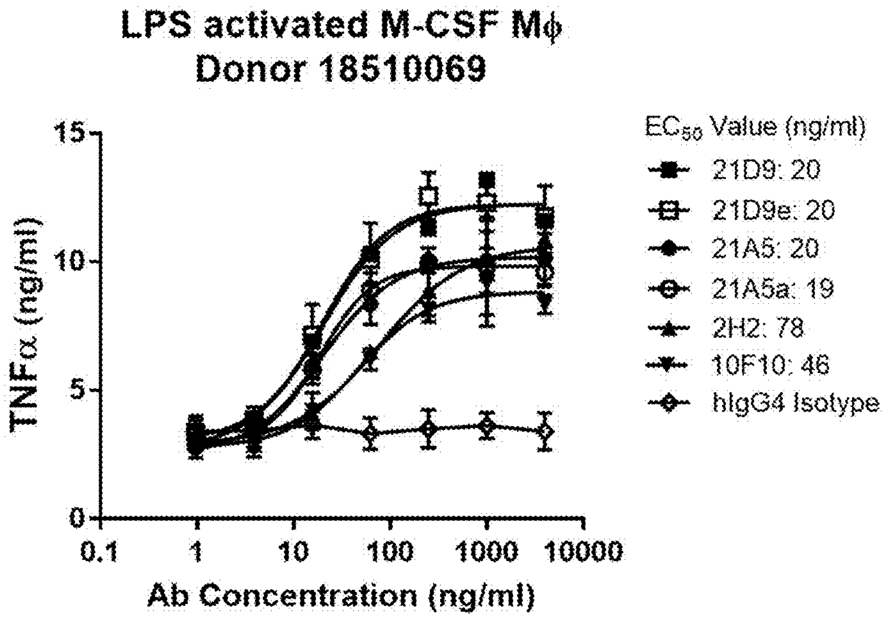
FIGS. 24A and B show the level of TNF-alpha secreted from in vitro differentiated macrophages activated by lipopolysaccharide (LPS) (FIG. 24A) or STING agonist 2'3'-cGAMP (FIG. 24B). Anti-ILT4 antibodies 21D9, 21D9.e, 21A5, 21A5.a, 2H2 and 10F10 or isotype control were included during activation.
Figure 24B:
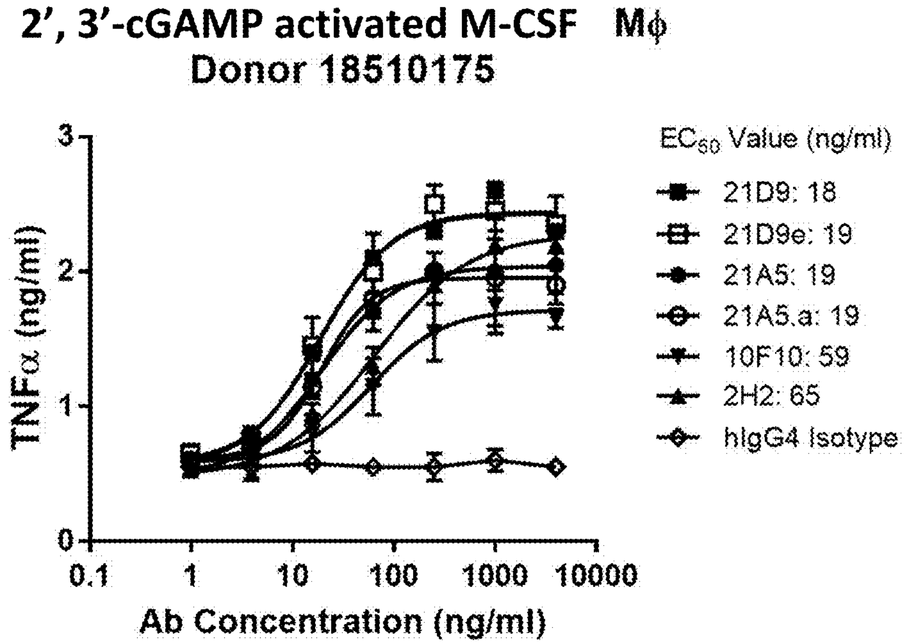

Example 8: Anti-ILT4 Antibodies Potentiate TNFα Secretion from In Vitro Differentiated Macrophages Isolated monocytes from human PBMC were differentiated to macrophages in presence of M-CSF for 5 days. The macrophages were treated with the indicated concentrations (next to their name and as ng/ml) of anti-ILT4 antibodies 21D9, 21D9.e, 21A5, 21A5.a, 2H2 and 10F10 or isotype control in the presence of 10 ng/ml of LPS (FIG. 24A) or 5 μg/ml of 2' 3'-cGAMP STING agonist (FIG. 24B). TNFα production was measured by ELISA 24 hours after treatment and the EC50 values in the presence of each antibody are noted next to the curves.

The results, which are shown in FIG. 24, indicate that the presence of ILT4 antibodies 21D9, 21D9.e, 21A5, 21A5.a, 2H2 and 10F10 potentiated TNFα secretion of the in vitro differentiated macrophages by either LPS or a STING agonist. Therefore, immunosuppressive macrophages show a shift to a more pro-inflammatory phenotype when ILT4 is blocked, which can potentially provide for an enhanced anti-cancer immune response. These results suggest that anti-ILT4 antibodies promote pro-inflammatory polarization towards M1 macrophages.

Example 9: Anti-ILT4 Antibodies Promote CD4 T Cell Responses in Macrophage: CD4+ T Cell Allo-MLR Monocytes isolated from peripheral PBMC were treated with M-CSF for 5 days to differentiate to macrophages. The macrophages were then co-cultured with allogeneic CD4+ T cells that were isolated from a different donor's PBMC, and labeled with CFSE dye. The indicated antibodies at 1 μg/ml (isotype control, anti-ILT4, or anti-PDL1) were included in the allo-MLR co-culture. At day 6, the supernatant was collected for analyzing IFNγ, and CD4+ T cell proliferation and was assessed by FACS based on CFSE dilution.

Figure 25A:
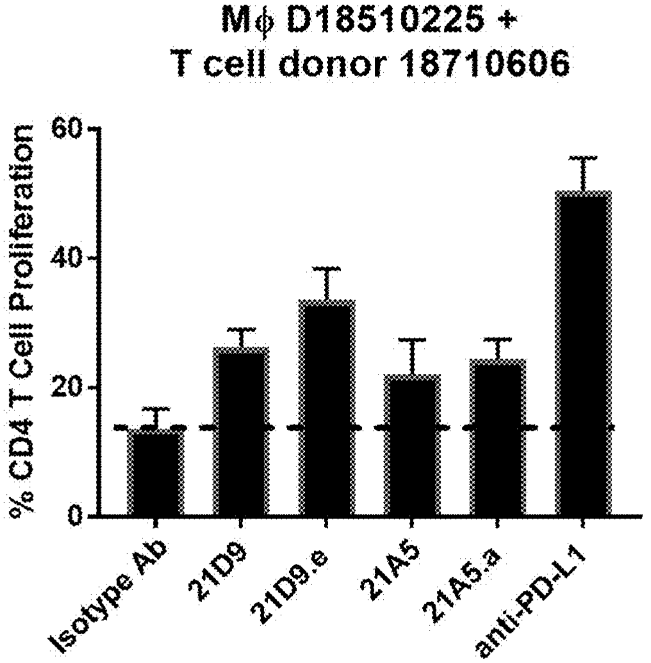
FIGS. 25A and B show the percentage of CD4 T cell proliferation (FIG. 25A) and amount of IFN-gamma (FIG. 25B) produced from the allo-MLR of CD4 T cells co-cultured with in vitro differentiated macrophages in the presence of anti-hILT4 antibodies 21D9, 21D9.e, 21A5 or 21A5.a or anti-PD-L1 antibody or isotype control antibody.
Figure 25B:
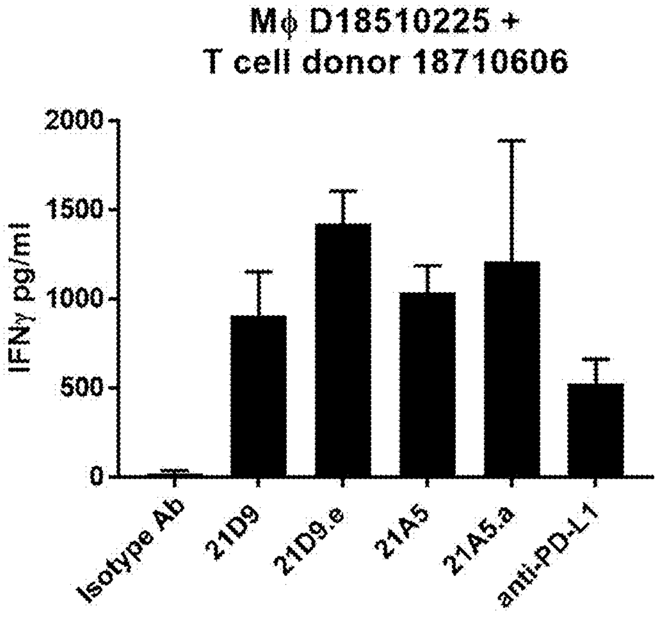
FIG. 25B shows IFNγ production measured by Alphalisa, both as a function of the ILT4 antibodies or controls.

The results, which are shown in FIG. 25A-B, indicate that the presence of the anti-ILT4 antibodies 21D9, 21D9.e, 21A5 or 21A5.a in allo-MLR of in vitro differentiated macrophages and CD4+ T cells promotes CD4+ T cell proliferation (FIG. 25A) and IFNγ production (FIG. 25B). These results suggest that the anti-ILT4 antibodies promote T cell activation either through modulating ILT4 suppressive signaling in macrophages or blocking its direct suppressive activity in T cells.

Example 10: Combined Effect of Anti-ILT4 and Anti-PD-L1 in Macrophages: CD4 T Cell Allo-MLR Monocytes isolated from peripheral PBMC were treated with M-CSF for 5 days to differentiate to macrophages, which were then co-cultured with allogeneic CD4+ T cells that were isolated from an allogeneic donor's PBMC. Anti-ILT4 antibody 21D9 and anti-PD-L1 antibody added alone or together at 10 μg/ml (isotype control, anti-ILT4, anti-PD-L1 or combined anti-ILT4 and anti-PD-L1) were included in the allo-MLR co-culture. At day 6, the supernatant was collected for analyzing IFNγ.

Figure 26A:
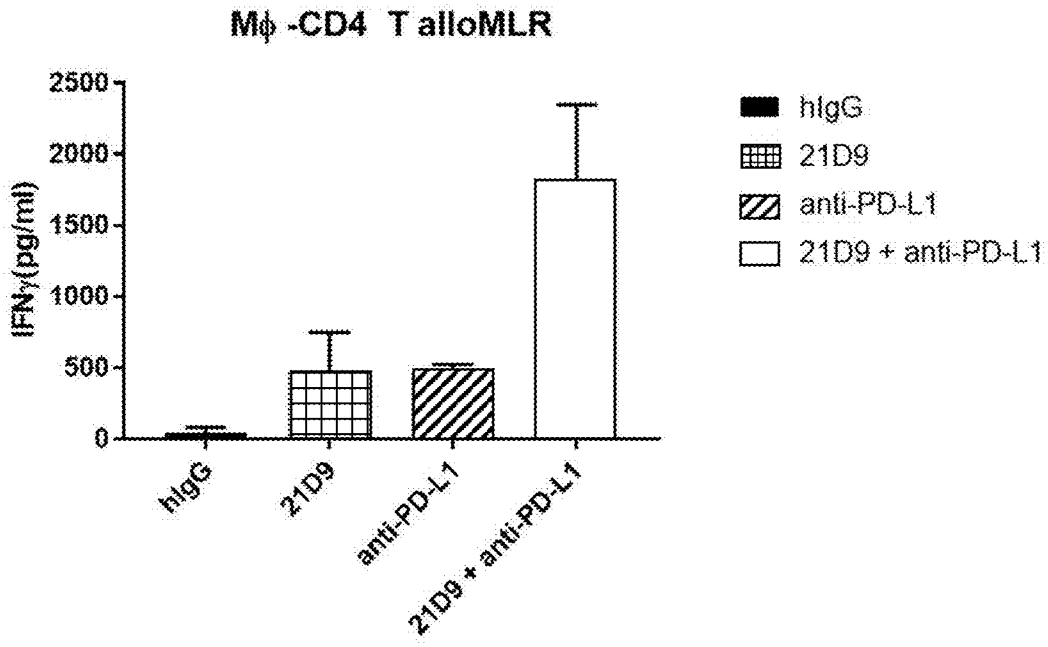
FIGS. 26A and B show that the combination of anti-ILT4 antibody 21D9 with the anti-PD-L1 antibody clone 29E.2A3 enhances the production of IFNγ to a higher level than relative to each antibody alone in a macrophage: CD4 T cell allo-MLR.
Figure 26B:
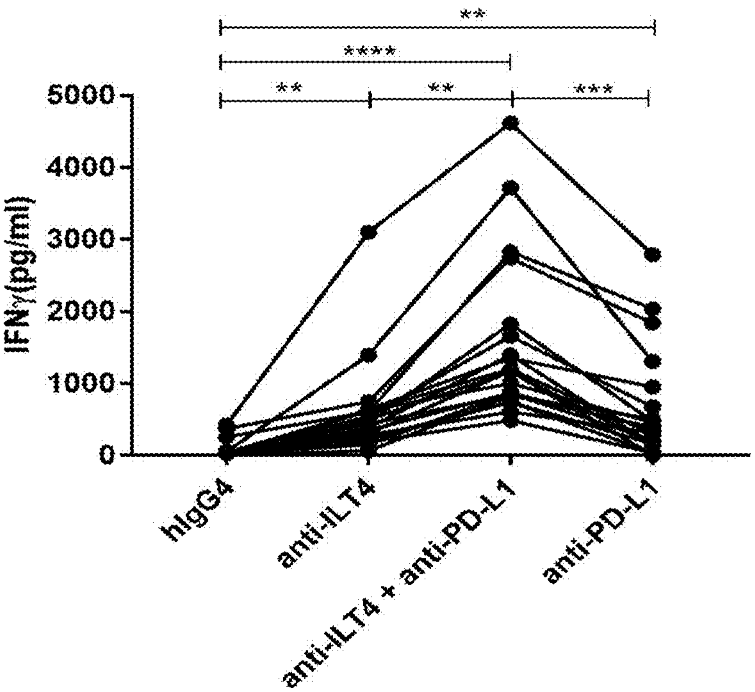
FIG. 26B shows responses from multiple allogeneic pairs, wherein each line denotes one experiment from one allogeneic pair. Statistical analyses were performed using the non-parametric one-way Anova multiple comparison (Friedman test). $^*p<0.05$, $^{}p<0.01$, $^{*}p<0.001$, $^{****}p<0.0001$.

The results, which are shown in FIG. 26, indicate that the combination of the anti-ILT4 antibody 21D9 with the anti-PD-L1 antibody stimulated an enhanced production of IFNγ from the macrophage: CD4+ T cell allo-MLR relative to each antibody alone.

Example 11: HDX Epitope Mapping of Anti-hILT4 Abs 21D9 and 2112 Fabs

HDX-MS was used to identify the areas of hILT4 to which anti-hILT4 antibodies 21D9 and 2H2 bind.

HDX-MS probes protein conformation and conformational dynamics in solution by monitoring the rate and extent of deuterium exchange of backbone amide hydrogen atoms (Huang and Chen (2014) Analytical and Bioanalytical Chem. 406:6541 and Wei et al. (2014) Drug Discovery Today 19:95). The level of HDX depends on the solvent accessibility of backbone amide hydrogen atoms and the protein hydrogen bonds. The mass increase of the protein upon HDX can be precisely measured by MS. When this technique is paired with enzymatic digestion, structural features at the peptide level can be resolved, enabling differentiation of surface exposed peptides from those folded inside, or from those sequestered at the interface of a protein-protein complex. Typically, the deuterium labeling and subsequent quenching experiments are performed, followed by enzymatic digestion, peptide separation, and MS analysis.

Prior to epitope mapping experiments, non-deuteriated experiments were carried out to generate a list of common peptides for recombinant human ILT4 (15 μM) and protein complexes of ILT4 with Fabs 21D9 and 2H2 (1:1 molar ratio). In the HDX-MS experiment, 5 μL of each sample (ILT4 or ILT4 with Fabs) was diluted into 55 μL of D20 buffer (10 mM phosphate buffer, D20, pH7.0) to start the labeling reactions. The reactions were carried out for different periods of time: 1 min, 10 min and 240 min. By the end of each labeling reaction period, the reaction was quenched by adding quenching buffer (6M Urea, 1M TCEP, pH 2.5, 1:1, v/v) and 50 μL of quenched sample was injected into Waters HDX-MS system for analysis. The deuterium uptake levels of common peptic peptides were monitored in the absence/presence of Fabs 21D9 and 2H2.

Figure 27A:
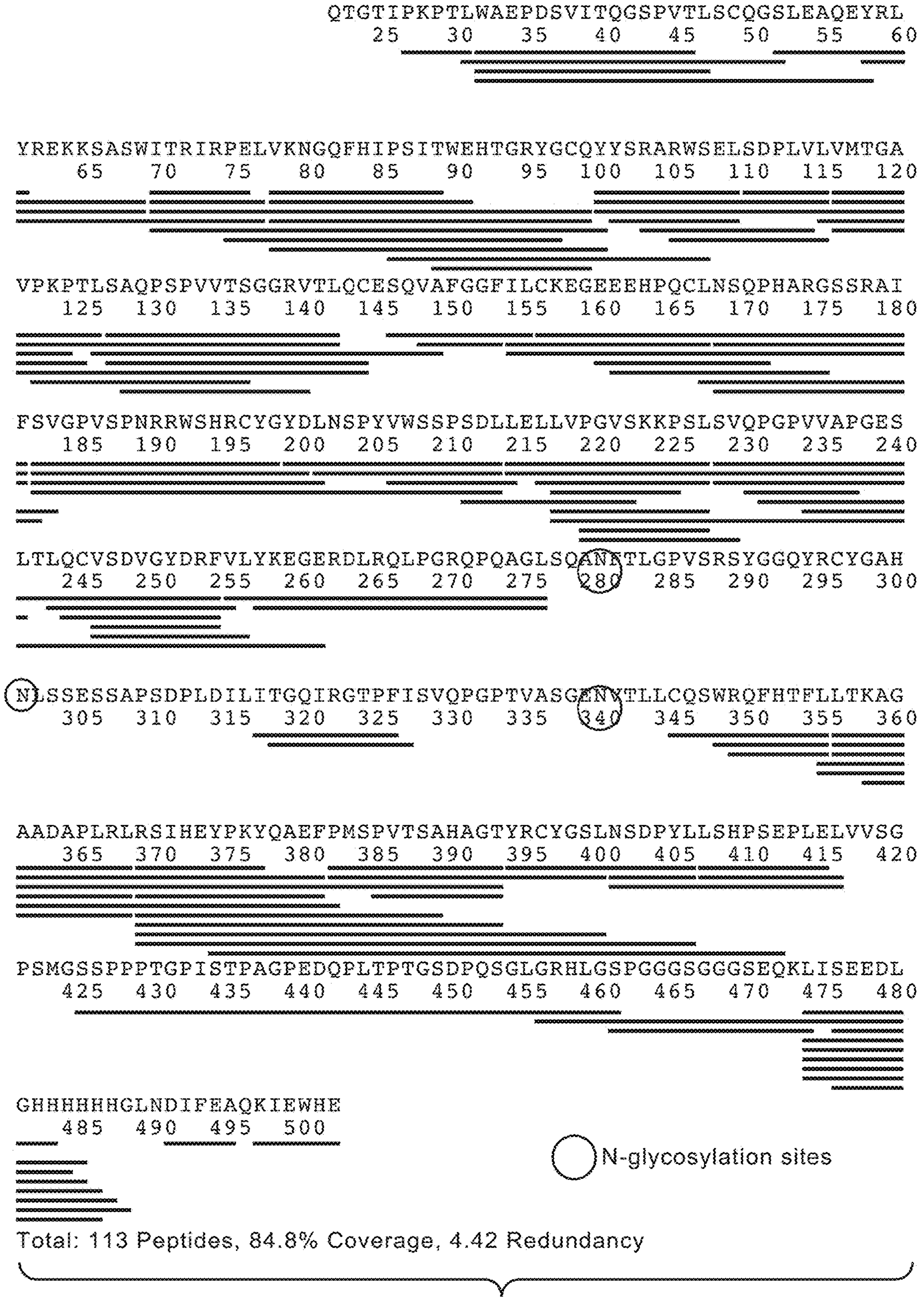
FIGS. 27A, B and C show HDX epitope mapping of anti-hILT4 Abs 21D9 and 2H2 Fabs.
Figure 27B:
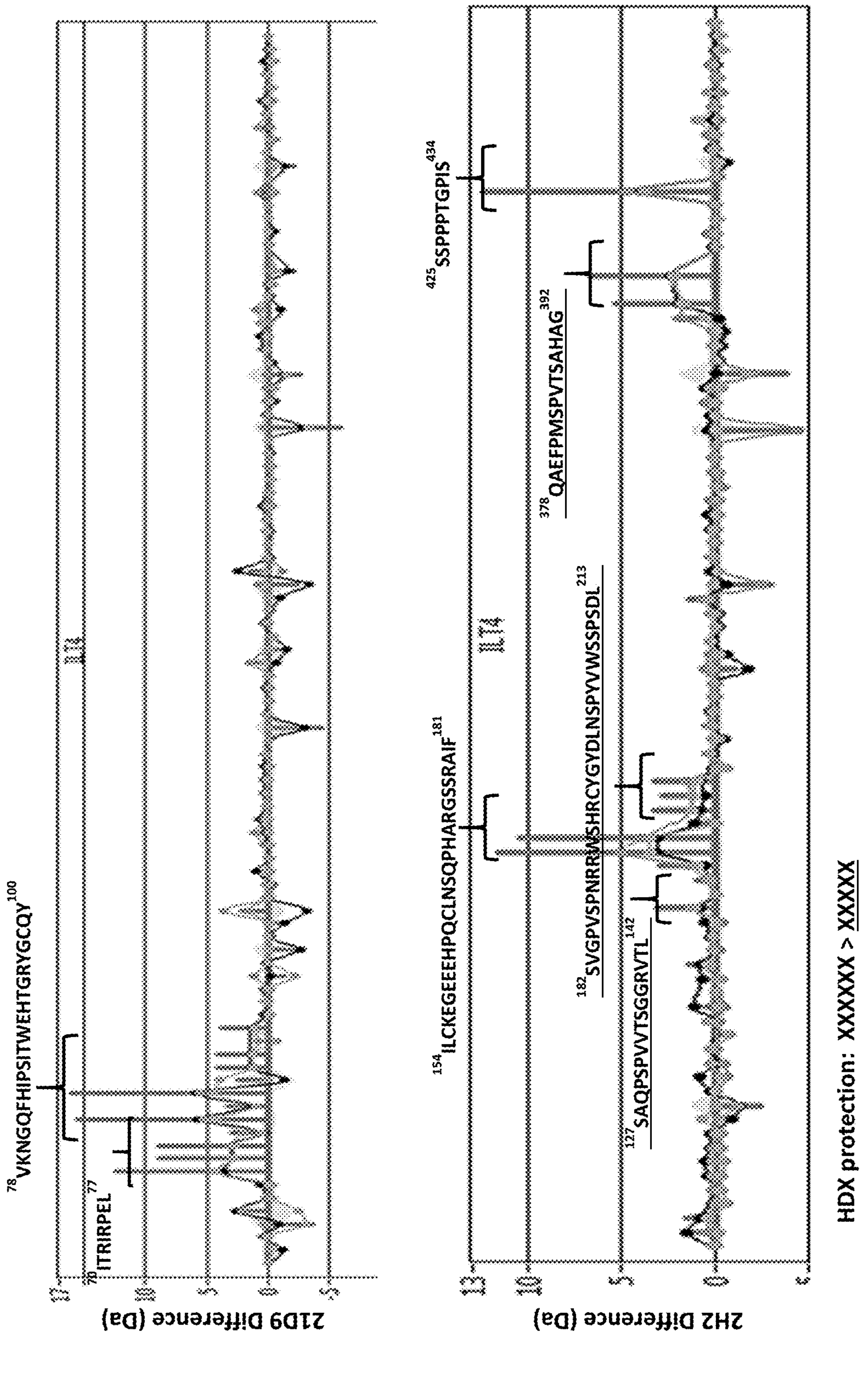
FIG. 27B shows differential HDX of the 21D9 and 2H2 Fabs. Sequences depicted are as follows: SEQ ID NO: 121 for ILT4 residues 78-100 at top left, SEQ ID NO: 120 for residues 70-77 at top, far left, SEQ ID NO: 123 for residues 154-181 at middle left, SEQ ID NO: 124 for residues 425-434 at middle right, SEQ ID NO: 173 for underlined residues 127-142 at lower left, SEQ ID NO: 174 for underlined residues 182-213 at lower middle, and SEQ ID NO: 175 for underlined residues 378-392 at lower right. Of the sequence portions delineated in the figure, those that are underlined have less HDX protection than those that are not underlined, as also noted below the figure drawing.
Figure 28A:
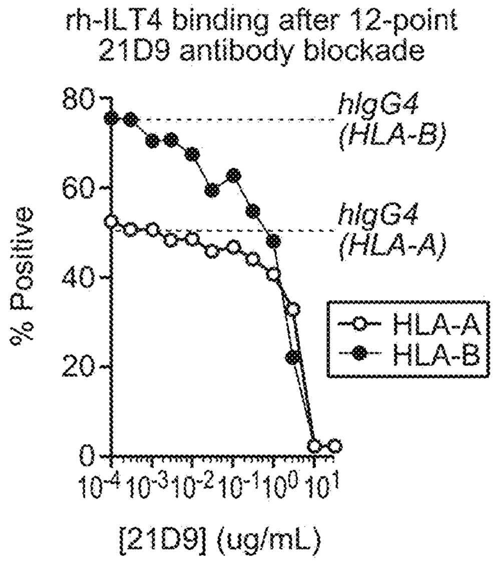
FIGS. 28A, B, C, and D show inhibition of binding of hILT4 to HLA-A and HLA-B by antibodies 21D9 (FIG. 28A), 2H2 (FIG. 28B), 10F10 (FIG. 28C) and 21A5 (FIG. 28D).
Figure 28B:
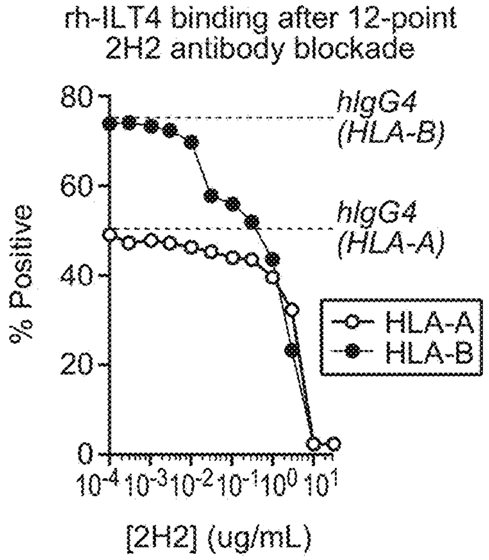
Figure 28C:
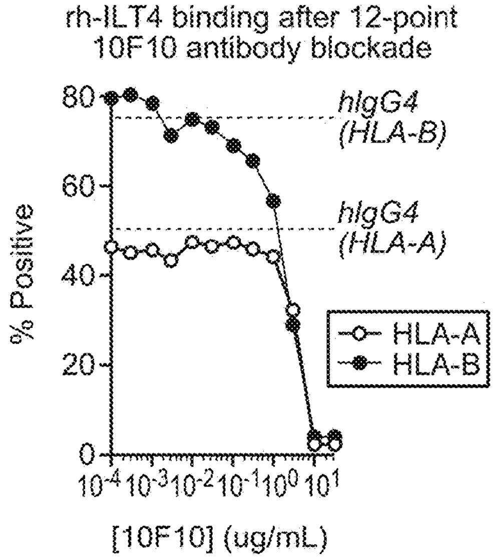
Figure 28D:
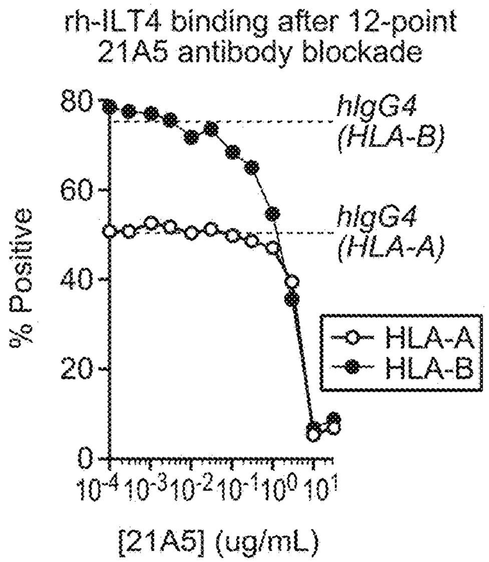
Figure 29A:
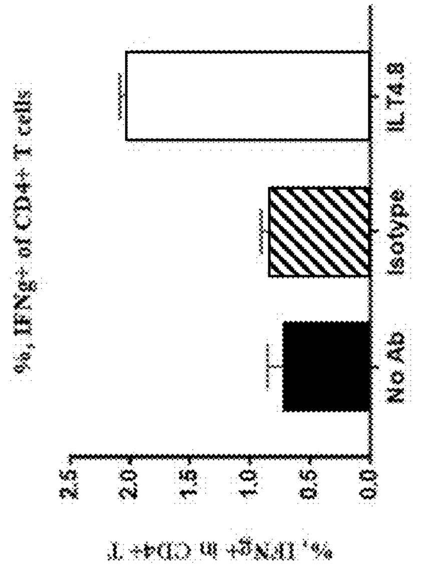
FIGS. 29A-D show that 21D9e.IgG1.3 enhances both IFN-γ and TNF-α secretion by CD4+ and CD8+ T cells, as determined by intracellular IFN-γ and TNF-α staining.
Figure 29B:
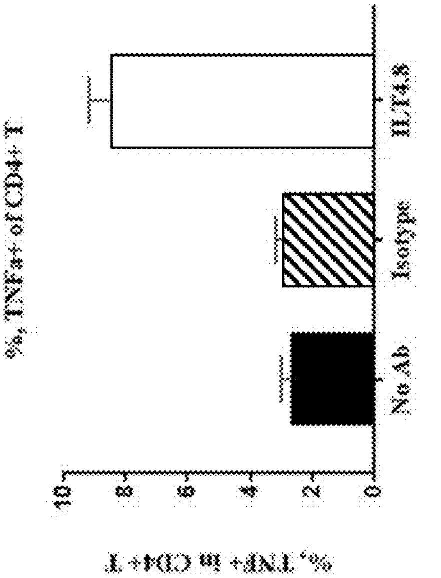
Figure 29C:
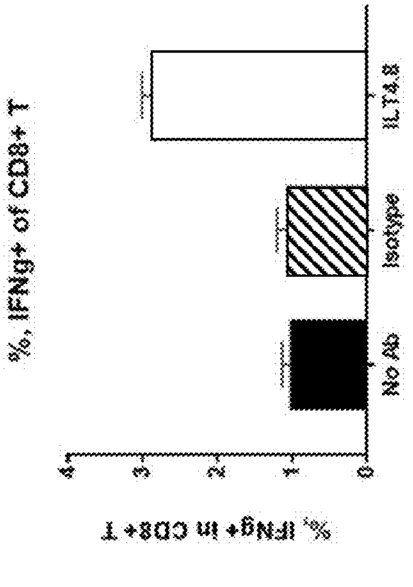
Figure 29D:
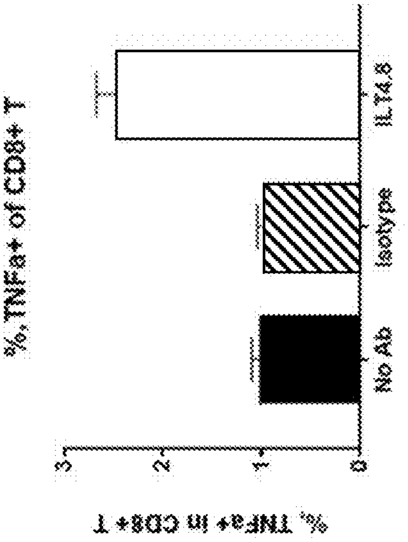

Human ILT4 (hILT4) was histidine tagged and mixed with 21D9 or 2H2 Fabs at a 1:1 ratio and subjected to HDX for 1 minute, 10 minutes or 4 hours. The sequence coverage of hILT4 by pepsin is shown in FIG. 27A. The areas of hILT4 (or hILT4 peptides) bound by each of the Fabs are shown in FIGS. 27B and C. Specifically, HDX-MS experiments provided 85% sequence coverage for human ILT4.

The HDX-MS data analysis on 21D9 and 2H2 in human ILT4 indicates that 21D9's epitope is comprised of one region of human ILT4 (residue numbers correspond to native human ILT4 sequence): Region: $^{70}$ITRIRPEL-VKNGQFHIPSITWEHTGRYGCQY$^{100}$ (SEQ ID NO: 122) in Ig domain 2. (See FIG. 27B, upper panel.)

The HDX-MS data analysis indicated that 2H2's epitope is comprised of five regions of human ILT4 with regions 2 and 5 being the primary epitope:

Region 1: (SEQ ID NO: 175)
$^{127}$SAQPSPVVTSGGRVTL$^{142}$

Region 2: (SEQ ID NO: 123)
$^{154}$ILCKEGEEEHPQCLNSQPHARGSSRAIF$^{181}$

Region 3: (SEQ ID NO: 176)
$^{182}$SVGPVSPNRRWSHRCYGYDLNSPYVWSSPSDL$^{213}$

Region 4: (SEQ ID NO: 177)
$^{378}$QAEFPMSPVTSAHAG$^{392}$

Region 5: (SEQ ID NO: 124)
$^{425}$SSPPPTGPIS$^{434}$
(See FIG. 27B, lower panel.)

Example 12: Anti-ILT4 Antibodies Block ILT4 Binding to MHC Class I Molecules A flow cytometry based antibody blocking assay was performed to determine the ability of anti-ILT4 antibodies to block rhILT4-Fc binding to HLA-A or HLA-B overexpressing CHO cells. rhILT4-Fc fusion protein was produced that contained a murine Fc tail. Anti-hILT4 antibodies 21D9, 2H2, 10F10 and 21A5 were titrated in the presence of a fixed 30 μg/ml concentration of rhILT4-Fc. The antibody and rhILT4-Fc mixture was incubated on ice for 30 minutes and then added to CHO cells engineered to overexpress HLA-A or HLA-B. The CHO cells were stained for 30 minutes on ice, washed and then stained with an anti-mouse-Ig secondary antibody to detect bound rhILT4-Fc.

The results, which are shown in FIGS. 28A-D, indicate that antibodies 21D9, 2H2, 10F10 and 21A5, respectively, inhibit binding of hILT4 to HLA-A and HLA-B.

Example 13: 21D9e.IgG1.3 Enhances Both IFN-γ and TNF-α Secretion by T Cells

This Example shows that 21D9e.IgG1.3 enhances IFN-gamma and TNF-alpha secretion of T cells in an autologous mixed lymphocyte reaction (MLR) of monocytes and T cells.

T cells and monocytes were isolated from peripheral blood mononuclear cells (PBMCs) and co-cultured at 1:1 ratio in the presence of 20 ng/mL anti-CD3 antibody (Clone: OKT3, BioLegend). 21D9e.IgG1.3 and isotype control (DT-1D12-g1.3f) was added at 10 ug/mL. Intracellular staining was performed to determine the frequencies of IFN-γ and TNF-α expressing T cells in each sample after an 88-hour incubation period using fluorochrome-conjugated IFN-γ antibody (Clone #B27, BioLegend) and TNF-α antibody (Clone #MAb11, BioLegend). The samples were acquired on a Cytoflex® cytometer (Beckmen Coulter) and analyzed with FlowJo™ software (Tree Star, Inc, Ashland, Oreg.).

The results, which are shown in FIGS. 29A-D, indicate that 21D9e.IgG1.3 enhances both IFN-γ and TNF-α secretion by CD4+ and CD8+ T cells in the autologous allo-MLR upon anti-CD3 stimulation.

Example 14: Anti-ILT4 Antibodies Enhance IFN-γ Secretion Upon Antigen Stimulation in a CMV Lysate Assay Peripheral blood mononuclear cells (PBMCs) from a cytomegalovirus (CMV) reactive donor were plated at 200,000 cells per well in the presence of 0.3 μg/mL of CMV Lysate (CMV Antigen 2, Microbix Cat #EL-02-01-001). Cells were treated with 8-point, 5-fold titration of anti-ILT4 antibodies 21D9.IgG1.3 and 21A5.IgG1.3 starting at 20 μg/mL. Nivolumab was added at 1 μg/mL as a positive control. 21D9-Fab and DT-1D12-g1.3 were added at 20 μg/mL. Supernatant from each sample was harvested and measured for IFN-γ level by ELISA (Human IFN-γ ELISA Kit, BD OptEIA Cat. 555142) after a 6-day incubation.

Figure 30:
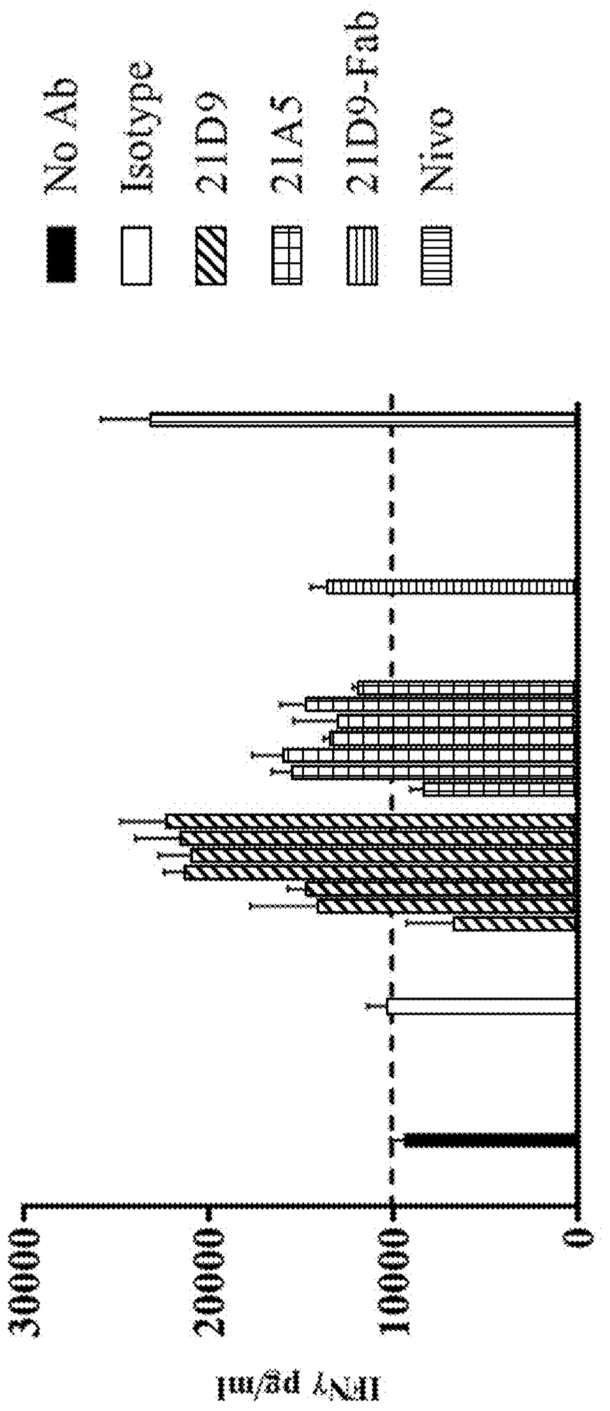
FIG. 30 shows that anti-ILT4 antibodies 21D9, 21A5, 21D9 Fab enhance IFN-g secretion upon antigen stimulation in a CMV Lysate Assay. Nivolumab was used as a positive control and the absence of antibody ("no Ab") and isotype control were used as negative controls. The concentrations of anti-ILT4 antibodies are, from left to right: 0.00128; 0.0064; 0.032; 0.16; 0.8; 4; and 20 μg/ml (a bar for each concentration is shown in the histogram). The antibodies and controls are shown from left to right in the same order as shown on the right of the histogram (e.g., "No Ab" corresponds to the bar on the left and "Nivo" corresponds to the bar on the right).

The results, which are shown in FIG. 30, indicate that the anti-ILT4 antibodies 21D9.IgG1.3, 21D9-Fab and 21A5.IgG1.3 enhance IFN-γ secretion upon antigen stimulation in the CMV lysate assay.

Example 15: ILT4 Antagonism Enhances T Cell Activation in Monocytes: T Allo-MLR T cells (100,000) from one donor and allogeneic monocytes were co-cultured at a 2:1 ratio per well in a 96-well U-bottom plate. Anti-ILT4 antibodies 2H2.IgG1.1f, 2H2 Fab, 21D9.IgG1.1f and 21D9 Fab were added in a 4-fold, 7-point titration starting at a concentration of 30 μg/mL for full length antibody or 80 μg/mL for Fab antibody. Anti-KLH-g1.1f (Anti-Hemocyanin antibody) was added at 30 μg/mL as an isotype control. The cell culture was incubated for 6 days. Cell proliferation was assessed by $^{3}H$-thymidine incorporation during the final 16 hours of culture.

Figure 31:
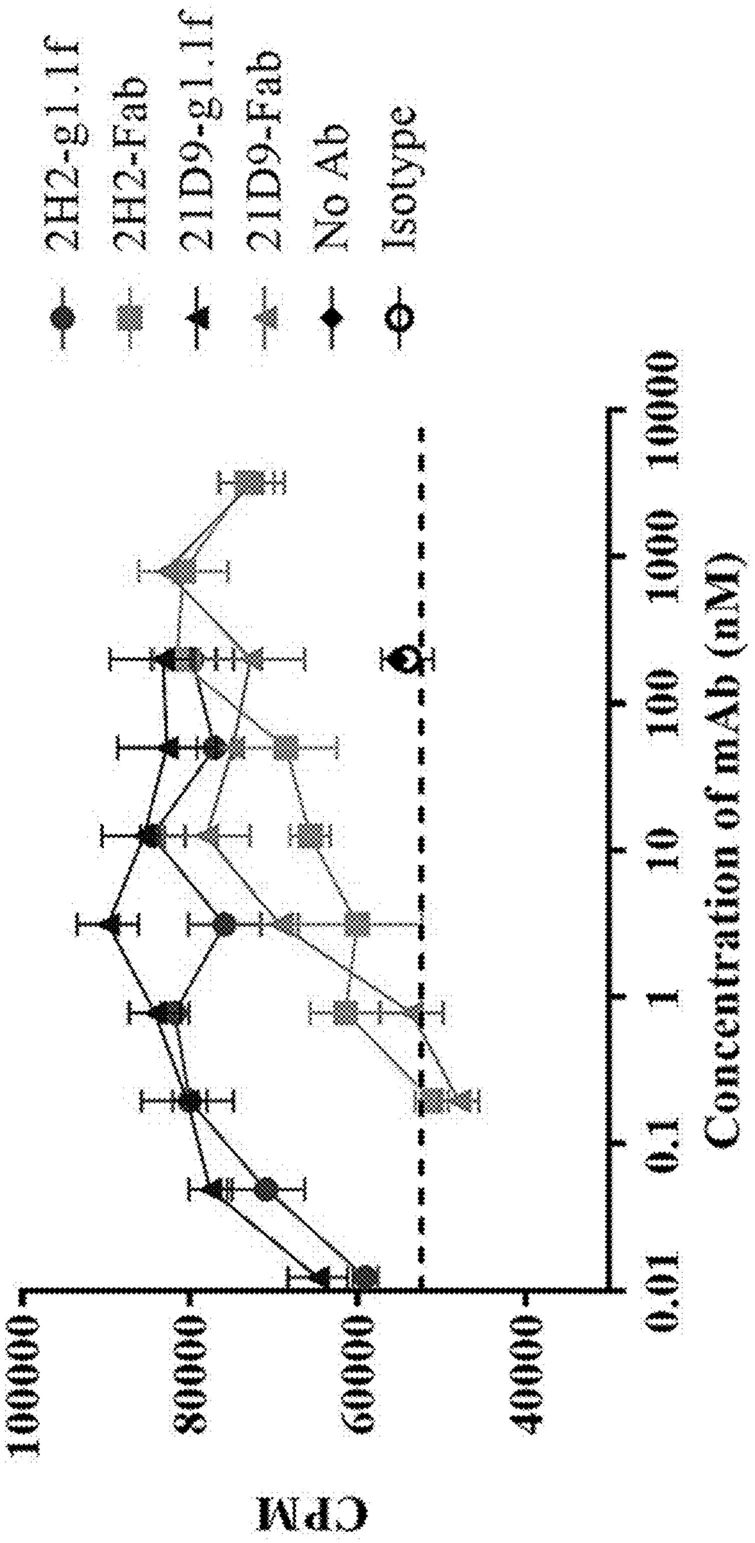
FIG. 31 shows that anti-ILT4 antibodies 2H2 and 21D9, either as IgG1.1f or as Fab, enhance T cell proliferation (measured by $^3$H incorporation) in a monocyte: T allo-MLR.

The results, which are shown in FIG. 31, indicate that both full length anti-ILT4 antibodies 21D9.IgG1.1f and 2H2.IgG1.1f, and their respective Fab fragments induce T cell proliferation.

Example 16: Binding of Anti-hILT4 Antibodies to Cyno ILT4

Several ILT family members were obtained via PCR from cynomolgus monkeys. Since sequence analysis of these proteins did not clearly indicate which was the closest match to hILT4, expression profiling and functional assays were conducted. These assays identified a clone named "9152" as the best match to hILT4 with regards to expression profiling and functional characteristics. The amino acid sequence of the extracellular region of 9152, including a His-Avi Tag, is the following: QAGILPKPMLWAEPDR-VITQGSPVTLRCQGNLEARGYHLYRERKSASWIT-LIRPE LVKKGQFPIPSITWED-AGRYRCQYYSHSWWSEHSDPLELVVTGAYRKPT LSALPS PVVASGGNVTLQCDSRVALDGFILCKEG-EDEHSQRLNSQPRTRGSSRAVFSVGPV SPSRRWSYRCYGYELHSRYVWSLPSDLLELLVPGV-SKKPSLSVQPGPVVAGGDK LTLQCGSD AGYDRFALYKEGERD-FLQRPGQQLQAGLAQANFTLDPVRGSHGGQ YRCYGAHNLSSEWSAPSDPLDILISAGPHSGLR-RECDPAVSVTGMDGHFLSDQGG SSSPGGGSGGGSE-QKLISEEDLGHHHHHHGLNDIFEAQKIEWHE (SEQ ID NO: 118). For binding to hILT4, the extracellular region (ECD) of hILT4-His-Avi tag; SEQ ID NO: 119, described in Example 2, was used.

The kinetics of 21D9.e antibody binding to cyno and human ILT4, using the above ILT4 constructs, was analyzed in a comparative SPR assay. The antibody was amine-coupled to a GLC sensor chip in a Proteon XPR36 instrument (BioRad). Human ILT4 and cyno ILT4 9152 were injected as analytes in a 5-membered, 5-fold dilution series with 1 μM maximum concentration (1.6 nM minimum concentration). All data were double-referenced, exported, and analyzed with BIAevaluation Software 4.1.1 using the kinetic titration model described by Karlsson et al (Karlsson et al. (2005) Analytical Biochem. 349:136). The running buffer consisted of 10 mM HEPES pH 7.4, 150 mM NaCl and 0.05% Tween-20. The assay temperature was 37° C.

The results, which are shown in Table 5, show that 21D9.e bound cyno ILT4 9152 with approximately 11-fold weaker affinity than human ILT4 ($K_D$ values of 3.5 nM for cyno and 0.33 nM for human ILT4). Similarly, the parental antibody, 21D9, bound cyno with approximately 12 fold weaker affinity than human ILT4. The difference was driven by a faster dissociation rate constant for cyno ILT4 ($K_D$ values of 4.0 nM for cyno and 0.32 nM for human ILT4).

TABLE 5

| Ligand | Analyte | Ka (M-1 s-1) | kd (s-1) | KD (M) |
|---|---|---|---|---|
| 21D9 | cyLILR 9152 | 8.8E+05 | 3.5E−03 | 4.0E−09 |
| 21D9 | hILT4 | 8.2E+05 | 2.6E−04 | 3.2E−10 |
| 21D9e | cyLILR 9152 | 7.3E+05 | 2.6E−03 | 3.5E−09 |
| 21D9e | hILT4 | 9.9E+05 | 3.3E−04 | 3.3E−10 |

Example 17: ILT4 Antibodies Promote Expression of Costimulatory Molecules and Activation Markers on Cynomolgus Monocyte-Derived Dendritic Cells In Vitro This Example shows that ILT4 antibodies 21D9.e.IgG1.3 (ILT4.8 in FIG. 32; see Table 1) and 9G4. hIgG1.3 (ILT4.1 in FIG. 32; see Table 1) stimulated the expression of CD80, CD83 and CD86 on monocyte derived dendritic cells.

Monocytes isolated from cynomolgus monkey PBMC (Non-human Primate CD14 Microbeads, Miltenyi) were cultured in the presence of 62.5 U/mL recombinant human GM-CSF (Peprotech) and 125 U/mL recombinant human IL-4 (Peprotech) for 5 days. Anti-ILT4 antibodies were added to the culture @ 10 ug/mL at the time the culture was set up. Cells were stained for their surface expression level of CD86, CD80, and CD83 using anti-CD86 (clone #IT2.2, BioLegend), anti-CD80 (clone #L307), and anti-CD83 (clone #HIB15e). The samples were acquired on a Cytoflex® cytometer (Beckmen Coulter) and analyzed with FlowJo™ software (Tree Star, Inc, Ashland, Oreg.).

Figure 32A:
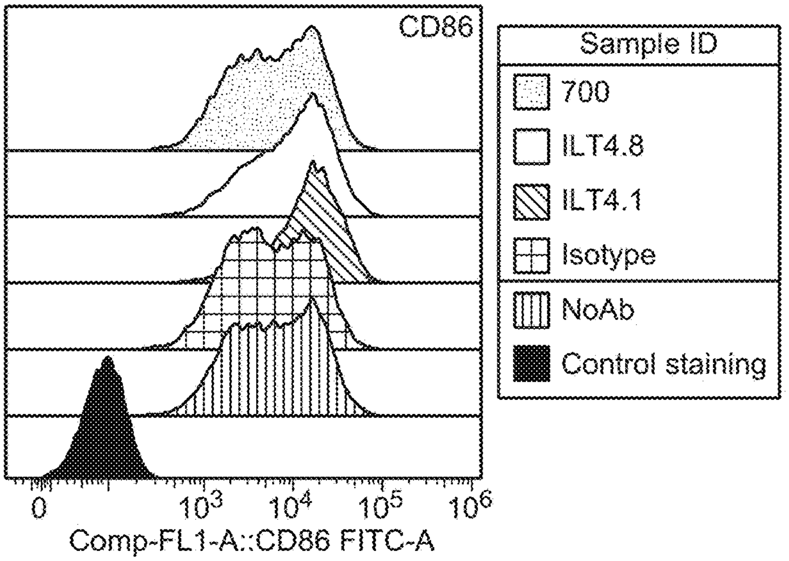
FIGS. 32A-C show that anti-ILT4 antibodies 21D9e.IgG1.3 ("ILT4.8" in the figure) and 9G4.IgG1.3 ("ILT4.1") (see Table 1 for nomenclature of antibodies) promote expression of the costimulatory molecules CD86 (FIG. 32A) and CD80 (FIG. 32B) and the dendritic cell activation marker CD83 (FIG. 32C) on cynomolgus monocyte-derived dendritic cells in vitro. Each antibody was added during cynomolgus monocyte differentiation to monocyte-derived dendritic cells (DC).
Figure 32B:
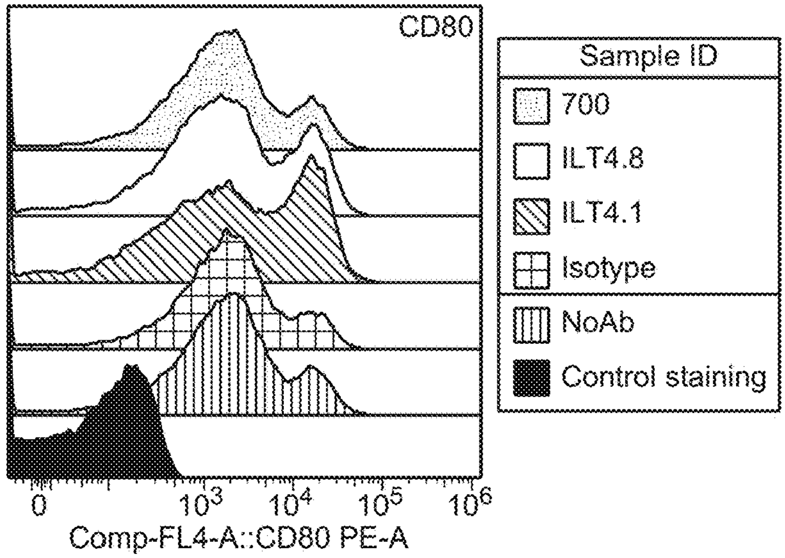
Figure 32C:
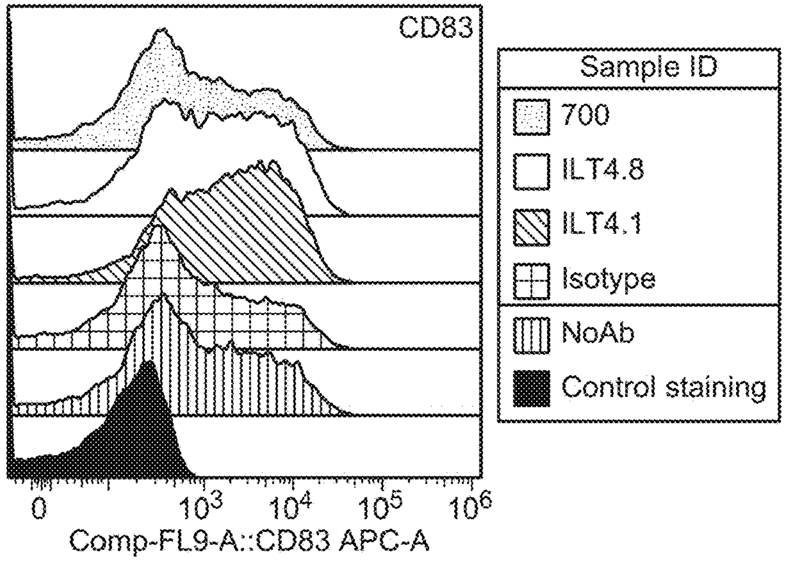

The results, which are shown in FIGS. 32A-C, indicate that ILT4 antibodies 21D9.e.IgG1.3 (aka. ILT4.8.IgG1.3; "ILT4.8" in the figure) and 9G4.IgG1.3 (aka. ILT4.1.IgG1.3; "ILT4.1" in the figure) promote expression of co-stimulatory molecules CD80 and CD86 as well as the dendritic cell maturation marker CD83 in monocyte-derived DC, as evidenced by the upregulation of CD80, CD83 and CD86 on the dendritic cells.

Example 18: Modified Anti-ILT4 Antibody 10F10.4

The tyrosine in F36Y in the light chain of 10F10.1 and 10F10.3 (see Example 2) is located near the heavy chain CDR3 in modeling of hILT4 and 10F10 antibodies. Therefore, substituting F36 with Y could cause a clash with an isoleucine in heavy chain CDR3, as evidenced by a faster off-rate of 10F10.1 and 10F10.3 relative to 10F10 (see Example 2). An additional mutant was created in which F36 of the light chain was not mutated and the only light chain framework region mutation made in 10F10 was T63S. The heavy chain was not mutated, and so is that of 10F10. This modified antibody is called 10F10.4, and the amino acid sequence of its light chain is set forth in the Sequence Table as SEQ ID NO: 116.

The binding kinetics of 10F10.4 were determined at 37° C. using a Biacore® T200 instrument. The running buffer was 10 mM HEPES pH 7.4 supplemented with 0.05% Tween-20 and 1 g/L BSA. All anti-ILT4 antibodies were captured on a CM4 chip with pre-immobilized anti-human Fc capture antibody from Southern Biotech (catalog number 2081-01). Human ILT4 (hILT4-His-Avi tag described in Example 2) was injected at 1.2 uM (only over 10F10, 10F10.4 and one replicate of 1E5 ILT4.15), 405 nM, 81 nM (in duplicate), 16 nM, 3 nM and 0.6 nM. All data were double-referenced and fitted to a 1:1 Langmuir model with mass transport using Biacore T200 Evaluation Software version 3.1.

The results, which are shown in Table 6, indicate that binding kinetics of 10F10.4 are very similar to those of 10F10. 21A5, 21A5a, 21D9, and 21D9.e were included as controls. The absolute values differ slightly from values shown in Table 2, which is due to the different capture reagent utilized in this assay.

TABLE 6

| Ligand | Sample | ka (1/Ms) | kd (1/s) | KD (M) | Rmax (RU) | Ligand Level (RU) | app. act. |
|---|---|---|---|---|---|---|---|
| 10F10 | hILT4 | 1.2E+06 | 2.6E−02 | 2.2E−08 | 35 | 50 | 100% |
| 10F10.4 | hILT4 | 1.2E+06 | 2.7E−02 | 2.2E−08 | 33 | 41 | 117% |
| 21A5 | hILT4 | 5.2E+05 | 1.2E−05 | 2.3E−11 | 81 | 119 | 98% |
| 21A5.a | hILT4 | 4.9E+05 | 1.7E−05 | 3.6E−11 | 76 | 109 | 100% |
| 21D9 | hILT4 | 1.1E+06 | 5.4E−04 | 5.0E−10 | 31 | 65 | 70% |
| 21D9.e | hILT4 | 1.0E+06 | 5.8E−04 | 5.8E−10 | 101 | 154 | 94% |

Figure 33A:
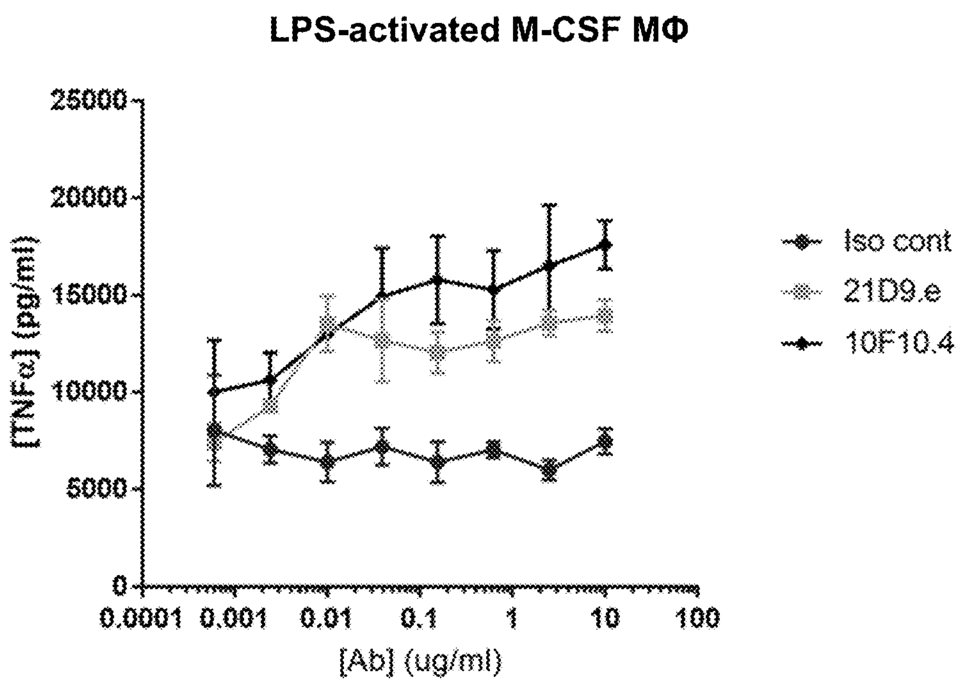
FIGS. 33A and B show the level of TNF-alpha secreted from in vitro differentiated macrophages activated by lipopolysaccharide (LPS) (FIG. 33A) or STING agonist 2'3'cGAMP (FIG. 33B). Anti-ILT4 antibodies 21D9.e and 10F10.4 or isotype control were included during activation.
Figure 33B:
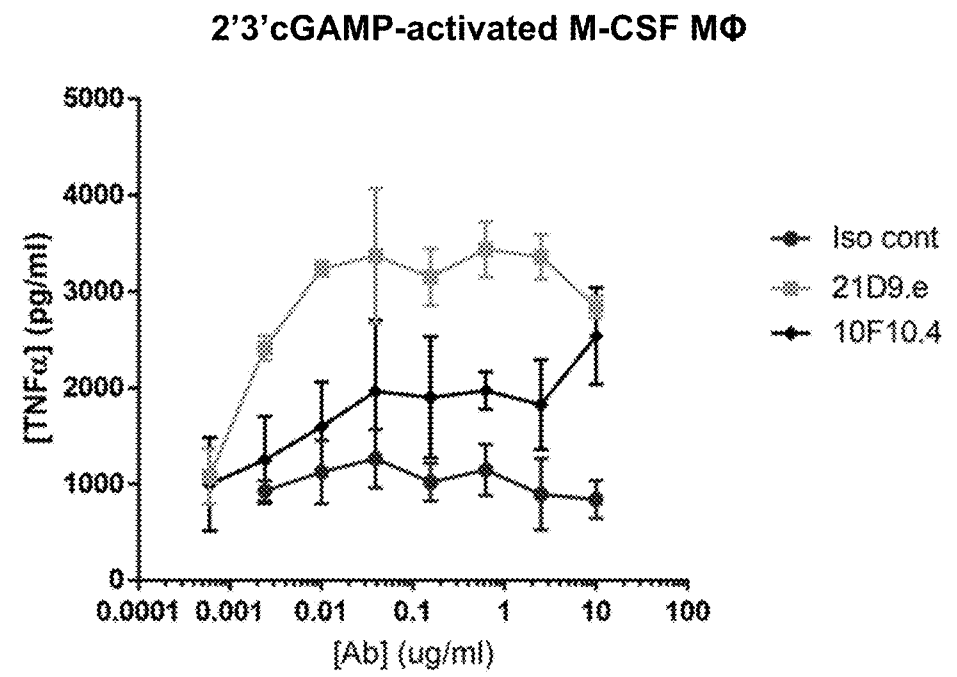

10F10.4 was shown to be functionally active by potentiating TNFα secretion from in vitro differentiated macrophages. This was demonstrated by incubating 10F10.4 with macrophages differentiated from PBMC monocytes as described in Example 8. 21D9.e was also included, as well as an isotype control. The results, which are shown in FIGS. 33A and B, indicate that the presence of ILT4 antibody 10F10.4 potentiated TNFα secretion during the in vitro differentiation of monocytes to macrophages by either LPS or a STING agonist.

Example 19: 21D9.e has Similar Potency in the Context of IgG1, IgG4 and IgG1.3

This Example shows that the potency of 21D9.e is similar in the context of an IgG1, IgG4 (S228P) and IgG1.3 heavy chain.

21D9.e antibodies were cloned in the context of an IgG1, IgG4 (with S228P) or IgG1.3 (SEQ ID Nos: 176, 178 and 13, respectively) and used in an assay measuring TNFα secretion, conducted as follows.

Figure 34:
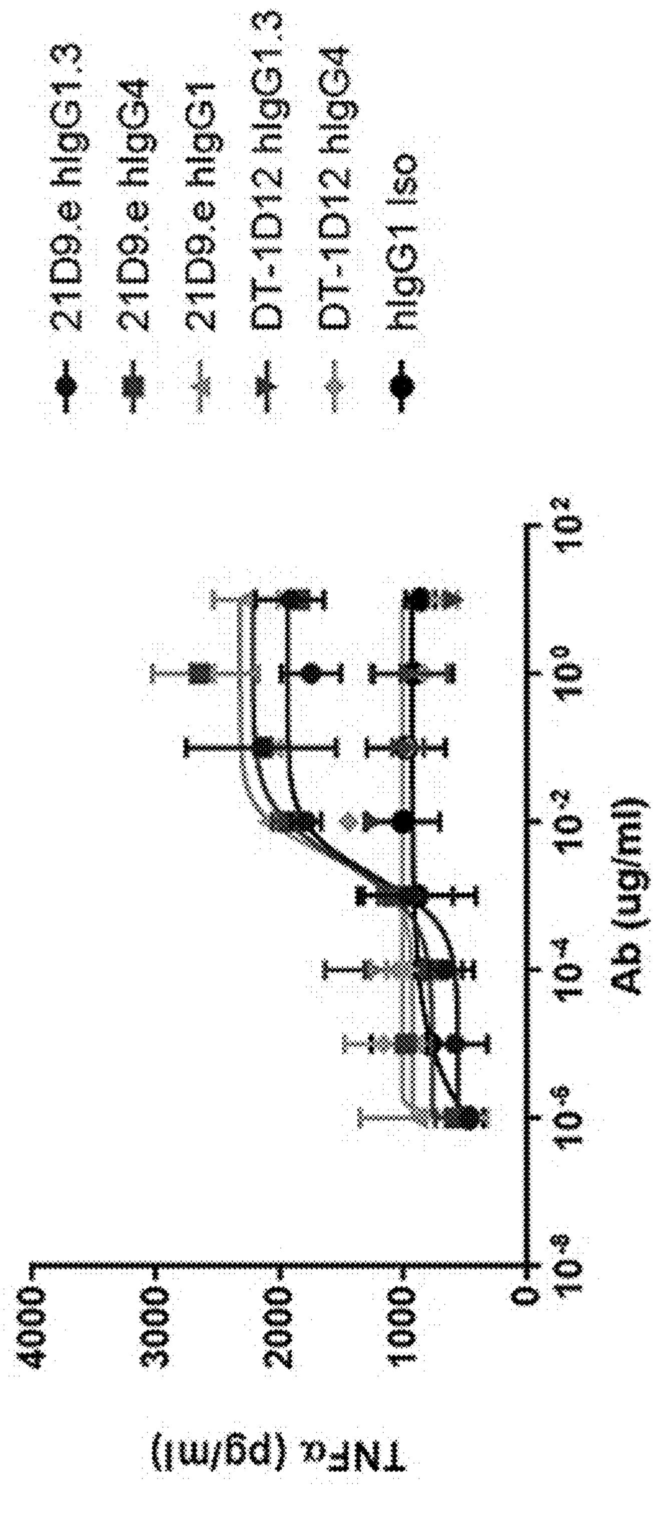

The results, which are shown in FIG. 34, indicate that a similar amount of TNFα is secreted for 21D9.e.IgG1, 21D9.e.IgG4.S228P and 21D9.e.IgG1.3. Thus, 21D9.e variable regions have similar functional potency in the context of these different Fc regions. DT-1D12 is an isotype control.

Example 20: 21D9e Binds to hILT4 Alleles

This Example describes assays to determine whether 21D9.e binds to alternative alleles of hILT4.

Only those alleles having a frequency over 1% were considered. Two alleles having amino acid changes in regions D1 and D2 were further considered: E161D and R103H (numbering according to SEQ ID NO: 107, i.e., ILT4 with signal sequence). As 3-dimensional modeling showed that both amino acid residues are not near the binding interface with MHC class I, amino acid changes at these residues were not expected to affect antibody binding to hILT4. To confirm this, a hILT4 protein with the substitutions E161D and R103H (hILT4 E161D/R103H) was made and tested for binding to 21D9.e.IgG1.3 and 21A5.a.IgG1.3 (ILT4.9.IgG1.3; see Table 1) via Octet BLI. Both proteins were found to bind similarly to hILT4 E161D/R103H and to hILT4 E161/R103.

Example 21: 21D9e.IgG1.3 does not Significantly Trigger Basophil Activation

The assay used for detection of basophil activation by anti-ILT4 antibodies involved the following steps. The assay was conducted by using the Buhlmann Laboratories AG methodology used in Flow CAST© Basophil Activation Test, generally as follows. Human basophils, derived from donor blood, were detected using anti-Ccr3. CD63 was used as an indicator of basophil activation. Stimulation buffer and the antibodies were added to whole blood. Following incubation, staining reagents were added to the blood; and following antibody incubation, erythrocytes were lysed and the samples were centrifuged, washed and analyzed on a BD FACS Canto II.

Based on this assay, Ccr3+CD63+ activated basophils from 8 donors were measured by FACS following incubation with either 21D9.e.IgG1.3 (ILT4.8.IgG1.3; see Table 1) 21.5Aa.IgG1.3, (ILT4.9.IgG1.3) or anti-DT at 4.5, 45.45 or 454.55 μg/mL for 180 minutes. Positive controls included anti-FcεRI and fMLP (N-formylmethionine-leucyl-phenyalanine). Negative control was DT1DT12-IgG1.3, which targets an irrelevant antigen, diphtheria toxin.

Figure 36:
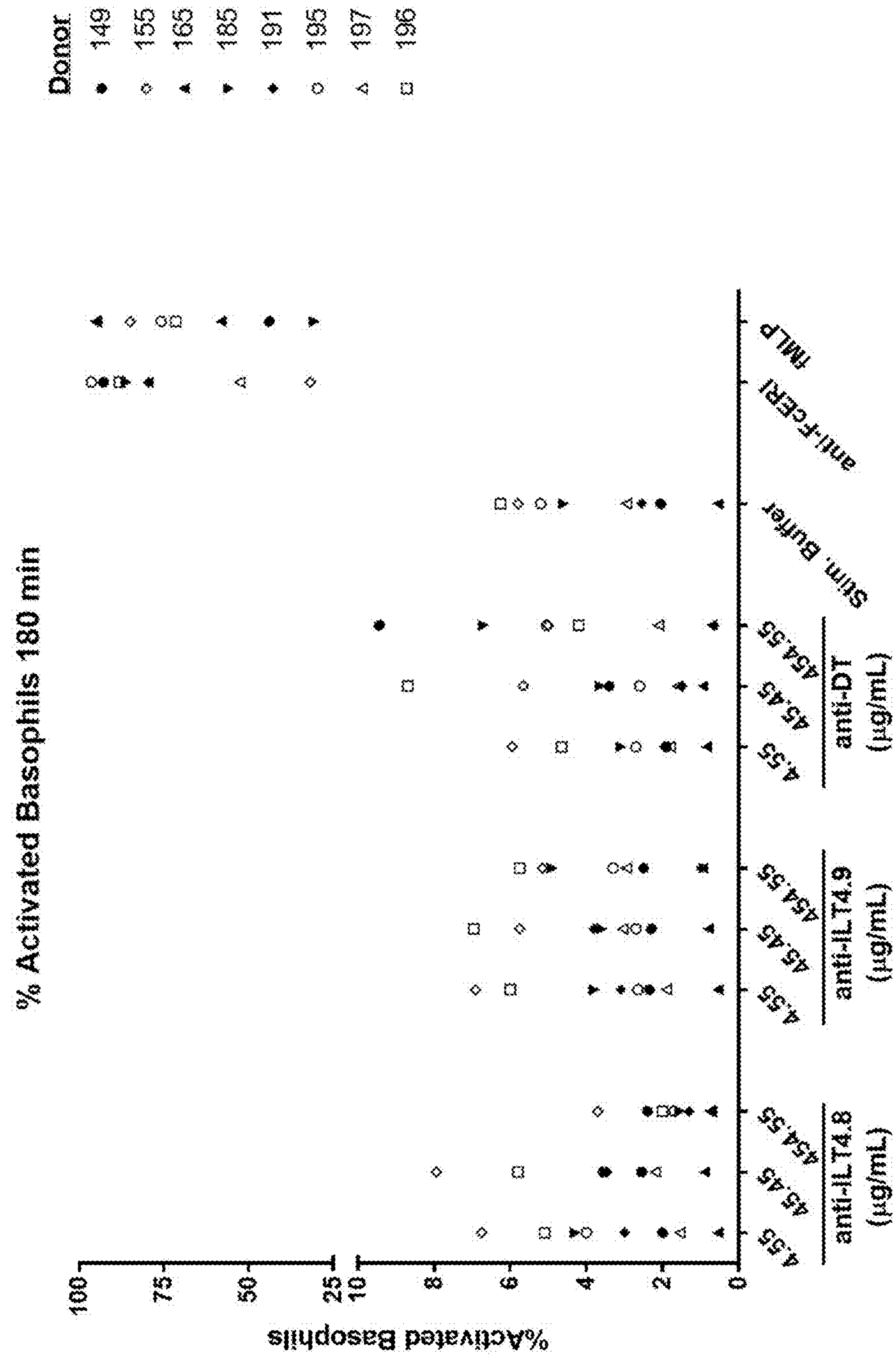
FIG. 36 shows the percentage of activated basophils of a total of 8 donors after incubation with 21D9e.IgG1.3 ("ILT4.8" in the figure), 21A5.a.IgG1.3 ("ILT4.9"), an isotype control antibody "anti-DT", anti-FcεRI or N-formylmethionine-leucyl-phenyalanine (fMLP), showing a lack of basophil activation by 21D9e.IgG1.3 (ILT4.8) and 21A5.a.IgG1.3 ("ILT4.9").

The results, which are shown in FIG. 36, indicate that 21D9.e.IgG1.3 (ILT4.8.IgG1.3) and 21.5Aa.IgG1.3 (ILT4.9.IgG1.3) do not induce basophil activation in the conditions tested. The lack of basophil activation represents an important safety feature.

Example 22: Anti-ILT4 Antibody 21D9.e.IgG1.3 is Stable

This Example describes 3 month stability studies performed with anti-ILT4 antibody 21D9.e.IgG1.3 (aka. ILT4.8.IgG1.3), which data show that the antibody is stable at least over 3 months.

Samples of 21D9.e.IgG1.3 were incubated at 25 or 40° C. at a concentration of 150 mg/mL. The samples were diluted with mobile phase (40 mM NaH2PO4, 60 mM Na2HPO4, 0.1 M Na2SO4, pH 6.8) to 1 mg/mL and forty microliters were analyzed using an Agilent 1200 Series HPLC System (Agilent Technologies, Santa Clara, Calif.) using a TSKgel Super3000SW column (4.6 mm ID×30 cm, 4 μm, Tosoh Bioscience, King of Prussia, Pa.) with an isocratic gradient (0.1 M Sodium Phosphate, 0.1M Sodium Sulfate, pH 6.8 at 0.2 mL/min). UV detection was set at 280 nM.

Figure 35:
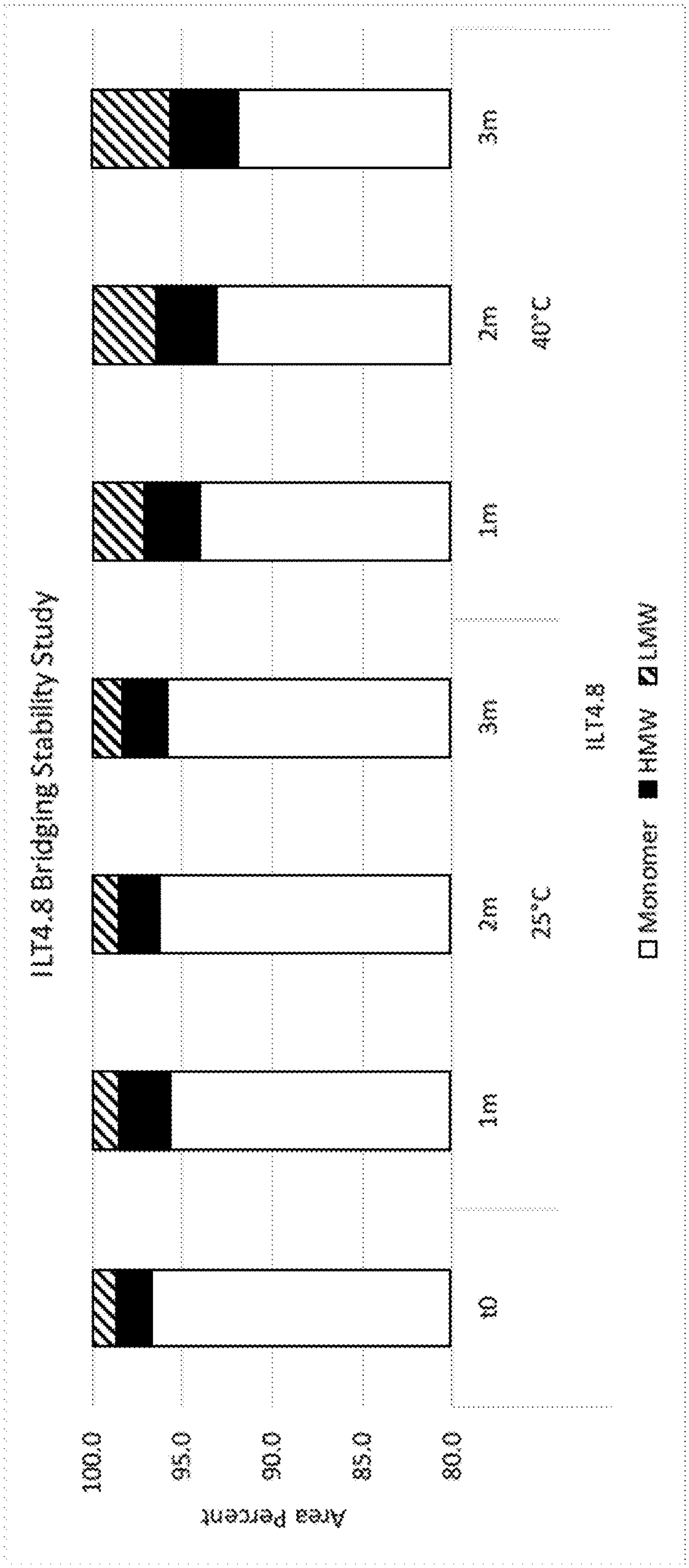
FIG. 35 shows the percentage of monomer, high molecular weight (HMW) species and low molecular weight (LMW) species of 21D9.e.IgG1.3 after 0, 1, 2 and 3 months at 25° C. or 40° C. The momoner, HMW and LMW species correspond to the bottom, middle and top portions of each of the bars, respectively, in the histogram.

The results, which are shown in FIG. 35, indicate that the 21D9.e.IgG1.3 (ILT4.8) antibody composition comprises less than 5% of high and low molecular weight species after 3 months incubation at 25° C. and less than 10% of high and low molecular weight species after 3 months incubation at 40° C.

Example 23: Cross-Blocking of 2112 and 21D9 by Anti-ILT4 Monoclonal Antibodies ILT4 overexpressing CHO cells were first pre-incubated with serial dilutions of unconjugated anti-ILT4 antibodies 10F10.IgG1.3 and 21A5.IgG1.3 (3-fold, 12-point, starting from 40 μg/mL). Anti-KLH-g1.1f (Anti-Hemocyanin antibody) was added as an isotype control while unconjugated 2H2.IgG1.1f or 21D9.IgG1.1f was added at 40 μg/mL as a positive control to demonstrate blocking activity. Following a 30-minute incubation period, PE conjugated 2H2.IgG1.1f or 21D9.IgG1.1f was spiked in at 1.5 μg/mL and incubated with cells for another 30 minutes. After washing, the samples were acquired on a FACSCanto™ cytometer (BD Bioscience, San Jose) and analyzed with Flowjo™ software (Tree Star, Inc, Ashland, Oreg.).

The results are shown in FIG. 37A (2H2 cross blocking) and FIG. 37B (21D9 cross blocking). The results indicate that 10F10 and 21A5 cross-block (or compete with) 2H2 for binding to hILT4 (FIG. 37A) and that 10F10, but not 21A5, cross-blocks (or competes with) 21D9 for binding to hILT4 (FIG. 37B). Thus, (i) 21A5 and 2H2 are in the same binning group (i.e., they compete with each other for binding to hILT4); (ii) 21D9 is in a separate binning group from that of 21A5/2H2; and (iii) 10F10 competes with both 21D9 and 2H2/21A5 for binding to hILT4.

A diagram showing the hILT4 binding regions of the antibodies on the crystal structure of hILT4 is shown in FIG. 37C. The Ig-like domain 1 corresponds to amino acid residues 27-110 of SEQ ID NO: 107, while Ig-like domain 2 corresponds to amino acid residues 111-229 of SEQ ID NO: 107. These two domains are shown in ribbon form in FIG. 37C. The results of these experiments indicate that antibody 21D9 binds to Ig-like domain 1, antibodies 2H2 and 21A5 bind to Ig-like domain 2, and antibody 10F10 binds to a region that is located in Ig-like domain 2, close to Ig-like domain 1, and can be competed away by antibodies that bind to Ig-like domain 1 or Ig-like domain 2. Antibodies differing from the antibodies used in these experiments only by germline mutations (e.g., 21D9.e, 29A5.a and 10F10.3 and 10F10.4) are expected to bind the same region as their parent antibodies (21D9, 29A5 and 10F10, respectively).

Example 24: Epitope Mapping Using Carbene Chemical Footprinting

The reagents for human ILT4 and anti-human ILT4 antibody Fab clones 10F10, 21D9, and 21A5 were buffer exchanged into 100 mM Tris-HCl and 50 mM NaCl at pH 7.5 at 1 mg/mL. Individual complexes of human ILT4 and each anti-human ILT4 antibody Fab were made by mixing at a 1:1 ratio. Triplicate experiments of 5 ug of ILT4 and 10 ug of the complexes were mixed 1:1 with 20 mM 4-[3-(Trifluoromethyl)-3H-diazirin-3-yl] benzoic acid in 100 mM Tris-HCl and 50 mM NaCl at pH 7.5. The resulting mixtures were snap frozen in liquid nitrogen. All samples were placed on dry ice and irradiated with light (300-800 nm) from an Atlas Suntest® CPS+ light box for 20 minutes to allow for covalent modification of the protein by the diazirine reagent. The irradiated samples were reduced, alkylated, and digested with chymotrypsin. LC-MS/MS analysis was performed on an Orbitrap Fusion Lumos® mass spectrometer using a Waters BEH C18 column. A 60 minute linear gradient at 10 μL/min of 0-35% buffer B (A: water with 0.1% formic acid; B: acetonitrile with 0.1% formic acid) was used to separate the peptides. The resulting eluent was mixed with 2 μL/min of acetonitrile mixed with 0.6% 3-nitrobenzyl alcohol. Modified peptides were identified and quantified using Byonic® and Byologic® from Protein Metrics. Chromatographic resolution and MS/MS identifications were used to localize and confirm the modified amino acids.

Figure 37D:
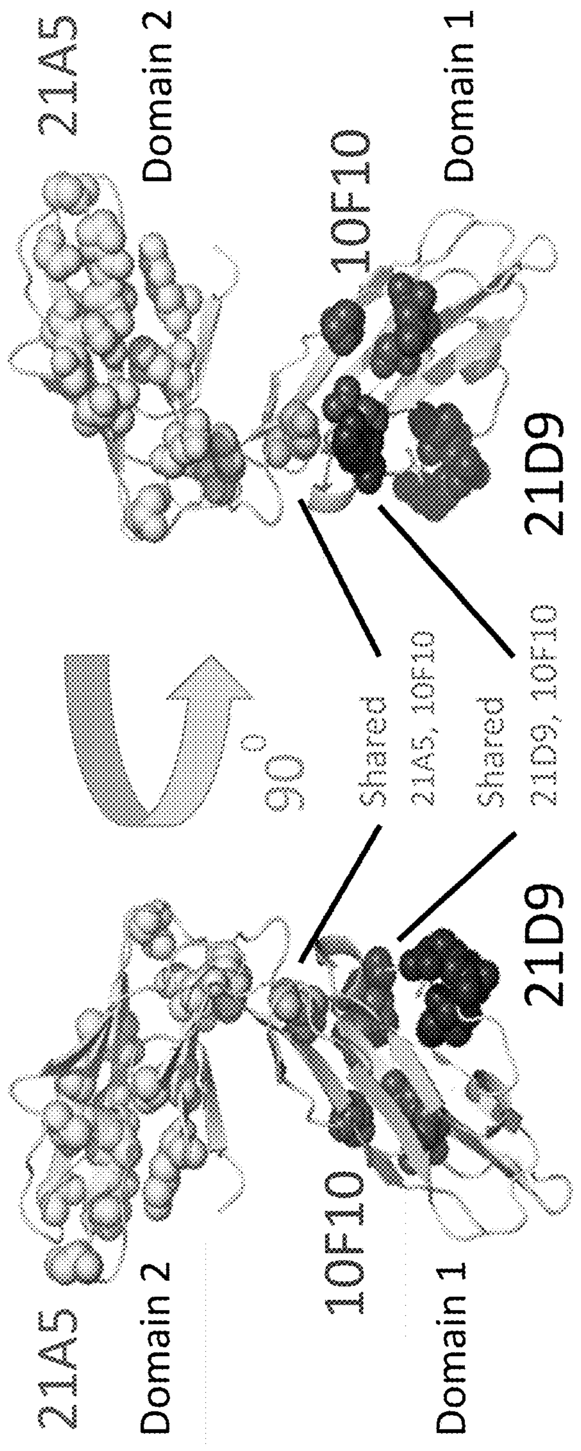

Diazirines are photoactive compounds that can react with any C-H bond in all 20 amino acids. The resulting covalent modification can be chromatographically separated from other amino acid sites in the same peptide. Comparisons of the triplicate peak areas for the unmodified peptides and singly modified peptides were used to determine differences in diazirine labeling for the antibody clones 10F10, 21A5, and 21A9 to identify the antibody epitope. Peptides with >50% decreases in labeling in one or more complexes were considered significant and used to localize the antibody epitopes. Significant peptides, or in cases where the comparison to the unmodified peptide could not be made due to a missed enzyme cleavage site, the modified peptide chromatogram for all samples were compared to each other with decreases of >50% of individual peptide peak elution chromatograms being used to determine differentially modified amino acids that are protected by the antibody epitope. The MS/MS spectra of the differentially modified amino acids were manually confirmed by MS/MS and marked on the human ILT4 x-ray crystallography structure (PDB: 2DYP). (FIG. 37D.) The antibody epitope for clone 21D9 was found to have differential labeling at two individual sites of 1 and 3 amino acids in domain 1 of human ILT4 and is marked in red and purple (due to an overlapping site with 10F10). The antibody epitope for clone 10F10 was found to have differential labeling at six individual sites of 1-2 amino acids in domain 1 and domain 2 of human ILT4 and as marked in FIG. 37D (due to overlapping sites with both 21A5 and 21D9). The antibody epitope for clone 21A5 was found to have differential labeling at 11 individual sites of 1-4 amino acids in domain 2 of human ILT4, as also marked in FIG. 37D (due to an overlapping site with both 10F10).

hILT4 amino acid residues Gly117, Val119, Try120, Leu134, Lys136, Gln149, Pro150, Ile159, Ser161, Val162, Gly163, Pro164, Pro167, His173, Try178, Pro183, and Tyr184 are depicted as balls in FIG. 37D with respect to antibody 21A5. Residues Glu42, Lys43, Gly76, Cys77, Leu88, Pro91, Pro183, and Tyr184 are depicted in FIG. 37D with respect to antibody 10F10. Residues Lys43, Ile49, Thr50, and Arg51 are depicted with respect to antibody 21A9.

Sequence Table

The following is a table of certain sequences referred to in this application. A number of the sequences below are also provided in FIGS. 1-15 and the VH and VL CDRs for the antibodies are denoted in FIGS. 1-15. Within the LC and HC sequences provided below, the component VL and VH sequences are underlined and bolded. Within the VL and VH sequences below, the CDRs are underlined and bolded, as depicted also in FIGS. 1-12, and within certain VH and VL sequences, reversion mutations are depicted. (See also FIGS. 13-15 for depiction of reversion mutations.) In some cases reversion mutations are shaded or are bold and underlined and grey-shaded.

| SEQ ID NO | Name | Sequence |
|---|---|---|
| 1 | 9G4 kappa LC (aka. ILT4.1-kappa) | **EIVLTQSPATLSLSPGERATLSCRASQSVSSYLAWYQQKPGQA**<br>**PRLLIYDASNRATGIPARFSGSGSGTDFTLTISSLEPEDFAGY**<br>**YCQQRSYWPWTFGQGTKVEIK**RTVAAPSVFIFPPSDEQLKSGT<br>ASVVCLLNNFYPREAKVQWKVDNALQSGNSQESVTEQDSKDST<br>YSLSSTLTLSKADYEKHKVYACEVTHQGLSSPVTKSFNRGEC |
| 2 | 9G4-IgG1.1f HC (aka. ILT4.1-IgG1.1f) | **QVQLQESGPGLVKPSETLSLTCTVSGGSISSYYWNWIRQPPGK**<br>**GLEWLGYIYYSGSTKYNPSLKSRVTISVDTSKNQFSLKLSSVT**<br>**AADTAVYYCASSGWYYFDYWGQGTLVTVSS**ASTKGPSVFPLAP<br>SSKSTSGGTAALGCLVKDYFPEPVTVSWNSGALTSGVHTFPAV<br>LQSSGLYSLSSVVTVPSSSLGTQTYICNVNHKPSNTKVDKRVE<br>PKSCDKTHTCPPCPAPEAEGAPSVFLFPPKPKDTLMISRTPEV<br>TCVVVDVSHEDPEVKFNWYVDGVEVHNAKTKPREEQYNSTYRV<br>VSVLTVLHQDWLNGKEYKCKVSNKALPSSIEKTISKAKGQPRE<br>PQVYTLPPSREEMTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPGK |
| 3 | 9C8 kappa LC ILT4.2-kappa | **AIQLTQSPSSLSASVGDRVTITCRASQGISSALAWYQQKPGKA**<br>**PKLLIYDASSLESGVPSRFSGSGSGTDFTLTISSLQPEDFATY**<br>**YCQQFNSYPFTFGPGTKVDIK**RTVAAPSVFIFPPSDEQLKSGT<br>ASVVCLLNNFYPREAKVQWKVDNALQSGNSQESVTEQDSKDST<br>YSLSSTLTLSKADYEKHKVYACEVTHQGLSSPVTKSFNRGEC |
| 4 | 9C8-IgG1.1f HC ILT4.2-IgG1.1f | **QVQLVQSGAEVKKPGASVKVSCKASGYTFTSSDINWVRQATGQ**<br>**GLEWMGWMNPNSGHTGYAQKFQDRVTLTRDTSISTAYMELSSL**<br>**RSEDSAVYYCARGGNSIDWGFSYYGLDVWGQGTTVTVSS**ASTK<br>GPSVFPLAPSSKSTSGGTAALGCLVKDYFPEPVTVSWNSGALT<br>SGVHTFPAVLQSSGLYSLSSVVTVPSSSLGTQTYICNVNHKPS<br>NTKVDKRVEPKSCDKTHTCPPCPAPEAEGAPSVFLFPPKPKDT<br>LMISRTPEVTCVVVDVSHEDPEVKFNWYVDGVEVHNAKTKPRE<br>EQYNSTYRVVSVLTVLHQDWLNGKEYKCKVSNKALPSSIEKTI<br>SKAKGQPREPQVYTLPPSREEMTKNQVSLTCLVKGFYPSDIAV<br>EWESNGQPENNYKTTPPVLDSDGSFFLYSKLTVDKSRWQQGNV<br>FSCSVMHEALHNHYTQKSLSLSPGK |
| 5 | 2H2 kappa LC ILT4.3-kappa | **EIVLTQSPGTLSLSPGERATLSCRASQSVSSSYLAWYQQKPGQ**<br>**APRLLIYGASSRATGIPDRFSGSGSGTDFTLTISRLEPEDFAV**<br>**YYCQQYGSSYTFGQGTKLEIK**RTVAAPSVFIFPPSDEQLKSGT<br>ASVVCLLNNFYPREAKVQWKVDNALQSGNSQESVTEQDSKDST<br>YSLSSILTLSKADYEKHKVYACEVTHQGLSSPVTKSFNRGEC |
| 6 | 2H2-IgG1.1fHC ILT4.3-IgG1.1f | **QVQLVQSGAEVKKPGSSVEVSCKASGGTFSNYAISWVRQAPGQ**<br>**GLEWMGGIIPILATANYAPKFQGRVTITADEFTSSAYMELSSL**<br>**RSEDTAVYYCAKSSITMIRGAYLYYYDGMDVWGQGTTVTVSS**A<br>STKGPSVFPLAPSSKSTSGGTAALGCLVKDYFPEPVTVSWNSG<br>ALTSGVHTFPAVLQSSGLYSLSSVVTVPSSSLGTQTYICNVNH<br>KPSNTKVDKRVEPKSCDKTHTCPPCPAPEAEGAPSVFLFPPKP |

-continued

| SEQ ID NO | Name | Sequence |
|---|---|---|
| | | KDTLMISRTPEVTCVVVDVSHEDPEVKFNWYVDGVEVHNAKTK<br>PREEQYNSTYRVVSVLTVLHQDWLNGKEYKCKVSNKALPSSIE<br>KTISKAKGQPREPQVYTLPPSREEMTKNQVSLTCLVKGFYPSD<br>IAVEWESNGQPENNYKTTPPVLDSDGSFFLYSKLTVDKSRWQQ<br>GNVFSCSVMHEALHNHYTQKSLSLSPGK |
| 7 | 2E5 kappa LC<br>ILT4.4-kappa | **EIVLTQSPATLSLSPGERATLSCRASQSVSSYLAWYQQKPGQA**<br>**PRLLIYDASNRATGIPARFSGSGSGTDFTLTISSLEPEDFAVY**<br>**YCQQRSNWPPWTFGQGTKVEIK**RTVAAPSVFIFPPSDEQLKSG<br>TASVVCLLNNFYPREAKVQWKVDNALQSGNSQESVTEQDSKDS<br>TYSLSSTLTLSKADYEKHKVYACEVTHQGLSSPVTKSFNRGEC |
| 8 | 2E5-IgG1.1f<br>HC<br>ILT4.4-<br>IgG1.1f | **QVQLVESGGGVVQPGRSLRLSCTASGFTFSNYGMHWVRQAPGK**<br>**GLEWVAVIWYDGSNEYYAESVKGRLTISRDNSKNTLYLQVNSL**<br>**RAEDTAVYYCARDPFYGSGNYFDYWGQGTLVTVSS**ASTKGPSV<br>FPLAPSSKSTSGGTAALGCLVKDYFPEPVTVSWNSGALTSGVH<br>TFPAVLQSSGLYSLSSVVTVPSSSLGTQTYICNVNHKPSNTKV<br>DKRVEPKSCDKTHTCPPCPAPEAEGAPSVFLFPPKPKDTLMIS<br>RTPEVTCVVVDVSHEDPEVKFNWYVDGVEVHNAKTKPREEQYN<br>STYRVVSVLTVLHQDWLNGKEYKCKVSNKALPSSIEKTISKAK<br>GQPREPQVYTLPPSREEMTKNQVSLTCLVKGFYPSDIAVEWES<br>NGQPENNYKTTPPVLDSDGSFFLYSKLTVDKSRWQQGNVFSCS<br>VMHEALHNHYTQKSLSLSPGK |
| 9 | 24E5 kappa LC<br>ILT4.5-kappa | **DIQMTQSPSSLSASVGDRVTITCRASQGISSWLAWYQQKPEKA**<br>**PKSLIYAASSLQSGVPSRFSGSGSGTDFTLTISSLQPEDFATY**<br>**YCQQYNSYPLTFGGGTKVEIK**RTVAAPSVFIFPPSDEQLKSGT<br>ASVVCLLNNFYPREAKVQWKVDNALQSGNSQESVTEQDSKDST<br>YSLSSTLTLSKADYEKHKVYACEVTHQGLSSPVTKSFNRGEC |
| 10 | 24E5-IgG1.1<br>HC<br>ILT4.5-<br>IgG1.1f | **EVQLLESGGGLVQPGGSLRLSCAASGFTFSSYVMSWVRQAPGK**<br>**GLEWVSGISGSGGSTYYADSVKGRFTISRDNSKNTLYLQMNSL**<br>**RAEDTAVYYCAKDQDIIAAYYFVYWGQGTLVTVSS**ASTKGPSV<br>FPLAPSSKSTSGGTAALGCLVKDYFPEPVTVSWNSGALTSGVH<br>TFPAVLQSSGLYSLSSVVTVPSSSLGTQTYICNVNHKPSNTKV<br>DKRVEPKSCDKTHTCPPCPAPEAEGAPSVFLFPPKPKDTLMIS<br>RTPEVTCVVVDVSHEDPEVKFNWYVDGVEVHNAKTKPREEQYN<br>STYRVVSVLTVLHQDWLNGKEYKCKVSNKALPSSIEKTISKAK<br>GQPREPQVYTLPPSREEMTKNQVSLTCLVKGFYPSDIAVEWES<br>NGQPENNYKTTPPVLDSDGSFFLYSKLTVDKSRWQQGNVFSCS<br>VMHEALHNHYTQKSLSLSPGK |
| 11 | 21D9 kappa LC<br>ILT4.6-kappa | **EIVLTQSPGTLSLSPGERATLSCRASQSVSSSYLAWYQQKPGQ**<br>**APRLLIYGASSRATGIPDRFSGSGSGTDFTLTISRLEPEDFAV**<br>**YYCQQYGSSPLTFGGGTKVEIK**RTVAAPSVFIFPPSDEQLKSG<br>TASVVCLLNNFYPREAKVQWKVDNALQSGNSQESVTEQDSKDS<br>TYSLSSTLTLSKADYEKHKVYACEVTHQGLSSPVTKSFNRGEC |
| 12 | 21D9-IgG1.1f<br>HC<br>ILT4.6-<br>IgG1.1f | **EGQLLESGGDLVQPGGSLRLSCATSGFTFSNYAMNWVRQAPGK**<br>**GLEWISVISVSGGSTYYADSVKGRFTISRDNSKNTLYLQMNSL**<br>**RAEDTAVYYCAKDYYYDSGSYYDSFFDYWGQGTLVTVSS**ASTK<br>GPSVFPLAPSSKSTSGGTAALGCLVKDYFPEPVTVSWNSGALT<br>SGVHTFPAVLQSSGLYSLSSVVTVPSSSLGTQTYICNVNHKPS<br>NTKVDKRVEPKSCDKTHTCPPCPAPEAEGAPSVFLFPPKPKDT<br>LMISRTPEVTCVVVDVSHEDPEVKFNWYVDGVEVHNAKTKPRE<br>EQYNSTYRVVSVLTVLHQDWLNGKEYKCKVSNKALPSSIEKTI<br>SKAKGQPREPQVYTLPPSREEMTKNQVSLTCLVKGFYPSDIAV<br>EWESNGQPENNYKTTPPVLDSDGSFFLYSKLTVDKSRWQQGNV<br>FSCSVMHEALHNHYTQKSLSLSPGK |
| 13 | 21D9.e.IgG1.3<br>HC<br>ILT4.8.IgG1.3 | **EVQLLESGGGLVQPGGSLRLSCAASGFTFSNYAMNWVRQAPGK**<br>**GLEWVSVISVSGGSTYYADSVKGRFTISRDNSKNTLYLQMNSL**<br>**RAEDTAVYYCAKDYYYDSGSYYDSFFDYWGQGTLVTVSS**ASTK<br>GPSVFPLAPSSKSTSGGTAALGCLVKDYFPEPVTVSWNSGALT<br>SGVHTFPAVLQSSGLYSLSSVVTVPSSSLGTQTYICNVNHKPS<br>NTKVDKRVEPKSCDKTHTCPPCPAPEAEGAPSVFLFPPKPKDT<br>LMISRTPEVTCVVVDVSHEDPEVKFNWYVDGVEVHNAKTKPRE<br>EQYNSTYRVVSVLTVLHQDWLNGKEYKCKVSNKALPAPIEKTI<br>SKAKGQPREPQVYTLPPSREEMTKNQVSLTCLVKGFYPSDIAV<br>EWESNGQPENNYKTTP<br>PVLDSDGSFFLYSKLTVDKSRWQQGNVFSCSVMHEALHNHYTQ<br>KSLSLSPG |

-continued

| SEQ ID NO | Name | Sequence |
|---|---|---|
| 14 | 21A5 kappa LC | EIALTQSPGTLSLSPGERATLSCRASQSVSSSYLAWYQQKPGQ<br>APRLLIYGASSRATGIPDRFSGSGSGTDFTLTISRLEPEDFAV<br>YYCQQYGSTFGGGTKVEIKRTVAAPSVFIFPPSDEQLKSGTAS<br>VVCLLNNFYPREAKVQWKVDNALQSGNSQESVTEQDSKDSTYS<br>LSSTLTLSKADYEKHKVYACEVTHQGLSSPVTKSFNRGEC |
| 15 | 21A5.IgG1.3 HC | QVQLVQSGAEVKKPGASVKVSCKASGYTFTDYYLHWVRQAPGQ<br>GLEWMGIFHPSGDITSSAQNFQGRVTMIRDTSTSTVYMELSSL<br>RSEDTAVYYCARGGVLRYLDWSHAFDIWGQGTMVTVSSASTKG<br>PSVFPLAPSSKSTSGGTAALGCLVKDYFPEPVTVSWNSGALTS<br>GVHTFPAVLQSSGLYSLSSVVTVPSSSLGTQTYICNVNHKPSN<br>TKVDKRVEPKSCDKTHTCPPCPAPEAEGAPSVFLFPPKPKDTL<br>MISRTPEVTCVVVDVSHEDPEVKFNWYVDGVEVHNAKTKPREE<br>QYNSTYRVVSVLTVLHQDWLNGKEYKCKVSNKALPAPIEKTIS<br>KAKGQPREPQVYTLPPSREEMTKNQVSLTCLVKGFYPSDIAVE<br>WESNGQPENNYKTTPPVLDSDGSFFLYSKLTVDKSRWQQGNVF<br>SCSVMHEALHNHYTQKSLSLSPG |
| 16 | 21A5.1 kappa LC (ILT4.9.1K) | EIVLTQSPGTLSLSPGERATLSCRASQSVSSSYLAWYQQKPGQ<br>APRLLIYGASSRATGIPDRFSGSGSGTDFTLTISRLEPEDFAV<br>YYCQQYGSTFGGGTKVEIKRTVAAPSVFIFPPSDEQLKSGTAS<br>VVCLLNNFYPREAKVQWKVDNALQSGNSQESVTEQDSKDSTYS<br>LSSILTLSKADYEKHKVYACEVTHQGLSSPVTKSFNRGEC |
| 17 | 21A5.a.IGg1.3 HC (Ilt4.9.IGg1.3) | QVQLVQSGAEVKKPGASVKVSCKASGYTFTDYYLHWVRQAPGQ<br>GLEWMGIFHPSGDITSSAQNFQGRVTMTRDTSTSTVYMELSSL<br>RSEDTAVYYCARGGVLRYLDWSHAFDIWGQGTMVTVSSASTKG<br>PSVFPLAPSSKSTSGGTAALGCLVKDYFPEPVTVSWNSGALTS<br>GVHTFPAVLQSSGLYSLSSVVTVPSSSLGTQTYICNVNHKPSN<br>TKVDKRVEPKSCDKTHTCPPCPAPEAEGAPSVFLFPPKPKDTL<br>MISRTPEVTCVVVDVSHEDPEVKFNWYVDGVEVHNAKTKPREE<br>QYNSTYRVVSVLTVLHQDWLNGKEYKCKVSNKALPAPIEKTIS<br>KAKGQPREPQVYTLPPSREEMTKNQVSLTCLVKGFYPSDIAVE<br>WESNGQPENNYKTTPPVLDSDGSFFLYSKLTVDKSRWQQGNVF<br>SCSVMHEALHNHYTQKSLSLSPG |
| 18 | 10F10 kappa LC | AIQLTQSPSSLSASVGDRVTITCRASQGISSALAWFQQKPGKA<br>PKLLIYDASSLESGVPSRFTGSGSGTDFTLTISSLQPEDFATY<br>YCQQFNSYPITFGQGTRLEIKRTVAAPSVFIFPPSDEQLKSGT<br>ASVVCLLNNFYPREAKVQWKVDNALQSGNSQESVTEQDSKDST<br>YSLSSILTLSKADYEKHKVYACEVTHQGLSSPVTKSFNRGEC |
| 19 | 10F10.IgG1.3 HC ILT4.10.IgG1.3 | QVQLVESGGGVVQPGRSLRLSCAASGFTFSSYAMHWVRQAPGK<br>GLEWVAIISYDEYNKYYADSVKGRFTISRDNSKNTLYLQMNSL<br>RAEDTAVYYCAREWVGIRYWGQGTLVTVSSASTKGPSVFPLAP<br>SSKSTSGGTAALGCLVKDYFPEPVTVSWNSGALTSGVHTFPAV<br>LQSSGLYSLSSVVTVPSSSLGTQTYICNVNHKPSNTKVDKRVE<br>PKSCDKTHTCPPCPAPEAEGAPSVFLFPPKPKDTLMISRTPEV<br>TCVVVDVSHEDPEVKFNWYVDGVEVHNAKTKPREEQYNSTYRV<br>VSVLTVLHQDWLNGKEYKCKVSNKALPAPIEKTISKAKGQPRE<br>PQVYTLPPSREEMTKNQVSLTCLVKGFYPSDIAVEWESNGQPE<br>NNYKTTPPVLDSDGSFFLYSKLTVDKSRWQQGNVFSCSVMHEA<br>LHNHYTQKSLSLSPG |
| 20 | 10E10.1 kappa LC | AIQLTQSPSSLSASVGDRVTITCRASQGISSALAWYQQKPGKA<br>PKLLIYDASSLESGVPSRFTGSGSGTDFTLTISSLQPEDFATY<br>YCQQFNSYPITFGQGTRLEIKRTVAAPSVFIFPPSDEQLKSGT<br>ASVVCLLNNFYPREAKVQWKVDNALQSGNSQESVTEQDSKDST<br>YSLSSTLTLSKADYEKHKVYACEVTHQGLSSPVIKSFNRGEC |
| 21 | 10E10.3 kappa LC | AIQLTQSPSSLSASVGDRVTITCRASQGISSALAWYQQKPGKA<br>PKLLIYDASSLESGVPSRFSGSGSGTDFTLTISSLQPEDFATY<br>YCQQFNSYPITFGQGTRLEIKRTVAAPSVFIFPPSDEQLKSGT<br>ASVVCLLNNFYPREAKVQWKVDNALQSGNSQESVTEQDSKDST<br>YSLSSILTLSKADYEKHKVYACEVTHQGLSSPVTKSFNRGEC |

-continued

| SEQ ID NO | Name | Sequence |
|---|---|---|
| 22 | 9G4 LC DNA<br>ILT4.1-kappa<br>DNA | GAAATTGTGTTGACACAGTCTCCAGCCACCCTGTCTTTGTCTC<br>CAGGGGAAAGAGCCACCCTCTCCTGCAGGGCCAGTCAGAGTGT<br>TAGCAGCTACTTAGCCTGGTACCAACAGAAACCTGGCCAGGCT<br>CCCAGGCTCCTCATCTATGATGCGTCCAACAGGGCCACTGGCA<br>TCCCAGCCAGGTTCAGTGGCAGTGGGTCTGGGACAGACTTCAC<br>TCTCACCATCAGCAGCCTAGAGCCTGAAGATTTTGCAGGTTAT<br>TACTGTCAGCAGCGTAGCTACTGGCCGTGGACGTTCGGCCAAG<br>GGACCAAGGTGGAAATCAAACGTACGGTGGCTGCACCATCTGT<br>CTTCATCTTCCCGCCATCTGATGAGCAGTTGAAATCTGGAACT<br>GCCTCTGTTGTGTGCCTGCTGAATAACTTCTATCCCAGAGAGG<br>CCAAAGTACAGTGGAAGGTGGATAACGCCCTCCAATCGGGTAA<br>CTCCCAGGAGAGTGTCACAGAGCAGGACAGCAAGGACAGCACC<br>TACAGCCTCAGCAGCACCCTGACGCTGAGCAAAGCAGACTACG<br>AGAAACACAAAGTCTACGCCTGCGAAGTCACCCATCAGGGCCT<br>GAGCTCGCCCGTCACAAAGAGCTTCAACAGGGGAGAGTGTTAG |
| 23 | 9G4 IgG1.1f<br>HC DNA<br>ILT4.1-<br>IgG1.1f DNA | CAGGTGCAGCTGCAGGAGTCGGGCCCAGGACTGGTGAAGCCTT<br>CGGAGACCCTGTCCCTCACCTGCACTGTCTCTGGTGGCTCCAT<br>CAGTAGTTACTACTGGAACTGGATTCGGCAGCCCCCAGGGAAG<br>GGACTGGAGTGGCTTGGGTACATCTATTACAGTGGGAGTACCA<br>AGTACAACCCCTCCCTCAAGAGTCGAGTCACCATATCAGTAGA<br>CACGTCCAAGAACCAGTTCTCCCTGAAGCTGAGCTCTGTGACC<br>GCTGCGGACACGGCCGTGTATTATTGTGCCAGCAGTGGCTGGT<br>ACTACTTTGACTATTGGGGCCAGGGAACCCTGGTCACCGTCTC<br>CTCAGCTAGCACCAAGGGCCCATCGGTCTTCCCCCTGGCACCC<br>TCCTCCAAGAGCACCTCTGGGGGCACAGCGGCCCTGGGCTGCC<br>TGGTCAAGGACTACTTCCCCGAACCGGTGACGGTGTCGTGGAA<br>CTCAGGCGCCCTGACCAGCGGCGTGCACACCTTCCCGGCTGTC<br>CTACAGTCCTCAGGACTCTACTCCCTCAGCAGCGTGGTGACCG<br>TGCCCTCCAGCAGCTTGGGCACCCAGACCTACATCTGCAACGT<br>GAATCACAAGCCCAGCAACACCAAGGTGGACAAGAGAGTTGAG<br>CCCAAATCTTGTGACAAAACTCACACATGCCCACCGTGCCCAG<br>CACCTGAAGCCGAAGGGGCCCCGTCAGTCTTCCTCTTCCCCCC<br>AAAACCCAAGGACACCCTCATGATCTCCCGGACCCCTGAGGTC<br>ACATGCGTGGTGGTGGACGTGAGCCACGAAGACCCTGAGGTCA<br>AGTTCAACTGGTACGTGGACGGCGTGGAGGTGCATAATGCCAA<br>GACAAAGCCGCGGGAGGAGCAGTACAACAGCACGTACCGTGTG<br>GTCAGCGTCCTCACCGTCCTGCACCAGGACTGGCTGAATGGCA<br>AGGAGTACAAGTGCAAGGTCTCCAACAAAGCCCTCCCAAGCAG<br>CATCGAGAAAACCATCTCCAAAGCCAAAGGGCAGCCCCGAGAA<br>CCACAGGTGTACACCCTGCCCCCATCCCGGGAGGAGATGACCA<br>AGAACCAGGTCAGCCTGACCTGCCTGGTCAAAGGCTTCTATCC<br>CAGCGACATCGCCGTGGAGTGGGAGAGCAATGGGCAGCCGGAG<br>AACAACTACAAGACCACGCCTCCCGTGCTGGACTCCGACGGCT<br>CCTTCTTCCTCTATAGCAAGCTCACCGTGGACAAGAGCAGGTG<br>GCAGCAGGGGAACGTCTTCTCATGCTCCGTGATGCATGAGGCT<br>CTGCACAACCACTACACGCAGAAGAGCCTCTCCCTGTCCCCGG<br>GTAAATGA |
| 24 | 9C8 kappa LC<br>DNA<br>ILT4.2-kappa<br>DNA | GCCATCCAGTTGACCCAGTCTCCATCCTCCCTGTCTGCATCTG<br>TAGGAGACAGAGTCACCATCACTTGCCGGGCAAGTCAGGGCAT<br>TAGCAGTGCTTTAGCCTGGTATCAGCAGAAACCAGGGAAAGCT<br>CCTAAGCTCCTGATCTATGATGCCTCCAGTTTGGAAAGTGGGG<br>TCCCATCAAGGTTCAGCGGCAGTGGATCTGGGACAGATTTCAC<br>TCTCACCATCAGCAGCCTGCAGCCTGAAGATTTTGCAACTTAT<br>TACTGTCAACAGTTTAATAGTTACCCATTCACTTTCGGCCCTG<br>GGACCAAAGTGGATATCAAACGTACGGTGGCTGCACCATCTGT<br>CTTCATCTTCCCGCCATCTGATGAGCAGTTGAAATCTGGAACT<br>GCCTCTGTTGTGTGCCTGCTGAATAACTTCTATCCCAGAGAGG<br>CCAAAGTACAGTGGAAGGTGGATAACGCCCTCCAATCGGGTAA<br>CTCCCAGGAGAGTGTCACAGAGCAGGACAGCAAGGACAGCACC<br>TACAGCCTCAGCAGCACCCTGACGCTGAGCAAAGCAGACTACG<br>AGAAACACAAAGTCTACGCCTGCGAAGTCACCCATCAGGGCCT<br>GAGCTCGCCCGTCACAAAGAGCTTCAACAGGGGAGAGTGTTAG |
| 25 | 9C8 IgG1.1f<br>DNA<br>ILT4.2-<br>CHECK THIS | CAGGTGCAACTGGTGCAGTCTGGGGCTGAGGTAAAGAAGCCTG<br>GGGCCTCAGTGAAGGTCTCCTGCAAGGCTTCTGGATACACCTT<br>CACCAGCTCTGATATCAACTGGGTGCGACAGGCCACTGGACAA<br>GGGCTTGAGTGGATGGGATGGATGAACCCTAACAGTGGTCACA<br>CAGGCTATGCACAGAAGTTCCAGGACAGAGTCACCTTGACCCG<br>GGACACCTCCATAAGCACAGCCTACATGGAGCTGAGCAGCCTG<br>AGATCTGAGGACTCGGCCGTGTATTACTGTGCGAGAGGTGGGA<br>ATAGCATTGACTGGGGGTTCTCCTACTACGGTCTGGACGTCTG<br>GGGCCAAGGGACCACGGTCACCGTCTCCTCAGCTAGCACCAAG |

-continued

| SEQ ID NO | Name | Sequence |
|---|---|---|
| | | GGCCCATCGGTCTTCCCCCTGGCACCCTCCTCCAAGAGCACCT CTGGGGGCACAGCGGCCCTGGGCTGCCTGGTCAAGGACTACTT CCCCGAACCGGTGACGGTGTCGTGGAACTCAGGCGCCCTGACC AGCGGCGTGCACACCTTCCCGGCTGTCCTACAGTCCTCAGGAC TCTACTCCCTCAGCAGCGTGGTGACCGTGCCCTCCAGCAGCTT GGGCACCCAGACCTACATCTGCAACGTGAATCACAAGCCCAGC AACACCAAGGTGGACAAGAGAGTTGAGCCCAAATCTTGTGACA AAACTCACACATGCCCACCGTGCCCAGCACCTGAAGCCGAAGG GGCCCCGTCAGTCTTCCTCTTCCCCCCAAAACCCAAGGACACC CTCATGATCTCCCGGACCCCTGAGGTCACATGCGTGGTGGTGG ACGTGAGCCACGAAGACCCTGAGGTCAAGTTCAACTGGTACGT GGACGGCGTGGAGGTGCATAATGCCAAGACAAAGCCGCGGGAG GAGCAGTACAACAGCACGTACCGTGTGGTCAGCGTCCTCACCG TCCTGCACCAGGACTGGCTGAATGGCAAGGAGTACAAGTGCAA GGTCTCCAACAAAGCCCTCCCAAGCAGCATCGAGAAAACCATC TCCAAAGCCAAAGGGCAGCCCCGAGAACCACAGGTGTACACCC TGCCCCCATCCCGGGAGGAGATGACCAAGAACCAGGTCAGCCT GACCTGCCTGGTCAAAGGCTTCTATCCCAGCGACATCGCCGTG GAGTGGGAGAGCAATGGGCAGCCGGAGAACAACTACAAGACCA CGCCTCCCGTGCTGGACTCCGACGGCTCCTTCTTCCTCTATAG CAAGCTCACCGTGGACAAGAGCAGGTGGCAGCAGGGGAACGTC TTCTCATGCTCCGTGATGCATGAGGCTCTGCACAACCACTACA CGCAGAAGAGCCTCTCCCTGTCCCCGGGTAAATGA |
| 26 | 2H2 kappa LC DNA ILT4.3-kappa DNA | GAAATTGTGTTGACGCAGTCTCCAGGCACCCTGTCTTTGTCTC CAGGGGAAAGAGCCACCCTCTCCTGCAGGGCCAGTCAGAGTGT TAGCAGCAGCTACTTAGCCTGGTACCAGCAGAAACCTGGCCAG GCTCCCAGGCTCCTCATCTATGGTGCATCCAGCAGGGCCACTG GCATCCCAGACAGGTTCAGTGGCAGTGGGTCTGGGACAGACTT CACTCTCACCATCAGCAGACTGGAGCCTGAAGATTTTGCAGTG TATTACTGTCAGCAGTATGGTAGCTCGTACACTTTTGGCCAGG GGACCAAGCTGGAGATCAAACGTACGGTGGCTGCACCATCTGT CTTCATCTTCCCGCCATCTGATGAGCAGTTGAAATCTGGAACT GCCTCTGTTGTGTGCCTGCTGAATAACTTCTATCCCAGAGAGG CCAAAGTACAGTGGAAGGTGGATAACGCCCTCCAATCGGGTAA CTCCCAGGAGAGTGTCACAGAGCAGGACAGCAAGGACAGCACC TACAGCCTCAGCAGCACCCTGACGCTGAGCAAAGCAGACTACG AGAAACACAAAGTCTACGCCTGCGAAGTCACCCATCAGGGCCT GAGCTCGCCCGTCACAAAGAGCTTCAACAGGGGAGAGTGTTAG |
| 27 | 2H2 IgG1.1f HC DNA ILT4.3-IgG1.1f DNA | CAGGTCCAGTTGGTGCAGTCTGGGGCTGAGGTGAAGAAGCCTG GGTCCTCGGTGGAGGTCTCCTGCAAGGCTTCTGGGGGCACCTT CAGCAACTATGCTATCAGCTGGGTGCGACAGGCCCCTGGACAA GGGCTTGAGTGGATGGGAGGGATCATCCCCATCTTGGCTACAG CAAACTACGCACCGAAGTTCCAGGGCAGAGTCACGATTACCGC GGACGAATTCACGAGCTCAGCTTACATGGAGCTGAGCAGCCTG AGATCTGAGGACACGGCCGTGTATTACTGTGCGAAGTCTAGTA TTACTATGATTCGGGGAGCCTATCTTTACTACTACGACGGTAT GGACGTCTGGGGCCAAGGGACCACGGTCACCGTCTCCTCAGCT AGCACCAAGGGCCCATCGGTCTTCCCCCTGGCACCCTCCTCCA AGAGCACCTCTGGGGGCACAGCGGCCCTGGGCTGCCTGGTCAA GGACTACTTCCCCGAACCGGTGACGGTGTCGTGGAACTCAGGC GCCCTGACCAGCGGCGTGCACACCTTCCCGGCTGTCCTACAGT CCTCAGGACTCTACTCCCTCAGCAGCGTGGTGACCGTGCCCTC CAGCAGCTTGGGCACCCAGACCTACATCTGCAACGTGAATCAC AAGCCCAGCAACACCAAGGTGGACAAGAGAGTTGAGCCCAAAT CTTGTGACAAAACTCACACATGCCCACCGTGCCCAGCACCTGA AGCCGAAGGGGCCCCGTCAGTCTTCCTCTTCCCCCCAAAACCC AAGGACACCCTCATGATCTCCCGGACCCCTGAGGTCACATGCG TGGTGGTGGACGTGAGCCACGAAGACCCTGAGGTCAAGTTCAA CTGGTACGTGGACGGCGTGGAGGTGCATAATGCCAAGACAAAG CCGCGGGAGGAGCAGTACAACAGCACGTACCGTGTGGTCAGCG TCCTCACCGTCCTGCACCAGGACTGGCTGAATGGCAAGGAGTA CAAGTGCAAGGTCTCCAACAAAGCCCTCCCAAGCAGCATCGAG AAAACCATCTCCAAAGCCAAAGGGCAGCCCCGAGAACCACAGG TGTACACCCTGCCCCCATCCCGGGAGGAGATGACCAAGAACCA GGTCAGCCTGACCTGCCTGGTCAAAGGCTTCTATCCCAGCGAC ATCGCCGTGGAGTGGGAGAGCAATGGGCAGCCGGAGAACAACT ACAAGACCACGCCTCCCGTGCTGGACTCCGACGGCTCCTTCTT CCTCTATAGCAAGCTCACCGTGGACAAGAGCAGGTGGCAGCAG GGGAACGTCTTCTCATGCTCCGTGATGCATGAGGCTCTGCACA ACCACTACACGCAGAAGAGCCTCTCCCTGTCCCCGGGTAAATG A |

-continued

| SEQ ID NO | Name | Sequence |
|---|---|---|
| 28 | 2E5 kappa LC DNA ILT4.4-kappa DNA | GAAATTGTGTTGACACAGTCTCCAGCCACCCTGTCTTTGTCTC CAGGGGAAAGAGCCACCCTCTCCTGCAGGGCCAGTCAGAGTGT TAGCAGCTACTTAGCCTGGTACCAACAGAAACCTGGCCAGGCT CCCAGGCTCCTCATCTATGATGCATCCAACAGGGCCACTGGCA TCCCAGCCAGGTTCAGTGGCAGTGGGTCTGGGACAGACTTCAC TCTCACCATCAGCAGCCTAGAGCCTGAAGATTTTGCAGTTTAT TACTGTCAGCAGCGTAGCAACTGGCCTCCGTGGACGTTCGGCC AAGGGACCAAGGTGGAAATCAAACGTACGGTGGCTGCACCATC TGTCTTCATCTTCCCGCCATCTGATGAGCAGTTGAAATCTGGA ACTGCCTCTGTTGTGTGCCTGCTGAATAACTTCTATCCCAGAG AGGCCAAAGTACAGTGGAAGGTGGATAACGCCCTCCAATCGGG TAACTCCCAGGAGAGTGTCACAGAGCAGGACAGCAAGGACAGC ACCTACAGCCTCAGCAGCACCCTGACGCTGAGCAAAGCAGACT ACGAGAAACACAAAGTCTACGCCTGCGAAGTCACCCATCAGGG CCTGAGCTCGCCCGTCACAAAGAGCTTCAACAGGGGAGAGTGT TAG |
| 29 | 2E5 IgG1.1f HC DNA ILT4.4-IgG1.1f DNA | CAGGTGCAGCTGGTGGAGTCTGGGGGAGGCGTGGTCCAGCCTG GGAGGTCCCTGAGACTCTCCTGTACAGCGTCTGGATTCACCTT CAGTAACTATGGCATGCACTGGGTCCGCCAGGCTCCAGGCAAG GGACTGGAGTGGGTGGCAGTTATCTGGTATGATGGAAGTAATG AATACTATGCAGAATCCGTGAAGGGCCGACTCACCATCTCCAG AGACAATTCCAAGAACACGCTGTATCTGCAAGTGAACAGCCTG AGAGCCGAGGACACGGCTGTGTATTATTGTGCGAGAGATCCTT TCTATGGTTCGGGGAATTACTTTGACTACTGGGGCCAGGGAAC CCTGGTCACCGTCTCCTCAGCTAGCACCAAGGGCCCATCGGTC TTCCCCCTGGCACCCTCCTCCAAGAGCACCTCTGGGGGCACAG CGGCCCTGGGCTGCCTGGTCAAGGACTACTTCCCCGAACCGGT GACGGTGTCGTGGAACTCAGGCGCCCTGACCAGCGGCGTGCAC ACCTTCCCGGCTGTCCTACAGTCCTCAGGACTCTACTCCCTCA GCAGCGTGGTGACCGTGCCCTCCAGCAGCTTGGGCACCCAGAC CTACATCTGCAACGTGAATCACAAGCCCAGCAACACCAAGGTG GACAAGAGAGTTGAGCCCAAATCTTGTGACAAAACTCACACAT GCCCACCGTGCCCAGCACCTGAAGCCGAAGGGGCCCCGTCAGT CTTCCTCTTCCCCCCAAAACCCAAGGACACCCTCATGATCTCC CGGACCCCTGAGGTCACATGCGTGGTGGTGGACGTGAGCCACG AAGACCCTGAGGTCAAGTTCAACTGGTACGTGGACGGCGTGGA GGTGCATAATGCCAAGACAAAGCCGCGGGAGGAGCAGTACAAC AGCACGTACCGTGTGGTCAGCGTCCTCACCGTCCTGCACCAGG ACTGGCTGAATGGCAAGGAGTACAAGTGCAAGGTCTCCAACAA AGCCCTCCCAAGCAGCATCGAGAAAACCATCTCCAAAGCCAAA GGGCAGCCCCGAGAACCACAGGTGTACACCCTGCCCCCATCCC GGGAGGAGATGACCAAGAACCAGGTCAGCCTGACCTGCCTGGT CAAAGGCTTCTATCCCAGCGACATCGCCGTGGAGTGGGAGAGC AATGGGCAGCCGGAGAACAACTACAAGACCACGCCTCCCGTGC TGGACTCCGACGGCTCCTTCTTCCTCTATAGCAAGCTCACCGT GGACAAGAGCAGGTGGCAGCAGGGGAACGTCTTCTCATGCTCC GTGATGCATGAGGCTCTGCACAACCACTACACGCAGAAGAGCC TCTCCCTGTCCCCGGGTAAATGA |
| 30 | 24E5 kappa LC DNA ILT4.5-kappa DNA | GACATCCAGATGACCCAGTCTCCATCCTCACTGTCTGCATCTG TAGGAGACAGAGTCACCATCACTTGTCGGGCGAGTCAGGGTAT TAGCAGCTGGTTAGCCTGGTATCAGCAGAAACCAGAGAAAGCC CCTAAGTCCCTGATCTATGCTGCATCCAGTTTGCAAAGTGGGG TCCCATCAAGGTTCAGCGGCAGTGGATCTGGGACAGATTTCAC TCTCACCATCAGCAGCCTGCAGCCTGAAGATTTTGCAACTTAT TACTGCCAACAGTATAATAGTTACCCTCTCACTTTCGGCGGAG GGACCAAGGTGGAGATCAAACGTACGGTGGCTGCACCATCTGT CTTCATCTTCCCGCCATCTGATGAGCAGTTGAAATCTGGAACT GCCTCTGTTGTGTGCCTGCTGAATAACTTCTATCCCAGAGAGG CCAAAGTACAGTGGAAGGTGGATAACGCCCTCCAATCGGGTAA CTCCCAGGAGAGTGTCACAGAGCAGGACAGCAAGGACAGCACC TACAGCCTCAGCAGCACCCTGACGCTGAGCAAAGCAGACTACG AGAAACACAAAGTCTACGCCTGCGAAGTCACCCATCAGGGCCT GAGCTCGCCCGTCACAAAGAGCTTCAACAGGGGAGAGTGTTAG |
| 31 | 24E5 IgG1.1f HC DNA ILT4.5-IgG1.1f DNA | GAGGTGCAGCTGTTGGAGTCTGGGGGAGGCTTGGTACAGCCTG GGGGGTCCCTGAGACTCTCCTGTGCAGCCTCTGGATTCACCTT TAGCAGCTATGTCATGAGCTGGGTCCGCCAGGCTCCAGGGAAG GGGCTGGAGTGGGTCTCAGGTATTAGTGGTAGTGGTGGTAGCA CATACTACGCAGACTCCGTGAAGGGCCGGTTCACCATCTCCAG AGACAATTCCAAGAACACGCTGTATCTGCAAATGAACAGCCTG AGAGCCGAGGACACGGCCGTATATTACTGTGCGAAAGATCAGG ATATTATAGCAGCATACTACTTTGTCTACTGGGGCCAGGGAAC |

-continued

| SEQ ID NO | Name | Sequence |
|---|---|---|
| | | CCTGGTCACCGTCTCCTCAGCTAGCACCAAGGGCCCATCGGTC TTCCCCCTGGCACCCTCCTCCAAGAGCACCTCTGGGGGCACAG CGGCCCTGGGCTGCCTGGTCAAGGACTACTTCCCCGAACCGGT GACGGTGTCGTGGAACTCAGGCGCCCTGACCAGCGGCGTGCAC ACCTTCCCGGCTGTCCTACAGTCCTCAGGACTCTACTCCCTCA GCAGCGTGGTGACCGTGCCCTCCAGCAGCTTGGGCACCCAGAC CTACATCTGCAACGTGAATCACAAGCCCAGCAACACCAAGGTG GACAAGAGAGTTGAGCCCAAATCTTGTGACAAAACTCACACAT GCCCACCGTGCCCAGCACCTGAAGCCGAAGGGGCCCCGTCAGT CTTCCTCTTCCCCCCAAAACCCAAGGACACCCTCATGATCTCC CGGACCCCTGAGGTCACATGCGTGGTGGTGGACGTGAGCCACG AAGACCCTGAGGTCAAGTTCAACTGGTACGTGGACGGCGTGGA GGTGCATAATGCCAAGACAAAGCCGCGGGAGGAGCAGTACAAC AGCACGTACCGTGTGGTCAGCGTCCTCACCGTCCTGCACCAGG ACTGGCTGAATGGCAAGGAGTACAAGTGCAAGGTCTCCAACAA AGCCCTCCCAAGCAGCATCGAGAAAACCATCTCCAAAGCCAAA GGGCAGCCCCGAGAACCACAGGTGTACACCCTGCCCCCATCCC GGGAGGAGATGACCAAGAACCAGGTCAGCCTGACCTGCCTGGT CAAAGGCTTCTATCCCAGCGACATCGCCGTGGAGTGGGAGAGC AATGGGCAGCCGGAGAACAACTACAAGACCACGCCTCCCGTGC TGGACTCCGACGGCTCCTTCTTCCTCTATAGCAAGCTCACCGT GGACAAGAGCAGGTGGCAGCAGGGGAACGTCTTCTCATGCTCC GTGATGCATGAGGCTCTGCACAACCACTACACGCAGAAGAGCC TCTCCCTGTCCCCGGGTAAATGA |
| 32 | 21D9 kappa LC DNA ILT4.6-kappa DNA | GAAATTGTGTTGACGCAGTCTCCAGGCACCCTGTCTTTGTCTC CAGGGGAAAGAGCCACCCTCTCCTGCAGGGCCAGTCAGAGTGT TAGCAGCAGCTACTTAGCCTGGTACCAGCAGAAACCTGGCCAG GCTCCCAGGCTCCTCATCTATGGTGCATCCAGCAGGGCCACTG GCATCCCAGACAGGTTCAGTGGCAGTGGGTCTGGGACAGACTT CACTCTCACCATCAGCAGACTGGAGCCTGAAGATTTTGCAGTG TATTACTGTCAGCAGTATGGTAGCTCACCTCTCACTTTCGGCG GAGGGACCAAGGTGGAGATCAAACGTACGGTGGCTGCACCATC TGTCTTCATCTTCCCGCCATCTGATGAGCAGTTGAAATCTGGA ACTGCCTCTGTTGTGTGCCTGCTGAATAACTTCTATCCCAGAG AGGCCAAAGTACAGTGGAAGGTGGATAACGCCCTCCAATCGGG TAACTCCCAGGAGAGTGTCACAGAGCAGGACAGCAAGGACAGC ACCTACAGCCTCAGCAGCACCCTGACGCTGAGCAAAGCAGACT ACGAGAAACACAAAGTCTACGCCTGCGAAGTCACCCATCAGGG CCTGAGCTCGCCCGTCACAAAGAGCTTCAACAGGGGAGAGTGT TAG |
| 33 | 21D9 IgG1.1f HC DNA ILT4.6- IgG1.1f DNA | GAGGGACAGCTGTTGGAGTCTGGGGGAGACTTGGTACAGCCTG GGGGGTCCCTGAGACTCTCCTGTGCAACCTCTGGATTCACCTT TAGCAACTATGCCATGAACTGGGTCCGCCAGGCTCCAGGGAAG GGGCTGGAGTGGATCTCAGTTATTAGTGTTAGTGGTGGTAGCA CATACTACGCAGACTCCGTGAAGGGCCGGTTCACCATCTCCAG AGACAATTCCAAGAACACGCTGTATCTGCAAATGAATAGCCTG AGAGCCGAGGACACGGCCGTATATTACTGTGCGAAAGATTATT ACTATGATTCGGGGAGTTATTATGACTCTTTCTTTGACTACTG GGGCCAGGGAACCCTGGTCACCGTCTCCTCAGCTAGCACCAAG GGCCCATCGGTCTTCCCCCTGGCACCCTCCTCCAAGAGCACCT CTGGGGGCACAGCGGCCCTGGGCTGCCTGGTCAAGGACTACTT CCCCGAACCGGTGACGGTGTCGTGGAACTCAGGCGCCCTGACC AGCGGCGTGCACACCTTCCCGGCTGTCCTACAGTCCTCAGGAC TCTACTCCCTCAGCAGCGTGGTGACCGTGCCCTCCAGCAGCTT GGGCACCCAGACCTACATCTGCAACGTGAATCACAAGCCCAGC AACACCAAGGTGGACAAGAGAGTTGAGCCCAAATCTTGTGACA AAACTCACACATGCCCACCGTGCCCAGCACCTGAAGCCGAAGG GGCCCCGTCAGTCTTCCTCTTCCCCCCAAAACCCAAGGACACC CTCATGATCTCCCGGACCCCTGAGGTCACATGCGTGGTGGTGG ACGTGAGCCACGAAGACCCTGAGGTCAAGTTCAACTGGTACGT GGACGGCGTGGAGGTGCATAATGCCAAGACAAAGCCGCGGGAG GAGCAGTACAACAGCACGTACCGTGTGGTCAGCGTCCTCACCG TCCTGCACCAGGACTGGCTGAATGGCAAGGAGTACAAGTGCAA GGTCTCCAACAAAGCCCTCCCAAGCAGCATCGAGAAAACCATC TCCAAAGCCAAAGGGCAGCCCCGAGAACCACAGGTGTACACCC TGCCCCCATCCCGGGAGGAGATGACCAAGAACCAGGTCAGCCT GACCTGCCTGGTCAAAGGCTTCTATCCCAGCGACATCGCCGTG GAGTGGGAGAGCAATGGGCAGCCGGAGAACAACTACAAGACCA CGCCTCCCGTGCTGGACTCCGACGGCTCCTTCTTCCTCTATAG CAAGCTCACCGTGGACAAGAGCAGGTGGCAGCAGGGGAACGTC TTCTCATGCTCCGTGATGCATGAGGCTCTGCACAACCACTACA CGCAGAAGAGCCTCTCCCTGTCCCCGGGTAAATGA |

-continued

| SEQ ID NO | Name | Sequence |
|---|---|---|
| 34 | 21D9.IgG1.3 HC DNA ILT4.6-IgG1.3 HC DNA (variable region is underlined and bold) | **GAGGGACAGCTGTTGGAGTCTGGGGGAGACTTGGTACAGCCTG**<br>**GGGGGTCCCTGAGACTCTCCTGTGCAACCTCTGGATTCACCTT**<br>**TAGCAACTATGCCATGAACTGGGTCCGCCAGGCTCCAGGGAAG**<br>**GGGCTGGAGTGGATCTCAGTTATTAGTGTTAGTGGTGGTAGCA**<br>**CATACTACGCAGACTCCGTGAAGGGCCGGTTCACCATCTCCAG**<br>**AGACAATTCCAAGAACACGCTGTATCTGCAAATGAATAGCCTG**<br>**AGAGCCGAGGACACGGCCGTATATTACTGTGCGAAAGATTATT**<br>**ACTATGATTCGGGGAGTTATTATGACTCTTTCTTTGACTACTG**<br>**GGGCCAGGGAACCCTGGTCACCGTCTCCTCA**<br>GCTAGCACCAAGGGCCCATCGGTCTTCCCCCTGGCACCCTCCT<br>CCAAGAGCACCTCTGGGGGCACAGCGGCCCTGGGCTGCCTGGT<br>CAAGGACTACTTCCCCGAACCGGTGACGGTGTCGTGGAACTCA<br>GGCGCCCTGACCAGCGGCGTGCACACCTTCCCGGCTGTCCTAC<br>AGTCCTCAGGACTCTACTCCCTCAGCAGCGTGGTGACCGTGCC<br>CTCCAGCAGCTTGGGCACCCAGACCTACATCTGCAACGTGAAT<br>CACAAGCCCAGCAACACCAAGGTGGACAAGAGAGTTGAGCCCA<br>AATCTTGTGACAAAACTCACACATGCCCACCGTGCCCAGCACC<br>TGAAGCCGAAGGGGCCCCGTCAGTCTTCCTCTTCCCCCCAAAA<br>CCCAAGGACACCCTCATGATCTCCCGGACCCCTGAGGTCACAT<br>GCGTGGTGGTGGACGTGAGCCACGAAGACCCTGAGGTCAAGTT<br>CAACTGGTACGTGGACGGCGTGGAGGTGCATAATGCCAAGACA<br>AAGCCGCGGGAGGAGCAGTACAACAGCACGTACCGTGTGGTCA<br>GCGTCCTCACCGTCCTGCACCAGGACTGGCTGAATGGCAAGGA<br>GTACAAGTGCAAGGTCTCCAACAAAGCCCTCCCAGCCCCCATC<br>GAGAAAACCATCTCCAAAGCCAAAGGGCAGCCCCGAGAACCAC<br>AGGTGTACACCCTGCCCCCATCCCGGGAGGAGATGACCAAGAA<br>CCAGGTCAGCCTGACCTGCCTGGTCAAAGGCTTCTATCCCAGC<br>GACATCGCCGTGGAGTGGGAGAGCAATGGGCAGCCGGAGAACA<br>ACTACAAGACCACGCCTCCCGTGCTGGACTCCGACGGCTCCTT<br>CTTCCTCTATAGCAAGCTCACCGTGGACAAGAGCAGGTGGCAG<br>CAGGGGAACGTCTTCTCATGCTCCGTGATGCATGAGGCTCTGC<br>ACAACCACTACACGCAGAAGAGCCTCTCCCTGTCCCCGGGTTG<br>A |
| 35 | 21D9.b.IgG1.3 HC DNA | GAGGTGCAGCTGCTGGAGTCTGGAGGAGGACTGGTGCAGCCAG<br>GAGGCAGCCTGAGGCTGTCCTGCGCCACCTCTGGCTTCACATT<br>TTCCAACTATGCCATGAATTGGGTGCGCCAGGCACCTGGCAAG<br>GGACTGGAGTGGATCTCTGTGATCTCTGTGAGCGGCGGCTCTA<br>CCTACTATGCCGACAGCGTGAAGGGCCGGTTCACCATCAGCAG<br>AGATAACTCCAAGAATACACTGTATCTGCAGATGAACAGCCTG<br>CGGGCCGAGGACACAGCCGTGTACTATTGTGCCAAGGACTACT<br>ATTACGATTCCGGCTCTTATTACGACTCCTTCTTTGATTACTG<br>GGGCCAGGGCACCCTGGTGACAGTGAGCTCCGCTAGCACCAAG<br>GGCCCATCGGTCTTCCCCCTGGCACCCTCCTCCAAGAGCACCT<br>CTGGGGGCACAGCGGCCCTGGGCTGCCTGGTCAAGGACTACTT<br>CCCCGAACCGGTGACGGTGTCGTGGAACTCAGGCGCCCTGACC<br>AGCGGCGTGCACACCTTCCCGGCTGTCCTACAGTCCTCAGGAC<br>TCTACTCCCTCAGCAGCGTGGTGACCGTGCCCTCCAGCAGCTT<br>GGGCACCCAGACCTACATCTGCAACGTGAATCACAAGCCCAGC<br>AACACCAAGGTGGACAAGAGAGTTGAGCCCAAATCTTGTGACA<br>AAACTCACACATGCCCACCGTGCCCAGCACCTGAAGCCGAAGG<br>GGCCCCGTCAGTCTTCCTCTTCCCCCCAAAACCCAAGGACACC<br>CTCATGATCTCCCGGACCCCTGAGGTCACATGCGTGGTGGTGG<br>ACGTGAGCCACGAAGACCCTGAGGTCAAGTTCAACTGGTACGT<br>GGACGGCGTGGAGGTGCATAATGCCAAGACAAAGCCGCGGGAG<br>GAGCAGTACAACAGCACGTACCGTGTGGTCAGCGTCCTCACCG<br>TCCTGCACCAGGACTGGCTGAATGGCAAGGAGTACAAGTGCAA<br>GGTCTCCAACAAAGCCCTCCCAGCCCCCATCGAGAAAACCATC<br>TCCAAAGCCAAAGGGCAGCCCCGAGAACCACAGGTGTACACCC<br>TGCCCCCATCCCGGGAGGAGATGACCAAGAACCAGGTCAGCCT<br>GACCTGCCTGGTCAAAGGCTTCTATCCCAGCGACATCGCCGTG<br>GAGTGGGAGAGCAATGGGCAGCCGGAGAACAACTACAAGACCA<br>CGCCTCCCGTGCTGGACTCCGACGGCTCCTTCTTCCTCTATAG<br>CAAGCTCACCGTGGACAAGAGCAGGTGGCAGCAGGGGAACGTC<br>TTCTCATGCTCCGTGATGCATGAGGCTCTGCACAACCACTACA<br>CGCAGAAGAGCCTCTCCCTGTCCCCGGGTTGA |
| 36 | 21D9.b.IgG1.3 HC | EVQLLESGGGLVQPGGSLRLSCATSGFTFSNYAMNWVRQAPGK<br>GLEWISVISVSGGSTYY<br>ADSVKGRFTISRDNSKNTLYLQMNSLRAEDTAVYYCAKDYYYD<br>SGSYYDSFFDYWGQGTL<br>VTVSSASTKGPSVFPLAPSSKSTSGGTAALGCLVKDYFPEPVT<br>VSWNSGALTSGVHTFPAVLQSSGLYSLSSVVTVPSSSLGTQTY<br>ICNVNHKPSNTKVDKRVEPKSCDKTHTCPPCPAPEAEGAPSVF<br>LFPPKPKDTLMISRTPEVTCVVVDVSHEDPEVKFNWYVDGVEV |

-continued

| SEQ ID NO | Name | Sequence |
|---|---|---|
| | | HNAKTKPREEQYNSTYRVVSVLTVLHQDWLNGKEYKCKVSNKA LPAPIEKTISKAKGQPREPQVYTLPPSREEMTKNQVSLICLVK GFYPSDIAVEWESNGQPENNYKTTP PVLDSDGSFFLYSKLTVDKSRWQQGNVFSCSVMHEALHNHYTQ KSLSLSPG |
| 37 | 21D9.c.IgG1.3 HC DNA | GAGGTGCAGCTGCTGGAGTCTGGAGGAGACCTGGTGCAGCCAG GAGGCAGCCTGAGGCTGTCCTGCGCCGCCTCTGGCTTCACATT TTCCAACTATGCCATGAATTGGGTGCGCCAGGCACCTGGCAAG GGACTGGAGTGGATCTCTGTGATCTCTGTGAGCGGCGGCTCTA CCTACTATGCCGACAGCGTGAAGGGCCGGTTCACCATCAGCAG AGATAACTCCAAGAATACACTGTATCTGCAGATGAACAGCCTG CGGGCCGAGGACACAGCCGTGTACTATTGTGCCAAGGACTACT ATTACGATTCCGGCTCTTATTACGACTCCTTCTTTGATTACTG GGGCCAGGGCACCCTGGTGACAGTGAGCTCCGCTAGCACCAAG GGCCCATCGGTCTTCCCCCTGGCACCCTCCTCCAAGAGCACCT CTGGGGGCACAGCGGCCCTGGGCTGCCTGGTCAAGGACTACTT CCCCGAACCGGTGACGGTGTCGTGGAACTCAGGCGCCCTGACC AGCGGCGTGCACACCTTCCCGGCTGTCCTACAGTCCTCAGGAC TCTACTCCCTCAGCAGCGTGGTGACCGTGCCCTCCAGCAGCTT GGGCACCCAGACCTACATCTGCAACGTGAATCACAAGCCCAGC AACACCAAGGTGGACAAGAGAGTTGAGCCCAAATCTTGTGACA AAACTCACACATGCCCACCGTGCCCAGCACCTGAAGCCGAAGG GGCCCCGTCAGTCTTCCTCTTCCCCCCAAAACCCAAGGACACC CTCATGATCTCCCGGACCCCTGAGGTCACATGCGTGGTGGTGG ACGTGAGCCACGAAGACCCTGAGGTCAAGTTCAACTGGTACGT GGACGGCGTGGAGGTGCATAATGCCAAGACAAAGCCGCGGGAG GAGCAGTACAACAGCACGTACCGTGTGGTCAGCGTCCTCACCG TCCTGCACCAGGACTGGCTGAATGGCAAGGAGTACAAGTGCAA GGTCTCCAACAAAGCCCTCCCAGCCCCCATCGAGAAAACCATC TCCAAAGCCAAAGGGCAGCCCCGAGAACCACAGGTGTACACCC TGCCCCCATCCCGGGAGGAGATGACCAAGAACCAGGTCAGCCT GACCTGCCTGGTCAAAGGCTTCTATCCCAGCGACATCGCCGTG GAGTGGGAGAGCAATGGGCAGCCGGAGAACAACTACAAGACCA CGCCTCCCGTGCTGGACTCCGACGGCTCCTTCTTCCTCTATAG CAAGCTCACCGTGGACAAGAGCAGGTGGCAGCAGGGGAACGTC TTCTCATGCTCCGTGATGCATGAGGCTCTGCACAACCACTACA CGCAGAAGAGCCTCTCCCTGTCCCCGGGTTGA |
| 38 | 21D9.c.IgG1.3 HC | EVQLLESGGDLVQPGGSLRLSCAASGFTFSNYAMNWVRQAPGK GLEWISVISVSGGSTYY ADSVKGRFTISRDNSKNTLYLQMNSLRAEDTAVYYCAKDYYYD SGSYYDSFFDYWGQGTL VTVSSASTKGPSVFPLAPSSKSTSGGTAALGCLVKDYFPEPVT VSWNSGALTSGVHTFPAVLQSSGLYSLSSVVTVPSSSLGTQTY ICNVNHKPSNTKVDKRVEPKSCDKTHTCPPCPAPEAEGAPSVF LFPPKPKDTLMISRTPEVTCVVVDVSHEDPEVKFNWYVDGVEV HNAKTKPREEQYNSTYRVVSVLTVLHQDWLNGKEYKCKVSNKA LPAPIEKTISKAKGQPREPQVYTLPPSREEMTKNQVSLICLVK GFYPSDIAVEWESNGQPENNYKTTP PVLDSDGSFFLYSKLTVDKSRWQQGNVFSCSVMHEALHNHYTQ KSLSLSPG |
| 39 | 21D9.d.IgG1.3 HC DNA | GAGGTGCAGCTGCTGGAGTCTGGAGGAGACCTGGTGCAGCCAG GAGGCAGCCTGAGGCTGTCCTGCGCCACCTCTGGCTTCACATT TTCCAACTATGCCATGAATTGGGTGCGCCAGGCACCTGGCAAG GGACTGGAGTGGGTGTCTGTGATCTCTGTGAGCGGCGGCTCTA CCTACTATGCCGACAGCGTGAAGGGCCGGTTCACCATCAGCAG AGATAACTCCAAGAATACACTGTATCTGCAGATGAACAGCCTG CGGGCCGAGGACACAGCCGTGTACTATTGTGCCAAGGACTACT ATTACGATTCCGGCTCTTATTACGACTCCTTCTTTGATTACTG GGGCCAGGGCACCCTGGTGACAGTGAGCTCCGCTAGCACCAAG GGCCCATCGGTCTTCCCCCTGGCACCCTCCTCCAAGAGCACCT CTGGGGGCACAGCGGCCCTGGGCTGCCTGGTCAAGGACTACTT CCCCGAACCGGTGACGGTGTCGTGGAACTCAGGCGCCCTGACC AGCGGCGTGCACACCTTCCCGGCTGTCCTACAGTCCTCAGGAC TCTACTCCCTCAGCAGCGTGGTGACCGTGCCCTCCAGCAGCTT GGGCACCCAGACCTACATCTGCAACGTGAATCACAAGCCCAGC AACACCAAGGTGGACAAGAGAGTTGAGCCCAAATCTTGTGACA AAACTCACACATGCCCACCGTGCCCAGCACCTGAAGCCGAAGG GGCCCCGTCAGTCTTCCTCTTCCCCCCAAAACCCAAGGACACC CTCATGATCTCCCGGACCCCTGAGGTCACATGCGTGGTGGTGG ACGTGAGCCACGAAGACCCTGAGGTCAAGTTCAACTGGTACGT GGACGGCGTGGAGGTGCATAATGCCAAGACAAAGCCGCGGGAG GAGCAGTACAACAGCACGTACCGTGTGGTCAGCGTCCTCACCG |

-continued

| SEQ ID NO | Name | Sequence |
|---|---|---|
| | | TCCTGCACCAGGACTGGCTGAATGGCAAGGAGTACAAGTGCAA<br>GGTCTCCAACAAAGCCCTCCCAGCCCCCATCGAGAAAACCATC<br>TCCAAAGCCAAAGGGCAGCCCCGAGAACCACAGGTGTACACCC<br>TGCCCCCATCCCGGGAGGAGATGACCAAGAACCAGGTCAGCCT<br>GACCTGCCTGGTCAAAGGCTTCTATCCCAGCGACATCGCCGTG<br>GAGTGGGAGAGCAATGGGCAGCCGGAGAACAACTACAAGACCA<br>CGCCTCCCGTGCTGGACTCCGACGGCTCCTTCTTCCTCTATAG<br>CAAGCTCACCGTGGACAAGAGCAGGTGGCAGCAGGGGAACGTC<br>TTCTCATGCTCCGTGATGCATGAGGCTCTGCACAACCACTACA<br>CGCAGAAGAGCCTCTCCCTGTCCCCGGGTTGA |
| 40 | 21D9.d.IgG1.3 HC | EVQLLESGGDLVQPGGSLRLSCATSGFTFSNYAMNWVRQAPGK<br>GLEWVSVISVSGGSTYY<br>ADSVKGRFTISRDNSKNTLYLQMNSLRAEDTAVYYCAKDYYYD<br>SGSYYDSFFDYWGQGTL<br>VTVSSASTKGPSVFPLAPSSKSTSGGTAALGCLVKDYFPEPVT<br>VSWNSGALTSGVHTFPAVLQSSGLYSLSSVVTVPSSSLGTQTY<br>ICNVNHKPSNTKVDKRVEPKSCDKTHTCPPCPAPEAEGAPSVF<br>LFPPKPKDTLMISRTPEVTCVVVDVSHEDPEVKFNWYVDGVEV<br>HNAKTKPREEQYNSTYRVVSVLTVLHQDWLNGKEYKCKVSNKA<br>LPAPIEKTISKAKGQPREPQVYTLPPSREEMTKNQVSLICLVK<br>GFYPSDIAVEWESNGQPENNYKTTP<br>PVLDSDGSFFLYSKLTVDKSRWQQGNVFSCSVMHEALHNHYTQ<br>KSLSLSPG |
| 41 | 21D9.e.IgG1.3 HC DNA ILT4.8.IgG1.3 HC DNA With signal peptide (signal peptide encoding sequence is underlined) | ATGAGGGCTTGGATCTTCTTTCTGCTCTGCCTGGCCGGGAGAG<br>CGCTCGCAGAGGTGCAGCTGTTGGAGTCTGGGGGAGGCTTGGT<br>ACAGCCTGGGGGGTCCCTGAGACTCTCCTGTGCAGCCTCTGGA<br>TTCACCTTTAGCAACTATGCCATGAACTGGGTCCGCCAGGCTC<br>CAGGGAAGGGGCTGGAGTGGGTCTCAGTTATTAGTGTTAGTGG<br>TGGTAGCACATACTACGCAGACTCCGTGAAGGGCCGGTTCACC<br>ATCTCCAGAGACAATTCCAAGAACACGCTGTATCTGCAAATGA<br>ATAGCCTGAGAGCCGAGGACACGGCCGTATATTACTGTGCGAA<br>AGATTATTACTATGATTCGGGGAGTTATTATGACTCTTTCTTT<br>GACTACTGGGGCCAGGGAACCCTGGTCACCGTCTCCTCAGCTA<br>GCACCAAGGGCCCATCGGTCTTCCCCCTGGCACCCTCCTCCAA<br>GAGCACCTCTGGGGGCACAGCGGCCCTGGGCTGCCTGGTCAAG<br>GACTACTTCCCCGAACCGGTGACGGTGTCGTGGAACTCAGGCG<br>CCCTGACCAGCGGCGTGCACACCTTCCCGGCTGTCCTACAGTC<br>CTCAGGACTCTACTCCCTCAGCAGCGTGGTGACCGTGCCCTCC<br>AGCAGCTTGGGCACCCAGACCTACATCTGCAACGTGAATCACA<br>AGCCCAGCAACACCAAGGTGGACAAGAGAGTTGAGCCCAAATC<br>TTGTGACAAAACTCACACATGCCCACCGTGCCCAGCACCTGAA<br>GCCGAAGGGGCCCCGTCAGTCTTCCTCTTCCCCCCAAAACCCA<br>AGGACACCCTCATGATCTCCCGGACCCCTGAGGTCACATGCGT<br>GGTGGTGGACGTGAGCCACGAAGACCCTGAGGTCAAGTTCAAC<br>TGGTACGTGGACGGCGTGGAGGTGCATAATGCCAAGACAAAGC<br>CGCGGGAGGAGCAGTACAACAGCACGTACCGTGTGGTCAGCGT<br>CCTCACCGTCCTGCACCAGGACTGGCTGAATGGCAAGGAGTAC<br>AAGTGCAAGGTCTCCAACAAAGCCCTCCCAGCCCCCATCGAGA<br>AAACCATCTCCAAAGCCAAAGGGCAGCCCCGAGAACCACAGGT<br>GTACACCCTGCCCCCATCCCGGGAGGAGATGACCAAGAACCAG<br>GTCAGCCTGACCTGCCTGGTCAAAGGCTTCTATCCCAGCGACA<br>TCGCCGTGGAGTGGGAGAGCAATGGGCAGCCGGAGAACAACTA<br>CAAGACCACGCCTCCCGTGCTGGACTCCGACGGCTCCTTCTTC<br>CTCTATAGCAAGCTCACCGTGGACAAGAGCAGGTGGCAGCAGG<br>GGAACGTCTTCTCATGCTCCGTGATGCATGAGGCTCTGCACAA<br>CCACTACACGCAGAAGAGCCTCTCCCTGTCCCCGGGT |
| 42 | 21A5 LC DNA (variable region coding sequence underlined and bold) | **GAGATCGTGCTGACCCAGAGCCCAGGCACACTGTCTCTGAGCC<br>CAGGAGAGAGGGCCACCCTGTCCTGCAGAGCCTCCCAGTCTGT<br>GAGCTCCTCTTACCTGGCCTGGTATCAGCAGAAGCCAGGACAG<br>GCACCTAGGCTGCTGATCTACGGAGCCAGCTCCAGGGCAACCG<br>GCATCCCTGACCGCTTCAGCGGCTCCGGCTCTGGCACAGACTT<br>CACCCTGACAATCTCTAGGCTGGAGCCCGAGGACTTCGCCGTG<br>TACTATTGTCAGCAGTATGGCTCCACCTTTGGCGGCGGCACAA<br>AGGTGGAGATCAAG**<br>GAATTCGCCACCATGAGGGCTTGGATCTTCTTTCTGCTCTGCC<br>TGGCCGGGCGCGCCCTCGCAGAGATCGTGCTGACCCAGAGCCC<br>AGGCACACTGTCTCTGAGCCCAGGAGAGAGGGCCACCCTGTCC<br>TGCAGAGCCTCCCAGTCTGTGAGCTCCTCTTACCTGGCCTGGT<br>ATCAGCAGAAGCCAGGACAGGCACCTAGGCTGCTGATCTACGG<br>AGCCAGCTCCAGGGCAACCGGCATCCCTGACCGCTTCAGCGGC<br>TCCGGCTCTGGCACAGACTTCACCCTGACAATCTCTAGGCTGG<br>AGCCCGAGGACTTCGCCGTGTACTATTGTCAGCAGTATGGCTC |

-continued

| SEQ ID NO | Name | Sequence |
|---|---|---|
| | | CACCTTTGGCGGCGGCACAAAGGTGGAGATCAAGCGTACGGTG<br>GCCGCCCCGTCCGTGTTTATCTTCCCTCCATCGGACGAGCAGC<br>TCAAGTCCGGTACCGCGAGCGTGGTCTGCCTGCTGAACAATTT<br>CTACCCGCGCGAAGCTAAAGTGCAATGGAAGGTCGATAACGCA<br>CTTCAGTCCGGGAACAGCCAGGAATCTGTGACCGAGCAGGACT<br>CCAAGGATTCGACCTATTCCCTGTCCTCGACTCTCACCCTGTC<br>AAAGGCCGACTACGAGAAGCACAAGGTCTACGCCTGCGAAGTG<br>ACCCATCAGGGCTTGTCCTCACCCGTGACTAAGAGCTTCAACC<br>GGGGAGAGTGTTAGTGA |
| 43 | 21A5.IgG1.3 HC DNA (variable region bold and underlined) | **CAGGTGCAGCTGGTGCAGTCCGGAGCAGAGGTGAAGAAGCCAG<br>GAGCCTCTGTGAAGGTGAGCTGCAAGGCCTCCGGCTACACCTT<br>CACAGATTACTATCTGCACTGGGTGCGGCAGGCACCAGGACAG<br>GGACTGGAGTGGATGGGCATCTTCCACCCTTCTGGCGACATCA<br>CAAGCTCCGCCCAGAACTTTCAGGGCCGGGTGACCATGACAAG<br>AGATACCAGCACATCCACCGTGTACATGGAGCTGTCTAGCCTG<br>AGGTCTGAGGACACCGCCGTGTACTATTGTGCAAGGGGAGGCG<br>TGCTGAGGTATCTGGACTGGAGCCACGCCTTTGATATCTGGGG<br>CCAGGGCACAATGGTGACCGTGTCCTCT**<br>GCTAGCACCAAAGGACCTTCAGTGTTCCCGCTCGCGCCGTCAT<br>CCAAGTCCACCTCCGGCGGAACCGCTGCCCTGGGATGCCTTGT<br>GAAGGACTACTTCCCTGAGCCTGTGACTGTGTCCTGGAACTCC<br>GGAGCCCTGACCTCCGGCGTGCATACCTTCCCTGCTGTGCTGC<br>AATCAAGCGGCCTCTACTCATTGAGCTCCGTCGTGACCGTGCC<br>GAGCTCCAGCCTCGGTACTCAAACCTACATCTGCAATGTCAAC<br>CACAAGCCCAGCAACACCAAGGTCGATAAGAGAGTGGAGCCCA<br>AGTCGTGCGACAAGACTCACACTTGTCCCCCATGCCCGGCCCC<br>CGAGGCCGAGGGGGCCCCGAGCGTCTTTCTGTTCCCGCCTAAG<br>CCCAAGGATACCCTGATGATTTCGCGGACTCCCGAAGTGACCT<br>GTGTCGTGGTGGACGTGTCCCACGAAGATCCCGAAGTCAAGTT<br>CAACTGGTACGTGGACGGAGTCGAGGTGCACAACGCAAAGACC<br>AAGCCTCGCGAGGAACAGTACAACTCGACCTATCGGGTGGTGT<br>CCGTGCTGACAGTGCTGCATCAGGACTGGCTCAACGGAAAGGA<br>GTACAAGTGCAAAGTGTCCAACAAGGCCCTGCCAGCGCCCATT<br>GAAAAGACTATCAGCAAGGCCAAGGGGCAGCCAAGGGAACCCC<br>AAGTGTACACCCTGCCTCCGTCCCGCGAAGAAATGACCAAGAA<br>CCAGGTGTCCCTGACGTGCTTGGTCAAGGGCTTTTACCCTTCC<br>GACATCGCCGTGGAGTGGGAGTCGAACGGGCAGCCGGAAAACA<br>ACTACAAGACCACTCCACCGGTGCTCGACTCGGATGGCTCGTT<br>CTTCCTGTATTCGAAGCTGACTGTCGACAAAAGCCGGTGGCAG<br>CAGGGCAATGTGTTCTCCTGCTCCGTGATGCATGAGGCCCTCC<br>ACAACCACTACACCCAGAAGTCTCTGAGCCTTTCCCCGGGATG<br>A |
| 44 | 21A5.1 kappa LC DNA (ILT4.9.1K) DNA With signal peptide | ATGAGGGCTTGGATCTTCTTTCTGCTCTGCCTGGCCGGGCGCG<br>CCTTGGCCGAAATTGTGTTGACGCAGTCTCCAGGCACCCTGTC<br>TTTGTCTCCAGGGGAAAGAGCCACCCTCTCCTGCAGGGCCAGT<br>CAGAGTGTTAGCAGCAGCTACTTAGCCTGGTACCAGCAGAAAC<br>CTGGCCAGGCTCCCAGGCTCCTCATCTATGGTGCATCCAGCAG<br>GGCCACTGGCATCCCAGACAGGTTCAGTGGCAGTGGGTCTGGG<br>ACAGACTTCACTCTCACCATCAGCAGACTGGAGCCTGAAGATT<br>TTGCAGTGTATTACTGTCAGCAGTATGGTAGCACTTTCGGCGG<br>AGGGACCAAGGTGGAGATCAAACGTACGGTGGCTGCACCATCT<br>GTCTTCATCTTCCCGCCATCTGATGAGCAGTTGAAATCTGGAA<br>CTGCCTCTGTTGTGTGCCTGCTGAATAACTTCTATCCCAGAGA<br>GGCCAAAGTACAGTGGAAGGTGGATAACGCCCTCCAATCGGGT<br>AACTCCCAGGAGAGTGTCACAGAGCAGGACAGCAAGGACAGCA<br>CCTACAGCCTCAGCAGCACCCTGACGCTGAGCAAAGCAGACTA<br>CGAGAAACACAAAGTCTACGCCTGCGAAGTCACCCATCAGGGC<br>CTGAGCTCGCCCGTCACAAAGAGCTTCAACAGGGGAGAGTGT |
| 45 | 21A5.a.IgG1.3 HC DNA (ILT4.9.IgG1.3) DNA With signal peptide | ATGAGGGCTTGGATCTTCTTTCTGCTCTGCCTGGCCGGGAGAG<br>CGCTCGCACAGGTGCAGCTGGTGCAGTCTGGGGCTGAGGTGAA<br>GAAGCCTGGGGCCTCAGTGAAGGTTTCCTGCAAGGCATCTGGA<br>TACACCTTCACCGACTACTATTTGCACTGGGTGCGACAGGCCC<br>CTGGACAAGGGCTTGAGTGGATGGGAATATTCCACCCTAGTGG<br>TGATATCACAAGCTCCGCACAGAACTTCCAGGGCAGAGTCACC<br>ATGACCAGGGACACGTCCACGAGCACAGTCTACATGGAGCTGA<br>GCAGCCTGAGATCTGAGGACACGGCCGTGTATTACTGTGCGAG<br>AGGAGGCGTGCTGAGGTATCTGGACTGGAGCCATGCTTTTGAT<br>ATCTGGGGCCAAGGGACAATGGTCACCGTCTCTTCAGCTAGCA<br>CCAAGGGCCCATCGGTCTTCCCCCTGGCACCCTCCTCCAAGAG<br>CACCTCTGGGGGCACAGCGGCCCTGGGCTGCCTGGTCAAGGAC<br>TACTTCCCCGAACCGGTGACGGTGTCGTGGAACTCAGGCGCCC<br>TGACCAGCGGCGTGCACACCTTCCCGGCTGTCCTACAGTCCTC |

-continued

| SEQ ID NO | Name | Sequence |
|---|---|---|
| | | AGGACTCTACTCCCTCAGCAGCGTGGTGACCGTGCCCTCCAGC<br>AGCTTGGGCACCCAGACCTACATCTGCAACGTGAATCACAAGC<br>CCAGCAACACCAAGGTGGACAAGAGAGTTGAGCCCAAATCTTG<br>TGACAAAACTCACACATGCCCACCGTGCCCAGCACCTGAAGCC<br>GAAGGGGCCCCGTCAGTCTTCCTCTTCCCCCCAAAACCCAAGG<br>ACACCCTCATGATCTCCCGGACCCCTGAGGTCACATGCGTGGT<br>GGTGGACGTGAGCCACGAAGACCCTGAGGTCAAGTTCAACTGG<br>TACGTGGACGGCGTGGAGGTGCATAATGCCAAGACAAAGCCGC<br>GGGAGGAGCAGTACAACAGCACGTACCGTGTGGTCAGCGTCCT<br>CACCGTCCTGCACCAGGACTGGCTGAATGGCAAGGAGTACAAG<br>TGCAAGGTCTCCAACAAAGCCCTCCCAGCCCCCATCGAGAAAA<br>CCATCTCCAAAGCCAAAGGGCAGCCCCGAGAACCACAGGTGTA<br>CACCCTGCCCCCATCCCGGGAGGAGATGACCAAGAACCAGGTC<br>AGCCTGACCTGCCTGGTCAAAGGCTTCTATCCCAGCGACATCG<br>CCGTGGAGTGGGAGAGCAATGGGCAGCCGGAGAACAACTACAA<br>GACCACGCCTCCCGTGCTGGACTCCGACGGCTCCTTCTTCCTC<br>TATAGCAAGCTCACCGTGGACAAGAGCAGGTGGCAGCAGGGGA<br>ACGTCTTCTCATGCTCCGTGATGCATGAGGCTCTGCACAACCA<br>CTACACGCAGAAGAGCCTCTCCCTGTCCCCGGGT |
| 46 | 10F10 kappa<br>LC DNA<br>ILT4.10K<br>DNA<br>With signal<br>peptide | ATGAGGGCTTGGATCTTCTTTCTGCTCTGCCTGGCCGGGCGCG<br>CCCTCGCAGCCATCCAGCTGACCCAGTCTCCTAGCTCCCTGTC<br>TGCCAGCGTGGGCGACAGGGTGACCATCACATGCAGAGCCTCC<br>CAGGGAATCTCTAGCGCCCTGGCCTGGTTCCAGCAGAAGCCAG<br>GCAAGGCCCCTAAGCTGCTGATCTACGATGCCTCCTCTCTGGA<br>GAGCGGAGTGCCATCCAGGTTCACCGGCTCCGGCTCTGGCACA<br>GACTTTACCCTGACAATCAGCTCCCTGCAGCCAGAGGATTTTG<br>CCACATACTATTGTCAGCAGTTCAACAGCTATCCCATCACCTT<br>TGGCCAGGGCACACGGCTGGAGATCAAGCGTACGGTGGCCGCC<br>CCGTCCGTGTTTATCTTCCCTCCATCGGACGAGCAGCTCAAGT<br>CCGGTACCGCGAGCGTGGTCTGCCTGCTGAACAATTTCTACCC<br>GCGCGAAGCTAAAGTGCAATGGAAGGTCGATAACGCACTTCAG<br>TCCGGGAACAGCCAGGAATCTGTGACCGAGCAGGACTCCAAGG<br>ATTCGACCTATTCCCTGTCCTCGACTCTCACCCTGTCAAAGGC<br>CGACTACGAGAAGCACAAGGTCTACGCCTGCGAAGTGACCCAT<br>CAGGGCTTGTCCTCACCCGTGACTAAGAGCTTCAACCGGGGAG<br>AGTGT |
| 47 | 10F10.IgG1.3<br>HC DNA<br>ILT4.10.IgG1.3<br>DNA<br>With signal<br>peptide | ATGAGGGCTTGGATCTTCTTTCTGCTCTGCCTGGCCGGGCGCG<br>CCCTCGCACAGGTGCAGCTGGTGGAGTCTGGAGGAGGAGTGGT<br>GCAGCCAGGCCGGTCCCTGAGACTGTCTTGCGCCGCCAGCGGC<br>TTCACCTTTAGCTCCTACGCAATGCACTGGGTGAGGCAGGCAC<br>CTGGCAAGGGACTGGAGTGGGTGGCCATCATCAGCTACGACGA<br>GTATAACAAGTACTATGCCGATTCCGTGAAGGGCAGGTTCACC<br>ATCTCCCGCGACAACTCTAAGAATACACTGTACCTGCAGATGA<br>ATAGCCTGAGAGCCGAGGATACAGCCGTGTACTATTGTGCCCG<br>GGAGTGGGTGGGCATCAGATATTGGGGCCAGGGCACCCTGGTG<br>ACAGTGTCTAGCGCTAGCACCAAAGGACCTTCAGTGTTCCCGC<br>TCGCGCCGTCATCCAAGTCCACCTCCGGCGGAACCGCTGCCCT<br>GGGATGCCTTGTGAAGGACTACTTCCCTGAGCCTGTGACTGTG<br>TCCTGGAACTCCGGAGCCCTGACCTCCGGCGTGCATACCTTCC<br>CTGCTGTGCTGCAATCAAGCGGCCTCTACTCATTGAGCTCCGT<br>CGTGACCGTGCCGAGCTCCAGCCTCGGTACTCAAACCTACATC<br>TGCAATGTCAACCACAAGCCCAGCAACACCAAGGTCGATAAGA<br>GAGTGGAGCCCAAGTCGTGCGACAAGACTCACACTTGTCCCCC<br>ATGCCCGGCCCCCGAGGCCGAGGGGGCCCCGAGCGTCTTTCTG<br>TTCCCGCCTAAGCCCAAGGATACCCTGATGATTTCGCGGACTC<br>CCGAAGTGACCTGTGTCGTGGTGGACGTGTCCCACGAAGATCC<br>CGAAGTCAAGTTCAACTGGTACGTGGACGGAGTCGAGGTGCAC<br>AACGCAAAGACCAAGCCTCGCGAGGAACAGTACAACTCGACCT<br>ATCGGGTGGTGTCCGTGCTGACAGTGCTGCATCAGGACTGGCT<br>CAACGGAAAGGAGTACAAGTGCAAAGTGTCCAACAAGGCCCTG<br>CCAGCGCCCATTGAAAAGACTATCAGCAAGGCCAAGGGGCAGC<br>CAAGGGAACCCCAAGTGTACACCCTGCCTCCGTCCCGCGAAGA<br>AATGACCAAGAACCAGGTGTCCCTGACGTGCTTGGTCAAGGGC<br>TTTTACCCTTCCGACATCGCCGTGGAGTGGGAGTCGAACGGGC<br>AGCCGGAAAACAACTACAAGACCACTCCACCGGTGCTCGACTC<br>GGATGGCTCGTTCTTCCTGTATTCGAAGCTGACTGTCGACAAA<br>AGCCGGTGGCAGCAGGGCAATGTGTTCTCCTGCTCCGTGATGC<br>ATGAGGCCCTCCACAACCACTACACCCAGAAGTCTCTGAGCCT<br>TTCCCCGGGA |

-continued

| SEQ ID NO | Name | Sequence |
|---|---|---|
| 48 | 10F10.1 kappa<br>LC<br>DNA | GCCATCCAGCTGACCCAGTCTCCTAGCTCCCTGTCTGCCAGCG<br>TGGGCGACAGGGTGACCATCACATGCAGAGCCTCCCAGGGAAT<br>CTCTAGCGCCCTGGCCTGGTACCAGCAGAAGCCAGGCAAGGCC<br>CCTAAGCTGCTGATCTATGATGCCTCCTCTCTGGAGAGCGGAG<br>TGCCATCCAGGTTCACCGGCTCCGGCTCTGGCACAGACTTTAC<br>CCTGACAATCAGCTCCCTGCAGCCAGAGGATTTCGCCACATAC<br>TATTGTCAGCAGTTCAACAGCTACCCCATCACCTTTGGCCAGG<br>GCACACGGCTGGAGATCAAGCGTACGGTGGCCGCCCCGTCCGT<br>GTTTATCTTCCCTCCATCGGACGAGCAGCTCAAGTCCGGTACC<br>GCGAGCGTGGTCTGCCTGCTGAACAATTTCTACCCGCGCGAAG<br>CTAAAGTGCAATGGAAGGTCGATAACGCACTTCAGTCCGGGAA<br>CAGCCAGGAATCTGTGACCGAGCAGGACTCCAAGGATTCGACC<br>TATTCCCTGTCCTCGACTCTCACCCTGTCAAAGGCCGACTACG<br>AGAAGCACAAGGTCTACGCCTGCGAAGTGACCCATCAGGGCTT<br>GTCCTCACCCGTGACTAAGAGCTTCAACCGGGGAGAGTGT |
| 49 | 10F10.3 kappa<br>LC DNA<br>ILT4.11K<br>DNA<br>With signal<br>peptide | ATGAGGGCTTGGATCTTCTTTCTGCTCTGCCTGGCCGGGCGCG<br>CCCTCGCAGCCATCCAGCTGACCCAGTCTCCTAGCTCCCTGTC<br>TGCCAGCGTGGGCGACAGGGTGACCATCACATGCAGAGCCTCC<br>CAGGGAATCTCTAGCGCCCTGGCCTGGTACCAGCAGAAGCCAG<br>GCAAGGCCCCTAAGCTGCTGATCTATGATGCCTCCTCTCTGGA<br>GAGCGGAGTGCCATCCAGGTTCAGCGGCTCCGGCTCTGGCACA<br>GACTTTACCCTGACAATCAGCTCCCTGCAGCCAGAGGATTTCG<br>CCACATACTATTGTCAGCAGTTCAACAGCTACCCCATCACCTT<br>TGGCCAGGGCACACGGCTGGAGATCAAGCGTACGGTGGCCGCC<br>CCGTCCGTGTTTATCTTCCCTCCATCGGACGAGCAGCTCAAGT<br>CCGGTACCGCGAGCGTGGTCTGCCTGCTGAACAATTTCTACCC<br>GCGCGAAGCTAAAGTGCAATGGAAGGTCGATAACGCACTTCAG<br>TCCGGGAACAGCCAGGAATCTGTGACCGAGCAGGACTCCAAGG<br>ATTCGACCTATTCCCTGTCCTCGACTCTCACCCTGTCAAAGGC<br>CGACTACGAGAAGCACAAGGTCTACGCCTGCGAAGTGACCCAT<br>CAGGGCTTGTCCTCACCCGTGACTAAGAGCTTCAACCGGGGAG<br>AGTGT |
| 50 | 9G4 VL<br>ILT4.1K<br>VL (including<br>signal<br>sequence,<br>residues 1-18) | APAQLLFLLLLWLPDTTGEIVLTQSPATLSLSPGERATLSC**RA**<br>**SQSVSSYLA**WYQQKPGQAPRLLIY**DASNRAT**GIPARFSGSGSG<br>TDFTLTISSLEPEDFAGYYC**QQRSYWPWT**FGQGTKVEIK |
| 51 | 9G4.IgG1.1 VH<br>ILT4.1.IgG1.1<br>VH (including<br>signal<br>sequence,<br>residues 1-19) | MKHLWFFLLLVAAPRWVLSQVQLQESGPGLVKPSETLSLTCTV<br>SGGSIS**SYYWN**WIRQPPGKGLEWLG**YIYYSGSTKYNPSLKS**RV<br>TISVDTSKNQFSLKLSSVTAADTAVYYCAS**SGWYYFDY**WGQGT<br>LVTVSS |
| 52 | 9G4 VL DNA<br>ILT4.1K<br>VL DNA | GCCCCAGCTCAGCTTCTCTTCCTCCTGCTACTCTGGCTCCCAG<br>ATACCACCGGAGAAATTGTGTTGACACAGTCTCCAGCCACCCT<br>GTCTTTGTCTCCAGGGGAAAGAGCCACCCTCTCCTGCAGGGCC<br>AGTCAGAGTGTTAGCAGCTACTTAGCCTGGTACCAACAGAAAC<br>CTGGCCAGGCTCCCAGGCTCCTCATCTATGATGCGTCCAACAG<br>GGCCACTGGCATCCCAGCCAGGTTCAGTGGCAGTGGGTCTGGG<br>ACAGACTTCACTCTCACCATCAGCAGCCTAGAGCCTGAAGATT<br>TTGCAGGTTATTACTGTCAGCAGCGTAGCTACTGGCCGTGGAC<br>GTTCGGCCAAGGGACCAAGGTGGAAATCAAA |
| 53 | 9G4.IgG1.1 VH<br>DNA<br>ILT4.1.IgG1.1<br>VH DNA | ATGAAACATCTGTGGTTCTTCCTTCTCCTGGTGGCAGCTCCCA<br>GATGGGTCCTGTCCCAGGTGCAGCTGCAGGAGTCGGGCCCAGG<br>ACTGGTGAAGCCTTCGGAGACCCTGTCCCTCACCTGCACTGTC<br>TCTGGTGGCTCCATCAGTAGTTACTACTGGAACTGGATCCGGC<br>AGCCCCCAGGGAAGGGACTGGAGTGGCTTGGGTACATCTATTA<br>CAGTGGGAGTACCAAGTACAACCCCTCCCTCAAGAGTCGAGTC<br>ACCATATCAGTAGACACGTCCAAGAACCAGTTCTCCCTGAAGC<br>TGAGCTCTGTGACCGCTGCGGACACGGCCGTGTATTATTGTGC<br>CAGCAGTGGCTGGTACTACTTTGACTATTGGGGCCAGGGAACC<br>CTGGTCACCGTCTCCTCA |
| 54 | 9C8 kappa VL<br>ILT4.2K<br>VL | AIQLTQSPSSLSASVGDRVTITC**RASQGISSALA**WYQQKPGKA<br>PKLLIY**DASSLES**GVPSRFSGSGSGTDFTLTISSLQPEDFATY<br>YC**QQFNSYPFT**FGPGTKVDIK |

-continued

| SEQ ID NO | Name | Sequence |
|---|---|---|
| 55 | 9C8.IgG1.1 VH ILT4.2.IgG1.1 VH | QVQLVQSGAEVKKPGASVKVSCKASGYTFT**SSDIN**WVRQATGQ GLEWMG**WMNPNSGHTGYAQKFQD**RVTLTRDTSISTAYMELSSL RSEDSAVYYCAR**GGNSIDWGFSYYGLDV**WGQGTTVTVSS |
| 56 | 9C8 kappa VL DNA ILT4.2K VL DNA | GCCATCCAGTTGACCCAGTCTCCATCCTCCCTGTCTGCATCTG TAGGAGACAGAGTCACCATCACTTGCCGGGCAAGTCAGGGCAT TAGCAGTGCTTTAGCCTGGTATCAGCAGAAACCAGGGAAAGCT CCTAAGCTCCTGATCTATGATGCCTCCAGTTTGGAAAGTGGGG TCCCATCAAGGTTCAGCGGCAGTGGATCTGGGACAGATTTCAC TCTCACCATCAGCAGCCTGCAGCCTGAAGATTTTGCAACTTAT TACTGTCAACAGTTTAATAGTTACCCATTCACTTTCGGCCCTG GGACCAAAGTGGATATCAAA |
| 57 | 9C8.IgG1.1 VH DNA ILT4.2.IgG1.1 VH DNA | CAGGTGCAACTGGTGCAGTCTGGGGCTGAGGTAAAGAAGCCTG GGGCCTCAGTGAAGGTCTCCTGCAAGGCTTCTGGATACACCTT CACCAGCTCTGATATCAACTGGGTGCGACAGGCCACTGGACAA GGGCTTGAGTGGATGGGATGGATGAACCCTAACAGTGGTCACA CAGGCTATGCACAGAAGTTCCAGGACAGAGTCACCTTGACCCG GGACACCTCCATAAGCACAGCCTACATGGAGCTGAGCAGCCTG AGATCTGAGGACTCGGCCGTGTATTACTGTGCGAGAGGTGGGA ATAGCATTGACTGGGGGTTCTCCTACTACGGTCTGGACGTCTG GGGCCAAGGGACCACGGTCACCGTCTCCTCA |
| 58 | 2H2.IgG1.1 VH ILT4.3.IgG1.1 VH | QVQLVQSGAEVKKPGSSVEVSCKASGGTFS**NYAIS**WVRQAPGQ GLEWMG**GIIPILATANYAPKFQG**RVTITADEFTSSAYMELSSL RSEDTAVYYCAK**SSITMIRGAYLYYYDGMDV**WGQGTTVTVSS |
| 59 | 2H2 kappa VL ILT4.3K VL | EIVLTQSPGTLSLSPGERATLSC**RASQSVSSSYLA**WYQQKPGQ APRLLIY**GASSRAT**GIPDRFSGSGSGTDFTLTISRLEPEDFAV YYC**QQYGSSYT**FGQGTKLEIK |
| 60 | 2H2.IgG1.1 VH DNA ILT4.3.IgG1.1 VH DNA | CAGGTCCAGTTGGTGCAGTCTGGGGCTGAGGTGAAGAAGCCTG GGTCCTCGGTGGAGGTCTCCTGCAAGGCTTCTGGGGGCACCTT CAGCAACTATGCTATCAGCTGGGTGCGACAGGCCCCTGGACAA GGGCTTGAGTGGATGGGAGGGATCATCCCCATCTTGGCTACAG CAAACTACGCACCGAAGTTCCAGGGCAGAGTCACGATTACCGC GGACGAATTCACGAGCTCAGCTTACATGGAGCTGAGCAGCCTG AGATCTGAGGACACGGCCGTGTATTACTGTGCGAAGTCTAGTA TTACTATGATTCGGGGAGCCTATCTTTACTACTACGACGGTAT GGACGTCTGGGGCCAAGGGACCACGGTCACCGTCTCCTCA |
| 61 | 2H2 kappa VL DNA ILT4.3K VL DNA | GAAATTGTGTTGACGCAGTCTCCAGGCACCCTGTCTTTGTCTC CAGGGGAAAGAGCCACCCTCTCCTGCAGGGCCAGTCAGAGTGT TAGCAGCAGCTACTTAGCCTGGTACCAGCAGAAACCTGGCCAG GCTCCCAGGCTCCTCATCTATGGTGCATCCAGCAGGGCCACTG GCATCCCAGACAGGTTCAGTGGCAGTGGGTCTGGGACAGACTT CACTCTCACCATCAGCAGACTGGAGCCTGAAGATTTTGCAGTG TATTACTGTCAGCAGTATGGTAGCTCGTACACTTTTGGCCAGG GGACCAAGCTGGAGATCAAA |
| 62 | 2E5 kappa VL ILT4.4K VL | EIVLTQSPATLSLSPGERATLSC**RASQSVSSYLA**WYQQKPGQA PRLLIY**DASNRAT**GIPARFSGSGSGTDFTLTISSLEPEDFAVY YC**QQRSNWPPWT**FGQGTKVEIK |
| 63 | 2E5.IgG1.1 VH ILT4.4.IgG1.1 VH | QVQLVESGGGVVQPGRSLRLSCTASGFTFS**NYGMH**WVRQAPGK GLEWVA**VIWYDGSNEYYAESVKG**RLTISRDNSKNTLYLQVNSL RAEDTAVYYCAR**DPFYGSGNYFDY**WGQGTLVTVSS |
| 64 | 2E5 kappa VL DNA ILT4.4K VL | GAAATTGTGTTGACACAGTCTCCAGCCACCCTGTCTTTGTCTC CAGGGGAAAGAGCCACCCTCTCCTGCAGGGCCAGTCAGAGTGT TAGCAGCTACTTAGCCTGGTACCAACAGAAACCTGGCCAGGCT CCCAGGCTCCTCATCTATGATGCATCCAACAGGGCCACTGGCA TCCCAGCCAGGTTCAGTGGCAGTGGGTCTGGGACAGACTTCAC TCTCACCATCAGCAGCCTAGAGCCTGAAGATTTTGCAGTTTAT TACTGTCAGCAGCGTAGCAACTGGCCTCCGTGGACGTTCGGCC AAGGGACCAAGGTGGAAATCAAA |
| 65 | 2E5.IgG1.1 VH DNA ILT4.4.IgG1.1 VH | CAGGTGCAGCTGGTGGAGTCTGGGGGAGGCGTGGTCCAGCCTG GGAGGTCCCTGAGACTCTCCTGTACAGCGTCTGGATTCACCTT CAGTAACTATGGCATGCACTGGGTCCGCCAGGCTCCAGGCAAG GGACTGGAGTGGGTGGCAGTTATCTGGTATGATGGAAGTAATG AATACTATGCAGAATCCGTGAAGGGCCGACTCACCATCTCCAG AGACAATTCCAAGAACACGCTGTATCTGCAAGTGAACAGCCTG AGAGCCGAGGACACGGCTGTGTATTATTGTGCGAGAGATCCTT |

-continued

| SEQ ID NO | Name | Sequence |
|---|---|---|
| | | TCTATGGTTCGGGGAATTACTTTGACTACTGGGGCCAGGGAAC<br>CCTGGTCACCGTCTCCTCA |
| 66 | 24E5 kappa VL<br>ILT4.5K<br>VL | DIQMTQSPSSLSASVGDRVTITC**RASQGISSWLA**WYQQKPEKA<br>PKSLIY**AASSLQS**GVPSRFSGSGSGTDFTLTISSLQPEDFATY<br>YC**QQYNSYPLT**FGGGTKVEIK |
| 67 | 24E5.IgG1.1<br>VH<br>ILT4.5.IgG1.1<br>VH | EVQLLESGGGLVQPGGSLRLSCAASGFTFS**SYVMS**WVRQAPGK<br>GLEWVS**GISGSGGSTYYADSVKG**RFTISRDNSKNTLYLQMNSL<br>RAEDTAVYYCAK**DQDIIAAYYFVY**WGQGTLVTVSS |
| 68 | 24E5 kappa VL<br>DNA<br>ILT4.5K<br>VL | GACATCCAGATGACCCAGTCTCCATCCTCACTGTCTGCATCTG<br>TAGGAGACAGAGTCACCATCACTTGTCGGGCGAGTCAGGGTAT<br>TAGCAGCTGGTTAGCCTGGTATCAGCAGAAACCAGAGAAAGCC<br>CCTAAGTCCCTGATCTATGCTGCATCCAGTTTGCAAAGTGGGG<br>TCCCATCAAGGTTCAGCGGCAGTGGATCTGGGACAGATTTCAC<br>TCTCACCATCAGCAGCCTGCAGCCTGAAGATTTTGCAACTTAT<br>TACTGCCAACAGTATAATAGTTACCCTCTCACTTTCGGCGGAG<br>GGACCAAGGTGGAGATCAAA |
| 69 | 24E5.IgG1.1<br>VH DNA<br>ILT4.5.IgG1.1<br>VH | GAGGTGCAGCTGTTGGAGTCTGGGGGAGGCTTGGTACAGCCTG<br>GGGGGTCCCTGAGACTCTCCTGTGCAGCCTCTGGATTCACCTT<br>TAGCAGCTATGTCATGAGCTGGGTCCGCCAGGCTCCAGGGAAG<br>GGGCTGGAGTGGGTCTCAGGTATTAGTGGTAGTGGTGGTAGCA<br>CATACTACGCAGACTCCGTGAAGGGCCGGTTCACCATCTCCAG<br>AGACAATTCCAAGAACACGCTGTATCTGCAAATGAACAGCCTG<br>AGAGCCGAGGACACGGCCGTATATTACTGTGCGAAAGATCAGG<br>ATATTATAGCAGCATACTACTTTGTCTACTGGGGCCAGGGAAC<br>CCTGGTCACCGTCTCCTCA |
| 70 | 21D9K kappa<br>VL<br>ILT4.6K<br>VL | EIVLTQSPGTLSLSPGERATLSC**RASQSVSSSYLA**WYQQKPGQ<br>APRLLIY**GASSRAT**GIPDRFSGSGSGTDFTLTISRLEPEDFAV<br>YYC**QQYGSSPLT**FGGGTKVEIK |
| 71 | 21D9.IgG1.1<br>VH<br>ILT4.6.IgG1.1<br>VH | EGQLLESGGDLVQPGGSLRLSCATSGFTFS**NYAMN**WVRQAPGK<br>GLEWIS**VISVSGGSTYYADSVKG**RFTISRDNSKNTLYLQMNSL<br>RAEDTAVYYCAK**DYYYDSGSYYDSFFDY**WGQGTLVTVSS |
| 72 | 21D9K kappa<br>VL DNA<br>ILT4.6K<br>VL DNA | GAAATTGTGTTGACGCAGTCTCCAGGCACCCTGTCTTTGTCTC<br>CAGGGGAAAGAGCCACCCTCTCCTGCAGGGCCAGTCAGAGTGT<br>TAGCAGCAGCTACTTAGCCTGGTACCAGCAGAAACCTGGCCAG<br>GCTCCCAGGCTCCTCATCTATGGTGCATCCAGCAGGGCCACTG<br>GCATCCCAGACAGGTTCAGTGGCAGTGGGTCTGGGACAGACTT<br>CACTCTCACCATCAGCAGACTGGAGCCTGAAGATTTTGCAGTG<br>TATTACTGTCAGCAGTATGGTAGCTCACCTCTCACTTTCGGCG<br>GAGGGACCAAGGTGGAGATCAAA |
| 73 | 21D9.IgG1.1<br>VH DNA<br>ILT4.6.IgG1.1<br>VH DNA | GAGGGACAGCTGTTGGAGTCTGGGGGAGACTTGGTACAGCCTG<br>GGGGGTCCCTGAGACTCTCCTGTGCAACCTCTGGATTCACCTT<br>TAGCAACTATGCCATGAACTGGGTCCGCCAGGCTCCAGGGAAG<br>GGGCTGGAGTGGATCTCAGTTATTAGTGTTAGTGGTGGTAGCA<br>CATACTACGCAGACTCCGTGAAGGGCCGGTTCACCATCTCCAG<br>AGACAATTCCAAGAACACGCTGTATCTGCAAATGAATAGCCTG<br>AGAGCCGAGGACACGGCCGTATATTACTGTGCGAAAGATTATT<br>ACTATGATTCGGGGAGTTATTATGACTCTTTCTTTGACTACTG<br>GGGCCAGGGAACCCTGGTCACCGTCTCCTCA |
| 74 | 21D9.b.IgG1.3<br>VH | EVQLLESGGGLVQPGGSLRLSCATSGFTFSNYAMNWVRQAPGK<br>GLEWISVISVSGGSTYYADSVKGRFTISRDNSKNTLYLQMNSL<br>RAEDTAVYYCAKDYYYDSGSYYDSFFDYWGQGTLVTVSS |
| 75 | 21D9.c.IgG1.3<br>VH | EVQLLESGGDLVQPGGSLRLSCAASGFTFSNYAMNWVRQAPGK<br>GLEWISVISVSGGSTYYADSVKGRFTISRDNSKNTLYLQMNSL<br>RAEDTAVYYCAKDYYYDSGSYYDSFFDYWGQGTLVTVSS |
| 76 | 21D9.b.IgG1.3<br>VH DNA | GAGGTGCAGCTGCTGGAGTCTGGAGGAGGACTGGTGCAGCCAG<br>GAGGCAGCCTGAGGCTGTCCTGCGCCACCTCTGGCTTCACATT<br>TTCCAACTATGCCATGAATTGGGTGCGCCAGGCACCTGGCAAG<br>GGACTGGAGTGGATCTCTGTGATCTCTGTGAGCGGCGGCTCTA<br>CCTACTATGCCGACAGCGTGAAGGGCCGGTTCACCATCAGCAG<br>AGATAACTCCAAGAATACACTGTATCTGCAGATGAACAGCCTG<br>CGGGCCGAGGACACAGCCGTGTACTATTGTGCCAAGGACTACT |

-continued

| SEQ ID NO | Name | Sequence |
|---|---|---|
| | | ATTACGATTCCGGCTCTTATTACGACTCCTTCTTTGATTACTG<br>GGGCCAGGGCACCCTGGTGACAGTGAGCTCC |
| 77 | 21D9.c.IgG1.3<br>VH DNA | GAGGTGCAGCTGCTGGAGTCTGGAGGAGACCTGGTGCAGCCAG<br>GAGGCAGCCTGAGGCTGTCCTGCGCCGCCTCTGGCTTCACATT<br>TTCCAACTATGCCATGAATTGGGTGCGCCAGGCACCTGGCAAG<br>GGACTGGAGTGGATCTCTGTGATCTCTGTGAGCGGCGGCTCTA<br>CCTACTATGCCGACAGCGTGAAGGGCCGGTTCACCATCAGCAG<br>AGATAACTCCAAGAATACACTGTATCTGCAGATGAACAGCCTG<br>CGGGCCGAGGACACAGCCGTGTACTATTGTGCCAAGGACTACT<br>ATTACGATTCCGGCTCTTATTACGACTCCTTCTTTGATTACTG<br>GGGCCAGGGCACCCTGGTGACAGTGAGCTCC |
| 78 | 21D9.d.IgG1.3<br>VH | EVQLLESGGDLVQPGGSLRLSCATSGFTFSNYAMNWVRQAPGK<br>GLEWVSVISVSGGSTYYADSVKGRFTISRDNSKNTLYLQMNSL<br>RAEDTAVYYCAKDYYYDSGSYYDSFFDYWGQGTLVTVSS |
| 79 | 21D9.d.IgG1.3<br>VH DNA | GAGGTGCAGCTGCTGGAGTCTGGAGGAGACCTGGTGCAGCCAG<br>GAGGCAGCCTGAGGCTGTCCTGCGCCACCTCTGGCTTCACATT<br>TTCCAACTATGCCATGAATTGGGTGCGCCAGGCACCTGGCAAG<br>GGACTGGAGTGGGTGTCTGTGATCTCTGTGAGCGGCGGCTCTA<br>CCTACTATGCCGACAGCGTGAAGGGCCGGTTCACCATCAGCAG<br>AGATAACTCCAAGAATACACTGTATCTGCAGATGAACAGCCTG<br>CGGGCCGAGGACACAGCCGTGTACTATTGTGCCAAGGACTACT<br>ATTACGATTCCGGCTCTTATTACGACTCCTTCTTTGATTACTG<br>GGGCCAGGGCACCCTGGTGACAGTGAGCTCC |
| 80 | 21D9.e.IgG1.3<br>VH<br>ILT4.8.IgG1.3<br>VH | EVQLLESGGGLVQPGGSLRLSCAASGFTFSNYAMNWVRQAPGK<br>GLEWVSVISVSGGSTYYADSVKGRFTISRDNSKNTLYLQMNSL<br>RAEDTAVYYCAKDYYYDSGSYYDSFFDYWGQGTLVTVSS |
| 81 | 21D9.e.IgG1.3<br>VH DNA<br>ILT4.8.IgG1.3<br>VH DNA | GAGGTGCAGCTGCTGGAGTCTGGAGGAGGACTGGTGCAGCCAG<br>GAGGCAGCCTGAGGCTGTCCTGCGCCGCCTCTGGCTTCACATT<br>TTCCAACTATGCCATGAATTGGGTGCGCCAGGCACCTGGCAAG<br>GGACTGGAGTGGGTGTCTGTGATCTCTGTGAGCGGCGGCTCTA<br>CCTACTATGCCGACAGCGTGAAGGGCCGGTTCACCATCAGCAG<br>AGATAACTCCAAGAATACACTGTATCTGCAGATGAACAGCCTG<br>CGGGCCGAGGACACAGCCGTGTACTATTGTGCCAAGGACTACT<br>ATTACGATTCCGGCTCTTATTACGACTCCTTCTTTGATTACTG<br>GGGCCAGGGCACCCTGGTGACAGTGAGCTCC |
| 82 | 21A5 kappa VL | EI**A**LTQSPGTLSLSPGERATLSC**RASQSVSSSYLA**WYQQKPGQ<br>APRLLIY**GASSRAT**GIPDRFSGSGSGTDFTLTISRLEPEDFAV<br>YYC**QQYGST**FGGGTKVEIK |
| 83 | 21A5.IgG1.3<br>VH | QVQLVQSGAEVKKPGASVKVSCKASGYTFT**DYYLH**WVRQAPGQ<br>GLEWMG**IFHPSGDITSSAQNFQG**RVTM**I**RDTSTSTVYMELSSL<br>RSEDTAVYYCAR**GGVLRYLDWSHAFDI**WGQGTMVTVSS |
| 84 | 21A5 kappa VL<br>DNA | GAAATTGCGTTGACGCAGTCTCCAGGCACCCTGTCTTTGTCTC<br>CAGGGGAAAGAGCCACCCTCTCCTGCAGGGCCAGTCAGAGTGT<br>TAGCAGCAGCTACTTAGCCTGGTACCAGCAGAAACCTGGCCAG<br>GCTCCCAGGCTCCTCATCTATGGTGCATCCAGCAGGGCCACTG<br>GCATCCCAGACAGGTTCAGTGGCAGTGGGTCTGGGACAGACTT<br>CACTCTCACCATCAGCAGACTGGAGCCTGAAGATTTTGCAGTG<br>TATTACTGTCAGCAGTATGGTAGCACTTTCGGCGGAGGGACCA<br>AGGTGGAGATCAAA |
| 85 | 21A5.IgG1.3<br>VH DNA | CAGGTGCAGCTGGTGCAGTCTGGGGCTGAGGTGAAGAAGCCTG<br>GGGCCTCAGTGAAGGTTTCCTGCAAGGCATCTGGATACACCTT<br>CACCGACTACTATTTACACTGGGTGCGACAGGCCCCTGGACAA<br>GGGCTTGAGTGGATGGGAATATTCCACCCTAGTGGTGATATCA<br>CAAGCAGCGCACAGAACTTCCAGGGCAGAGTCACCATGATCAG<br>GGACACGTCCACGAGCACCGTCTACATGGAACTGAGCAGCCTG<br>AGATCTGAAGACACGGCCGTGTATTACTGTGCGAGAGGGGGTG<br>TATTACGATATCTTGACTGGTCCCATGCTTTTGATATCTGGGG<br>CCAAGGGACAATGGTCACCGTCTCTTCA |

-continued

| SEQ ID NO | Name | Sequence |
|---|---|---|
| 86 | 21A5.a kappa<br>VL<br>21A5.1K<br>ILT4.9K<br>VL | EI**V**ITQSPGTLSLSPGERATLSC**RASQSVSSSYLA**WYQQKPGQ<br>APRLLIY**GASSRAT**GIPDRFSGSGSGTDFTLTISRLEPEDFAV<br>YYC**QQYGST**FGGGTKVEIK |
| 87 | 21A5.a.IgG1.3<br>VH<br>ILT4.9.IgG1.3<br>VH | QVQLVQSGAEVKKPGASVKVSCKASGYTFT**DYYLH**WVRQAPGQ<br>GLEWMG**IFHPSGDITSSAQNFQG**RVTM**T**RDTSTSTVYMELSSL<br>RSEDTAVYYCAR**GGVLRYLDWSHAFDI**WGQGTMVTVSS |
| 88 | 21A5.a kappa<br>VL DNA<br>21A5.1K<br>ILT4.9K<br>VL | GAGATCGTGCTGACCCAGAGCCCAGGCACACTGTCTCTGAGCC<br>CAGGAGAGAGGGCCACCCTGTCCTGCAGAGCCTCCCAGTCTGT<br>GAGCTCCTCTTACCTGGCCTGGTATCAGCAGAAGCCAGGACAG<br>GCACCTAGGCTGCTGATCTACGGAGCCAGCTCCAGGGCAACCG<br>GCATCCCTGACCGCTTCAGCGGCTCCGGCTCTGGCACAGACTT<br>CACCCTGACAATCTCTAGGCTGGAGCCCGAGGACTTCGCCGTG<br>TACTATTGTCAGCAGTATGGCTCCACCTTTGGCGGCGGCACAA<br>AGGTGGAGATCAAG |
| 89 | 21A5.a.IgG1.3<br>VH DNA<br>ILT4.9.IgG1.3<br>VH | CAGGTGCAGCTGGTGCAGTCCGGAGCAGAGGTGAAGAAGCCAG<br>GAGCCTCTGTGAAGGTGAGCTGCAAGGCCTCCGGCTACACCTT<br>CACAGATTACTATCTGCACTGGGTGCGGCAGGCACCAGGACAG<br>GGACTGGAGTGGATGGGCATCTTCCACCCTTCTGGCGACATCA<br>CAAGCTCCGCCCAGAACTTTCAGGGCCGGGTGACCATGACAAG<br>AGATACCAGCACATCCACCGTGTACATGGAGCTGTCTAGCCTG<br>AGGTCTGAGGACACCGCCGTGTACTATTGTGCAAGGGGAGGCG<br>TGCTGAGGTATCTGGACTGGAGCCACGCCTTTGATATCTGGGG<br>CCAGGGCACAATGGTGACCGTGTCCTCT |
| 90 | 10F10 kappa<br>VL<br>ILT4.10K<br>VL | AIQLTQSPSSLSASVGDRVTITC**RASQGISSALA**W**F**QQKPGKA<br>PKLLIY**DASSLES**GVPSRF**T**GSGSGTDFTLTISSLQPEDFATY<br>YC**QQFNSYPIT**FGQGTRLEIK |
| 91 | 10F10.IgG1.3<br>VH<br>ILT4.10.IgG1.3<br>VH | QVQLVESGGGVVQPGRSLRLSCAASGFTFS**SYAMH**WVRQAPGK<br>GLEWVA**IISYDEYNKYYADSVKG**RFTISRDNSKNTLYLQMNSL<br>RAEDTAVYYCAR**EWVGIRY**WGQGTLVTVSS |
| 92 | 10F10 kappa<br>VL DNA<br>ILT4.10K<br>VL | GCCATCCAGTTGACCCAGTCTCCATCCTCCCTGTCTGCATCTG<br>TAGGAGACAGAGTCACCATCACTTGCCGGGCAAGTCAGGGCAT<br>TAGCAGTGCTTTAGCCTGGTTTCAGCAGAAACCAGGGAAAGCT<br>CCTAAGCTCCTGATCTATGATGCCTCCAGTTTGGAAAGTGGGG<br>TCCCATCAAGGTTCACCGGCAGTGGATCTGGGACAGATTTCAC<br>TCTCACCATCAGCAGCCTGCAGCCTGAAGATTTTGCAACTTAT<br>TACTGTCAACAGTTTAATAGTTACCCGATCACCTTCGGCCAAG<br>GGACACGACTGGAGATTAAA |
| 93 | 10F10.IgG1.3<br>VH DNA<br>ILT4.10.IgG1.3<br>VH | CAGGTGCAGCTGGTGGAGTCTGGGGGAGGCGTGGTCCAGCCTG<br>GGAGGTCCCTGAGACTCTCCTGTGCAGCCTCTGGATTCACCTT<br>CAGTAGCTATGCTATGCACTGGGTCCGCCAGGCTCCAGGCAAG<br>GGGCTGGAGTGGGTGGCAATTATATCATATGATGAATACAATA<br>AATACTACGCAGACTCCGTGAAGGGCCGATTCACCATCTCCAG<br>AGACAATTCCAAGAACACGCTGTATCTGCAAATGAACAGCCTG<br>AGAGCTGAGGACACGGCTGTGTATTACTGTGCGAGAGAGTGGG<br>TGGGGATACGTTACTGGGGCCAGGGAACCCTGGTCACCGTCTC<br>CTCA |
| 94 | 10F10.1 kappa<br>VL | AIQLTQSPSSLSASVGDRVTITC**RASQGISSALA**W**Y**QQKPGKA<br>PKLLIY**DASSLES**GVPSRF**T**GSGSGTDFTLTISSLQPEDFATY<br>YC**QQFNSYPIT**FGQGTRLEIK |
| 95 | 10F10.1 kappa<br>VL DNA | GCCATCCAGCTGACCCAGTCTCCTAGCTCCCTGTCTGCCAGCG<br>TGGGCGACAGGGTGACCATCACATGCAGAGCCTCCCAGGGAAT<br>CTCTAGCGCCCTGGCCTGGTACCAGCAGAAGCCAGGCAAGGCC<br>CCTAAGCTGCTGATCTATGATGCCTCCTCTCTGGAGAGCGGAG<br>TGCCATCCAGGTTCACCGGCTCCGGCTCTGGCACAGACTTTAC<br>CCTGACAATCAGCTCCCTGCAGCCAGAGGATTTCGCCACATAC<br>TATTGTCAGCAGTTCAACAGCTACCCCATCACCTTTGGCCAGG<br>GCACACGGCTGGAGATCAAG |

-continued

| SEQ ID NO | Name | Sequence |
|---|---|---|
| 96 | 10F10.3 kappa VL ILT4.11K VL | AIQLTQSPSSLSASVGDRVTITC**RASQGISSALA**WYQQKPGKAPKLLIY**DASSLES**GVPSRFSGSGSGTDFTLTISSLQPEDFATYYC**QQFNSYPIT**FGQGTRLEIK |
| 97 | 10F10.3 kappa VL DNA ILT4.11K VL DNA | GCCATCCAGCTGACCCAGTCTCCTAGCTCCCTGTCTGCCAGCGTGGGCGACAGGGTGACCATCACATGCAGAGCCTCCCAGGGAATCTCTAGCGCCCTGGCCTGGTACCAGCAGAAGCCAGGCAAGGCCCCTAAGCTGCTGATCTATGATGCCTCCTCTCTGGAGAGCGGAGTGCCATCCAGGTTCAGCGGCTCCGGCTCTGGCACAGACTTTACCCTGACAATCAGCTCCCTGCAGCCAGAGGATTTCGCCACATACTATTGTCAGCAGTTCAACAGCTACCCCATCACCTTTGGCCAGGGCACACGGCTGGAGATCAAG |
| 98 | Human IgG1f Constant Region | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 99 | IgG1f Consant Region DNA | GCTAGCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAGAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTATAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCCCCGGGTAAATGA |
| 100 | IgG1.3 (or IgG1.3f) heavy chain constant region (L234A, L235E, G237A) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAEGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 101 | Exemplary light chain constant region | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 102 | IgG1f (human wild-type allotype f) heavy chain constant region | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |

-continued

| SEQ ID NO | Name | Sequence |
|---|---|---|
| 103 | IgG1.1f Heavy chain constant region (L234A, L235E, G237A, A3305, P3315) | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPEAEGAPSVFLFPPK<br>PKDTLMISRTPEVTCVVVDVSHEDPEVKFNWYVDGVEVHNAKT<br>KPREEQYNSTYRVVSVLTVLHQDWLNGKEYKCKVSNKALPSSI<br>EKTISKAKGQPREPQVYTLPPSREEMTKNQVSLTCLVKGFYPS<br>DIAVEWESNGQPENNYKTTPPVLDSDGSFFLYSKLTVDKSRWQ<br>QGNVFSCSVMHEALHNHYTQKSLSLSPG |
| 104 | IgG1fa.P238K (or IgG1.P238K) heavy chain constant region | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKRVEPKSCDKTHTCPPCPAPELLGGKSVFLFPPK<br>PKDTLMISRTPEVTCVVVDVSHEDPEVKFNWYVDGVEVHNAKT<br>KPREEQYNSTYRVVSVLTVLHQDWLNGKEYKCKVSNKALPAPI<br>EKTISKAKGQPREPQVYTLPPSRDELTKNQVSLTCLVKGFYPS<br>DIAVEWESNGQPENNYKTTPPVLDSDGSFFLYSKLTVDKSRWQ<br>QGNVFSCSVMHEALHNHYTQKSLSLSPG |
| 105 | IgG1.3 heavy chain constant region DNA | GCGTCGACCAAGGGCCCATCGGTCTTCCCCCTGGCACCCTCCT<br>CCAAGAGCACCTCTGGGGGCACAGCGGCCCTGGGCTGCCTGGT<br>CAAGGACTACTTCCCCGAACCGGTGACGGTGTCGTGGAACTCA<br>GGCGCCCTGACCAGCGGCGTGCACACCTTCCCGGCTGTCCTAC<br>AGTCCTCAGGACTCTACTCCCTCAGCAGCGTGGTGACCGTGCC<br>CTCCAGCAGCTTGGGCACCCAGACCTACATCTGCAACGTGAAT<br>CACAAGCCCAGCAACACCAAGGTGGACAAGAGAGTTGAGCCCA<br>AATCTTGTGACAAAACTCACACATGCCCACCGTGCCCAGCACC<br>TGAAGCCGAAGGGGCCCCGTCAGTCTTCCTCTTCCCCCCAAAA<br>CCCAAGGACACCCTCATGATCTCCCGGACCCCTGAGGTCACAT<br>GCGTGGTGGTGGACGTGAGCCACGAAGACCCTGAGGTCAAGTT<br>CAACTGGTACGTGGACGGCGTGGAGGTGCATAATGCCAAGACA<br>AAGCCGCGGGAGGAGCAGTACAACAGCACGTACCGTGTGGTCA<br>GCGTCCTCACCGTCCTGCACCAGGACTGGCTGAATGGCAAGGA<br>GTACAAGTGCAAGGTCTCCAACAAAGCCCTCCCAGCCCCCATC<br>GAGAAAACCATCTCCAAAGCCAAAGGGCAGCCCCGAGAACCAC<br>AGGTGTACACCCTGCCCCCATCCCGGGAGGAGATGACCAAGAA<br>CCAGGTCAGCCTGACCTGCCTGGTCAAAGGCTTCTATCCCAGC<br>GACATCGCCGTGGAGTGGGAGAGCAATGGGCAGCCGGAGAACA<br>ACTACAAGACCACGCCTCCCGTGCTGGACTCCGACGGCTCCTT<br>CTTCCTCTATAGCAAGCTCACCGTGGACAAGAGCAGGTGGCAG<br>CAGGGGAACGTCTTCTCATGCTCCGTGATGCATGAGGCTCTGC<br>ACAACCACTACACGCAGAAGAGCCTCTCCCTGTCCCCGGGTTG<br>A |
| 106 | Exemplary light chain constant region DNA | CGTACGGTGGCTGCACCATCTGTCTTCATCTTCCCGCCATCTG<br>ATGAGCAGTTGAAATCTGGAACTGCCTCTGTTGTGTGCCTGCT<br>GAATAACTTCTATCCCAGAGAGGCCAAAGTACAGTGGAAGGTG<br>GATAACGCCCTCCAATCGGGTAACTCCCAGGAGAGTGTCACAG<br>AGCAGGACAGCAAGGACAGCACCTACAGCCTCAGCAGCACCCT<br>GACGCTGAGCAAAGCAGACTACGAGAAACACAAAGTCTACGCC<br>TGCGAAGTCACCCATCAGGGCCTGAGCTCGCCCGTCACAAAGA<br>GCTTCAACAGGGGAGAGTGTTAG |
| 107 | Human ILT4 precursor, with signal peptide (UniProtKB Ref. Q8N423.4, 24 JUL. 2013) | MTPIVTVLIC LGLSLGPRTH VQTGTIPKPT LWAEPDSVIT<br>QGSPVTLSCQ GSLEAQEYRL YREKKSASWI TRIRPELVKN<br>GQFHIPSITW EHTGRYGCQY YSRARWSELS DPLVLVMTGA<br>YPKPTLSAQP SPVVTSGGRV TLQCESQVAF GGFILCKEGE<br>EEHPQCLNSQ PHARGSSRAI FSVGPVSPNR RWSHRCYGYD<br>LNSPYVWSSP SDLLELLVPG VSKKPSLSVQ PGPVVAPGES<br>LTLQCVSDVG YDRFVLYKEG ERDLRQLPGR QPQAGLSQAN<br>FTLGPVSRSY GGQYRCYGAH NLSSECSAPS DPLDILITGQ<br>IRGTPFISVQ PGPTVASGEN VTLLCQSWRQ FHTFLLTKAG<br>AADAPLRLRS IHEYPKYQAE FPMSPVTSAH AGTYRCYGSL<br>NSDPYLLSHP SEPLELVVSG PSMGSSPPPT GPISTPAGPE<br>DQPLTPTGSD PQSGLGRHLG VVIGILVAVV LLLLLLLLLF<br>LILRHRRQGK HWTSTQRKAD FQHPAGAVGP EPTDRGLQWR<br>SSPAADAQEE NLYAAVKDTQ PEDGVEMDTR AAASEAPQDV<br>TYAQLHSLTL RRKATEPPPS QEREPPAEPS IYATLAIH |
| 108 | Human mature ILT4, without signal peptide | QTGTIPKPTL WAEPDSVITQ GSPVTLSCQG SLEAQEYRLY<br>REKKSASWIT RIRPELVKNG QFHIPSITWE HTGRYGCQYY<br>SRARWSELSD PLVLVMTGAY PKPTLSAQPS PVVTSGGRVT<br>LQCESQVAFG GFILCKEGEE EHPQCLNSQP HARGSSRAIF<br>SVGPVSPNRR WSHRCYGYDL NSPYVWSSPS DLLELLVPGV<br>SKKPSLSVQP GPVVAPGESL TLQCVSDVGY DRFVLYKEGE |

-continued

| SEQ ID NO | Name | Sequence |
|---|---|---|
| | | RDLRQLPGRQ PQAGLSQANF TLGPVSRSYG GQYRCYGAHN LSSECSAPSD PLDILITGQI RGTPFISVQP GPTVASGENV TLLCQSWRQF HTFLLTKAGA ADAPLRLRSI HEYPKYQAEF PMSPVTSAHA GTYRCYGSLN SDPYLLSHPS EPLELVVSGP SMGSSPPPTG PISTPAGPED QPLTPTGSDP QSGLGRHLGV VIGILVAVVL LLLLLLLLFL ILRHRRQGKH WTSTQRKADF QHPAGAVGPE PTDRGLQWRS SPAADAQEEN LYAAVKDTQP EDGVEMDTRA AASEAPQDVT YAQLHSLTLR RKATEPPPSQ EREPPAEPSI YATLAIH |
| 109 | Human ILT4 ECD region | GTIPKPTL WAEPDSVITQ GSPVTLSCQG SLEAQEYRLY REKKSASWIT RIRPELVKNG QFHIPSITWE HTGRYGCQYY SRARWSELSD PLVLVMTGAY PKPTLSAQPS PVVTSGGRVT LQCESQVAFG GFILCKEGEE EHPQCLNSQP HARGSSRAIF SVGPVSPNRR WSHRCYGYDL NSPYVWSSPS DLLELLVPGV SKKPSLSVQP GPVVAPGESL TLQCVSDVGY DRFVLYKEGE RDLRQLPGRQ PQAGLSQANF TLGPVSRSYG GQYRCYGAHN LSSECSAPSD PLDILITGQI RGTPFISVQP GPTVASGENV TLLCQSWRQF HTFLLTKAGA ADAPLRLRSI HEYPKYQAEF PMSPVTSAHA GTYRCYGSLN SDPYLLSHPS EPLELVVSGP SMGSSPPPTG PISTPAGPED QPLTPTGSDP QSGLGRHLGV |
| 110 | Human ILT4 precursor, with signal peptide, isoform 2 (NCBI Ref. NP_001074447.1, 12 SEP. 2013) | MTPIVTVLIC LGLSLGPRTH VQTGTIPKPT LWAEPDSVIT QGSPVTLSCQ GSLEAQEYRL YREKKSASWI TRIRPELVKN GQFHIPSITW EHTGRYGCQY YSRARWSELS DPLVLVMTGA YPKPTLSAQP SPVVTSGGRV TLQCESQVAF GGFILCKEGE EEHPQCLNSQ PHARGSSRAI FSVGPVSPNR RWSHRCYGYD LNSPYVWSSP SDLLELLVPG VSKKPSLSVQ PGPVVAPGES LTLQCVSDVG YDRFVLYKEG ERDLRQLPGR QPQAGLSQAN FTLGPVSRSY GGQYRCYGAH NLSSECSAPS DPLDILITGQ IRGTPFISVQ PGPTVASGEN VTLLCQSWRQ FHTFLLTKAG AADAPLRLRS IHEYPKYQAE FPMSPVTSAH AGTYRCYGSL NSDPYLLSHP SEPLELVVSG PSMGSSPPPT GPISTPGPED QPLTPTGSDP QSGLGRHLGV VIGILVAVVL LLLLLLLLFL ILRHRRQGKH WTSTQRKADF QHPAGAVGPE PTDRGLQWRS SPAADAQEEN LYAAVKDTQP EDGVEMDTRA AASEAPQDVT YAQLHSLTLR RKATEPPPSQ EREPPAEPSI YATLAIH |
| 111 | Human mature ILT4, isoform 2, without signal peptide | QTGTIPKPTL WAEPDSVITQ GSPVTLSCQG SLEAQEYRLY REKKSASWIT RIRPELVKNG QFHIPSITWE HTGRYGCQYY SRARWSELSD PLVLVMTGAY PKPTLSAQPS PVVTSGGRVT LQCESQVAFG GFILCKEGEE EHPQCLNSQP HARGSSRAIF SVGPVSPNRR WSHRCYGYDL NSPYVWSSPS DLLELLVPGV SKKPSLSVQP GPVVAPGESL TLQCVSDVGY DRFVLYKEGE RDLRQLPGRQ PQAGLSQANF TLGPVSRSYG GQYRCYGAHN LSSECSAPSD PLDILITGQI RGTPFISVQP GPTVASGENV TLLCQSWRQF HTFLLTKAGA ADAPLRLRSI HEYPKYQAEF PMSPVTSAHA GTYRCYGSLN SDPYLLSHPS EPLELVVSGP SMGSSPPPTG PISTPGPEDQ PLTPTGSDPQ SGLGRHLGVV IGILVAVVLL LLLLLLLFLI LRHRRQGKHW TSTQRKADFQ HPAGAVGPEP TDRGLQWRSS PAADAQEENL YAAVKDTQPE DGVEMDTRAA ASEAPQDVTY AQLHSLTLRR KATEPPPSQE REPPAEPSIY ATLAIH |
| 112 | Human ILT4 isoform 2, ECD | GTIPKPTL WAEPDSVITQ GSPVTLSCQG SLEAQEYRLY REKKSASWIT RIRPELVKNG QFHIPSITWE HTGRYGCQYY SRARWSELSD PLVLVMTGAY PKPTLSAQPS PVVTSGGRVT LQCESQVAFG GFILCKEGEE EHPQCLNSQP HARGSSRAIF SVGPVSPNRR WSHRCYGYDL NSPYVWSSPS DLLELLVPGV SKKPSLSVQP GPVVAPGESL TLQCVSDVGY DRFVLYKEGE RDLRQLPGRQ PQAGLSQANF TLGPVSRSYG GQYRCYGAHN LSSECSAPSD PLDILITGQI RGTPFISVQP GPTVASGENV TLLCQSWRQF HTFLLTKAGA ADAPLRLRSI HEYPKYQAEF PMSPVTSAHA GTYRCYGSLN SDPYLLSHPS EPLELVVSGP SMGSSPPPTG PISTPGPEDQ PLTPTGSDPQ SGLGRHLGV |
| 113 | 21D9.IgG1.3 HC | EGQLLESGGD LVQPGGSLRL SCATSGFTFS NYAMNWVRQA PGKGLEWISV ISVSGGSTYY ADSVKGRFTI SRDNSKNTLY LQMNSLRAED TAVYYCAKDY YYDSGSYYDS FFDYWGQGTL VTVSSASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KRVEPKSCDK THTCPPCPAPEAEGAPSVFL FPPKPKDTLM ISRTPEVTCV VVDVSHEDPE VKFNWYVDGV EVHNAKTKPREEQYNSTYRV VSVLTVLHQD WLNGKEYKCK |

-continued

| SEQ ID NO | Name | Sequence |
|---|---|---|
| | | VSNKALPAPI EKTISKAKGQ PREPQVYTLPPSREEMTKNQ<br>VSLTCLVKGF YPSDIAVEWE SNGQPENNYK TTPPVLDSDG<br>SFFLYSKLTVDKSRWQQGNV FSCSVMHEAL HNHYTQKSLS<br>LSPG |
| 114 | 10F10.4 VL | AIQLTQSPSSLSASVGDRVTITC**RASQGISSALA**W**F**QQKPGKA<br>PKLLIY**DASSLES**GVPSRF**S**GSGSGTDFTLTISSLQPEDFATY<br>YC**QQFNSYPIT**FGQGTRLEIK |
| 115 | 10F10.4 VL DNA | GCCATCCAGCTGACCCAGAGCCCTAGCTCCCTGTCTGCCAGCG<br>TGGGCGACAGGGTGACCATCACATGCAGAGCCTCCCAGGGAAT<br>CTCTAGCGCCCTGGCCTGGTTCCAGCAGAAGCCAGGCAAGGCC<br>CCTAAGCTGCTGATCTACGATGCCTCCTCTCTGGAGTCCGGCG<br>TGCCCTCTAGGTTCTCCGGCTCTGGCAGCGGCACCGACTTTAC<br>CCTGACAATCAGCTCCCTGCAGCCAGAGGATTTTGCCACATAC<br>TATTGTCAGCAGTTCAACTCTTATCCCATCACCTTTGGCCAGG<br>GCACACGGCTGGAGATCAAG |
| 116 | 10F10.4 LC | **AIQLTQSPSSLSASVGDRVTITCRASQGISSALAWFQQKPGKA**<br>**PKLLIYDASSLESGVPSRFSGSGSGTDFTLTISSLQPEDFATY**<br>**YCQQFNSYPITFGQGTRLEIK**RTVAAPSVFIFPPSDEQLKSGT<br>ASVVCLLNNFYPREAKVQWKVDNALQSGNSQESVTEQDSKDST<br>YSLSSTLTLSKADYEKHKVYACEVTHQGLSSPVTKSFNRGEC |
| 117 | 10F10.4 LC DNA | GCCATCCAGCTGACCCAGAGCCCTAGCTCCCTGTCTGCCAGCG<br>TGGGCGACAGGGTGACCATCACATGCAGAGCCTCCCAGGGAAT<br>CTCTAGCGCCCTGGCCTGGTTCCAGCAGAAGCCAGGCAAGGCC<br>CCTAAGCTGCTGATCTACGATGCCTCCTCTCTGGAGTCCGGCG<br>TGCCCTCTAGGTTCTCCGGCTCTGGCAGCGGCACCGACTTTAC<br>CCTGACAATCAGCTCCCTGCAGCCAGAGGATTTTGCCACATAC<br>TATTGTCAGCAGTTCAACTCTTATCCCATCACCTTTGGCCAGG<br>GCACACGGCTGGAGATCAAGCGTACGGTGGCCGCCCCGTCCGT<br>GTTTATCTTCCCTCCATCGGACGAGCAGCTCAAGTCCGGTACC<br>GCGAGCGTGGTCTGCCTGCTGAACAATTTCTACCCGCGCGAAG<br>CTAAAGTGCAATGGAAGGTCGATAACGCACTTCAGTCCGGGAA<br>CAGCCAGGAATCTGTGACCGAGCAGGACTCCAAGGATTCGACC<br>TATTCCCTGTCCTCGACTCTCACCCTGTCAAAGGCCGACTACG<br>AGAAGCACAAGGTCTACGCCTGCGAAGTGACCCATCAGGGCTT<br>GTCCTCACCCGTGACTAAGAGCTTCAACCGGGGAGAGTGT |
| 118 | Cyno ILT4 9152 extracellular domain, including His-Avi Tag | QAGILPKPMLWAEPDRVITQGSPVTLRCQGNLEARGYHLYRER<br>KSASWITLIRPELVKKGQFPIPSITWEDAGRYRCQYYSHSWWS<br>EHSDPLELVVTGAYRKPTLSALPSPVVASGGNVTLQCDSRVAL<br>DGFILCKEGEDEHSQRLNSQPRTRGSSRAVFSVGPVSPSRRWS<br>YRCYGYELHSRYVWSLPSDLLELLVPGVSKKPSLSVQPGPVVA<br>GGDKLTLQCGSDAGYDRFALYKEGERDFLQRPGQQLQAGLAQA<br>NFTLDPVRGSHGGQYRCYGAHNLSSEWSAPSDPLDILISAGPH<br>SGLRRECDPAVSVTGMDGHFLSDQGGSSSPGGGSGGGSEQKLI<br>SEEDLGHHHHHHGLNDIFEAQKIEWHE |
| 119 | hILT4H extracellular domain plus HIS-Avi tag (used in Example 2) | QTGTIPKPTLWAEPDSVITQGSPVTLSCQGSLEAQEYRLYREK<br>KSASWITRIRPELVKNGQFHIPSITWEHTGRYGCQYYSRARWS<br>ELSDPLVLVMTGAYPKPTLSAQPSPVVTSGGRVTLQCESQVAF<br>GGFILCKEGEEEHPQCLNSQPHARGSSRAIFSVGPVSPNRRWS<br>HRCYGYDLNSPYVWSSPSDLLELLVPGVSKKPSLSVQPGPVVA<br>PGESLTLQCVSDVGYDRFVLYKEGERDLRQLPGRQPQAGLSQA<br>NFTLGPVSRSYGGQYRCYGAHNLSSESSAPSDPLDILITGQIR<br>GTPFISVQPGPTVASGENVTLLCQSWRQFHTFLLTKAGAADAP<br>LRLRSIHEYPKYQAEFPMSPVTSAHAGTYRCYGSLNSDPYLLS<br>HPSEPLELVVSGPSMGSSPPPTGPISTPAGPEDQPLTPTGSDP<br>QSGLGRHLGSPGGGSGGGSEQKLISEEDLGHHHHHHGLNDIFE<br>AQKIEWHE |
| 120 | Residues 70-77 of hILT4 | ITRIRPEL |
| 121 | Residues 78-100 of hILT4 | VKNGQFHIPSITWEHTGRYGCQY |
| 122 | Residues 70-100 of hILT4 | ITRIRPELVKNGQFHIPSITWEHTGRYGCQY |

-continued

| SEQ ID NO | Name | Sequence |
|---|---|---|
| 123 | Residues 154 to 181 of hILT4 | ILCKEGEEEHPQCLNSQPHARGSSRAIF |
| 124 | Residues 425 to 434 of hILT4 | SSPPPTGPIS |
| 125 | 9G4 (ILT4.1) VH CDR1 | SYYWN |
| 126 | 9G4 VH CDR2 | YIYYSGSTKYNPSLKS |
| 127 | 9G4 VH CDR3 | SGWYYFDY |
| 128 | 9G4 VL CDR1 | RASQSVSSYLA |
| 129 | 9G4 VL CDR2 | DASNRAT |
| 130 | 9G4 VL CDR3 | QQRSYWPWT |
| 131 | 9C8 VH CDR1 | SSDIN |
| 132 | 9C8 VH CDR2 | WMNPNSGHTGYAQKFQD |
| 133 | 9C8 VH CDR3 | GGNSIDWGFSYYGLDV |
| 134 | 9C8 VL CDR1 | RASQGISSALA |
| 135 | 9C8 VL CDR2 | DASSLES |
| 136 | 9C8 VL CDR3 | QQFNSYPFT |
| 137 | 2H2 VH CDR1 | NYAIS |
| 138 | 2H2 VH CDR2 | GIIPILATANYAPKFQG |
| 139 | 2H2 VH CDR3 | SSITMIRGAYLYYYDGMDV |
| 140 | 2H2 VL CDR1 | RASQSVSSSYLA |
| 141 | 2H2 VL CDR2 | GASSRAT |
| 142 | 2H2 VL CDR3 | QQYGSSYT |
| 143 | 2E5 VH CDR1 | NYGMH |
| 144 | 2E5 VH CDR2 | VIWYDGSNEYYAESVKG |
| 145 | 2E5 VH CDR3 | DPFYGSGNYFDY |
| 146 | 2E5 VL CDR1 | RASQSVSSYLA |
| 147 | 2E5 VL CDR2 | DASNRAT |
| 148 | 2E5 VL CDR3 | QQRSNWPPWT |
| 149 | 24E5 VH CDR1 | SYVMS |
| 150 | 24E5 VH CDR2 | GISGSGGSTYYADSVKG |
| 151 | 24E5 VH CDR3 | DQDIIAAYYFVY |
| 152 | 24E5 VL CDR1 | RASQGISSWLA |
| 153 | 24E5 VL CDR2 | AASSLQS |
| 154 | 24E5 VL CDR3 | QQYNSYPLT |
| 155 | 21D9 VH CDR1 | NYAMN |
| 156 | 21D9 VH CDR2 | VISVSGGSTYYADSVKG |
| 157 | 21D9 VH CDR3 | DYYYDSGSYYDSFFDY |

-continued

| SEQ ID NO | Name | Sequence |
|---|---|---|
| 158 | 21D9 VL CDR1 | RASQSVSSSYLA |
| 159 | 21D9 VL CDR2 | GASSRAT |
| 160 | 21D9 VL CDR3 | QQYGSSPLT |
| 161 | 21A5 VH CDR1 | DYYLH |
| 162 | 21A5 VH CDR2 | IFHPSGDITSSAQNFQG |
| 163 | 21A5 VH CDR3 | GGVLRYLDWSHAFDI |
| 164 | 21A5 VL CDR1 | RASQSVSSSYLA |
| 165 | 21A5 VL CDR2 | GASSRAT |
| 166 | 21A5 VL CDR3 | QQYGST |
| 167 | 10F10 VH CDR1 | SYAMH |
| 168 | 10F10 VH CDR2 | IISYDEYNKYYADSVKG |
| 169 | 10F10 VH CDR3 | EWVGIRY |
| 170 | 10F10 VL CDR1 | RASQGISSALA |
| 171 | 10F10 VL CDR2 | DASSLES |
| 172 | 10F10 VL CDR3 | QQFNSYPIT |
| 173 | Residues 127-142 of hILT4 | SAQPSPVVTSGGRVTL |
| 174 | Residues 182-213 of hILT4 | SVGPVSPNRRWSHRCYGYDLNSPYVWSSPSDL |
| 175 | Residues 378-392 of hILT4 | QAEFPMSPVTSAHAG |
| 176 | 21D9.e, IgG1f (Same Fc as SEQ ID NO: 98 w/o C-term. K) | **EVQLLESGGGLVQPGGSLRLSCAASGFTFSNYAMNWVRQAPGK GLEWVSVISVSGGSTYYADSVKGRFTISRDNSKNTLYLQMNSL RAEDTAVYYCAKDYYYDSGSYYDSFFDYWGQGTLVTVSS**ASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKRVEPKSCDKTHTCPPCPAPELLGGPSVFLFPPKPKDT LMISRTPEVTCVVVDVSHEDPEVKFNWYVDGVEVHNAKTKPRE EQYNSTYRVVSVLTVLHQDWLNGKEYKCKVSNKALPAPIEKTI SKAKGQPREPQVYTLPPSREEMTKNQVSLTCLVKGFYPSDIAV EWESNGQPENNYKTTPPVLDSDGSFFLYSKLTVDKSRWQQGNV FSCSVMHEALHNHYTQKSLSLSPG |
| 177 | 21D9.e.IgG1.1f (Fc is the same as SEQ ID NO: 103) | **EVQLLESGGGLVQPGGSLRLSCAASGFTFSNYAMNWVRQAPGK GLEWVSVISVSGGSTYYADSVKGRFTISRDNSKNTLYLQMNSL RAEDTAVYYCAKDYYYDSGSYYDSFFDYWGQGTLVTVSS**ASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKRVEPKSCDKTHTCPPCPAPEAEGAPSVFLFPPKPKDT LMISRTPEVTCVVVDVSHEDPEVKFNWYVDGVEVHNAKTKPRE EQYNSTYRVVSVLTVLHQDWLNGKEYKCKVSNKALPSSIEKTI SKAKGQPREPQVYTLPPSREEMTKNQVSLTCLVKGFYPSDIAV EWESNGQPENNYKTTPPVLDSDGSFFLYSKLTVDKSRWQQGNV FSCSVMHEALHNHYTQKSLSLSPG |
| 178 | 21D9.e.IgG4_S228P | **EVQLLESGGGLVQPGGSLRLSCAASGFTFSNYAMNWVRQAPGK GLEWVSVISVSGGSTYYADSVKGRFTISRDNSKNTLYLQMNSL RAEDTAVYYCAKDYYYDSGSYYDSFFDYWGQGTLVTVSS**ASTK GPSVFPLAPCSRSTSESTAALGCLVKDYFPEPVTVSWNSGALT SGVHTFPAVLQSSGLYSLSSVVTVPSSSLGTKTYTCNVDHKPS NTKVDKRVESKYGPPCPPCPAPEFLGGPSVFLFPPKPKDTLMI SRTPEVTCVVVDVSQEDPEVQFNWYVDGVEVHNAKTKPREEQF NSTYRVVSVLTVLHQDWLNGKEYKCKVSNKGLPSSIEKTISKA KGQPREPQVYTLPPSQEEMTKNQVSLTCLVKGFYPSDIAVEWE SNGQPENNYKTTPPVLDSDGSFFLYSRLTVDKSRWQQGNVFSC SVMHEALHNHYTQKSLSLS |

-continued

| SEQ ID NO | Name | Sequence |
| --- | --- | --- |
| 179 | hIgG4 S228P (Fc of SEQ ID NO: 178) | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEFLGGPSVFLFPPKPKD TLMISRTPEVTCVVVDVSQEDPEVQFNWYVDGVEVHNAKTKPR EEQFNSTYRVVSVLTVLHQDWLNGKEYKCKVSNKGLPSSIEKT ISKAKGQPREPQVYTLPPSQEEMTKNQVSLTCLVKGFYPSDIA VEWESNGQPENNYKTTPPVLDSDGSFFLYSRLTVDKSRWQQGN VFSCSVMHEALHNHYTQKSLSLS |

The invention claimed is:

1. An isolated antibody that specifically binds to human ILT4 (hILT4), the antibody comprising a heavy chain and a light chain, wherein the heavy chain comprises a heavy chain variable region (VH) comprising VH complementary determining region 1 (CDR1), CDR2 and CDR3 comprising the amino acid sequences of SEQ ID Nos: 155, 156, and 157, respectively, and wherein the light chain comprises a light chain variable region (VL) comprising VL CDR1, CDR2 and CDR3 comprising the amino acid sequences of SEQ ID Nos: 158, 159, and 160, respectively.

2. The isolated antibody of claim 1, wherein:

a. the VH comprises an amino acid sequence that is at least 90% identical to the amino acid sequence of SEQ ID NO: 71 and the VL comprises an amino acid sequence that is at least 90% identical to the amino acid sequence of SEQ ID NO: 70;

b. the VH comprises an amino acid sequence that is at least 90% identical to the amino acid sequence of SEQ ID NO: 74 and the VL comprises an amino acid sequence that is at least 90% identical to the amino acid sequence of SEQ ID NO: 70;

c. the VH comprises an amino acid sequence that is at least 90% identical to the amino acid sequence of SEQ ID NO: 75 and the VL comprises an amino acid sequence that is at least 90% identical to the amino acid sequence of SEQ ID NO: 70;

d. the VH comprises an amino acid sequence that is at least 90% identical to the amino acid sequence of SEQ ID NO: 78 and the VL comprises an amino acid sequence that is at least 90% identical to the amino acid sequence of SEQ ID NO: 70; or e. the VH comprises an amino acid sequence that is at least 90% identical to the amino acid sequence of SEQ ID NO: 80 and the VL comprises an amino acid sequence that is at least 90% identical to the amino acid sequence of SEQ ID NO: 70.

3. The isolated antibody of claim 1, wherein:

a. the VH comprises an amino acid sequence that is at least 95% identical to the amino acid sequence of SEQ ID NO: 71 and the VL comprises an amino acid sequence that is at least 95% identical to the amino acid sequence of SEQ ID NO: 70;

b. the VH comprises an amino acid sequence that is at least 95% identical to the amino acid sequence of SEQ ID NO: 74 and the VL comprises an amino acid sequence that is at least 95% identical to the amino acid sequence of SEQ ID NO: 70;

c. the VH comprises an amino acid sequence that is at least 95% identical to the amino acid sequence of SEQ ID NO: 75 and the VL comprises an amino acid sequence that is at least 95% identical to the amino acid sequence of SEQ ID NO: 70;

d. the VH comprises an amino acid sequence that is at least 95% identical to the amino acid sequence of SEQ ID NO: 78 and the VL comprises an amino acid sequence that is at least 95% identical to the amino acid sequence of SEQ ID NO: 70; or e. the VH comprises an amino acid sequence that is at least 95% identical to the amino acid sequence of SEQ ID NO: 80 and the VL comprises an amino acid sequence that is at least 95% identical to the amino acid sequence of SEQ ID NO: 70.

4. The isolated antibody of claim 1, wherein:

a. the VH comprises the amino acid sequence of SEQ ID NO: 71;

b. the VH comprises the amino acid sequence of SEQ ID NO: 74;

c. the VH comprises the amino acid sequence of SEQ ID NO: 75;

d. the VH comprises the amino acid sequence of SEQ ID NO: 78; or e. the VH comprises the amino acid sequence of SEQ ID NO: 80.

5. The isolated antibody of claim 4, comprising a heavy chain constant region comprising the amino acid sequence of any one of SEQ ID Nos: 98, 100, 102, 103, 104 or 179.

6. The isolated antibody of claim 5, wherein the heavy chain constant region comprises the amino acid sequence of any one of SEQ ID Nos: 100, 102, 103, 104 or 179 and further comprises a C-terminal lysine residue.

7. The isolated antibody of claim 5, wherein the heavy chain constant region comprises the amino acid sequence of SEQ ID NO: 100.

8. The isolated antibody of claim 7, wherein the heavy chain constant region further comprises a C-terminal lysine residue.

9. The isolated antibody of claim 1, wherein the VL comprises the amino acid sequence of SEQ ID NO: 70.

10. The isolated antibody of claim 1, wherein:

a. the VH comprises the amino acid sequence of SEQ ID NO: 71 and the VL comprises the amino acid sequence of SEQ ID NO: 70;

b. the VH comprises the amino acid sequence of SEQ ID NO: 74 and the VL comprises the amino acid sequence of SEQ ID NO: 70;

c. the VH comprises the amino acid sequence of SEQ ID NO: 75 and the VL comprises the amino acid sequence of SEQ ID NO: 70;

d. the VH comprises the amino acid sequence of SEQ ID NO: 78 and the VL comprises the amino acid sequence of SEQ ID NO: 70; or e. the VH comprises the amino acid sequence of SEQ ID NO: 80 and the VL comprises the amino acid sequence of SEQ ID NO: 70.

11. The isolated antibody of claim 10, comprising a heavy chain constant region comprising the amino acid sequence of any one of SEQ ID Nos: 98, 100, 102, 103, 104 or 179.

12. The isolated antibody of claim 11, wherein the heavy chain constant region comprises the amino acid sequence of any one of SEQ ID Nos: 100, 102, 103, 104 or 179 and further comprises a C-terminal lysine residue.

13. The isolated antibody of claim 11, wherein the heavy chain constant region comprises the amino acid sequence of SEQ ID NO: 100.

14. The isolated antibody of claim 13, wherein the heavy chain constant region further comprises a C-terminal lysine residue.

15. The isolated antibody of claim 1, which is an IgG antibody.

16. The isolated antibody of claim 15, which is an IgG1, IgG2 or IgG4 antibody.

17. The isolated antibody of claim 16, wherein the antibody is a human IgG4 antibody comprising an S228P substitution (EU numbering).

18. The isolated antibody of claim 1, wherein the heavy chain lacks a C-terminal lysine residue.

19. The isolated antibody of claim 1, which is a full length antibody, and wherein the heavy chain comprises or does not comprise a C-terminal lysine residue.

20. The isolated antibody of claim 1, wherein the heavy chain comprises the amino acid sequence of SEQ ID NO: 13.

21. The isolated antibody of claim 20, wherein the heavy chain further comprises a C-terminal lysine residue.

22. The isolated antibody of claim 1, wherein the light chain comprises the amino acid sequence of SEQ ID NO: 11.

23. The isolated antibody of claim 1, wherein the heavy chain comprises the amino acid sequence of SEQ ID NO: 12, SEQ ID NO: 13, SEQ ID NO: 36, SEQ ID NO: 38, SEQ ID NO: 40, SEQ ID NO: 176, SEQ ID NO: 177, or SEQ ID NO: 178.

24. The isolated antibody of claim 1, wherein: (a) the heavy chain comprises the amino acid sequence of SEQ ID NO: 12 and the light chain comprises the amino acid sequence of SEQ ID NO: 11, (b) the heavy chain comprises the amino acid sequence of SEQ ID NO: 13 and the light chain comprises the amino acid sequence of SEQ ID NO: 11, (c) the heavy chain comprises the amino acid sequence of SEQ ID NO: 36 and the light chain comprises the amino acid sequence of SEQ ID NO: 11, (d) the heavy chain comprises the amino acid sequence of SEQ ID NO: 38 and the light chain comprises the amino acid sequence of SEQ ID NO: 11, (e) the heavy chain comprises the amino acid sequence of SEQ ID NO: 40 and the light chain comprises the amino acid sequence of SEQ ID NO: 11, (f) the heavy chain comprises the amino acid sequence of SEQ ID NO: 176 and the light chain comprises the amino acid sequence of SEQ ID NO: 11, (g) the heavy chain comprises the amino acid sequence of SEQ ID NO: 177 and the light chain comprises the amino acid sequence of SEQ ID NO: 11, or (h) the heavy chain comprises the amino acid sequence of SEQ ID NO: 178 and the light chain comprises the amino acid sequence of SEQ ID NO: 11.

25. The isolated antibody of claim 1, wherein the VH comprises the amino acid sequence of SEQ ID NO: 80.

26. The isolated antibody of claim 25, comprising a heavy chain constant region comprising the amino acid sequence of any one of SEQ ID Nos: 98, 100, 102, 103, 104 or 179.

27. The isolated antibody of claim 26, wherein the heavy chain constant region comprises the amino acid sequence of any one of SEQ ID Nos: 100, 102, 103, 104 or 179 and further comprises a C-terminal lysine residue.

28. An isolated antibody that specifically binds to hILT4, the antibody comprising a VH comprising the amino acid sequence of SEQ ID NO: 80 and a VL comprising the amino acid sequence of SEQ ID NO: 70.

29. The isolated antibody of claim 28, which is an IgG antibody.

30. The isolated antibody of claim 29, which is an IgG1, IgG2 or IgG4 antibody.

31. The isolated antibody of claim 30, wherein the antibody is a human IgG4 antibody comprising an S228P substitution (EU numbering).

32. The isolated antibody of claim 28, comprising a heavy chain that lacks a C-terminal lysine residue.

33. The isolated antibody of claim 28, which is a full length antibody comprising a heavy chain that comprises or does not comprise a C-terminal lysine residue.

34. The isolated antibody of claim 28, comprising a heavy chain constant region comprising the amino acid sequence of any one of SEQ ID Nos: 98, 100, 102, 103, 104 or 179.

35. The isolated antibody of claim 34, wherein the heavy chain constant region comprises the amino acid sequence of any one of SEQ ID Nos: 100, 102, 103, 104 or 179 and further comprises a C-terminal lysine residue.

36. An isolated antibody that specifically binds to hILT4, the antibody comprising a VH comprising the amino acid sequence of SEQ ID NO: 80, a VL comprising the amino acid sequence of SEQ ID NO: 70, and a heavy chain constant region comprising the amino acid sequence of SEQ ID NO: 100.

37. The isolated antibody of claim 36, wherein the heavy chain constant region further comprises a C-terminal lysine residue.

38. An isolated antibody that specifically binds to hILT4, the antibody comprising a heavy chain comprising the amino acid sequence of SEQ ID NO: 13 and a light chain comprising the amino acid sequence of SEQ ID NO: 11.

39. The isolated antibody of claim 38, wherein the heavy chain further comprises a C-terminal lysine residue.

40. The isolated antibody of claim 38, which comprises a heavy chain consisting of the amino acid sequence of SEQ ID NO: 13 and a light chain consisting of the amino acid sequence of SEQ ID NO: 11.

41. The isolated antibody of claim 38, which comprises a heavy chain consisting of the amino acid sequence of SEQ ID NO: 13 and a C-terminal lysine, and a light chain consisting of the amino acid sequence of SEQ ID NO: 11.

* * * * *

UNITED STATES PATENT AND TRADEMARK OFFICE

CERTIFICATE OF CORRECTION

PATENT NO. : 11,401,328 B2
APPLICATION NO. : 16/506754
DATED : August 2, 2022
INVENTOR(S) : Schebye et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 309 days.

Signed and Sealed this
Eleventh Day of February, 2025

Coke Morgan Stewart
*Acting Director of the United States Patent and Trademark Office*

SEQUENCE LISTING

<160> NUMBER OF SEQ ID NOS: 193

<210> SEQ ID NO 1
<211> LENGTH: 214
<212> TYPE: PRT
<213> ORGANISM: Artificial Sequence
<220> FEATURE:
<223> OTHER INFORMATION: Synthetic: 9G4 kappa LC (aka. ILT4.1-kappa)

<400> SEQUENCE: 1

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Gly Tyr Tyr Cys Gln Gln Arg Ser Tyr Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 2
<211> LENGTH: 446
<212> TYPE: PRT
<213> ORGANISM: Artificial Sequence
<220> FEATURE:
<223> OTHER INFORMATION: Synthetic: 9G4-IgG1.1f HC (aka. ILT4.1-IgG1.1f)

<400> SEQUENCE: 2

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Asn Trp Ile Arg Gln Pro Pro Gly Lys Gly Leu Glu Trp Leu
        35                  40                  45

Gly Tyr Ile Tyr Tyr Ser Gly Ser Thr Lys Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ser Gly Trp Tyr Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Glu Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp

```
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 3
<211> LENGTH: 214
<212> TYPE: PRT
<213> ORGANISM: Artificial Sequence
<220> FEATURE:
<223> OTHER INFORMATION: Synthetic: 9C8 kappa LC ILT4.2-kappa

<400> SEQUENCE: 3

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 4
<211> LENGTH: 455
<212> TYPE: PRT
<213> ORGANISM: Artificial Sequence
<220> FEATURE:
<223> OTHER INFORMATION: Synthetic: 9C8-IgG1.1f HC ILT4.2-IgG1.1f

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Val Arg Gln Ala Thr Gly Gln Gly Leu Glu Trp Met
        35                  40                  45
```

-continued

```
Gly Trp Met Asn Pro Asn Ser Gly His Thr Gly Tyr Ala Gln Lys Phe
    50                  55                  60

Gln Asp Arg Val Thr Leu Thr Arg Asp Thr Ser Ile Ser Thr Ala Tyr
65                  70                  75                  80

Met Glu Leu Ser Ser Leu Arg Ser Glu Asp Ser Ala Val Tyr Tyr Cys
                85                  90                  95

Ala Arg Gly Gly Asn Ser Ile Asp Trp Gly Phe Ser Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455
```

<210> SEQ ID NO 5
<211> LENGTH: 214
<212> TYPE: PRT
<213> ORGANISM: Artificial Sequence
<220> FEATURE:
<223> OTHER INFORMATION: Synthetic: 2H2 kappa LC ILT4.3-kappa

<400> SEQUENCE: 5

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 6
<211> LENGTH: 458
<212> TYPE: PRT
<213> ORGANISM: Artificial Sequence
<220> FEATURE:
<223> OTHER INFORMATION: Synthetic: 2H2-IgG1.1fHC ILT4.3-IgG1.1f

<400> SEQUENCE: 6

```
Gln Val Gln Leu Val Gln Ser Gly Ala Glu Val Lys Lys Pro Gly Ser
1               5                   10                  15

Ser Val Glu Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Ala Thr Ala Asn Tyr Ala Pro Lys Phe
    50                  55                  60

Gln Gly Arg Val Thr Ile Thr Ala Asp Glu Phe Thr Ser Ser Ala Tyr
65                  70                  75                  80

Met Glu Leu Ser Ser Leu Arg Ser Glu Asp Thr Ala Val Tyr Tyr Cys
                85                  90                  95
```

-continued

```
Ala Lys Ser Ser Ile Thr Met Ile Arg Gly Ala Tyr Leu Tyr Tyr Tyr
            100                 105                 110

Asp Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240

Pro Ala Pro Glu Ala Glu Gly Ala Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ser Ser Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 7
<211> LENGTH: 215
<212> TYPE: PRT
<213> ORGANISM: Artificial Sequence
<220> FEATURE:
<223> OTHER INFORMATION: Synthetic: 2E5 kappa LC ILT4.4-kappa

<400> SEQUENCE: 7

-continued

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Pro
85 90 95

Trp Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 8
<211> LENGTH: 451
<212> TYPE: PRT
<213> ORGANISM: Artificial Sequence
<220> FEATURE:
<223> OTHER INFORMATION: Synthetic: 2E5-IgG1.1f HC ILT4.4-IgG1.1f

<400> SEQUENCE: 8

Gln Val Gln Leu Val Glu Ser Gly Gly Gly Val Val Gln Pro Gly Arg
1 5 10 15

Ser Leu Arg Leu Ser Cys Thr Ala Ser Gly Phe Thr Phe Ser Asn Tyr
20 25 30

Gly Met His Trp Val Arg Gln Ala Pro Gly Lys Gly Leu Glu Trp Val
35 40 45

Ala Val Ile Trp Tyr Asp Gly Ser Asn Glu Tyr Tyr Ala Glu Ser Val
50 55 60

Lys Gly Arg Leu Thr Ile Ser Arg Asp Asn Ser Lys Asn Thr Leu Tyr
65 70 75 80

Leu Gln Val Asn Ser Leu Arg Ala Glu Asp Thr Ala Val Tyr Tyr Cys
85 90 95

Ala Arg Asp Pro Phe Tyr Gly Ser Gly Asn Tyr Phe Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

-continued

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Arg Val Glu Pro Lys Ser Cys
210 215 220

Asp Lys Thr His Thr Cys Pro Pro Cys Pro Ala Pro Glu Ala Glu Gly
225 230 235 240

Ala Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ser Ser Ile
325 330 335

Glu Lys Thr Ile Ser Lys Ala Lys Gly Gln Pro Arg Glu Pro Gln Val
340 345 350

Tyr Thr Leu Pro Pro Ser Arg Glu Glu Met Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 9
<211> LENGTH: 214
<212> TYPE: PRT
<213> ORGANISM: Artificial Sequence
<220> FEATURE:
<223> OTHER INFORMATION: Synthetic: 24E5 kappa LC ILT4.5-kappa

<400> SEQUENCE: 9

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 10
<211> LENGTH: 451
<212> TYPE: PRT
<213> ORGANISM: Artificial Sequence
<220> FEATURE:
<223> OTHER INFORMATION: Synthetic: 24E5-IgG1.1 HC ILT4.5-IgG1.1f

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gln Asp Ile Ile Ala Ala Tyr Tyr Phe Val Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Glu Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 11
<211> LENGTH: 215
<212> TYPE: PRT
<213> ORGANISM: Artificial Sequence
<220> FEATURE:
<223> OTHER INFORMATION: Synthetic: 21D9 kappa LC ILT4.6-kappa

<400> SEQUENCE: 11

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

Leu Thr Phe Gly Gly Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 12
<211> LENGTH: 455
<212> TYPE: PRT
<213> ORGANISM: Artificial Sequence
<220> FEATURE:
<223> OTHER INFORMATION: Synthetic: 21D9-IgG1.1f HC ILT4.6-IgG1.1f

<400> SEQUENCE: 12

Glu Gly Gln Leu Leu Glu Ser Gly Gly Asp Leu Val Gln Pro Gly Gly
1 5 10 15

Ser Leu Arg Leu Ser Cys Ala Thr Ser Gly Phe Thr Phe Ser Asn Tyr
20 25 30

Ala Met Asn Trp Val Arg Gln Ala Pro Gly Lys Gly Leu Glu Trp Ile
35 40 45

Ser Val Ile Ser Val Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Tyr Tyr Tyr Asp Ser Gly Ser Tyr Tyr Asp Ser Phe Phe
100 105 110

Asp Tyr Trp Gly Gln Gly Thr Leu Val Thr Val Ser Ser Ala Ser Thr
115 120 125

Lys Gly Pro Ser Val Phe Pro Leu Ala Pro Ser Ser Lys Ser Thr Ser
130 135 140

Gly Gly Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Arg Val Glu
210 215 220

Pro Lys Ser Cys Asp Lys Thr His Thr Cys Pro Pro Cys Pro Ala Pro
225 230 235 240

-continued

Glu Ala Glu Gly Ala Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr
290 295 300

Asn Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Ala Leu
325 330 335

Pro Ser Ser Ile Glu Lys Thr Ile Ser Lys Ala Lys Gly Gln Pro Arg
340 345 350

Glu Pro Gln Val Tyr Thr Leu Pro Pro Ser Arg Glu Glu Met Thr Lys
355 360 365

Asn Gln Val Ser Leu Thr Cys Leu Val Lys Gly Phe Tyr Pro Ser Asp
370 375 380

Ile Ala Val Glu Trp Glu Ser Asn Gly Gln Pro Glu Asn Asn Tyr Lys
385 390 395 400

Thr Thr Pro Pro Val Leu Asp Ser Asp Gly Ser Phe Phe Leu Tyr Ser
405 410 415

Lys Leu Thr Val Asp Lys Ser Arg Trp Gln Gln Gly Asn Val Phe Ser
420 425 430

Cys Ser Val Met His Glu Ala Leu His Asn His Tyr Thr Gln Lys Ser
435 440 445

Leu Ser Leu Ser Pro Gly Lys
450 455

<210> SEQ ID NO 13
<211> LENGTH: 454
<212> TYPE: PRT
<213> ORGANISM: Artificial Sequence
<220> FEATURE:
<223> OTHER INFORMATION: Synthetic: 21D9.e.IgG1.3 HC ILT4.8.IgG1.3

<400> SEQUENCE: 13

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Asn Trp Val Arg Gln Ala Pro Gly Lys Gly Leu Glu Trp Val
35 40 45

Ser Val Ile Ser Val Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Tyr Tyr Tyr Asp Ser Gly Ser Tyr Tyr Asp Ser Phe Phe
100 105 110

Asp Tyr Trp Gly Gln Gly Thr Leu Val Thr Val Ser Ser Ala Ser Thr
115 120 125

Lys Gly Pro Ser Val Phe Pro Leu Ala Pro Ser Ser Lys Ser Thr Ser
130 135 140

-continued

```
Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450
```

<210> SEQ ID NO 14
<211> LENGTH: 212
<212> TYPE: PRT
<213> ORGANISM: Artificial Sequence
<220> FEATURE:
<223> OTHER INFORMATION: Synthetic: 21A5 kappa LC

<400> SEQUENCE: 14

```
Glu Ile Ala Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Thr Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210


<210> SEQ ID NO 15
<211> LENGTH: 453
<212> TYPE: PRT
<213> ORGANISM: Artificial Sequence
<220> FEATURE:
<223> OTHER INFORMATION: Synthetic: 21A5.IgG1.3 HC

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Ile Phe His Pro Ser Gly Asp Ile Thr Ser Ser Ala Gln Asn Phe
    50                  55                  60

Gln Gly Arg Val Thr Met Ile Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Val Leu Arg Tyr Leu Asp Trp Ser His Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

```
Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Glu Gly Ala Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 16
<211> LENGTH: 212
<212> TYPE: PRT
<213> ORGANISM: Artificial Sequence
<220> FEATURE:
<223> OTHER INFORMATION: Synthetic: 21A5.1 kappa LC (ILT4.9.1K)

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Thr Phe
                85                  90                  95
```

```
Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210


<210> SEQ ID NO 17
<211> LENGTH: 453
<212> TYPE: PRT
<213> ORGANISM: Artificial Sequence
<220> FEATURE:
<223> OTHER INFORMATION: Synthetic: 21A5.a.IgG1.3 HC (ILT4.9.IgG1.3)

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Ile Phe His Pro Ser Gly Asp Ile Thr Ser Ser Ala Gln Asn Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Val Leu Arg Tyr Leu Asp Trp Ser His Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240
```

```
Ala Glu Gly Ala Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 18
<211> LENGTH: 214
<212> TYPE: PRT
<213> ORGANISM: Artificial Sequence
<220> FEATURE:
<223> OTHER INFORMATION: Synthetic: 10F10 kappa LC

<400> SEQUENCE: 18

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Phe Gln Gln Lys Pro Gly Lys Ala Pro Lys Leu Leu Ile
        35                  40                  45

Tyr Asp Ala Ser Ser Leu Glu Ser Gly Val Pro Ser Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 19
<211> LENGTH: 445
<212> TYPE: PRT
<213> ORGANISM: Artificial Sequence
<220> FEATURE:
<223> OTHER INFORMATION: Synthetic: 10F10.IgG1.3 HC ILT4.10.IgG1.3

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Ile Ile Ser Tyr Asp Glu Tyr Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Val Gly Ile Arg Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Ala Glu Gly Ala Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285
```

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 20
<211> LENGTH: 214
<212> TYPE: PRT
<213> ORGANISM: Artificial Sequence
<220> FEATURE:
<223> OTHER INFORMATION: Synthetic: 10F10.1 kappa LC

<400> SEQUENCE: 20

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 21
<211> LENGTH: 214
<212> TYPE: PRT
<213> ORGANISM: Artificial Sequence
<220> FEATURE:
<223> OTHER INFORMATION: Synthetic: 10F10.3 kappa LC

<400> SEQUENCE: 21

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Tyr Gln Gln Lys Pro Gly Lys Ala Pro Lys Leu Leu Ile
35 40 45

Tyr Asp Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Ile
85 90 95

Thr Phe Gly Gln Gly Thr Arg Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 22
<211> LENGTH: 645
<212> TYPE: DNA
<213> ORGANISM: Artificial Sequence
<220> FEATURE:
<223> OTHER INFORMATION: Synthetic: 9G4 LC DNA ILT4.1-kappa DNA

<400> SEQUENCE: 22
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat gcgtccaaca gggccactgg catcccagcc 180
aggttcagtg gcagtgggtc tgggacagac ttcactctca ccatcagcag cctagagcct 240
gaagattttg caggttatta ctgtcagcag cgtagctact ggccgtggac gttcggccaa 300
gggaccaagg tggaaatcaa acgtacggtg gctgcaccat ctgtcttcat cttcccgcca 360
tctgatgagc agttgaaatc tggaactgcc tctgttgtgt gcctgctgaa taacttctat 420

```
cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                   645


<210> SEQ ID NO 23
<211> LENGTH: 1341
<212> TYPE: DNA
<213> ORGANISM: Artificial Sequence
<220> FEATURE:
<223> OTHER INFORMATION: Synthetic: 9G4 IgG1.1f HC DNA ILT4.1-IgG1.1f
      DNA

<400> SEQUENCE: 23

caggtgcagc tgcaggagtc gggcccagga ctggtgaagc cttcggagac cctgtccctc     60

acctgcactg tctctggtgg ctccatcagt agttactact ggaactggat tcggcagccc    120

ccagggaagg gactggagtg gcttgggtac atctattaca gtgggagtac caagtacaac    180

ccctccctca agagtcgagt caccatatca gtagacacgt ccaagaacca gttctccctg    240

aagctgagct ctgtgaccgc tgcggacacg gccgtgtatt attgtgccag cagtggctgg    300

tactactttg actattgggg ccagggaacc ctggtcaccg tctcctcagc tagcaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gacaagagag ttgagcccaa atcttgtgac    660

aaaactcaca catgcccacc gtgcccagca cctgaagccg aagggggccc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cccaagcagc atcgagaaaa ccatctccaa agccaaaggg   1020

cagccccgag aaccacaggt gtacaccctg cccccatccc gggaggagat gaccaagaac   1080

caggtcagcc tgacctgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctatag caagctcacc gtggacaaga gcaggtggca gcaggggaac   1260

gtcttctcat gctccgtgat gcatgaggct ctgcacaacc actacacgca gaagagcctc   1320

tccctgtccc cgggtaaatg a                                             1341


<210> SEQ ID NO 24
<211> LENGTH: 645
<212> TYPE: DNA
<213> ORGANISM: Artificial Sequence
<220> FEATURE:
<223> OTHER INFORMATION: Synthetic: 9C8 kappa LC DNA ILT4.2-kappa DNA

<400> SEQUENCE: 24

gccatccagt tgacccagtc tccatcctcc ctgtctgcat ctgtaggaga cagagtcacc     60

atcacttgcc gggcaagtca gggcattagc agtgctttag cctggtatca gcagaaacca    120
```

```
gggaaagctc ctaagctcct gatctatgat gcctccagtt tggaaagtgg ggtcccatca    180

aggttcagcg gcagtggatc tgggacagat ttcactctca ccatcagcag cctgcagcct    240

gaagattttg caacttatta ctgtcaacag tttaatagtt acccattcac tttcggccct    300

gggaccaaag tggatatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 25
<211> LENGTH: 1368
<212> TYPE: DNA
<213> ORGANISM: Artificial Sequence
<220> FEATURE:
<223> OTHER INFORMATION: Synthetic: 9C8 IgG1.1f DNA ILT4.2-IgG1.1f DNA

<400> SEQUENCE: 25

```
caggtgcaac tggtgcagtc tggggctgag gtaaagaagc ctggggcctc agtgaaggtc     60

tcctgcaagg cttctggata caccttcacc agctctgata tcaactgggt gcgacaggcc    120

actggacaag ggcttgagtg gatgggatgg atgaacccta acagtggtca cacaggctat    180

gcacagaagt tccaggacag agtcaccttg acccgggaca cctccataag cacagcctac    240

atggagctga gcagcctgag atctgaggac tcggccgtgt attactgtgc gagaggtggg    300

aatagcattg actggggggtt ctcctactac ggtctggacg tctggggcca agggaccacg    360

gtcaccgtct cctcagctag caccaagggc ccatcggtct tccccctggc accctcctcc    420

aagagcacct ctgggggcac agcggccctg ggctgcctgg tcaaggacta cttccccgaa    480

ccggtgacgg tgtcgtggaa ctcaggcgcc ctgaccagcg gcgtgcacac cttcccggct    540

gtcctacagt cctcaggact ctactccctc agcagcgtgg tgaccgtgcc ctccagcagc    600

ttgggcaccc agacctacat ctgcaacgtg aatcacaagc ccagcaacac caaggtggac    660

aagagagttg agcccaaatc ttgtgacaaa actcacacat gcccaccgtg cccagcacct    720

gaagccgaag ggggcccgtc agtcttcctc ttccccccaa aacccaagga caccctcatg    780

atctcccgga cccctgaggt cacatgcgtg gtggtggacg tgagccacga agaccctgag    840

gtcaagttca actggtacgt ggacggcgtg gaggtgcata atgccaagac aaagccgcgg    900

gaggagcagt acaacagcac gtaccgtgtg gtcagcgtcc tcaccgtcct gcaccaggac    960

tggctgaatg gcaaggagta caagtgcaag gtctccaaca aagccctccc aagcagcatc   1020

gagaaaacca tctccaaagc caaagggcag ccccgagaac cacaggtgta caccctgccc   1080

ccatcccggg aggagatgac caagaaccag gtcagcctga cctgcctggt caaaggcttc   1140

tatcccagcg acatcgccgt ggagtgggag agcaatgggc agccggagaa caactacaag   1200

accacgcctc ccgtgctgga ctccgacggc tccttcttcc tctatagcaa gctcaccgtg   1260

gacaagagca ggtggcagca ggggaacgtc ttctcatgct ccgtgatgca tgaggctctg   1320

cacaaccact acacgcagaa gagcctctcc ctgtccccgg gtaaatga                1368
```

<210> SEQ ID NO 26
<211> LENGTH: 645
<212> TYPE: DNA
<213> ORGANISM: Artificial Sequence
<220> FEATURE:
<223> OTHER INFORMATION: Synthetic: 2H2 kappa LC DNA ILT4.3-kappa DNA

<400> SEQUENCE: 26

```
gaaattgtgt tgacgcagtc tccaggcacc ctgtctttgt ctccagggga aagagccacc     60

ctctcctgca gggccagtca gagtgttagc agcagctact tagcctggta ccagcagaaa    120

cctggccagg ctcccaggct cctcatctat ggtgcatcca gcagggccac tggcatccca    180

gacaggttca gtggcagtgg gtctgggaca gacttcactc tcaccatcag cagactggag    240

cctgaagatt ttgcagtgta ttactgtcag cagtatggta gctcgtacac ttttggccag    300

gggaccaagc tggagatcaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 27
<211> LENGTH: 1377
<212> TYPE: DNA
<213> ORGANISM: Artificial Sequence
<220> FEATURE:
<223> OTHER INFORMATION: Synthetic: 2H2 IgG1.1f HC DNA ILT4.3-IgG1.1f
DNA

<400> SEQUENCE: 27

```
caggtccagt tggtgcagtc tggggctgag gtgaagaagc ctgggtcctc ggtgaaggtc     60

tcctgcaagg cttctggggg caccttcagc aactatgcta tcagctgggt gcgacaggcc    120

cctggacaag ggcttgagtg gatgggaggg atcatcccca tcttggctac agcaaactac    180

gcaccgaagt tccagggcag agtcacgatt accgcggacg aattcacgag ctcagcttac    240

atggagctga gcagcctgag atctgaggac acggccgtgt attactgtgc gaagtctagt    300

attactatga ttcggggagc ctatctttac tactacgacg gtatggacgt ctggggccaa    360

gggaccacgg tcaccgtctc ctcagctagc accaagggcc catcggtctt ccccctggca    420

ccctcctcca agagcacctc tgggggcaca gcggccctgg gctgcctggt caaggactac    480

ttccccgaac cggtgacggt gtcgtggaac tcaggcgccc tgaccagcgg cgtgcacacc    540

ttcccggctg tcctacagtc ctcaggactc tactccctca gcagcgtggt gaccgtgccc    600

tccagcagct tgggcaccca gacctacatc tgcaacgtga atcacaagcc cagcaacacc    660

aaggtggaca agagagttga gcccaaatct tgtgacaaaa ctcacacatg cccaccgtgc    720

ccagcacctg aagccgaagg ggccccgtca gtcttcctct tccccccaaa acccaaggac    780

accctcatga tctcccggac ccctgaggtc acatgcgtgg tggtggacgt gagccacgaa    840

gaccctgagg tcaagttcaa ctggtacgtg gacggcgtgg aggtgcataa tgccaagaca    900

aagccgcggg aggagcagta caacagcacg taccgtgtgg tcagcgtcct caccgtcctg    960

caccaggact ggctgaatgg caaggagtac aagtgcaagg tctccaacaa agccctccca   1020

agcagcatcg agaaaaccat ctccaaagcc aaagggcagc cccgagaacc acaggtgtac   1080

accctgcccc catcccggga ggagatgacc aagaaccagg tcagcctgac ctgcctggtc   1140

aaaggcttct atcccagcga catcgccgtg gagtgggaga gcaatgggca gccggagaac   1200

aactacaaga ccacgcctcc cgtgctggac tccgacggct ccttcttcct ctatagcaag   1260
```

ctcaccgtgg acaagagcag gtggcagcag gggaacgtct tctcatgctc cgtgatgcat 1320
gaggctctgc acaaccacta cacgcagaag agcctctccc tgtccccggg taaatga 1377

<210> SEQ ID NO 28
<211> LENGTH: 648
<212> TYPE: DNA
<213> ORGANISM: Artificial Sequence
<220> FEATURE:
<223> OTHER INFORMATION: Synthetic: 2E5 kappa LC DNA ILT4.4-kappa DNA

<400> SEQUENCE: 28
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag cgtagcaact ggcctccgtg gacgttcggc 300
caagggacca aggtggaaat caaacgtacg gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgttag 648

<210> SEQ ID NO 29
<211> LENGTH: 1356
<212> TYPE: DNA
<213> ORGANISM: Artificial Sequence
<220> FEATURE:
<223> OTHER INFORMATION: Synthetic: 2E5 IgG1.1f HC DNA ILT4.4-IgG1.1f DNA

<400> SEQUENCE: 29
caggtgcagc tggtggagtc tgggggaggc gtggtccagc ctgggaggtc cctgagactc 60
tcctgtacag cgtctggatt caccttcagt aactatggca tgcactgggt ccgccaggct 120
ccaggcaagg gactggagtg ggtggcagtt atctggtatg atggaagtaa tgaatactat 180
gcagaatccg tgaagggccg actcaccatc tccagagaca attccaagaa cacgctgtat 240
ctgcaagtga acagcctgag agccgaggac acggctgtgt attattgtgc gagagatcct 300
ttctatggtt cggggaatta ctttgactac tggggccagg gaaccctggt caccgtctcc 360
tcagctagca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtgcacacct tcccggctgt cctacagtcc 540
tcaggactct actccctcag cagcgtggtg accgtgccct ccagcagctt gggcacccag 600
acctacatct gcaacgtgaa tcacaagccc agcaacacca aggtggacaa gagagttgag 660
cccaaatctt gtgacaaaac tcacacatgc ccaccgtgcc cagcacctga agccgaaggg 720
gccccgtcag tcttcctctt ccccccaaaa cccaaggaca ccctcatgat ctcccggacc 780
cctgaggtca catgcgtggt ggtggacgtg agccacgaag accctgaggt caagttcaac 840
tggtacgtgg acggcgtgga ggtgcataat gccaagacaa agccgcggga ggagcagtac 900
aacagcacgt accgtgtggt cagcgtcctc accgtcctgc accaggactg gctgaatggc 960
aaggagtaca agtgcaaggt ctccaacaaa gccctcccaa gcagcatcga gaaaaccatc 1020
tccaaagcca aagggcagcc ccgagaacca caggtgtaca ccctgccccc atcccgggag 1080
gagatgacca agaaccaggt cagcctgacc tgcctggtca aaggcttcta tcccagcgac 1140
atcgccgtgg agtgggagag caatgggcag ccggagaaca actacaagac cacgcctccc 1200
gtgctggact ccgacggctc cttcttcctc tatagcaagc tcaccgtgga caagagcagg 1260
tggcagcagg ggaacgtctt ctcatgctcc gtgatgcatg aggctctgca caaccactac 1320
acgcagaaga gcctctccct gtccccgggt aaatga 1356

<210> SEQ ID NO 30
<211> LENGTH: 645
<212> TYPE: DNA
<213> ORGANISM: Artificial Sequence
<220> FEATURE:
<223> OTHER INFORMATION: Synthetic: 24E5 kappa LC DNA ILT4.5-kappa DNA

<400> SEQUENCE: 30
gacatccaga tgacccagtc tccatcctca ctgtctgcat ctgtaggaga cagagtcacc 60
atcacttgtc gggcgagtca gggtattagc agctggttag cctggtatca gcagaaacca 120
gagaaagccc ctaagtccct gatctatgct gcatccagtt tgcaaagtgg ggtcccatca 180
aggttcagcg gcagtggatc tgggacagat ttcactctca ccatcagcag cctgcagcct 240
gaagattttg caacttatta ctgccaacag tataatagtt accctctcac tttcggcgga 300
gggaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gttag 645

<210> SEQ ID NO 31
<211> LENGTH: 1356
<212> TYPE: DNA
<213> ORGANISM: Artificial Sequence
<220> FEATURE:
<223> OTHER INFORMATION: Synthetic: 24E5 IgG1.1f HC DNA ILT4.5-IgG1.1f
DNA

<400> SEQUENCE: 31
gaggtgcagc tgttggagtc tgggggaggc ttggtacagc ctggggggtc cctgagactc 60
tcctgtgcag cctctggatt cacctttagc agctatgtca tgagctgggt ccgccaggct 120
ccagggaagg ggctggagtg ggtctcaggt attagtggta gtggtggtag cacatactac 180
gcagactccg tgaagggccg gttcaccatc tccagagaca attccaagaa cacgctgtat 240
ctgcaaatga acagcctgag agccgaggac acggccgtat attactgtgc gaaagatcag 300
gatattatag cagcatacta ctttgtctac tggggccagg gaaccctggt caccgtctcc 360
tcagctagca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtgcacacct tcccggctgt cctacagtcc 540
tcaggactct actccctcag cagcgtggtg accgtgccct ccagcagctt gggcacccag 600
acctacatct gcaacgtgaa tcacaagccc agcaacacca aggtggacaa gagagttgag 660
cccaaatctt gtgacaaaac tcacacatgc ccaccgtgcc cagcacctga agccgaaggg 720
gccccgtcag tcttcctctt ccccccaaaa cccaaggaca ccctcatgat ctcccggacc 780
cctgaggtca catgcgtggt ggtggacgtg agccacgaag accctgaggt caagttcaac 840
tggtacgtgg acggcgtgga ggtgcataat gccaagacaa agccgcggga ggagcagtac 900
aacagcacgt accgtgtggt cagcgtcctc accgtcctgc accaggactg gctgaatggc 960
aaggagtaca agtgcaaggt ctccaacaaa gccctcccaa gcagcatcga gaaaaccatc 1020
tccaaagcca aagggcagcc ccgagaacca caggtgtaca ccctgccccc atcccgggag 1080
gagatgacca agaaccaggt cagcctgacc tgcctggtca aaggcttcta tcccagcgac 1140
atcgccgtgg agtgggagag caatgggcag ccggagaaca actacaagac cacgcctccc 1200
gtgctggact ccgacggctc cttcttcctc tatagcaagc tcaccgtgga caagagcagg 1260
tggcagcagg ggaacgtctt ctcatgctcc gtgatgcatg aggctctgca caaccactac 1320
acgcagaaga gcctctccct gtccccgggt aaatga 1356

<210> SEQ ID NO 32
<211> LENGTH: 648
<212> TYPE: DNA
<213> ORGANISM: Artificial Sequence
<220> FEATURE:
<223> OTHER INFORMATION: Synthetic: 21D9 kappa LC DNA ILT4.6-kappa DNA

<400> SEQUENCE: 32
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcacctct cactttcggc 300
ggagggacca aggtggagat caaacgtacg gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgttag 648

<210> SEQ ID NO 33
<211> LENGTH: 1368
<212> TYPE: DNA
<213> ORGANISM: Artificial Sequence
<220> FEATURE:
<223> OTHER INFORMATION: Synthetic: 21D9 IgG1.1f HC DNA ILT4.6-IgG1.1f
DNA

<400> SEQUENCE: 33
gagggacagc tgttggagtc tgggggagac ttggtacagc ctgggggtc cctgagactc 60 tcctgtgcaa cctctggatt cacctttagc aactatgcca tgaactgggt ccgccaggct 120
ccagggaagg ggctggagtg gatctcagtt attagtgtta gtggtggtag cacatactac 180
gcagactccg tgaagggccg gttcaccatc tccagagaca attccaagaa cacgctgtat 240
ctgcaaatga atagcctgag agccgaggac acggccgtat attactgtgc gaaagattat 300
tactatgatt cggggagtta ttatgactct ttctttgact actggggcca gggaaccctg 360
gtcaccgtct cctcagctag caccaagggc ccatcggtct tcccctggc accctcctcc 420 aagagcacct ctgggggcac agcggccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcaccc agacctacat ctgcaacgtg aatcacaagc ccagcaacac caaggtggac 660
aagagagttg agcccaaatc ttgtgacaaa actcacacat gcccaccgtg cccagcacct 720
gaagccgaag ggccccgtc agtcttcctc ttccccccaa aacccaagga caccctcatg 780
atctcccgga cccctgaggt cacatgcgtg gtggtggacg tgagccacga agaccctgag 840
gtcaagttca actggtacgt ggacggcgtg gaggtgcata atgccaagac aaagccgcgg 900
gaggagcagt acaacagcac gtaccgtgtg gtcagcgtcc tcaccgtcct gcaccaggac 960
tggctgaatg gcaaggagta caagtgcaag gtctccaaca aagccctccc aagcagcatc 1020
gagaaaacca tctccaaagc caaagggcag ccccgagaac cacaggtgta caccctgccc 1080
ccatcccggg aggagatgac caagaaccag gtcagcctga cctgcctggt caaaggcttc 1140
tatcccagcg acatcgccgt ggagtgggag agcaatgggc agccggagaa caactacaag 1200
accacgcctc ccgtgctgga ctccgacggc tccttcttcc tctatagcaa gctcaccgtg 1260
gacaagagca ggtggcagca ggggaacgtc ttctcatgct ccgtgatgca tgaggctctg 1320
cacaaccact acacgcagaa gagcctctcc ctgtccccgg gtaaatga 1368

<210> SEQ ID NO 34
<211> LENGTH: 1365
<212> TYPE: DNA
<213> ORGANISM: Artificial Sequence
<220> FEATURE:
<223> OTHER INFORMATION: Synthetic: 21D9.IgG1.3 HC DNA ILT4.6-IgG1.3 HC DNA

<400> SEQUENCE: 34
gagggacagc tgttggagtc tgggggagac ttggtacagc ctggggggtc cctgagactc 60
tcctgtgcaa cctctggatt cacctttagc aactatgcca tgaactgggt ccgccaggct 120
ccagggaagg ggctggagtg gatctcagtt attagtgtta gtggtggtag cacatactac 180
gcagactccg tgaagggccg gttcaccatc tccagagaca attccaagaa cacgctgtat 240
ctgcaaatga atagcctgag agccgaggac acggccgtat attactgtgc gaaagattat 300
tactatgatt cggggagtta ttatgactct ttctttgact actggggcca gggaaccctg 360
gtcaccgtct cctcagctag caccaagggc ccatcggtct tcccctggc accctcctcc 420 aagagcacct ctgggggcac agcggccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcaccc agacctacat ctgcaacgtg aatcacaagc ccagcaacac caaggtggac 660
aagagagttg agcccaaatc ttgtgacaaa actcacacat gcccaccgtg cccagcacct 720
gaagccgaag ggccccgtc agtcttcctc ttccccccaa aacccaagga caccctcatg 780
atctcccgga cccctgaggt cacatgcgtg gtggtggacg tgagccacga agaccctgag 840
gtcaagttca actggtacgt ggacggcgtg gaggtgcata atgccaagac aaagccgcgg 900
gaggagcagt acaacagcac gtaccgtgtg gtcagcgtcc tcaccgtcct gcaccaggac 960
tggctgaatg gcaaggagta caagtgcaag gtctccaaca aagccctccc agcccccatc 1020

```
gagaaaacca tctccaaagc caaagggcag ccccgagaac cacaggtgta caccctgccc   1080

ccatcccggg aggagatgac caagaaccag gtcagcctga cctgcctggt caaaggcttc   1140

tatcccagcg acatcgccgt ggagtgggag agcaatgggc agccggagaa caactacaag   1200

accacgcctc ccgtgctgga ctccgacggc tccttcttcc tctatagcaa gctcaccgtg   1260

gacaagagca ggtggcagca ggggaacgtc ttctcatgct ccgtgatgca tgaggctctg   1320

cacaaccact acacgcagaa gagcctctcc ctgtccccgg gttga                   1365
```

<210> SEQ ID NO 35
<211> LENGTH: 1365
<212> TYPE: DNA
<213> ORGANISM: Artificial Sequence
<220> FEATURE:
<223> OTHER INFORMATION: Synthetic: 21D9.b.IgG1.3 HC DNA

<400> SEQUENCE: 35

```
gaggtgcagc tgctggagtc tggaggagga ctggtgcagc caggaggcag cctgaggctg     60

tcctgcgcca cctctggctt cacattttcc aactatgcca tgaattgggt gcgccaggca    120

cctggcaagg gactggagtg gatctctgtg atctctgtga gcggcggctc tacctactat    180

gccgacagcg tgaagggccg gttcaccatc agcagagata actccaagaa tacactgtat    240

ctgcagatga acagcctgcg ggccgaggac acagccgtgt actattgtgc caaggactac    300

tattacgatt ccggctctta ttacgactcc ttctttgatt actggggcca gggcaccctg    360

gtgacagtga gctccgctag caccaagggc ccatcggtct tccccctggc accctcctcc    420

aagagcacct ctgggggcac agcggccctg ggctgcctgg tcaaggacta cttccccgaa    480

ccggtgacgg tgtcgtggaa ctcaggcgcc ctgaccagcg gcgtgcacac cttcccggct    540

gtcctacagt cctcaggact ctactccctc agcagcgtgg tgaccgtgcc ctccagcagc    600

ttgggcaccc agacctacat ctgcaacgtg aatcacaagc ccagcaacac caaggtggac    660

aagagagttg agcccaaatc ttgtgacaaa actcacacat gcccaccgtg cccagcacct    720

gaagccgaag ggggcccgtc agtcttcctc ttccccccaa aacccaagga caccctcatg    780

atctcccgga cccctgaggt cacatgcgtg gtggtggacg tgagccacga agaccctgag    840

gtcaagttca actggtacgt ggacggcgtg gaggtgcata atgccaagac aaagccgcgg    900

gaggagcagt acaacagcac gtaccgtgtg gtcagcgtcc tcaccgtcct gcaccaggac    960

tggctgaatg gcaaggagta caagtgcaag gtctccaaca aagccctccc agcccccatc   1020

gagaaaacca tctccaaagc caaagggcag ccccgagaac cacaggtgta caccctgccc   1080

ccatcccggg aggagatgac caagaaccag gtcagcctga cctgcctggt caaaggcttc   1140

tatcccagcg acatcgccgt ggagtgggag agcaatgggc agccggagaa caactacaag   1200

accacgcctc ccgtgctgga ctccgacggc tccttcttcc tctatagcaa gctcaccgtg   1260

gacaagagca ggtggcagca ggggaacgtc ttctcatgct ccgtgatgca tgaggctctg   1320

cacaaccact acacgcagaa gagcctctcc ctgtccccgg gttga                   1365
```

<210> SEQ ID NO 36
<211> LENGTH: 454
<212> TYPE: PRT
<213> ORGANISM: Artificial Sequence
<220> FEATURE:
<223> OTHER INFORMATION: Synthetic: 21D9.b.IgG1.3 HC

<400> SEQUENCE: 36

-continued

```
Glu Val Gln Leu Leu Glu Ser Gly Gly Gly Leu Val Gln Pro Gly Gly
1               5                   10                  15

Ser Leu Arg Leu Ser Cys Ala Thr Ser Gly Phe Thr Phe Ser Asn Tyr
            20                  25                  30

Ala Met Asn Trp Val Arg Gln Ala Pro Gly Lys Gly Leu Glu Trp Ile
        35                  40                  45

Ser Val Ile Ser Val Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Tyr Tyr Asp Ser Gly Ser Tyr Tyr Asp Ser Phe Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
```

```
            420                 425                 430

Cys Ser Val Met His Glu Ala Leu His Asn His Tyr Thr Gln Lys Ser
        435                 440                 445

Leu Ser Leu Ser Pro Gly
    450


<210> SEQ ID NO 37
<211> LENGTH: 1365
<212> TYPE: DNA
<213> ORGANISM: Artificial Sequence
<220> FEATURE:
<223> OTHER INFORMATION: Synthetic: 21D9.c.IgG1.3 HC DNA

<400> SEQUENCE: 37

gaggtgcagc tgctggagtc tggaggagac ctggtgcagc caggaggcag cctgaggctg      60

tcctgcgccg cctctggctt cacattttcc aactatgcca tgaattgggt gcgccaggca     120

cctggcaagg gactggagtg gatctctgtg atctctgtga gcggcggctc tacctactat     180

gccgacagcg tgaagggccg gttcaccatc agcagagata actccaagaa tacactgtat     240

ctgcagatga acagcctgcg ggccgaggac acagccgtgt actattgtgc caaggactac     300

tattacgatt ccggctctta ttacgactcc ttctttgatt actggggcca gggcaccctg     360

gtgacagtga gctccgctag caccaagggc ccatcggtct tccccctggc accctcctcc     420

aagagcacct ctgggggcac agcggccctg ggctgcctgg tcaaggacta cttccccgaa     480

ccggtgacgg tgtcgtggaa ctcaggcgcc ctgaccagcg gcgtgcacac cttcccggct     540

gtcctacagt cctcaggact ctactccctc agcagcgtgg tgaccgtgcc ctccagcagc     600

ttgggcaccc agacctacat ctgcaacgtg aatcacaagc ccagcaacac caaggtggac     660

aagagagttg agcccaaatc ttgtgacaaa actcacacat gcccaccgtg cccagcacct     720

gaagccgaag ggggcccgtc agtcttcctc ttccccccaa aacccaagga caccctcatg     780

atctcccgga cccctgaggt cacatgcgtg gtggtggacg tgagccacga agaccctgag     840

gtcaagttca actggtacgt ggacggcgtg gaggtgcata atgccaagac aaagccgcgg     900

gaggagcagt acaacagcac gtaccgtgtg gtcagcgtcc tcaccgtcct gcaccaggac     960

tggctgaatg gcaaggagta caagtgcaag gtctccaaca aagccctccc agcccccatc    1020

gagaaaacca tctccaaagc caaagggcag ccccgagaac cacaggtgta caccctgccc    1080

ccatcccggg aggagatgac caagaaccag gtcagcctga cctgcctggt caaaggcttc    1140

tatcccagcg acatcgccgt ggagtgggag agcaatgggc agccggagaa caactacaag    1200

accacgcctc ccgtgctgga ctccgacggc tccttcttcc tctatagcaa gctcaccgtg    1260

gacaagagca ggtggcagca ggggaacgtc ttctcatgct ccgtgatgca tgaggctctg    1320

cacaaccact acacgcagaa gagcctctcc ctgtccccgg gttga                    1365


<210> SEQ ID NO 38
<211> LENGTH: 454
<212> TYPE: PRT
<213> ORGANISM: Artificial Sequence
<220> FEATURE:
<223> OTHER INFORMATION: Synthetic: 21D9.c.IgG1.3 HC

<400> SEQUENCE: 38

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Asn Tyr
            20                  25                  30
```

Ala Met Asn Trp Val Arg Gln Ala Pro Gly Lys Gly Leu Glu Trp Ile
35 40 45

Ser Val Ile Ser Val Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Tyr Tyr Tyr Asp Ser Gly Ser Tyr Tyr Asp Ser Phe Phe
100 105 110

Asp Tyr Trp Gly Gln Gly Thr Leu Val Thr Val Ser Ser Ala Ser Thr
115 120 125

Lys Gly Pro Ser Val Phe Pro Leu Ala Pro Ser Ser Lys Ser Thr Ser
130 135 140

Gly Gly Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Arg Val Glu
210 215 220

Pro Lys Ser Cys Asp Lys Thr His Thr Cys Pro Pro Cys Pro Ala Pro
225 230 235 240

Glu Ala Glu Gly Ala Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr
290 295 300

Asn Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Ala Leu
325 330 335

Pro Ala Pro Ile Glu Lys Thr Ile Ser Lys Ala Lys Gly Gln Pro Arg
340 345 350

Glu Pro Gln Val Tyr Thr Leu Pro Pro Ser Arg Glu Glu Met Thr Lys
355 360 365

Asn Gln Val Ser Leu Thr Cys Leu Val Lys Gly Phe Tyr Pro Ser Asp
370 375 380

Ile Ala Val Glu Trp Glu Ser Asn Gly Gln Pro Glu Asn Asn Tyr Lys
385 390 395 400

Thr Thr Pro Pro Val Leu Asp Ser Asp Gly Ser Phe Phe Leu Tyr Ser
405 410 415

Lys Leu Thr Val Asp Lys Ser Arg Trp Gln Gln Gly Asn Val Phe Ser
420 425 430

Cys Ser Val Met His Glu Ala Leu His Asn His Tyr Thr Gln Lys Ser
435 440 445

Leu Ser Leu Ser Pro Gly
    450

<210> SEQ ID NO 39
<211> LENGTH: 1365
<212> TYPE: DNA
<213> ORGANISM: Artificial Sequence
<220> FEATURE:
<223> OTHER INFORMATION: Synthetic: 21D9.d.IgG1.3 HC DNA

<400> SEQUENCE: 39
gaggtgcagc tgctggagtc tggaggagac ctggtgcagc caggaggcag cctgaggctg 60
tcctgcgcca cctctggctt cacattttcc aactatgcca tgaattgggt gcgccaggca 120
cctggcaagg gactggagtg ggtgtctgtg atctctgtga gcggcggctc tacctactat 180
gccgacagcg tgaagggccg gttcaccatc agcagagata actccaagaa tacactgtat 240
ctgcagatga acagcctgcg ggccgaggac acagccgtgt actattgtgc caaggactac 300
tattacgatt ccggctctta ttacgactcc ttctttgatt actggggcca gggcaccctg 360
gtgacagtga gctccgctag caccaagggc ccatcggtct tccccctggc accctcctcc 420
aagagcacct ctgggggcac agcggccctg ggctgcctgg tcaaggacta cttccccgaa 480
ccggtgacgg tgtcgtggaa ctcaggcgcc ctgaccagcg gcgtgcacac cttcccggct 540
gtcctacagt cctcaggact ctactccctc agcagcgtgg tgaccgtgcc ctccagcagc 600
ttgggcaccc agacctacat ctgcaacgtg aatcacaagc ccagcaacac caaggtggac 660
aagagagttg agcccaaatc ttgtgacaaa actcacacat gcccaccgtg cccagcacct 720
gaagccgaag ggggccccgtc agtcttcctc ttccccccaa aacccaagga caccctcatg 780
atctcccgga cccctgaggt cacatgcgtg gtggtggacg tgagccacga agaccctgag 840
gtcaagttca actggtacgt ggacggcgtg gaggtgcata atgccaagac aaagccgcgg 900
gaggagcagt acaacagcac gtaccgtgtg gtcagcgtcc tcaccgtcct gcaccaggac 960
tggctgaatg gcaaggagta caagtgcaag gtctccaaca aagccctccc agcccccatc 1020
gagaaaacca tctccaaagc caaagggcag ccccgagaac cacaggtgta caccctgccc 1080
ccatcccggg aggagatgac caagaaccag gtcagcctga cctgcctggt caaaggcttc 1140
tatcccagcg acatcgccgt ggagtgggag agcaatgggc agccggagaa caactacaag 1200
accacgcctc ccgtgctgga ctccgacggc tccttcttcc tctatagcaa gctcaccgtg 1260
gacaagagca ggtggcagca ggggaacgtc ttctcatgct ccgtgatgca tgaggctctg 1320
cacaaccact acacgcagaa gagcctctcc ctgtccccgg gttga 1365

<210> SEQ ID NO 40
<211> LENGTH: 454
<212> TYPE: PRT
<213> ORGANISM: Artificial Sequence
<220> FEATURE:
<223> OTHER INFORMATION: Synthetic: 21D9.d.IgG1.3 HC

<400> SEQUENCE: 40

Glu Val Gln Leu Leu Glu Ser Gly Gly Asp Leu Val Gln Pro Gly Gly
1               5                   10                  15

Ser Leu Arg Leu Ser Cys Ala Thr Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Val Ile Ser Val Ser Gly Gly Ser Thr Tyr Tyr Ala Asp Ser Val

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Tyr Tyr Asp Ser Gly Ser Tyr Tyr Asp Ser Phe Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450
```

<210> SEQ ID NO 41

```
<211> LENGTH: 1413
<212> TYPE: DNA
<213> ORGANISM: Artificial Sequence
<220> FEATURE:
<223> OTHER INFORMATION: Synthetic: 21D9.e.IgG1.3 HC DNA ILT4.8.IgG1.3
      HC DNA With signal peptide

<400> SEQUENCE: 41

atgagggctt ggatcttctt tctgctctgc ctggccggga gagcgctcgc agaggtgcag     60

ctgttggagt ctgggggagg cttggtacag cctggggggt ccctgagact ctcctgtgca    120

gcctctggat tcacctttag caactatgcc atgaactggg tccgccaggc tccagggaag    180

gggctggagt gggtctcagt tattagtgtt agtggtggta gcacatacta cgcagactcc    240

gtgaagggcc ggttcaccat ctccagagac aattccaaga acacgctgta tctgcaaatg    300

aatagcctga gagccgagga cacggccgta tattactgtg cgaaagatta ttactatgat    360

tcggggagtt attatgactc tttctttgac tactggggcc agggaaccct ggtcaccgtc    420

tcctcagcta gcaccaaggg cccatcggtc ttccccctgg caccctcctc caagagcacc    480

tctgggggca cagcggccct gggctgcctg gtcaaggact acttccccga accggtgacg    540

gtgtcgtgga actcaggcgc cctgaccagc ggcgtgcaca ccttcccggc tgtcctacag    600

tcctcaggac tctactccct cagcagcgtg gtgaccgtgc cctccagcag cttgggcacc    660

cagacctaca tctgcaacgt gaatcacaag cccagcaaca ccaaggtgga caagagagtt    720

gagcccaaat cttgtgacaa aactcacaca tgcccaccgt gcccagcacc tgaagccgaa    780

ggggccccgt cagtcttcct cttcccccca aaacccaagg acaccctcat gatctcccgg    840

acccctgagg tcacatgcgt ggtggtggac gtgagccacg aagaccctga ggtcaagttc    900

aactggtacg tggacggcgt ggaggtgcat aatgccaaga caaagccgcg ggaggagcag    960

tacaacagca cgtaccgtgt ggtcagcgtc ctcaccgtcc tgcaccagga ctggctgaat   1020

ggcaaggagt acaagtgcaa ggtctccaac aaagccctcc cagcccccat cgagaaaacc   1080

atctccaaag ccaaagggca gccccgagaa ccacaggtgt acaccctgcc cccatcccgg   1140

gaggagatga ccaagaacca ggtcagcctg acctgcctgg tcaaaggctt ctatcccagc   1200

gacatcgccg tggagtggga gagcaatggg cagccggaga acaactacaa gaccacgcct   1260

cccgtgctgg actccgacgg ctccttcttc ctctatagca agctcaccgt ggacaagagc   1320

aggtggcagc aggggaacgt cttctcatgc tccgtgatgc atgaggctct gcacaaccac   1380

tacacgcaga agagcctctc cctgtccccg ggt                                1413


<210> SEQ ID NO 42
<211> LENGTH: 1020
<212> TYPE: DNA
<213> ORGANISM: Artificial Sequence
<220> FEATURE:
<223> OTHER INFORMATION: Synthetic: 21A5 LC DNA

<400> SEQUENCE: 42

gagatcgtgc tgacccagag cccaggcaca ctgtctctga gcccaggaga gagggccacc     60

ctgtcctgca gagcctccca gtctgtgagc tcctcttacc tggcctggta tcagcagaag    120

ccaggacagg cacctaggct gctgatctac ggagccagct ccagggcaac cggcatccct    180

gaccgcttca gcggctccgg ctctggcaca gacttcaccc tgacaatctc taggctggag    240

cccgaggact tcgccgtgta ctattgtcag cagtatggct ccacctttgg cggcggcaca    300

aaggtggaga tcaaggaatt cgccaccatg agggcttgga tcttctttct gctctgcctg    360
```

```
gccgggcgcg ccctcgcaga gatcgtgctg acccagagcc caggcacact gtctctgagc    420

ccaggagaga gggccaccct gtcctgcaga gcctcccagt ctgtgagctc ctcttacctg    480

gcctggtatc agcagaagcc aggacaggca cctaggctgc tgatctacgg agccagctcc    540

agggcaaccg gcatccctga ccgcttcagc ggctccggct ctggcacaga cttcaccctg    600

acaatctcta ggctggagcc cgaggacttc gccgtgtact attgtcagca gtatggctcc    660

acctttggcg gcggcacaaa ggtggagatc aagcgtacgg tggccgcccc gtccgtgttt    720

atcttccctc catcggacga gcagctcaag tccggtaccg cgagcgtggt ctgcctgctg    780

aacaatttct acccgcgcga agctaaagtg caatggaagg tcgataacgc acttcagtcc    840

gggaacagcc aggaatctgt gaccgagcag gactccaagg attcgaccta ttccctgtcc    900

tcgactctca ccctgtcaaa ggccgactac gagaagcaca aggtctacgc ctgcgaagtg    960

acccatcagg gcttgtcctc acccgtgact aagagcttca accggggaga gtgttagtga   1020
```

```
<210> SEQ ID NO 43
<211> LENGTH: 1362
<212> TYPE: DNA
<213> ORGANISM: Artificial Sequence
<220> FEATURE:
<223> OTHER INFORMATION: Synthetic: 21A5.IgG1.3 HC DNA

<400> SEQUENCE: 43

caggtgcagc tggtgcagtc cggagcagag gtgaagaagc caggagcctc tgtgaaggtg     60

agctgcaagg cctccggcta caccttcaca gattactatc tgcactgggt gcggcaggca    120

ccaggacagg gactggagtg gatgggcatc ttccaccctt ctggcgacat cacaagctcc    180

gcccagaact ttcagggccg ggtgaccatg acaagagata ccagcacatc caccgtgtac    240

atggagctgt ctagcctgag gtctgaggac accgccgtgt actattgtgc aaggggaggc    300

gtgctgaggt atctggactg gagccacgcc tttgatatct ggggccaggg cacaatggtg    360

accgtgtcct ctgctagcac caaaggacct tcagtgttcc cgctcgcgcc gtcatccaag    420

tccacctccg gcggaaccgc tgccctggga tgccttgtga aggactactt ccctgagcct    480

gtgactgtgt cctggaactc cggagccctg acctccggcg tgcatacctt ccctgctgtg    540

ctgcaatcaa gcggcctcta ctcattgagc tccgtcgtga ccgtgccgag ctccagcctc    600

ggtactcaaa cctacatctg caatgtcaac cacaagccca gcaacaccaa ggtcgataag    660

agagtggagc ccaagtcgtg cgacaagact cacacttgtc ccccatgccc ggcccccgag    720

gccgaggggg ccccgagcgt ctttctgttc ccgcctaagc ccaaggatac cctgatgatt    780

tcgcggactc ccgaagtgac ctgtgtcgtg gtggacgtgt cccacgaaga tcccgaagtc    840

aagttcaact ggtacgtgga cggagtcgag gtgcacaacg caaagaccaa gcctcgcgag    900

gaacagtaca actcgaccta tcgggtggtg tccgtgctga cagtgctgca tcaggactgg    960

ctcaacggaa aggagtacaa gtgcaaagtg tccaacaagg ccctgccagc gcccattgaa   1020

aagactatca gcaaggccaa ggggcagcca agggaacccc aagtgtacac cctgcctccg   1080

tcccgcgaag aaatgaccaa gaaccaggtg tccctgacgt gcttggtcaa gggcttttac   1140

ccttccgaca tcgccgtgga gtgggagtcg aacgggcagc cggaaaacaa ctacaagacc   1200

actccaccgg tgctcgactc ggatggctcg ttcttcctgt attcgaagct gactgtcgac   1260

aaaagccggt ggcagcaggg caatgtgttc tcctgctccg tgatgcatga ggccctccac   1320

aaccactaca cccagaagtc tctgagcctt tccccgggat ga                      1362
```

<210> SEQ ID NO 44
<211> LENGTH: 687
<212> TYPE: DNA
<213> ORGANISM: Artificial Sequence
<220> FEATURE:
<223> OTHER INFORMATION: Synthetic: 21A5.1 kappa LC DNA (ILT4.9.1K) DNA
With signal peptide

<400> SEQUENCE: 44
atgagggctt ggatcttctt tctgctctgc ctggccgggc gcgccttggc cgaaattgtg 60
ttgacgcagt ctccaggcac cctgtctttg tctccagggg aaagagccac cctctcctgc 120
agggccagtc agagtgttag cagcagctac ttagcctggt accagcagaa acctggccag 180
gctcccaggc tcctcatcta tggtgcatcc agcagggcca ctggcatccc agacaggttc 240
agtggcagtg ggtctgggac agacttcact ctcaccatca gcagactgga gcctgaagat 300
tttgcagtgt attactgtca gcagtatggt agcactttcg gcggagggac caaggtggag 360
atcaaacgta cggtggctgc accatctgtc ttcatcttcc cgccatctga tgagcagttg 420
aaatctggaa ctgcctctgt tgtgtgcctg ctgaataact tctatcccag agaggccaaa 480
gtacagtgga aggtggataa cgccctccaa tcgggtaact cccaggagag tgtcacagag 540
caggacagca aggacagcac ctacagcctc agcagcaccc tgacgctgag caaagcagac 600
tacgagaaac acaaagtcta cgcctgcgaa gtcacccatc agggcctgag ctcgcccgtc 660
acaaagagct tcaacagggg agagtgt 687

<210> SEQ ID NO 45
<211> LENGTH: 1410
<212> TYPE: DNA
<213> ORGANISM: Artificial Sequence
<220> FEATURE:
<223> OTHER INFORMATION: Synthetic: 21A5.a.IgG1.3 HC DNA (ILT4.9.IgG1.3)
DNA With signal peptide

<400> SEQUENCE: 45
atgagggctt ggatcttctt tctgctctgc ctggccggga gagcgctcgc acaggtgcag 60
ctggtgcagt ctggggctga ggtgaagaag cctggggcct cagtgaaggt ttcctgcaag 120
gcatctggat acaccttcac cgactactat ttgcactggg tgcgacaggc ccctggacaa 180
gggcttgagt ggatgggaat attccaccct agtggtgata tcacaagctc cgcacagaac 240
ttccagggca gagtcaccat gaccagggac acgtccacga gcacagtcta catggagctg 300
agcagcctga gatctgagga cacggccgtg tattactgtg cgagaggagg cgtgctgagg 360
tatctggact ggagccatgc ttttgatatc tggggccaag ggacaatggt caccgtctct 420
tcagctagca ccaagggccc atcggtcttc cccctggcac cctcctccaa gagcacctct 480
gggggcacag cggccctggg ctgcctggtc aaggactact tccccgaacc ggtgacggtg 540
tcgtggaact caggcgccct gaccagcggc gtgcacacct tcccggctgt cctacagtcc 600
tcaggactct actccctcag cagcgtggtg accgtgccct ccagcagctt gggcacccag 660
acctacatct gcaacgtgaa tcacaagccc agcaacacca aggtggacaa gagagttgag 720
cccaaatctt gtgacaaaac tcacacatgc ccaccgtgcc cagcacctga agccgaaggg 780
gccccgtcag tcttcctctt ccccccaaaa cccaaggaca ccctcatgat ctcccggacc 840
cctgaggtca catgcgtggt ggtggacgtg agccacgaag accctgaggt caagttcaac 900
tggtacgtgg acggcgtgga ggtgcataat gccaagacaa agccgcggga ggagcagtac 960
aacagcacgt accgtgtggt cagcgtcctc accgtcctgc accaggactg gctgaatggc 1020

```
aaggagtaca agtgcaaggt ctccaacaaa gccctcccag cccccatcga gaaaaccatc   1080

tccaaagcca aagggcagcc ccgagaacca caggtgtaca ccctgccccc atcccgggag   1140

gagatgacca agaaccaggt cagcctgacc tgcctggtca aaggcttcta tcccagcgac   1200

atcgccgtgg agtgggagag caatgggcag ccggagaaca actacaagac cacgcctccc   1260

gtgctggact ccgacggctc cttcttcctc tatagcaagc tcaccgtgga caagagcagg   1320

tggcagcagg ggaacgtctt ctcatgctcc gtgatgcatg aggctctgca caaccactac   1380

acgcagaaga gcctctccct gtccccgggt                                    1410
```

<210> SEQ ID NO 46
<211> LENGTH: 693
<212> TYPE: DNA
<213> ORGANISM: Artificial Sequence
<220> FEATURE:
<223> OTHER INFORMATION: Synthetic: 10F10 kappa LC DNA ILT4.10K DNA With signal peptide

<400> SEQUENCE: 46

```
atgagggctt ggatcttctt tctgctctgc ctggccgggc gcgccctcgc agccatccag     60

ctgacccagt ctcctagctc cctgtctgcc agcgtgggcg acagggtgac catcacatgc    120

agagcctccc agggaatctc tagcgccctg gcctggttcc agcagaagcc aggcaaggcc    180

cctaagctgc tgatctacga tgcctcctct ctggagagcg gagtgccatc caggttcacc    240

ggctccggct ctggcacaga ctttaccctg acaatcagct ccctgcagcc agaggatttt    300

gccacatact attgtcagca gttcaacagc tatcccatca cctttggcca gggcacacgg    360

ctggagatca agcgtacggt ggccgccccg tccgtgttta tcttccctcc atcggacgag    420

cagctcaagt ccggtaccgc gagcgtggtc tgcctgctga acaatttcta cccgcgcgaa    480

gctaaagtgc aatggaaggt cgataacgca cttcagtccg ggaacagcca ggaatctgtg    540

accgagcagg actccaagga ttcgacctat tccctgtcct cgactctcac cctgtcaaag    600

gccgactacg agaagcacaa ggtctacgcc tgcgaagtga cccatcaggg cttgtcctca    660

cccgtgacta agagcttcaa ccggggagag tgt                                693
```

<210> SEQ ID NO 47
<211> LENGTH: 1386
<212> TYPE: DNA
<213> ORGANISM: Artificial Sequence
<220> FEATURE:
<223> OTHER INFORMATION: Synthetic: 10F10.IgG1.3 HC DNA ILT4.10.IgG1.3 DNA  With signal peptide

<400> SEQUENCE: 47

```
atgagggctt ggatcttctt tctgctctgc ctggccgggc gcgccctcgc acaggtgcag     60

ctggtggagt ctggaggagg agtggtgcag ccaggccggt ccctgagact gtcttgcgcc    120

gccagcggct tcacctttag ctcctacgca atgcactggg tgaggcaggc acctggcaag    180

ggactggagt gggtggccat catcagctac gacgagtata acaagtacta tgccgattcc    240

gtgaagggca ggttcaccat ctcccgcgac aactctaaga atacactgta cctgcagatg    300

aatagcctga gagccgagga tacagccgtg tactattgtg cccgggagtg ggtgggcatc    360

agatattggg gccagggcac cctggtgaca gtgtctagcg ctagcaccaa aggaccttca    420

gtgttcccgc tcgcgccgtc atccaagtcc acctccggcg gaaccgctgc cctgggatgc    480

cttgtgaagg actacttccc tgagcctgtg actgtgtcct ggaactccgg agccctgacc    540

tccggcgtgc ataccttccc tgctgtgctg caatcaagcg gcctctactc attgagctcc    600
```

gtcgtgaccg tgccgagctc cagcctcggt actcaaacct acatctgcaa tgtcaaccac 660
aagcccagca acaccaaggt cgataagaga gtggagccca agtcgtgcga caagactcac 720
acttgtcccc catgcccggc ccccgaggcc gagggggccc cgagcgtctt tctgttcccg 780
cctaagccca aggataccct gatgatttcg cggactcccg aagtgacctg tgtcgtggtg 840
gacgtgtccc acgaagatcc cgaagtcaag ttcaactggt acgtggacgg agtcgaggtg 900
cacaacgcaa agaccaagcc tcgcgaggaa cagtacaact cgacctatcg ggtggtgtcc 960
gtgctgacag tgctgcatca ggactggctc aacggaaagg agtacaagtg caaagtgtcc 1020
aacaaggccc tgccagcgcc cattgaaaag actatcagca aggccaaggg gcagccaagg 1080
gaaccccaag tgtacaccct gcctccgtcc cgcgaagaaa tgaccaagaa ccaggtgtcc 1140
ctgacgtgct tggtcaaggg cttttaccct tccgacatcg ccgtggagtg ggagtcgaac 1200
gggcagccgg aaaacaacta caagaccact ccaccggtgc tcgactcgga tggctcgttc 1260
ttcctgtatt cgaagctgac tgtcgacaaa agccggtggc agcagggcaa tgtgttctcc 1320
tgctccgtga tgcatgaggc cctccacaac cactacaccc agaagtctct gagcctttcc 1380
ccggga 1386

<210> SEQ ID NO 48
<211> LENGTH: 642
<212> TYPE: DNA
<213> ORGANISM: Artificial Sequence
<220> FEATURE:
<223> OTHER INFORMATION: Synthetic: 10F10.1 kappa LC DNA

<400> SEQUENCE: 48
gccatccagc tgacccagtc tcctagctcc ctgtctgcca gcgtgggcga cagggtgacc 60
atcacatgca gagcctccca gggaatctct agcgccctgg cctggtacca gcagaagcca 120
ggcaaggccc ctaagctgct gatctatgat gcctcctctc tggagagcgg agtgccatcc 180
aggttcaccg gctccggctc tggcacagac tttaccctga caatcagctc cctgcagcca 240
gaggatttcg ccacatacta ttgtcagcag ttcaacagct accccatcac ctttggccag 300
ggcacacggc tggagatcaa gcgtacggtg gccgccccgt ccgtgtttat cttccctcca 360
tcggacgagc agctcaagtc cggtaccgcg agcgtggtct gcctgctgaa caatttctac 420
ccgcgcgaag ctaaagtgca atggaaggtc gataacgcac ttcagtccgg gaacagccag 480
gaatctgtga ccgagcagga ctccaaggat tcgacctatt ccctgtcctc gactctcacc 540
ctgtcaaagg ccgactacga gaagcacaag gtctacgcct gcgaagtgac ccatcagggc 600
ttgtcctcac ccgtgactaa gagcttcaac cggggagagt gt 642

<210> SEQ ID NO 49
<211> LENGTH: 693
<212> TYPE: DNA
<213> ORGANISM: Artificial Sequence
<220> FEATURE:
<223> OTHER INFORMATION: Synthetic: 10F10.3 kappa LC DNA ILT4.11K DNA
With signal peptide

<400> SEQUENCE: 49
atgagggctt ggatcttctt tctgctctgc ctggccgggc gcgccctcgc agccatccag 60
ctgacccagt ctcctagctc cctgtctgcc agcgtgggcg acagggtgac catcacatgc 120
agagcctccc agggaatctc tagcgccctg gcctggtacc agcagaagcc aggcaaggcc 180
cctaagctgc tgatctatga tgcctcctct ctggagagcg gagtgccatc caggttcagc 240

```
ggctccggct ctggcacaga ctttaccctg acaatcagct ccctgcagcc agaggatttc    300

gccacatact attgtcagca gttcaacagc taccccatca cctttggcca gggcacacgg    360

ctggagatca agcgtacggt ggccgccccg tccgtgttta tcttccctcc atcggacgag    420

cagctcaagt ccggtaccgc gagcgtggtc tgcctgctga acaatttcta cccgcgcgaa    480

gctaaagtgc aatggaaggt cgataacgca cttcagtccg ggaacagcca ggaatctgtg    540

accgagcagg actccaagga ttcgacctat tccctgtcct cgactctcac cctgtcaaag    600

gccgactacg agaagcacaa ggtctacgcc tgcgaagtga cccatcaggg cttgtcctca    660

cccgtgacta agagcttcaa ccggggagag tgt                                 693


<210> SEQ ID NO 50
<211> LENGTH: 125
<212> TYPE: PRT
<213> ORGANISM: Artificial Sequence
<220> FEATURE:
<223> OTHER INFORMATION: Synthetic: 9G4 VL ILT4.1K VL (including signal
      sequence, residues 1-18)

<400> SEQUENCE: 50

Ala Pro Ala Gln Leu Leu Phe Leu Leu Leu Leu Trp Leu Pro Asp Thr
1               5                   10                  15

Thr Gly Glu Ile Val Leu Thr Gln Ser Pro Ala Thr Leu Ser Leu Ser
            20                  25                  30

Pro Gly Glu Arg Ala Thr Leu Ser Cys Arg Ala Ser Gln Ser Val Ser
        35                  40                  45

Ser Tyr Leu Ala Trp Tyr Gln Gln Lys Pro Gly Gln Ala Pro Arg Leu
    50                  55                  60

Leu Ile Tyr Asp Ala Ser Asn Arg Ala Thr Gly Ile Pro Ala Arg Phe
65                  70                  75                  80

Ser Gly Ser Gly Ser Gly Thr Asp Phe Thr Leu Thr Ile Ser Ser Leu
                85                  90                  95

Glu Pro Glu Asp Phe Ala Gly Tyr Tyr Cys Gln Gln Arg Ser Tyr Trp
            100                 105                 110

Pro Trp Thr Phe Gly Gln Gly Thr Lys Val Glu Ile Lys
        115                 120                 125


<210> SEQ ID NO 51
<211> LENGTH: 135
<212> TYPE: PRT
<213> ORGANISM: Artificial Sequence
<220> FEATURE:
<223> OTHER INFORMATION: Synthetic: 9G4.IgG1.1 VH ILT4.1.IgG1.1 VH
      (including signal sequence, residues 1-19)

<400> SEQUENCE: 51

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Tyr Tyr Trp Asn Trp Ile Arg Gln Pro Pro Gly Lys Gly Leu
    50                  55                  60

Glu Trp Leu Gly Tyr Ile Tyr Tyr Ser Gly Ser Thr Lys Tyr Asn Pro
65                  70                  75                  80

Ser Leu Lys Ser Arg Val Thr Ile Ser Val Asp Thr Ser Lys Asn Gln
```

-continued

```
                85                  90                  95

Phe Ser Leu Lys Leu Ser Ser Val Thr Ala Ala Asp Thr Ala Val Tyr
            100                 105                 110

Tyr Cys Ala Ser Ser Gly Trp Tyr Tyr Phe Asp Tyr Trp Gly Gln Gly
        115                 120                 125

Thr Leu Val Thr Val Ser Ser
    130                 135
```

<210> SEQ ID NO 52
<211> LENGTH: 375
<212> TYPE: DNA
<213> ORGANISM: Artificial Sequence
<220> FEATURE:
<223> OTHER INFORMATION: Synthetic: 9G4 VL DNA ILT4.1K VL DNA

<400> SEQUENCE: 52

```
gccccagctc agcttctctt cctcctgcta ctctggctcc cagataccac cggagaaatt     60

gtgttgacac agtctccagc caccctgtct ttgtctccag gggaaagagc caccctctcc    120

tgcagggcca gtcagagtgt tagcagctac ttagcctggt accaacagaa acctggccag    180

gctcccaggc tcctcatcta tgatgcgtcc aacagggcca ctggcatccc agccaggttc    240

agtggcagtg ggtctgggac agacttcact ctcaccatca gcagcctaga gcctgaagat    300

tttgcaggtt attactgtca gcagcgtagc tactggccgt ggacgttcgg ccaagggacc    360

aaggtggaaa tcaaa                                                     375
```

<210> SEQ ID NO 53
<211> LENGTH: 405
<212> TYPE: DNA
<213> ORGANISM: Artificial Sequence
<220> FEATURE:
<223> OTHER INFORMATION: Synthetic: 9G4.IgG1.1 VH DNA ILT4.1.IgG1.1 VH DNA

<400> SEQUENCE: 53

```
atgaaacatc tgtggttctt ccttctcctg gtggcagctc ccagatgggt cctgtcccag     60

gtgcagctgc aggagtcggg cccaggactg gtgaagcctt cggagaccct gtccctcacc    120

tgcactgtct ctggtggctc catcagtagt tactactgga actggatccg gcagccccca    180

gggaagggac tggagtggct tgggtacatc tattacagtg ggagtaccaa gtacaacccc    240

tccctcaaga gtcgagtcac catatcagta gacacgtcca agaaccagtt ctccctgaag    300

ctgagctctg tgaccgctgc ggacacggcc gtgtattatt gtgccagcag tggctggtac    360

tactttgact attggggcca gggaaccctg gtcaccgtct cctca                    405
```

<210> SEQ ID NO 54
<211> LENGTH: 107
<212> TYPE: PRT
<213> ORGANISM: Artificial Sequence
<220> FEATURE:
<223> OTHER INFORMATION: Synthetic: 9C8 kappa VL ILT4.2K VL

<400> SEQUENCE: 54

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45
```

```
Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105


<210> SEQ ID NO 55
<211> LENGTH: 125
<212> TYPE: PRT
<213> ORGANISM: Artificial Sequence
<220> FEATURE:
<223> OTHER INFORMATION: Synthetic: 9C8.IgG1.1 VH ILT4.2.IgG1.1 VH

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Val Arg Gln Ala Thr Gly Gln Gly Leu Glu Trp Met
        35                  40                  45

Gly Trp Met Asn Pro Asn Ser Gly His Thr Gly Tyr Ala Gln Lys Phe
    50                  55                  60

Gln Asp Arg Val Thr Leu Thr Arg Asp Thr Ser Ile Ser Thr Ala Tyr
65                  70                  75                  80

Met Glu Leu Ser Ser Leu Arg Ser Glu Asp Ser Ala Val Tyr Tyr Cys
                85                  90                  95

Ala Arg Gly Gly Asn Ser Ile Asp Trp Gly Phe Ser Tyr Tyr Gly Leu
            100                 105                 110

Asp Val Trp Gly Gln Gly Thr Thr Val Thr Val Ser Ser
        115                 120                 125


<210> SEQ ID NO 56
<211> LENGTH: 321
<212> TYPE: DNA
<213> ORGANISM: Artificial Sequence
<220> FEATURE:
<223> OTHER INFORMATION: Synthetic: 9C8 kappa VL DNA ILT4.2K VL DNA

<400> SEQUENCE: 56

gccatccagt tgacccagtc tccatcctcc ctgtctgcat ctgtaggaga cagagtcacc     60

atcacttgcc gggcaagtca gggcattagc agtgctttag cctggtatca gcagaaacca    120

gggaaagctc ctaagctcct gatctatgat gcctccagtt tggaaagtgg ggtcccatca    180

aggttcagcg gcagtggatc tgggacagat ttcactctca ccatcagcag cctgcagcct    240

gaagattttg caacttatta ctgtcaacag tttaatagtt acccattcac tttcggccct    300

gggaccaaag tggatatcaa a                                              321


<210> SEQ ID NO 57
<211> LENGTH: 375
<212> TYPE: DNA
<213> ORGANISM: Artificial Sequence
<220> FEATURE:
<223> OTHER INFORMATION: Synthetic: 9C8.IgG1.1 VH DNA ILT4.2.IgG1.1 VH
      DNA

<400> SEQUENCE: 57
```

```
caggtgcaac tggtgcagtc tggggctgag gtaaagaagc ctggggcctc agtgaaggtc     60

tcctgcaagg cttctggata caccttcacc agctctgata tcaactgggt gcgacaggcc    120

actggacaag ggcttgagtg gatgggatgg atgaacccta acagtggtca cacaggctat    180

gcacagaagt tccaggacag agtcaccttg acccgggaca cctccataag cacagcctac    240

atggagctga gcagcctgag atctgaggac tcggccgtgt attactgtgc gagaggtggg    300

aatagcattg actgggggtt ctcctactac ggtctggacg tctggggcca agggaccacg    360

gtcaccgtct cctca                                                      375
```

<210> SEQ ID NO 58
<211> LENGTH: 128
<212> TYPE: PRT
<213> ORGANISM: Artificial Sequence
<220> FEATURE:
<223> OTHER INFORMATION: Synthetic: 2H2.IgG1.1 VH ILT4.3.IgG1.1 VH

<400> SEQUENCE: 58

```
Gln Val Gln Leu Val Gln Ser Gly Ala Glu Val Lys Lys Pro Gly Ser
1               5                   10                  15

Ser Val Glu Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Ala Thr Ala Asn Tyr Ala Pro Lys Phe
    50                  55                  60

Gln Gly Arg Val Thr Ile Thr Ala Asp Glu Phe Thr Ser Ser Ala Tyr
65                  70                  75                  80

Met Glu Leu Ser Ser Leu Arg Ser Glu Asp Thr Ala Val Tyr Tyr Cys
                85                  90                  95

Ala Lys Ser Ser Ile Thr Met Ile Arg Gly Ala Tyr Leu Tyr Tyr Tyr
            100                 105                 110

Asp Gly Met Asp Val Trp Gly Gln Gly Thr Thr Val Thr Val Ser Ser
        115                 120                 125
```

<210> SEQ ID NO 59
<211> LENGTH: 107
<212> TYPE: PRT
<213> ORGANISM: Artificial Sequence
<220> FEATURE:
<223> OTHER INFORMATION: Synthetic: 2H2 kappa VL ILT4.3K VL

<400> SEQUENCE: 59

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Tyr
                85                  90                  95

Thr Phe Gly Gln Gly Thr Lys Leu Glu Ile Lys
            100                 105
```

<210> SEQ ID NO 60
<211> LENGTH: 384
<212> TYPE: DNA
<213> ORGANISM: Artificial Sequence
<220> FEATURE:
<223> OTHER INFORMATION: Synthetic: 2H2.IgG1.1 VH DNA ILT4.3.IgG1.1 VH DNA

<400> SEQUENCE: 60
caggtccagt tggtgcagtc tggggctgag gtgaagaagc ctgggtcctc ggtgaaggtc 60
tcctgcaagg cttctggggg caccttcagc aactatgcta tcagctgggt gcgacaggcc 120
cctggacaag ggcttgagtg gatgggaggg atcatcccca tcttggctac agcaaactac 180
gcaccgaagt tccagggcag agtcacgatt accgcggacg aattcacgag ctcagcttac 240
atggagctga gcagcctgag atctgaggac acggccgtgt attactgtgc gaagtctagt 300
attactatga ttcggggagc ctatctttac tactacgacg gtatggacgt ctggggccaa 360
gggaccacgg tcaccgtctc ctca 384

<210> SEQ ID NO 61
<211> LENGTH: 321
<212> TYPE: DNA
<213> ORGANISM: Artificial Sequence
<220> FEATURE:
<223> OTHER INFORMATION: Synthetic: 2H2 kappa VL DNA ILT4.3K VL DNA

<400> SEQUENCE: 61
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcgtacac ttttggccag 300
gggaccaagc tggagatcaa a 321

<210> SEQ ID NO 62
<211> LENGTH: 108
<212> TYPE: PRT
<213> ORGANISM: Artificial Sequence
<220> FEATURE:
<223> OTHER INFORMATION: Synthetic: 2E5 kappa VL ILT4.4K VL

<400> SEQUENCE: 62

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Trp Thr Phe Gly Gln Gly Thr Lys Val Glu Ile Lys
            100                 105

<210> SEQ ID NO 63
<211> LENGTH: 121
<212> TYPE: PRT
<213> ORGANISM: Artificial Sequence
<220> FEATURE:
<223> OTHER INFORMATION: Synthetic: 2E5.IgG1.1 VH ILT4.4.IgG1.1 VH

<400> SEQUENCE: 63

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Glu Tyr Tyr Ala Glu Ser Val
    50                  55                  60

Lys Gly Arg Leu Thr Ile Ser Arg Asp Asn Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Ala Arg Asp Pro Phe Tyr Gly Ser Gly Asn Tyr Phe Asp Tyr Trp Gly
            100                 105                 110

Gln Gly Thr Leu Val Thr Val Ser Ser
        115                 120
```

<210> SEQ ID NO 64
<211> LENGTH: 324
<212> TYPE: DNA
<213> ORGANISM: Artificial Sequence
<220> FEATURE:
<223> OTHER INFORMATION: Synthetic: 2E5 kappa VL DNA ILT4.4K VL

<400> SEQUENCE: 64

```
gaaattgtgt tgacacagtc tccagccacc ctgtctttgt ctccagggga aagagccacc      60

ctctcctgca gggccagtca gagtgttagc agctacttag cctggtacca acagaaacct     120

ggccaggctc ccaggctcct catctatgat gcatccaaca gggccactgg catcccagcc     180

aggttcagtg gcagtgggtc tgggacagac ttcactctca ccatcagcag cctagagcct     240

gaagattttg cagtttatta ctgtcagcag cgtagcaact ggcctccgtg gacgttcggc     300

caagggacca aggtggaaat caaa                                            324
```

<210> SEQ ID NO 65
<211> LENGTH: 363
<212> TYPE: DNA
<213> ORGANISM: Artificial Sequence
<220> FEATURE:
<223> OTHER INFORMATION: Synthetic: 2E5.IgG1.1 VH DNA ILT4.4.IgG1.1 VH

<400> SEQUENCE: 65

```
caggtgcagc tggtggagtc tgggggaggc gtggtccagc ctgggaggtc cctgagactc      60

tcctgtacag cgtctggatt caccttcagt aactatggca tgcactgggt ccgccaggct     120

ccaggcaagg gactggagtg ggtggcagtt atctggtatg atggaagtaa tgaatactat     180

gcagaatccg tgaagggccg actcaccatc tccagagaca attccaagaa cacgctgtat     240

ctgcaagtga acagcctgag agccgaggac acggctgtgt attattgtgc gagagatcct     300

ttctatggtt cggggaatta ctttgactac tggggccagg gaaccctggt caccgtctcc     360

tca                                                                   363
```

<210> SEQ ID NO 66
<211> LENGTH: 107
<212> TYPE: PRT
<213> ORGANISM: Artificial Sequence
<220> FEATURE:
<223> OTHER INFORMATION: Synthetic: 24E5 kappa VL ILT4.5K VL

<400> SEQUENCE: 66

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 67
<211> LENGTH: 121
<212> TYPE: PRT
<213> ORGANISM: Artificial Sequence
<220> FEATURE:
<223> OTHER INFORMATION: Synthetic: 24E5.IgG1.1 VH ILT4.5.IgG1.1 VH

<400> SEQUENCE: 67

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gln Asp Ile Ile Ala Ala Tyr Tyr Phe Val Tyr Trp Gly
            100                 105                 110

Gln Gly Thr Leu Val Thr Val Ser Ser
        115                 120
```

<210> SEQ ID NO 68
<211> LENGTH: 321
<212> TYPE: DNA
<213> ORGANISM: Artificial Sequence
<220> FEATURE:
<223> OTHER INFORMATION: Synthetic: 24E5 kappa VL DNA ILT4.5K VL

<400> SEQUENCE: 68

```
gacatccaga tgacccagtc tccatcctca ctgtctgcat ctgtaggaga cagagtcacc     60

atcacttgtc gggcgagtca gggtattagc agctggttag cctggtatca gcagaaacca    120
```

-continued

```
gagaaagccc ctaagtccct gatctatgct gcatccagtt tgcaaagtgg ggtcccatca    180

aggttcagcg gcagtggatc tgggacagat ttcactctca ccatcagcag cctgcagcct    240

gaagattttg caacttatta ctgccaacag tataatagtt accctctcac tttcggcgga    300

gggaccaagg tggagatcaa a                                              321
```

<210> SEQ ID NO 69
<211> LENGTH: 363
<212> TYPE: DNA
<213> ORGANISM: Artificial Sequence
<220> FEATURE:
<223> OTHER INFORMATION: Synthetic: 24E5.IgG1.1 VH DNA ILT4.5.IgG1.1 VH

<400> SEQUENCE: 69

```
gaggtgcagc tgttggagtc tgggggaggc ttggtacagc ctggggggtc cctgagactc     60

tcctgtgcag cctctggatt cacctttagc agctatgtca tgagctgggt ccgccaggct    120

ccagggaagg ggctggagtg ggtctcaggt attagtggta gtggtggtag cacatactac    180

gcagactccg tgaagggccg gttcaccatc tccagagaca attccaagaa cacgctgtat    240

ctgcaaatga acagcctgag agccgaggac acggccgtat attactgtgc gaaagatcag    300

gatattatag cagcatacta ctttgtctac tggggccagg gaaccctggt caccgtctcc    360

tca                                                                  363
```

<210> SEQ ID NO 70
<211> LENGTH: 108
<212> TYPE: PRT
<213> ORGANISM: Artificial Sequence
<220> FEATURE:
<223> OTHER INFORMATION: Synthetic: 21D9K kappa VL ILT4.6K VL

<400> SEQUENCE: 70

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105
```

<210> SEQ ID NO 71
<211> LENGTH: 125
<212> TYPE: PRT
<213> ORGANISM: Artificial Sequence
<220> FEATURE:
<223> OTHER INFORMATION: Synthetic: 21D9.IgG1.1 VH ILT4.6.IgG1.1 VH

<400> SEQUENCE: 71

```
Glu Gly Gln Leu Leu Glu Ser Gly Gly Asp Leu Val Gln Pro Gly Gly
1               5                   10                  15

Ser Leu Arg Leu Ser Cys Ala Thr Ser Gly Phe Thr Phe Ser Asn Tyr
            20                  25                  30
```

```
Ala Met Asn Trp Val Arg Gln Ala Pro Gly Lys Gly Leu Glu Trp Ile
         35                  40                  45

Ser Val Ile Ser Val Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Lys Asp Tyr Tyr Tyr Asp Ser Gly Ser Tyr Tyr Asp Ser Phe Phe
             100                 105                 110

Asp Tyr Trp Gly Gln Gly Thr Leu Val Thr Val Ser Ser
         115                 120                 125

<210> SEQ ID NO 72
<211> LENGTH: 324
<212> TYPE: DNA
<213> ORGANISM: Artificial Sequence
<220> FEATURE:
<223> OTHER INFORMATION: Synthetic: 21D9K kappa VL DNA ILT4.6K VL DNA

<400> SEQUENCE: 72

gaaattgtgt tgacgcagtc tccaggcacc ctgtctttgt ctccagggga aagagccacc      60

ctctcctgca gggccagtca gagtgttagc agcagctact tagcctggta ccagcagaaa     120

cctggccagg ctcccaggct cctcatctat ggtgcatcca gcagggccac tggcatccca     180

gacaggttca gtggcagtgg gtctgggaca gacttcactc tcaccatcag cagactggag     240

cctgaagatt ttgcagtgta ttactgtcag cagtatggta gctcacctct cactttcggc     300

ggagggacca aggtggagat caaa                                             324

<210> SEQ ID NO 73
<211> LENGTH: 375
<212> TYPE: DNA
<213> ORGANISM: Artificial Sequence
<220> FEATURE:
<223> OTHER INFORMATION: Synthetic: 21D9.IgG1.1 VH DNA ILT4.6.IgG1.1 VH
      DNA

<400> SEQUENCE: 73

gagggacagc tgttggagtc tgggggagac ttggtacagc ctggggggtc cctgagactc      60

tcctgtgcaa cctctggatt cacctttagc aactatgcca tgaactgggt ccgccaggct     120

ccagggaagg ggctggagtg gatctcagtt attagtgtta gtggtggtag cacatactac     180

gcagactccg tgaagggccg gttcaccatc tccagagaca attccaagaa cacgctgtat     240

ctgcaaatga atagcctgag agccgaggac acggccgtat attactgtgc gaaagattat     300

tactatgatt cggggagtta ttatgactct ttctttgact actggggcca gggaaccctg     360

gtcaccgtct cctca                                                       375

<210> SEQ ID NO 74
<211> LENGTH: 125
<212> TYPE: PRT
<213> ORGANISM: Artificial Sequence
<220> FEATURE:
<223> OTHER INFORMATION: Synthetic: 21D9.b.IgG1.3 VH

<400> SEQUENCE: 74

Glu Val Gln Leu Leu Glu Ser Gly Gly Gly Leu Val Gln Pro Gly Gly
 1               5                  10                  15

Ser Leu Arg Leu Ser Cys Ala Thr Ser Gly Phe Thr Phe Ser Asn Tyr
```

```
            20                  25                  30

Ala Met Asn Trp Val Arg Gln Ala Pro Gly Lys Gly Leu Glu Trp Ile
        35                  40                  45

Ser Val Ile Ser Val Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Tyr Tyr Asp Ser Gly Ser Tyr Tyr Asp Ser Phe Phe
            100                 105                 110

Asp Tyr Trp Gly Gln Gly Thr Leu Val Thr Val Ser Ser
        115                 120                 125


<210> SEQ ID NO 75
<211> LENGTH: 125
<212> TYPE: PRT
<213> ORGANISM: Artificial Sequence
<220> FEATURE:
<223> OTHER INFORMATION: Synthetic: 21D9.c.IgG1.3 VH

<400> SEQUENCE: 75

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Ile
        35                  40                  45

Ser Val Ile Ser Val Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Tyr Tyr Asp Ser Gly Ser Tyr Tyr Asp Ser Phe Phe
            100                 105                 110

Asp Tyr Trp Gly Gln Gly Thr Leu Val Thr Val Ser Ser
        115                 120                 125


<210> SEQ ID NO 76
<211> LENGTH: 375
<212> TYPE: DNA
<213> ORGANISM: Artificial Sequence
<220> FEATURE:
<223> OTHER INFORMATION: Synthetic: 21D9.b.IgG1.3 VH DNA

<400> SEQUENCE: 76

gaggtgcagc tgctggagtc tggaggagga ctggtgcagc caggaggcag cctgaggctg      60

tcctgcgcca cctctggctt cacattttcc aactatgcca tgaattgggt gcgccaggca     120

cctggcaagg gactggagtg gatctctgtg atctctgtga gcggcggctc tacctactat     180

gccgacagcg tgaagggccg gttcaccatc agcagagata actccaagaa tacactgtat     240

ctgcagatga acagcctgcg ggccgaggac acagccgtgt actattgtgc caaggactac     300

tattacgatt ccggctctta ttacgactcc ttctttgatt actggggcca gggcaccctg     360

gtgacagtga gctcc                                                      375
```

<210> SEQ ID NO 77
<211> LENGTH: 375
<212> TYPE: DNA
<213> ORGANISM: Artificial Sequence
<220> FEATURE:
<223> OTHER INFORMATION: Synthetic: 21D9.c.IgG1.3 VH DNA

<400> SEQUENCE: 77

```
gaggtgcagc tgctggagtc tggaggagac ctggtgcagc caggaggcag cctgaggctg     60

tcctgcgccg cctctggctt cacattttcc aactatgcca tgaattgggt gcgccaggca    120

cctggcaagg gactggagtg gatctctgtg atctctgtga gcggcggctc tacctactat    180

gccgacagcg tgaagggccg gttcaccatc agcagagata actccaagaa tacactgtat    240

ctgcagatga acagcctgcg ggccgaggac acagccgtgt actattgtgc caaggactac    300

tattacgatt ccggctctta ttacgactcc ttctttgatt actggggcca gggcaccctg    360

gtgacagtga gctcc                                                     375
```

<210> SEQ ID NO 78
<211> LENGTH: 125
<212> TYPE: PRT
<213> ORGANISM: Artificial Sequence
<220> FEATURE:
<223> OTHER INFORMATION: Synthetic: 21D9.d.IgG1.3 VH

<400> SEQUENCE: 78

```
Glu Val Gln Leu Leu Glu Ser Gly Gly Asp Leu Val Gln Pro Gly Gly
1               5                   10                  15

Ser Leu Arg Leu Ser Cys Ala Thr Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Val Ile Ser Val Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Tyr Tyr Asp Ser Gly Ser Tyr Tyr Asp Ser Phe Phe
            100                 105                 110

Asp Tyr Trp Gly Gln Gly Thr Leu Val Thr Val Ser Ser
        115                 120                 125
```

<210> SEQ ID NO 79
<211> LENGTH: 375
<212> TYPE: DNA
<213> ORGANISM: Artificial Sequence
<220> FEATURE:
<223> OTHER INFORMATION: Synthetic: 21D9.d.IgG1.3 VH DNA

<400> SEQUENCE: 79

```
gaggtgcagc tgctggagtc tggaggagac ctggtgcagc caggaggcag cctgaggctg     60

tcctgcgcca cctctggctt cacattttcc aactatgcca tgaattgggt gcgccaggca    120

cctggcaagg gactggagtg ggtgtctgtg atctctgtga gcggcggctc tacctactat    180

gccgacagcg tgaagggccg gttcaccatc agcagagata actccaagaa tacactgtat    240

ctgcagatga acagcctgcg ggccgaggac acagccgtgt actattgtgc caaggactac    300

tattacgatt ccggctctta ttacgactcc ttctttgatt actggggcca gggcaccctg    360
```

gtgacagtga gctcc 375

<210> SEQ ID NO 80
<211> LENGTH: 125
<212> TYPE: PRT
<213> ORGANISM: Artificial Sequence
<220> FEATURE:
<223> OTHER INFORMATION: Synthetic: 21D9.e.IgG1.3 VH ILT4.8.IgG1.3 VH

<400> SEQUENCE: 80

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Val Ile Ser Val Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Tyr Tyr Asp Ser Gly Ser Tyr Tyr Asp Ser Phe Phe
            100                 105                 110

Asp Tyr Trp Gly Gln Gly Thr Leu Val Thr Val Ser Ser
        115                 120                 125
```

<210> SEQ ID NO 81
<211> LENGTH: 375
<212> TYPE: DNA
<213> ORGANISM: Artificial Sequence
<220> FEATURE:
<223> OTHER INFORMATION: Synthetic: 21D9.e.IgG1.3 VH DNA ILT4.8.IgG1.3 VH DNA

<400> SEQUENCE: 81

```
gaggtgcagc tgctggagtc tggaggagga ctggtgcagc caggaggcag cctgaggctg     60

tcctgcgccg cctctggctt cacattttcc aactatgcca tgaattgggt gcgccaggca    120

cctggcaagg gactggagtg ggtgtctgtg atctctgtga gcggcggctc tacctactat    180

gccgacagcg tgaagggccg gttcaccatc agcagagata actccaagaa tacactgtat    240

ctgcagatga acagcctgcg ggccgaggac acagccgtgt actattgtgc caaggactac    300

tattacgatt ccggctctta ttacgactcc ttctttgatt actggggcca gggcaccctg    360

gtgacagtga gctcc                                                     375
```

<210> SEQ ID NO 82
<211> LENGTH: 105
<212> TYPE: PRT
<213> ORGANISM: Artificial Sequence
<220> FEATURE:
<223> OTHER INFORMATION: Synthetic: 21A5 kappa VL

<400> SEQUENCE: 82

```
Glu Ile Ala Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Thr Phe
                85                  90                  95

Gly Gly Gly Thr Lys Val Glu Ile Lys
            100                 105


<210> SEQ ID NO 83
<211> LENGTH: 124
<212> TYPE: PRT
<213> ORGANISM: Artificial Sequence
<220> FEATURE:
<223> OTHER INFORMATION: Synthetic: 21A5.IgG1.3 VH

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Ile Phe His Pro Ser Gly Asp Ile Thr Ser Ser Ala Gln Asn Phe
    50                  55                  60

Gln Gly Arg Val Thr Met Ile Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Val Leu Arg Tyr Leu Asp Trp Ser His Ala Phe Asp
            100                 105                 110

Ile Trp Gly Gln Gly Thr Met Val Thr Val Ser Ser
        115                 120


<210> SEQ ID NO 84
<211> LENGTH: 315
<212> TYPE: DNA
<213> ORGANISM: Artificial Sequence
<220> FEATURE:
<223> OTHER INFORMATION: Synthetic: 21A5 kappa VL DNA

<400> SEQUENCE: 84

gaaattgcgt tgacgcagtc tccaggcacc ctgtctttgt ctccagggga aagagccacc      60

ctctcctgca gggccagtca gagtgttagc agcagctact tagcctggta ccagcagaaa     120

cctggccagg ctcccaggct cctcatctat ggtgcatcca gcagggccac tggcatccca     180

gacaggttca gtggcagtgg gtctgggaca gacttcactc tcaccatcag cagactggag     240

cctgaagatt ttgcagtgta ttactgtcag cagtatggta gcactttcgg cggagggacc     300

aaggtggaga tcaaa                                                      315


<210> SEQ ID NO 85
<211> LENGTH: 372
<212> TYPE: DNA
<213> ORGANISM: Artificial Sequence
<220> FEATURE:
<223> OTHER INFORMATION: Synthetic: 21A5.IgG1.3 VH DNA

<400> SEQUENCE: 85
```

-continued caggtgcagc tggtgcagtc tggggctgag gtgaagaagc ctggggcctc agtgaaggtt 60
tcctgcaagg catctggata caccttcacc gactactatt tacactgggt gcgacaggcc 120
cctggacaag ggcttgagtg gatgggaata ttccacccta gtggtgatat cacaagcagc 180
gcacagaact tccagggcag agtcaccatg atcagggaca cgtccacgag caccgtctac 240
atggaactga gcagcctgag atctgaagac acggccgtgt attactgtgc gagagggggt 300
gtattacgat atcttgactg gtcccatgct tttgatatct ggggccaagg gacaatggtc 360
accgtctctt ca 372

<210> SEQ ID NO 86
<211> LENGTH: 105
<212> TYPE: PRT
<213> ORGANISM: Artificial Sequence
<220> FEATURE:
<223> OTHER INFORMATION: Synthetic: 21A5.a kappa VL 21A5.1K ILT4.9K VL

<400> SEQUENCE: 86

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Thr Phe
85 90 95

Gly Gly Gly Thr Lys Val Glu Ile Lys
100 105

<210> SEQ ID NO 87
<211> LENGTH: 124
<212> TYPE: PRT
<213> ORGANISM: Artificial Sequence
<220> FEATURE:
<223> OTHER INFORMATION: Synthetic: 21A5.a.IgG1.3 VH ILT4.9.IgG1.3 VH

<400> SEQUENCE: 87

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Tyr Leu His Trp Val Arg Gln Ala Pro Gly Gln Gly Leu Glu Trp Met
35 40 45

Gly Ile Phe His Pro Ser Gly Asp Ile Thr Ser Ser Ala Gln Asn Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Gly Val Leu Arg Tyr Leu Asp Trp Ser His Ala Phe Asp
100 105 110

Ile Trp Gly Gln Gly Thr Met Val Thr Val Ser Ser
115 120

<210> SEQ ID NO 88
<211> LENGTH: 315
<212> TYPE: DNA
<213> ORGANISM: Artificial Sequence
<220> FEATURE:
<223> OTHER INFORMATION: Synthetic: 21A5.a kappa VL DNA 21A5.1K ILT4.9K VL

<400> SEQUENCE: 88
gagatcgtgc tgacccagag cccaggcaca ctgtctctga gcccaggaga gagggccacc 60
ctgtcctgca gagcctccca gtctgtgagc tcctcttacc tggcctggta tcagcagaag 120
ccaggacagg cacctaggct gctgatctac ggagccagct ccagggcaac cggcatccct 180
gaccgcttca gcggctccgg ctctggcaca gacttcaccc tgacaatctc taggctggag 240
cccgaggact tcgccgtgta ctattgtcag cagtatggct ccacctttgg cggcggcaca 300
aaggtggaga tcaag 315

<210> SEQ ID NO 89
<211> LENGTH: 372
<212> TYPE: DNA
<213> ORGANISM: Artificial Sequence
<220> FEATURE:
<223> OTHER INFORMATION: Synthetic: 21A5.a.IgG1.3 VH DNA ILT4.9.IgG1.3 VH

<400> SEQUENCE: 89
caggtgcagc tggtgcagtc cggagcagag gtgaagaagc caggagcctc tgtgaaggtg 60
agctgcaagg cctccggcta caccttcaca gattactatc tgcactgggt gcggcaggca 120
ccaggacagg gactggagtg gatgggcatc ttccaccctt ctggcgacat cacaagctcc 180
gcccagaact ttcagggccg ggtgaccatg acaagagata ccagcacatc caccgtgtac 240
atggagctgt ctagcctgag gtctgaggac accgccgtgt actattgtgc aaggggaggc 300
gtgctgaggt atctggactg gagccacgcc tttgatatct ggggccaggg cacaatggtg 360
accgtgtcct ct 372

<210> SEQ ID NO 90
<211> LENGTH: 107
<212> TYPE: PRT
<213> ORGANISM: Artificial Sequence
<220> FEATURE:
<223> OTHER INFORMATION: Synthetic: 10F10 kappa VL ILT4.10K VL

<400> SEQUENCE: 90

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Phe Gln Gln Lys Pro Gly Lys Ala Pro Lys Leu Leu Ile
35 40 45

Tyr Asp Ala Ser Ser Leu Glu Ser Gly Val Pro Ser Arg Phe Thr Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Ile
85 90 95

Thr Phe Gly Gln Gly Thr Arg Leu Glu Ile Lys
100 105

<210> SEQ ID NO 91
<211> LENGTH: 116
<212> TYPE: PRT
<213> ORGANISM: Artificial Sequence
<220> FEATURE:
<223> OTHER INFORMATION: Synthetic: 10F10.IgG1.3 VH ILT4.10.IgG1.3 VH

<400> SEQUENCE: 91

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Ile Ile Ser Tyr Asp Glu Tyr Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Val Gly Ile Arg Tyr Trp Gly Gln Gly Thr Leu Val
            100                 105                 110

Thr Val Ser Ser
        115
```

<210> SEQ ID NO 92
<211> LENGTH: 321
<212> TYPE: DNA
<213> ORGANISM: Artificial Sequence
<220> FEATURE:
<223> OTHER INFORMATION: Synthetic: 10F10 kappa VL DNA ILT4.10K VL

<400> SEQUENCE: 92

```
gccatccagt tgacccagtc tccatcctcc ctgtctgcat ctgtaggaga cagagtcacc     60

atcacttgcc gggcaagtca gggcattagc agtgctttag cctggtttca gcagaaacca    120

gggaaagctc ctaagctcct gatctatgat gcctccagtt tggaaagtgg ggtcccatca    180

aggttcaccg gcagtggatc tgggacagat ttcactctca ccatcagcag cctgcagcct    240

gaagattttg caacttatta ctgtcaacag tttaatagtt acccgatcac cttcggccaa    300

gggacacgac tggagattaa a                                              321
```

<210> SEQ ID NO 93
<211> LENGTH: 348
<212> TYPE: DNA
<213> ORGANISM: Artificial Sequence
<220> FEATURE:
<223> OTHER INFORMATION: Synthetic: 10F10.IgG1.3 VH DNA ILT4.10.IgG1.3
      VH

<400> SEQUENCE: 93

```
caggtgcagc tggtggagtc tgggggaggc gtggtccagc ctgggaggtc cctgagactc     60

tcctgtgcag cctctggatt caccttcagt agctatgcta tgcactgggt ccgccaggct    120

ccaggcaagg ggctggagtg ggtggcaatt atatcatatg atgaatacaa taaatactac    180

gcagactccg tgaagggccg attcaccatc tccagagaca attccaagaa cacgctgtat    240

ctgcaaatga acagcctgag agctgaggac acggctgtgt attactgtgc gagagagtgg    300

gtggggatac gttactgggg ccagggaacc ctggtcaccg tctcctca                 348
```

<210> SEQ ID NO 94
<211> LENGTH: 107
<212> TYPE: PRT
<213> ORGANISM: Artificial Sequence
<220> FEATURE:
<223> OTHER INFORMATION: Synthetic: 10F10.1 kappa VL

<400> SEQUENCE: 94

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys
            100                 105
```

<210> SEQ ID NO 95
<211> LENGTH: 321
<212> TYPE: DNA
<213> ORGANISM: Artificial Sequence
<220> FEATURE:
<223> OTHER INFORMATION: Synthetic: 10F10.1 kappa VL DNA

<400> SEQUENCE: 95

```
gccatccagc tgacccagtc tcctagctcc ctgtctgcca gcgtgggcga cagggtgacc      60

atcacatgca gagcctccca gggaatctct agcgccctgg cctggtacca gcagaagcca     120

ggcaaggccc ctaagctgct gatctatgat gcctcctctc tggagagcgg agtgccatcc     180

aggttcaccg gctccggctc tggcacagac tttaccctga caatcagctc cctgcagcca     240

gaggatttcg ccacatacta ttgtcagcag ttcaacagct accccatcac ctttggccag     300

ggcacacggc tggagatcaa g                                               321
```

<210> SEQ ID NO 96
<211> LENGTH: 107
<212> TYPE: PRT
<213> ORGANISM: Artificial Sequence
<220> FEATURE:
<223> OTHER INFORMATION: Synthetic: 10F10.3 kappa VL ILT4.11K VL

<400> SEQUENCE: 96

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
```

```
                85                  90                  95

Thr Phe Gly Gln Gly Thr Arg Leu Glu Ile Lys
            100                 105
```

<210> SEQ ID NO 97
<211> LENGTH: 321
<212> TYPE: DNA
<213> ORGANISM: Artificial Sequence
<220> FEATURE:
<223> OTHER INFORMATION: Synthetic: 10F10.3 kappa VL DNA ILT4.11K VL DNA

<400> SEQUENCE: 97

```
gccatccagc tgacccagtc tcctagctcc ctgtctgcca gcgtgggcga cagggtgacc      60

atcacatgca gagcctccca gggaatctct agcgccctgg cctggtacca gcagaagcca     120

ggcaaggccc ctaagctgct gatctatgat gcctcctctc tggagagcgg agtgccatcc     180

aggttcagcg gctccggctc tggcacagac tttaccctga caatcagctc cctgcagcca     240

gaggatttcg ccacatacta ttgtcagcag ttcaacagct accccatcac ctttggccag     300

ggcacacggc tggagatcaa g                                               321
```

<210> SEQ ID NO 98
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: Human IgG1f Constant Region

<400> SEQUENCE: 98

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 99
<211> LENGTH: 993
<212> TYPE: DNA
<213> ORGANISM: Artificial Sequence
<220> FEATURE:
<223> OTHER INFORMATION: Synthetic: IgG1f Constant Region DNA

<400> SEQUENCE: 99

```
gctagcacca agggcccatc ggtcttcccc ctggcaccct cctccaagag cacctctggg      60

ggcacagcgg ccctgggctg cctggtcaag gactacttcc ccgaaccggt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacccagacc     240

tacatctgca acgtgaatca caagcccagc aacaccaagg tggacaagag agttgagccc     300

aaatcttgtg acaaaactca cacatgccca ccgtgcccag cacctgaact cctgggggga     360

ccgtcagtct tcctcttccc cccaaaaccc aaggacaccc tcatgatctc ccggacccct     420

gaggtcacat gcgtggtggt ggacgtgagc cacgaagacc ctgaggtcaa gttcaactgg     480

tacgtggacg gcgtggaggt gcataatgcc aagacaaagc cgcgggagga gcagtacaac     540

agcacgtacc gtgtggtcag cgtcctcacc gtcctgcacc aggactggct gaatggcaag     600

gagtacaagt gcaaggtctc caacaaagcc ctcccagccc ccatcgagaa aaccatctcc     660

aaagccaaag ggcagccccg agaaccacag gtgtacaccc tgcccccatc ccgggaggag     720

atgaccaaga accaggtcag cctgacctgc ctggtcaaag gcttctatcc cagcgacatc     780

gccgtggagt gggagagcaa tgggcagccg gagaacaact acaagaccac gcctcccgtg     840

ctggactccg acggctcctt cttcctctat agcaagctca ccgtggacaa gagcaggtgg     900

cagcagggga acgtcttctc atgctccgtg atgcatgagg ctctgcacaa ccactacacg     960

cagaagagcc tctccctgtc cccgggtaaa tga                                  993
```

<210> SEQ ID NO 100
<211> LENGTH: 329
<212> TYPE: PRT
<213> ORGANISM: Artificial Sequence
<220> FEATURE:
<223> OTHER INFORMATION: Synthetic: IgG1.3 (or IgG1.3f) heavy chain
      constant region (L234A, L235E, G237A)

<400> SEQUENCE: 100

```
Ala Ser Thr Lys Gly Pro Ser Val Phe Pro Leu Ala Pro Ser Ser Lys
```

-continued

```
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 101
<211> LENGTH: 107
<212> TYPE: PRT
<213> ORGANISM: Artificial Sequence
<220> FEATURE:
<223> OTHER INFORMATION: Synthetic: Exemplary light chain constant
      region

<400> SEQUENCE: 101

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

```
Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 102
<211> LENGTH: 329
<212> TYPE: PRT
<213> ORGANISM: Homo sapiens
<220> FEATURE:
<221> NAME/KEY: misc_feature
<222> LOCATION: (1)..(329)
<223> OTHER INFORMATION: IgG1f (human wild-type allotype f) heavy chain
      constant region

<400> SEQUENCE: 102

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

-continued

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 103
<211> LENGTH: 329
<212> TYPE: PRT
<213> ORGANISM: Artificial Sequence
<220> FEATURE:
<223> OTHER INFORMATION: Synthetic: IgG1.1f  Heavy chain constant region
      (L234A, L235E, G237A, A330S, P331S)

<400> SEQUENCE: 103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly
                325
```

```
<210> SEQ ID NO 104
<211> LENGTH: 329
<212> TYPE: PRT
<213> ORGANISM: Artificial Sequence
<220> FEATURE:
<223> OTHER INFORMATION: Synthetic: IgG1fa.P238K (or IgG1.P238K) heavy
      chain constant region

<400> SEQUENCE: 104

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Lys Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
```

325

<210> SEQ ID NO 105
<211> LENGTH: 990
<212> TYPE: DNA
<213> ORGANISM: Artificial Sequence
<220> FEATURE:
<223> OTHER INFORMATION: Synthetic: IgG1.3 heavy chain constant region
DNA

<400> SEQUENCE: 105
gcgtcgacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagag agttgagccc 300
aaatcttgtg acaaaactca cacatgccca ccgtgcccag cacctgaagc cgaaggggcc 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctat agcaagctca ccgtggacaa gagcaggtgg 900
cagcagggga acgtcttctc atgctccgtg atgcatgagg ctctgcacaa ccactacacg 960
cagaagagcc tctccctgtc cccgggttga 990

<210> SEQ ID NO 106
<211> LENGTH: 324
<212> TYPE: DNA
<213> ORGANISM: Artificial Sequence
<220> FEATURE:
<223> OTHER INFORMATION: Synthetic: Exemplary light chain constant
region DNA

<400> SEQUENCE: 106
cgtacggtgg ctgcaccatc tgtcttcatc ttcccgccat ctgatgagca gttgaaatct 60
ggaactgcct ctgttgtgtg cctgctgaat aacttctatc ccagagaggc caaagtacag 120
tggaaggtgg ataacgccct ccaatcgggt aactcccagg agagtgtcac agagcaggac 180
agcaaggaca gcacctacag cctcagcagc accctgacgc tgagcaaagc agactacgag 240
aaacacaaag tctacgcctg cgaagtcacc catcagggcc tgagctcgcc cgtcacaaag 300
agcttcaaca ggggagagtg ttag 324

<210> SEQ ID NO 107
<211> LENGTH: 598
<212> TYPE: PRT
<213> ORGANISM: Homo sapiens
<220> FEATURE:
<221> NAME/KEY: misc_feature
<222> LOCATION: (1)..(598)
<223> OTHER INFORMATION: Human ILT4 precursor, with signal peptide -continued

<400> SEQUENCE: 107

Met Thr Pro Ile Val Thr Val Leu Ile Cys Leu Gly Leu Ser Leu Gly
1               5                   10                  15

Pro Arg Thr His Val Gln Thr Gly Thr Ile Pro Lys Pro Thr Leu Trp
            20                  25                  30

Ala Glu Pro Asp Ser Val Ile Thr Gln Gly Ser Pro Val Thr Leu Ser
        35                  40                  45

Cys Gln Gly Ser Leu Glu Ala Gln Glu Tyr Arg Leu Tyr Arg Glu Lys
    50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
        115                 120                 125

Gln Pro Ser Pro Val Val Thr Ser Gly Gly Arg Val Thr Leu Gln Cys
    130                 135                 140

Glu Ser Gln Val Ala Phe Gly Gly Phe Ile Leu Cys Lys Glu Gly Glu
145                 150                 155                 160

Glu Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
        195                 200                 205

Ser Pro Ser Asp Leu Leu Glu Leu Leu Val Pro Gly Val Ser Lys Lys
    210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
        275                 280                 285

Ser Tyr Gly Gly Gln Tyr Arg Cys Tyr Gly Ala His Asn Leu Ser Ser
    290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
        355                 360                 365

Arg Ser Ile His Glu Tyr Pro Lys Tyr Gln Ala Glu Phe Pro Met Ser
    370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu

-continued

```
                405                 410                 415

Val Val Ser Gly Pro Ser Met Gly Ser Ser Pro Pro Pro Thr Gly Pro
            420                 425                 430

Ile Ser Thr Pro Ala Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Val Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
        515                 520                 525

Glu Glu Asn Leu Tyr Ala Ala Val Lys Asp Thr Gln Pro Glu Asp Gly
    530                 535                 540

Val Glu Met Asp Thr Arg Ala Ala Ala Ser Glu Ala Pro Gln Asp Val
545                 550                 555                 560

Thr Tyr Ala Gln Leu His Ser Leu Thr Leu Arg Arg Lys Ala Thr Glu
                565                 570                 575

Pro Pro Pro Ser Gln Glu Arg Glu Pro Pro Ala Glu Pro Ser Ile Tyr
            580                 585                 590

Ala Thr Leu Ala Ile His
        595


<210> SEQ ID NO 108
<211> LENGTH: 577
<212> TYPE: PRT
<213> ORGANISM: Homo sapiens
<220> FEATURE:
<221> NAME/KEY: misc_feature
<222> LOCATION: (1)..(577)
<223> OTHER INFORMATION: Human mature ILT4, without signal peptide

<400> SEQUENCE: 108

Gln Thr Gly Thr Ile Pro Lys Pro Thr Leu Trp Ala Glu Pro Asp Ser
1               5                   10                  15

Val Ile Thr Gln Gly Ser Pro Val Thr Leu Ser Cys Gln Gly Ser Leu
            20                  25                  30

Glu Ala Gln Glu Tyr Arg Leu Tyr Arg Glu Lys Lys Ser Ala Ser Trp
        35                  40                  45

Ile Thr Arg Ile Arg Pro Glu Leu Val Lys Asn Gly Gln Phe His Ile
    50                  55                  60

Pro Ser Ile Thr Trp Glu His Thr Gly Arg Tyr Gly Cys Gln Tyr Tyr
65                  70                  75                  80

Ser Arg Ala Arg Trp Ser Glu Leu Ser Asp Pro Leu Val Leu Val Met
                85                  90                  95

Thr Gly Ala Tyr Pro Lys Pro Thr Leu Ser Ala Gln Pro Ser Pro Val
            100                 105                 110

Val Thr Ser Gly Gly Arg Val Thr Leu Gln Cys Glu Ser Gln Val Ala
        115                 120                 125

Phe Gly Gly Phe Ile Leu Cys Lys Glu Gly Glu Glu His Pro Gln
    130                 135                 140

Cys Leu Asn Ser Gln Pro His Ala Arg Gly Ser Ser Arg Ala Ile Phe
145                 150                 155                 160
```

-continued

```
Ser Val Gly Pro Val Ser Pro Asn Arg Arg Trp Ser His Arg Cys Tyr
                165                 170                 175

Gly Tyr Asp Leu Asn Ser Pro Tyr Val Trp Ser Ser Pro Ser Asp Leu
            180                 185                 190

Leu Glu Leu Leu Val Pro Gly Val Ser Lys Lys Pro Ser Leu Ser Val
        195                 200                 205

Gln Pro Gly Pro Val Val Ala Pro Gly Glu Ser Leu Thr Leu Gln Cys
    210                 215                 220

Val Ser Asp Val Gly Tyr Asp Arg Phe Val Leu Tyr Lys Glu Gly Glu
225                 230                 235                 240

Arg Asp Leu Arg Gln Leu Pro Gly Arg Gln Pro Gln Ala Gly Leu Ser
                245                 250                 255

Gln Ala Asn Phe Thr Leu Gly Pro Val Ser Arg Ser Tyr Gly Gly Gln
            260                 265                 270

Tyr Arg Cys Tyr Gly Ala His Asn Leu Ser Ser Glu Cys Ser Ala Pro
        275                 280                 285

Ser Asp Pro Leu Asp Ile Leu Ile Thr Gly Gln Ile Arg Gly Thr Pro
    290                 295                 300

Phe Ile Ser Val Gln Pro Gly Pro Thr Val Ala Ser Gly Glu Asn Val
305                 310                 315                 320

Thr Leu Leu Cys Gln Ser Trp Arg Gln Phe His Thr Phe Leu Leu Thr
                325                 330                 335

Lys Ala Gly Ala Ala Asp Ala Pro Leu Arg Leu Arg Ser Ile His Glu
            340                 345                 350

Tyr Pro Lys Tyr Gln Ala Glu Phe Pro Met Ser Pro Val Thr Ser Ala
        355                 360                 365

His Ala Gly Thr Tyr Arg Cys Tyr Gly Ser Leu Asn Ser Asp Pro Tyr
    370                 375                 380

Leu Leu Ser His Pro Ser Glu Pro Leu Glu Leu Val Val Ser Gly Pro
385                 390                 395                 400

Ser Met Gly Ser Ser Pro Pro Pro Thr Gly Pro Ile Ser Thr Pro Ala
                405                 410                 415

Gly Pro Glu Asp Gln Pro Leu Thr Pro Thr Gly Ser Asp Pro Gln Ser
            420                 425                 430

Gly Leu Gly Arg His Leu Gly Val Val Ile Gly Ile Leu Val Ala Val
        435                 440                 445

Val Leu Leu Leu Leu Leu Leu Leu Leu Leu Phe Leu Ile Leu Arg His
    450                 455                 460

Arg Arg Gln Gly Lys His Trp Thr Ser Thr Gln Arg Lys Ala Asp Phe
465                 470                 475                 480

Gln His Pro Ala Gly Ala Val Gly Pro Glu Pro Thr Asp Arg Gly Leu
                485                 490                 495

Gln Trp Arg Ser Ser Pro Ala Ala Asp Ala Gln Glu Glu Asn Leu Tyr
            500                 505                 510

Ala Ala Val Lys Asp Thr Gln Pro Glu Asp Gly Val Glu Met Asp Thr
        515                 520                 525

Arg Ala Ala Ala Ser Glu Ala Pro Gln Asp Val Thr Tyr Ala Gln Leu
    530                 535                 540

His Ser Leu Thr Leu Arg Arg Lys Ala Thr Glu Pro Pro Pro Ser Gln
545                 550                 555                 560

Glu Arg Glu Pro Pro Ala Glu Pro Ser Ile Tyr Ala Thr Leu Ala Ile
                565                 570                 575
```

His

<210> SEQ ID NO 109
<211> LENGTH: 438
<212> TYPE: PRT
<213> ORGANISM: Homo sapiens
<220> FEATURE:
<221> NAME/KEY: misc_feature
<222> LOCATION: (1)..(438)
<223> OTHER INFORMATION: Human ILT4 ECD region

<400> SEQUENCE: 109

Gly Thr Ile Pro Lys Pro Thr Leu Trp Ala Glu Pro Asp Ser Val Ile
1               5                   10                  15

Thr Gln Gly Ser Pro Val Thr Leu Ser Cys Gln Gly Ser Leu Glu Ala
            20                  25                  30

Gln Glu Tyr Arg Leu Tyr Arg Glu Lys Lys Ser Ala Ser Trp Ile Thr
        35                  40                  45

Arg Ile Arg Pro Glu Leu Val Lys Asn Gly Gln Phe His Ile Pro Ser
    50                  55                  60

Ile Thr Trp Glu His Thr Gly Arg Tyr Gly Cys Gln Tyr Tyr Ser Arg
65                  70                  75                  80

Ala Arg Trp Ser Glu Leu Ser Asp Pro Leu Val Leu Val Met Thr Gly
                85                  90                  95

Ala Tyr Pro Lys Pro Thr Leu Ser Ala Gln Pro Ser Pro Val Val Thr
            100                 105                 110

Ser Gly Gly Arg Val Thr Leu Gln Cys Glu Ser Gln Val Ala Phe Gly
        115                 120                 125

Gly Phe Ile Leu Cys Lys Glu Gly Glu Glu Glu His Pro Gln Cys Leu
    130                 135                 140

Asn Ser Gln Pro His Ala Arg Gly Ser Ser Arg Ala Ile Phe Ser Val
145                 150                 155                 160

Gly Pro Val Ser Pro Asn Arg Arg Trp Ser His Arg Cys Tyr Gly Tyr
                165                 170                 175

Asp Leu Asn Ser Pro Tyr Val Trp Ser Ser Pro Ser Asp Leu Leu Glu
            180                 185                 190

Leu Leu Val Pro Gly Val Ser Lys Lys Pro Ser Leu Ser Val Gln Pro
        195                 200                 205

Gly Pro Val Val Ala Pro Gly Glu Ser Leu Thr Leu Gln Cys Val Ser
    210                 215                 220

Asp Val Gly Tyr Asp Arg Phe Val Leu Tyr Lys Glu Gly Glu Arg Asp
225                 230                 235                 240

Leu Arg Gln Leu Pro Gly Arg Gln Pro Gln Ala Gly Leu Ser Gln Ala
                245                 250                 255

Asn Phe Thr Leu Gly Pro Val Ser Arg Ser Tyr Gly Gly Gln Tyr Arg
            260                 265                 270

Cys Tyr Gly Ala His Asn Leu Ser Ser Glu Cys Ser Ala Pro Ser Asp
        275                 280                 285

Pro Leu Asp Ile Leu Ile Thr Gly Gln Ile Arg Gly Thr Pro Phe Ile
    290                 295                 300

Ser Val Gln Pro Gly Pro Thr Val Ala Ser Gly Glu Asn Val Thr Leu
305                 310                 315                 320

Leu Cys Gln Ser Trp Arg Gln Phe His Thr Phe Leu Leu Thr Lys Ala
                325                 330                 335

Gly Ala Ala Asp Ala Pro Leu Arg Leu Arg Ser Ile His Glu Tyr Pro
            340                 345                 350

Lys Tyr Gln Ala Glu Phe Pro Met Ser Pro Val Thr Ser Ala His Ala
355 360 365

Gly Thr Tyr Arg Cys Tyr Gly Ser Leu Asn Ser Asp Pro Tyr Leu Leu
370 375 380

Ser His Pro Ser Glu Pro Leu Glu Leu Val Val Ser Gly Pro Ser Met
385 390 395 400

Gly Ser Ser Pro Pro Pro Thr Gly Pro Ile Ser Thr Pro Ala Gly Pro
405 410 415

Glu Asp Gln Pro Leu Thr Pro Thr Gly Ser Asp Pro Gln Ser Gly Leu
420 425 430

Gly Arg His Leu Gly Val
435

<210> SEQ ID NO 110
<211> LENGTH: 597
<212> TYPE: PRT
<213> ORGANISM: Homo sapiens
<220> FEATURE:
<221> NAME/KEY: misc_feature
<222> LOCATION: (1)..(597)
<223> OTHER INFORMATION: Human ILT4 precursor, with signal peptide, isoform 2

<400> SEQUENCE: 110

Met Thr Pro Ile Val Thr Val Leu Ile Cys Leu Gly Leu Ser Leu Gly
1 5 10 15

Pro Arg Thr His Val Gln Thr Gly Thr Ile Pro Lys Pro Thr Leu Trp
20 25 30

Ala Glu Pro Asp Ser Val Ile Thr Gln Gly Ser Pro Val Thr Leu Ser
35 40 45

Cys Gln Gly Ser Leu Glu Ala Gln Glu Tyr Arg Leu Tyr Arg Glu Lys
50 55 60

Lys Ser Ala Ser Trp Ile Thr Arg Ile Arg Pro Glu Leu Val Lys Asn
65 70 75 80

Gly Gln Phe His Ile Pro Ser Ile Thr Trp Glu His Thr Gly Arg Tyr
85 90 95

Gly Cys Gln Tyr Tyr Ser Arg Ala Arg Trp Ser Glu Leu Ser Asp Pro
100 105 110

Leu Val Leu Val Met Thr Gly Ala Tyr Pro Lys Pro Thr Leu Ser Ala
115 120 125

Gln Pro Ser Pro Val Val Thr Ser Gly Gly Arg Val Thr Leu Gln Cys
130 135 140

Glu Ser Gln Val Ala Phe Gly Gly Phe Ile Leu Cys Lys Glu Gly Glu
145 150 155 160

Glu Glu His Pro Gln Cys Leu Asn Ser Gln Pro His Ala Arg Gly Ser
165 170 175

Ser Arg Ala Ile Phe Ser Val Gly Pro Val Ser Pro Asn Arg Arg Trp
180 185 190

Ser His Arg Cys Tyr Gly Tyr Asp Leu Asn Ser Pro Tyr Val Trp Ser
195 200 205

Ser Pro Ser Asp Leu Leu Glu Leu Leu Val Pro Gly Val Ser Lys Lys
210 215 220

Pro Ser Leu Ser Val Gln Pro Gly Pro Val Val Ala Pro Gly Glu Ser
225 230 235 240

Leu Thr Leu Gln Cys Val Ser Asp Val Gly Tyr Asp Arg Phe Val Leu
245 250 255

```
Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
        275                 280                 285

Ser Tyr Gly Gly Gln Tyr Arg Cys Tyr Gly Ala His Asn Leu Ser Ser
    290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
        355                 360                 365

Arg Ser Ile His Glu Tyr Pro Lys Tyr Gln Ala Glu Phe Pro Met Ser
    370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415

Val Val Ser Gly Pro Ser Met Gly Ser Ser Pro Pro Pro Thr Gly Pro
            420                 425                 430

Ile Ser Thr Pro Gly Pro Glu Asp Gln Pro Leu Thr Pro Thr Gly Ser
        435                 440                 445

Asp Pro Gln Ser Gly Leu Gly Arg His Leu Gly Val Val Ile Gly Ile
    450                 455                 460

Leu Val Ala Val Val Leu Leu Leu Leu Leu Leu Leu Leu Leu Phe Leu
465                 470                 475                 480

Ile Leu Arg His Arg Arg Gln Gly Lys His Trp Thr Ser Thr Gln Arg
                485                 490                 495

Lys Ala Asp Phe Gln His Pro Ala Gly Ala Val Gly Pro Glu Pro Thr
            500                 505                 510

Asp Arg Gly Leu Gln Trp Arg Ser Ser Pro Ala Ala Asp Ala Gln Glu
        515                 520                 525

Glu Asn Leu Tyr Ala Ala Val Lys Asp Thr Gln Pro Glu Asp Gly Val
    530                 535                 540

Glu Met Asp Thr Arg Ala Ala Ala Ser Glu Ala Pro Gln Asp Val Thr
545                 550                 555                 560

Tyr Ala Gln Leu His Ser Leu Thr Leu Arg Arg Lys Ala Thr Glu Pro
                565                 570                 575

Pro Pro Ser Gln Glu Arg Glu Pro Pro Ala Glu Pro Ser Ile Tyr Ala
            580                 585                 590

Thr Leu Ala Ile His
        595
```

<210> SEQ ID NO 111
<211> LENGTH: 576
<212> TYPE: PRT
<213> ORGANISM: Homo sapiens
<220> FEATURE:
<221> NAME/KEY: misc_feature
<222> LOCATION: (1)..(576)
<223> OTHER INFORMATION: Human mature ILT4, isoform 2, without signal peptide

<400> SEQUENCE: 111

```
Gln Thr Gly Thr Ile Pro Lys Pro Thr Leu Trp Ala Glu Pro Asp Ser
1               5                   10                  15

Val Ile Thr Gln Gly Ser Pro Val Thr Leu Ser Cys Gln Gly Ser Leu
            20                  25                  30

Glu Ala Gln Glu Tyr Arg Leu Tyr Arg Glu Lys Lys Ser Ala Ser Trp
        35                  40                  45

Ile Thr Arg Ile Arg Pro Glu Leu Val Lys Asn Gly Gln Phe His Ile
    50                  55                  60

Pro Ser Ile Thr Trp Glu His Thr Gly Arg Tyr Gly Cys Gln Tyr Tyr
65                  70                  75                  80

Ser Arg Ala Arg Trp Ser Glu Leu Ser Asp Pro Leu Val Leu Val Met
                85                  90                  95

Thr Gly Ala Tyr Pro Lys Pro Thr Leu Ser Ala Gln Pro Ser Pro Val
            100                 105                 110

Val Thr Ser Gly Gly Arg Val Thr Leu Gln Cys Glu Ser Gln Val Ala
        115                 120                 125

Phe Gly Gly Phe Ile Leu Cys Lys Glu Gly Glu Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Asn Arg Arg Trp Ser His Arg Cys Tyr
                165                 170                 175

Gly Tyr Asp Leu Asn Ser Pro Tyr Val Trp Ser Ser Pro Ser Asp Leu
            180                 185                 190

Leu Glu Leu Leu Val Pro Gly Val Ser Lys Lys Pro Ser Leu Ser Val
        195                 200                 205

Gln Pro Gly Pro Val Val Ala Pro Gly Glu Ser Leu Thr Leu Gln Cys
    210                 215                 220

Val Ser Asp Val Gly Tyr Asp Arg Phe Val Leu Tyr Lys Glu Gly Glu
225                 230                 235                 240

Arg Asp Leu Arg Gln Leu Pro Gly Arg Gln Pro Gln Ala Gly Leu Ser
                245                 250                 255

Gln Ala Asn Phe Thr Leu Gly Pro Val Ser Arg Ser Tyr Gly Gly Gln
            260                 265                 270

Tyr Arg Cys Tyr Gly Ala His Asn Leu Ser Ser Glu Cys Ser Ala Pro
        275                 280                 285

Ser Asp Pro Leu Asp Ile Leu Ile Thr Gly Gln Ile Arg Gly Thr Pro
    290                 295                 300

Phe Ile Ser Val Gln Pro Gly Pro Thr Val Ala Ser Gly Glu Asn Val
305                 310                 315                 320

Thr Leu Leu Cys Gln Ser Trp Arg Gln Phe His Thr Phe Leu Leu Thr
                325                 330                 335

Lys Ala Gly Ala Ala Asp Ala Pro Leu Arg Leu Arg Ser Ile His Glu
            340                 345                 350

Tyr Pro Lys Tyr Gln Ala Glu Phe Pro Met Ser Pro Val Thr Ser Ala
        355                 360                 365

His Ala Gly Thr Tyr Arg Cys Tyr Gly Ser Leu Asn Ser Asp Pro Tyr
    370                 375                 380

Leu Leu Ser His Pro Ser Glu Pro Leu Glu Leu Val Val Ser Gly Pro
385                 390                 395                 400

Ser Met Gly Ser Ser Pro Pro Pro Thr Gly Pro Ile Ser Thr Pro Gly
                405                 410                 415
```

```
Pro Glu Asp Gln Pro Leu Thr Pro Thr Gly Ser Asp Pro Gln Ser Gly
            420                 425                 430

Leu Gly Arg His Leu Gly Val Val Ile Gly Ile Leu Val Ala Val Val
        435                 440                 445

Leu Leu Leu Leu Leu Leu Leu Leu Leu Phe Leu Ile Leu Arg His Arg
    450                 455                 460

Arg Gln Gly Lys His Trp Thr Ser Thr Gln Arg Lys Ala Asp Phe Gln
465                 470                 475                 480

His Pro Ala Gly Ala Val Gly Pro Glu Pro Thr Asp Arg Gly Leu Gln
                485                 490                 495

Trp Arg Ser Ser Pro Ala Ala Asp Ala Gln Glu Glu Asn Leu Tyr Ala
            500                 505                 510

Ala Val Lys Asp Thr Gln Pro Glu Asp Gly Val Glu Met Asp Thr Arg
        515                 520                 525

Ala Ala Ala Ser Glu Ala Pro Gln Asp Val Thr Tyr Ala Gln Leu His
    530                 535                 540

Ser Leu Thr Leu Arg Arg Lys Ala Thr Glu Pro Pro Pro Ser Gln Glu
545                 550                 555                 560

Arg Glu Pro Pro Ala Glu Pro Ser Ile Tyr Ala Thr Leu Ala Ile His
                565                 570                 575


<210> SEQ ID NO 112
<211> LENGTH: 437
<212> TYPE: PRT
<213> ORGANISM: Homo sapiens
<220> FEATURE:
<221> NAME/KEY: misc_feature
<222> LOCATION: (1)..(437)
<223> OTHER INFORMATION: Human ILT4 isoform 2, ECD

<400> SEQUENCE: 112

Gly Thr Ile Pro Lys Pro Thr Leu Trp Ala Glu Pro Asp Ser Val Ile
1               5                   10                  15

Thr Gln Gly Ser Pro Val Thr Leu Ser Cys Gln Gly Ser Leu Glu Ala
            20                  25                  30

Gln Glu Tyr Arg Leu Tyr Arg Glu Lys Lys Ser Ala Ser Trp Ile Thr
        35                  40                  45

Arg Ile Arg Pro Glu Leu Val Lys Asn Gly Gln Phe His Ile Pro Ser
    50                  55                  60

Ile Thr Trp Glu His Thr Gly Arg Tyr Gly Cys Gln Tyr Tyr Ser Arg
65                  70                  75                  80

Ala Arg Trp Ser Glu Leu Ser Asp Pro Leu Val Leu Val Met Thr Gly
                85                  90                  95

Ala Tyr Pro Lys Pro Thr Leu Ser Ala Gln Pro Ser Pro Val Val Thr
            100                 105                 110

Ser Gly Gly Arg Val Thr Leu Gln Cys Glu Ser Gln Val Ala Phe Gly
        115                 120                 125

Gly Phe Ile Leu Cys Lys Glu Gly Glu Glu Glu His Pro Gln Cys Leu
    130                 135                 140

Asn Ser Gln Pro His Ala Arg Gly Ser Ser Arg Ala Ile Phe Ser Val
145                 150                 155                 160

Gly Pro Val Ser Pro Asn Arg Arg Trp Ser His Arg Cys Tyr Gly Tyr
                165                 170                 175

Asp Leu Asn Ser Pro Tyr Val Trp Ser Ser Pro Ser Asp Leu Leu Glu
            180                 185                 190

Leu Leu Val Pro Gly Val Ser Lys Lys Pro Ser Leu Ser Val Gln Pro
```

195 200 205

Gly Pro Val Val Ala Pro Gly Glu Ser Leu Thr Leu Gln Cys Val Ser
210 215 220

Asp Val Gly Tyr Asp Arg Phe Val Leu Tyr Lys Glu Gly Glu Arg Asp
225 230 235 240

Leu Arg Gln Leu Pro Gly Arg Gln Pro Gln Ala Gly Leu Ser Gln Ala
245 250 255

Asn Phe Thr Leu Gly Pro Val Ser Arg Ser Tyr Gly Gly Gln Tyr Arg
260 265 270

Cys Tyr Gly Ala His Asn Leu Ser Ser Glu Cys Ser Ala Pro Ser Asp
275 280 285

Pro Leu Asp Ile Leu Ile Thr Gly Gln Ile Arg Gly Thr Pro Phe Ile
290 295 300

Ser Val Gln Pro Gly Pro Thr Val Ala Ser Gly Glu Asn Val Thr Leu
305 310 315 320

Leu Cys Gln Ser Trp Arg Gln Phe His Thr Phe Leu Leu Thr Lys Ala
325 330 335

Gly Ala Ala Asp Ala Pro Leu Arg Leu Arg Ser Ile His Glu Tyr Pro
340 345 350

Lys Tyr Gln Ala Glu Phe Pro Met Ser Pro Val Thr Ser Ala His Ala
355 360 365

Gly Thr Tyr Arg Cys Tyr Gly Ser Leu Asn Ser Asp Pro Tyr Leu Leu
370 375 380

Ser His Pro Ser Glu Pro Leu Glu Leu Val Val Ser Gly Pro Ser Met
385 390 395 400

Gly Ser Ser Pro Pro Pro Thr Gly Pro Ile Ser Thr Pro Gly Pro Glu
405 410 415

Asp Gln Pro Leu Thr Pro Thr Gly Ser Asp Pro Gln Ser Gly Leu Gly
420 425 430

Arg His Leu Gly Val
435

<210> SEQ ID NO 113
<211> LENGTH: 454
<212> TYPE: PRT
<213> ORGANISM: Artificial Sequence
<220> FEATURE:
<223> OTHER INFORMATION: Synthetic: 21D9.IgG1.3 HC

<400> SEQUENCE: 113

Glu Gly Gln Leu Leu Glu Ser Gly Gly Asp Leu Val Gln Pro Gly Gly
1 5 10 15

Ser Leu Arg Leu Ser Cys Ala Thr Ser Gly Phe Thr Phe Ser Asn Tyr
20 25 30

Ala Met Asn Trp Val Arg Gln Ala Pro Gly Lys Gly Leu Glu Trp Ile
35 40 45

Ser Val Ile Ser Val Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Tyr Tyr Tyr Asp Ser Gly Ser Tyr Tyr Asp Ser Phe Phe
100 105 110

Asp Tyr Trp Gly Gln Gly Thr Leu Val Thr Val Ser Ser Ala Ser Thr

```
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450


<210> SEQ ID NO 114
<211> LENGTH: 107
<212> TYPE: PRT
<213> ORGANISM: Artificial Sequence
<220> FEATURE:
<223> OTHER INFORMATION: Synthetic: 10F10.4 VL

<400> SEQUENCE: 114

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
```

```
            20                  25                  30

Leu Ala Trp Phe Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys
            100                 105
```

<210> SEQ ID NO 115
<211> LENGTH: 321
<212> TYPE: DNA
<213> ORGANISM: Artificial Sequence
<220> FEATURE:
<223> OTHER INFORMATION: Synthetic: 10F10.4 VL DNA

<400> SEQUENCE: 115

```
gccatccagc tgacccagag ccctagctcc ctgtctgcca gcgtgggcga cagggtgacc      60

atcacatgca gagcctccca gggaatctct agcgccctgg cctggttcca gcagaagcca     120

ggcaaggccc ctaagctgct gatctacgat gcctcctctc tggagtccgg cgtgccctct     180

aggttctccg gctctggcag cggcaccgac tttaccctga caatcagctc cctgcagcca     240

gaggattttg ccacatacta ttgtcagcag ttcaactctt atcccatcac ctttggccag     300

ggcacacggc tggagatcaa g                                               321
```

<210> SEQ ID NO 116
<211> LENGTH: 214
<212> TYPE: PRT
<213> ORGANISM: Artificial Sequence
<220> FEATURE:
<223> OTHER INFORMATION: Synthetic: 10F10.4 LC

<400> SEQUENCE: 116

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Phe Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 117
<211> LENGTH: 642
<212> TYPE: DNA
<213> ORGANISM: Artificial Sequence
<220> FEATURE:
<223> OTHER INFORMATION: Synthetic: 10F10.4 LC DNA

<400> SEQUENCE: 117
gccatccagc tgacccagag ccctagctcc ctgtctgcca gcgtgggcga cagggtgacc 60
atcacatgca gagcctccca gggaatctct agcgccctgg cctggttcca gcagaagcca 120
ggcaaggccc ctaagctgct gatctacgat gcctcctctc tggagtccgg cgtgccctct 180
aggttctccg gctctggcag cggcaccgac tttaccctga caatcagctc cctgcagcca 240
gaggattttg ccacatacta ttgtcagcag ttcaactctt atcccatcac ctttggccag 300
ggcacacggc tggagatcaa gcgtacggtg gccgccccgt ccgtgtttat cttccctcca 360
tcggacgagc agctcaagtc cggtaccgcg agcgtggtct gcctgctgaa caatttctac 420
ccgcgcgaag ctaaagtgca atggaaggtc gataacgcac ttcagtccgg gaacagccag 480
gaatctgtga ccgagcagga ctccaaggat tcgacctatt ccctgtcctc gactctcacc 540
ctgtcaaagg ccgactacga gaagcacaag gtctacgcct gcgaagtgac ccatcagggc 600
ttgtcctcac ccgtgactaa gagcttcaac cggggagagt gt 642

<210> SEQ ID NO 118
<211> LENGTH: 371
<212> TYPE: PRT
<213> ORGANISM: Artificial Sequence
<220> FEATURE:
<223> OTHER INFORMATION: Synthetic: Cyno ILT4 9152 extracellular domain, including His-Avi Tag

<400> SEQUENCE: 118

Gln Ala Gly Ile Leu Pro Lys Pro Met Leu Trp Ala Glu Pro Asp Arg
1 5 10 15

Val Ile Thr Gln Gly Ser Pro Val Thr Leu Arg Cys Gln Gly Asn Leu
20 25 30

Glu Ala Arg Gly Tyr His Leu Tyr Arg Glu Arg Lys Ser Ala Ser Trp
35 40 45

Ile Thr Leu Ile Arg Pro Glu Leu Val Lys Lys Gly Gln Phe Pro Ile
50 55 60

Pro Ser Ile Thr Trp Glu Asp Ala Gly Arg Tyr Arg Cys Gln Tyr Tyr
65 70 75 80

Ser His Ser Trp Trp Ser Glu His Ser Asp Pro Leu Glu Leu Val Val
85 90 95

Thr Gly Ala Tyr Arg Lys Pro Thr Leu Ser Ala Leu Pro Ser Pro Val
100 105 110

Val Ala Ser Gly Gly Asn Val Thr Leu Gln Cys Asp Ser Arg Val Ala
115 120 125

Leu Asp Gly Phe Ile Leu Cys Lys Glu Gly Glu Asp Glu His Ser Gln
    130                 135                 140

Arg Leu Asn Ser Gln Pro Arg Thr Arg Gly Ser Ser Arg Ala Val Phe
145                 150                 155                 160

Ser Val Gly Pro Val Ser Pro Ser Arg Arg Trp Ser Tyr Arg Cys Tyr
                165                 170                 175

Gly Tyr Glu Leu His Ser Arg Tyr Val Trp Ser Leu Pro Ser Asp Leu
            180                 185                 190

Leu Glu Leu Leu Val Pro Gly Val Ser Lys Lys Pro Ser Leu Ser Val
        195                 200                 205

Gln Pro Gly Pro Val Val Ala Gly Gly Asp Lys Leu Thr Leu Gln Cys
    210                 215                 220

Gly Ser Asp Ala Gly Tyr Asp Arg Phe Ala Leu Tyr Lys Glu Gly Glu
225                 230                 235                 240

Arg Asp Phe Leu Gln Arg Pro Gly Gln Gln Leu Gln Ala Gly Leu Ala
                245                 250                 255

Gln Ala Asn Phe Thr Leu Asp Pro Val Arg Gly Ser His Gly Gly Gln
            260                 265                 270

Tyr Arg Cys Tyr Gly Ala His Asn Leu Ser Ser Glu Trp Ser Ala Pro
        275                 280                 285

Ser Asp Pro Leu Asp Ile Leu Ile Ser Ala Gly Pro His Ser Gly Leu
    290                 295                 300

Arg Arg Glu Cys Asp Pro Ala Val Ser Val Thr Gly Met Asp Gly His
305                 310                 315                 320

Phe Leu Ser Asp Gln Gly Gly Ser Ser Ser Pro Gly Gly Gly Ser Gly
                325                 330                 335

Gly Gly Ser Glu Gln Lys Leu Ile Ser Glu Glu Asp Leu Gly His His
            340                 345                 350

His His His His Gly Leu Asn Asp Ile Phe Glu Ala Gln Lys Ile Glu
        355                 360                 365

Trp His Glu
    370

<210> SEQ ID NO 119
<211> LENGTH: 481
<212> TYPE: PRT
<213> ORGANISM: Artificial Sequence
<220> FEATURE:
<223> OTHER INFORMATION: Synthetic: hILT4H extracellular domain plus
      HIS-Avi tag (used in Example 2)

<400> SEQUENCE: 119

Gln Thr Gly Thr Ile Pro Lys Pro Thr Leu Trp Ala Glu Pro Asp Ser
1               5                   10                  15

Val Ile Thr Gln Gly Ser Pro Val Thr Leu Ser Cys Gln Gly Ser Leu
            20                  25                  30

Glu Ala Gln Glu Tyr Arg Leu Tyr Arg Glu Lys Lys Ser Ala Ser Trp
        35                  40                  45

Ile Thr Arg Ile Arg Pro Glu Leu Val Lys Asn Gly Gln Phe His Ile
    50                  55                  60

Pro Ser Ile Thr Trp Glu His Thr Gly Arg Tyr Gly Cys Gln Tyr Tyr
65                  70                  75                  80

Ser Arg Ala Arg Trp Ser Glu Leu Ser Asp Pro Leu Val Leu Val Met
                85                  90                  95

Thr Gly Ala Tyr Pro Lys Pro Thr Leu Ser Ala Gln Pro Ser Pro Val
            100                 105                 110

```
Val Thr Ser Gly Gly Arg Val Thr Leu Gln Cys Glu Ser Gln Val Ala
        115                 120                 125

Phe Gly Gly Phe Ile Leu Cys Lys Glu Gly Glu Glu Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Asn Arg Arg Trp Ser His Arg Cys Tyr
                165                 170                 175

Gly Tyr Asp Leu Asn Ser Pro Tyr Val Trp Ser Ser Pro Ser Asp Leu
            180                 185                 190

Leu Glu Leu Leu Val Pro Gly Val Ser Lys Lys Pro Ser Leu Ser Val
        195                 200                 205

Gln Pro Gly Pro Val Val Ala Pro Gly Glu Ser Leu Thr Leu Gln Cys
    210                 215                 220

Val Ser Asp Val Gly Tyr Asp Arg Phe Val Leu Tyr Lys Glu Gly Glu
225                 230                 235                 240

Arg Asp Leu Arg Gln Leu Pro Gly Arg Gln Pro Gln Ala Gly Leu Ser
                245                 250                 255

Gln Ala Asn Phe Thr Leu Gly Pro Val Ser Arg Ser Tyr Gly Gly Gln
            260                 265                 270

Tyr Arg Cys Tyr Gly Ala His Asn Leu Ser Ser Glu Ser Ser Ala Pro
        275                 280                 285

Ser Asp Pro Leu Asp Ile Leu Ile Thr Gly Gln Ile Arg Gly Thr Pro
    290                 295                 300

Phe Ile Ser Val Gln Pro Gly Pro Thr Val Ala Ser Gly Glu Asn Val
305                 310                 315                 320

Thr Leu Leu Cys Gln Ser Trp Arg Gln Phe His Thr Phe Leu Leu Thr
                325                 330                 335

Lys Ala Gly Ala Ala Asp Ala Pro Leu Arg Leu Arg Ser Ile His Glu
            340                 345                 350

Tyr Pro Lys Tyr Gln Ala Glu Phe Pro Met Ser Pro Val Thr Ser Ala
        355                 360                 365

His Ala Gly Thr Tyr Arg Cys Tyr Gly Ser Leu Asn Ser Asp Pro Tyr
    370                 375                 380

Leu Leu Ser His Pro Ser Glu Pro Leu Glu Leu Val Val Ser Gly Pro
385                 390                 395                 400

Ser Met Gly Ser Ser Pro Pro Pro Thr Gly Pro Ile Ser Thr Pro Ala
                405                 410                 415

Gly Pro Glu Asp Gln Pro Leu Thr Pro Thr Gly Ser Asp Pro Gln Ser
            420                 425                 430

Gly Leu Gly Arg His Leu Gly Ser Pro Gly Gly Gly Ser Gly Gly Gly
        435                 440                 445

Ser Glu Gln Lys Leu Ile Ser Glu Glu Asp Leu Gly His His His His
    450                 455                 460

His His Gly Leu Asn Asp Ile Phe Glu Ala Gln Lys Ile Glu Trp His
465                 470                 475                 480

Glu
```

<210> SEQ ID NO 120
<211> LENGTH: 8
<212> TYPE: PRT
<213> ORGANISM: Artificial Sequence
<220> FEATURE:
<223> OTHER INFORMATION: Synthetic: Residues 70-77 of hILT4

<400> SEQUENCE: 120

Ile Thr Arg Ile Arg Pro Glu Leu
1 5

<210> SEQ ID NO 121
<211> LENGTH: 23
<212> TYPE: PRT
<213> ORGANISM: Artificial Sequence
<220> FEATURE:
<223> OTHER INFORMATION: Synthetic: Residues 78-100 of hILT4

<400> SEQUENCE: 121

Val Lys Asn Gly Gln Phe His Ile Pro Ser Ile Thr Trp Glu His Thr
1 5 10 15

Gly Arg Tyr Gly Cys Gln Tyr
20

<210> SEQ ID NO 122
<211> LENGTH: 31
<212> TYPE: PRT
<213> ORGANISM: Artificial Sequence
<220> FEATURE:
<223> OTHER INFORMATION: Synthetic: Residues 70-100 of hILT4

<400> SEQUENCE: 122

Ile Thr Arg Ile Arg Pro Glu Leu Val Lys Asn Gly Gln Phe His Ile
1 5 10 15

Pro Ser Ile Thr Trp Glu His Thr Gly Arg Tyr Gly Cys Gln Tyr
20 25 30

<210> SEQ ID NO 123
<211> LENGTH: 28
<212> TYPE: PRT
<213> ORGANISM: Artificial Sequence
<220> FEATURE:
<223> OTHER INFORMATION: Synthetic: Residues 154 to 181 of hILT4

<400> SEQUENCE: 123

Ile Leu Cys Lys Glu Gly Glu Glu Glu His Pro Gln Cys Leu Asn Ser
1 5 10 15

Gln Pro His Ala Arg Gly Ser Ser Arg Ala Ile Phe
20 25

<210> SEQ ID NO 124
<211> LENGTH: 10
<212> TYPE: PRT
<213> ORGANISM: Artificial Sequence
<220> FEATURE:
<223> OTHER INFORMATION: Synthetic: Residues 425 to 434 of hILT4

<400> SEQUENCE: 124

Ser Ser Pro Pro Pro Thr Gly Pro Ile Ser
1 5 10

<210> SEQ ID NO 125
<211> LENGTH: 5
<212> TYPE: PRT
<213> ORGANISM: Artificial Sequence
<220> FEATURE:
<223> OTHER INFORMATION: Synthetic: 9G4 (ILT4.1) VH CDR1

<400> SEQUENCE: 125

Ser Tyr Tyr Trp Asn
1 5

<210> SEQ ID NO 126
<211> LENGTH: 16
<212> TYPE: PRT
<213> ORGANISM: Artificial Sequence
<220> FEATURE:
<223> OTHER INFORMATION: Synthetic: 9G4 VH CDR2

<400> SEQUENCE: 126

Tyr Ile Tyr Tyr Ser Gly Ser Thr Lys Tyr Asn Pro Ser Leu Lys Ser
1 5 10 15

<210> SEQ ID NO 127
<211> LENGTH: 8
<212> TYPE: PRT
<213> ORGANISM: Artificial Sequence
<220> FEATURE:
<223> OTHER INFORMATION: Synthetic: 9G4 VH CDR3

<400> SEQUENCE: 127

Ser Gly Trp Tyr Tyr Phe Asp Tyr
1 5

<210> SEQ ID NO 128
<211> LENGTH: 11
<212> TYPE: PRT
<213> ORGANISM: Artificial Sequence
<220> FEATURE:
<223> OTHER INFORMATION: Synthetic: 9G4 VL CDR1

<400> SEQUENCE: 128

Arg Ala Ser Gln Ser Val Ser Ser Tyr Leu Ala
1 5 10

<210> SEQ ID NO 129
<211> LENGTH: 7
<212> TYPE: PRT
<213> ORGANISM: Artificial Sequence
<220> FEATURE:
<223> OTHER INFORMATION: Synthetic: 9G4 VL CDR2

<400> SEQUENCE: 129

Asp Ala Ser Asn Arg Ala Thr
1 5

<210> SEQ ID NO 130
<211> LENGTH: 9
<212> TYPE: PRT
<213> ORGANISM: Artificial Sequence
<220> FEATURE:
<223> OTHER INFORMATION: Synthetic: 9G4 VL CDR3

<400> SEQUENCE: 130

Gln Gln Arg Ser Tyr Trp Pro Trp Thr
1 5

<210> SEQ ID NO 131
<211> LENGTH: 5
<212> TYPE: PRT
<213> ORGANISM: Artificial Sequence
<220> FEATURE:
<223> OTHER INFORMATION: Synthetic: 9C8 VH CDR1

<400> SEQUENCE: 131

Ser Ser Asp Ile Asn
1 5

<210> SEQ ID NO 132
<211> LENGTH: 17
<212> TYPE: PRT
<213> ORGANISM: Artificial Sequence
<220> FEATURE:
<223> OTHER INFORMATION: Synthetic: 9C8 VH CDR2

<400> SEQUENCE: 132

```
Trp Met Asn Pro Asn Ser Gly His Thr Gly Tyr Ala Gln Lys Phe Gln
1               5                   10                  15

Asp
```

<210> SEQ ID NO 133
<211> LENGTH: 16
<212> TYPE: PRT
<213> ORGANISM: Artificial Sequence
<220> FEATURE:
<223> OTHER INFORMATION: Synthetic: 9C8 VH CDR3

<400> SEQUENCE: 133

```
Gly Gly Asn Ser Ile Asp Trp Gly Phe Ser Tyr Tyr Gly Leu Asp Val
1               5                   10                  15
```

<210> SEQ ID NO 134
<211> LENGTH: 11
<212> TYPE: PRT
<213> ORGANISM: Artificial Sequence
<220> FEATURE:
<223> OTHER INFORMATION: Synthetic: 9C8 VL CDR1

<400> SEQUENCE: 134

```
Arg Ala Ser Gln Gly Ile Ser Ser Ala Leu Ala
1               5                   10
```

<210> SEQ ID NO 135
<211> LENGTH: 7
<212> TYPE: PRT
<213> ORGANISM: Artificial Sequence
<220> FEATURE:
<223> OTHER INFORMATION: Synthetic: 9C8 VL CDR2

<400> SEQUENCE: 135

```
Asp Ala Ser Ser Leu Glu Ser
1               5
```

<210> SEQ ID NO 136
<211> LENGTH: 9
<212> TYPE: PRT
<213> ORGANISM: Artificial Sequence
<220> FEATURE:
<223> OTHER INFORMATION: Synthetic: 9C8 VL CDR3

<400> SEQUENCE: 136

```
Gln Gln Phe Asn Ser Tyr Pro Phe Thr
1               5
```

<210> SEQ ID NO 137
<211> LENGTH: 5
<212> TYPE: PRT
<213> ORGANISM: Artificial Sequence
<220> FEATURE:
<223> OTHER INFORMATION: Synthetic: 2H2 VH CDR1

<400> SEQUENCE: 137

```
Asn Tyr Ala Ile Ser
1               5
```

<210> SEQ ID NO 138
<211> LENGTH: 17
<212> TYPE: PRT
<213> ORGANISM: Artificial Sequence
<220> FEATURE:
<223> OTHER INFORMATION: Synthetic: 2H2 VH CDR2

<400> SEQUENCE: 138

Gly Ile Ile Pro Ile Leu Ala Thr Ala Asn Tyr Ala Pro Lys Phe Gln
1 5 10 15

Gly

<210> SEQ ID NO 139
<211> LENGTH: 19
<212> TYPE: PRT
<213> ORGANISM: Artificial Sequence
<220> FEATURE:
<223> OTHER INFORMATION: Synthetic: 2H2 VH CDR3

<400> SEQUENCE: 139

Ser Ser Ile Thr Met Ile Arg Gly Ala Tyr Leu Tyr Tyr Tyr Asp Gly
1 5 10 15

Met Asp Val

<210> SEQ ID NO 140
<211> LENGTH: 12
<212> TYPE: PRT
<213> ORGANISM: Artificial Sequence
<220> FEATURE:
<223> OTHER INFORMATION: Synthetic: 2H2 VL CDR1

<400> SEQUENCE: 140

Arg Ala Ser Gln Ser Val Ser Ser Ser Tyr Leu Ala
1 5 10

<210> SEQ ID NO 141
<211> LENGTH: 7
<212> TYPE: PRT
<213> ORGANISM: Artificial Sequence
<220> FEATURE:
<223> OTHER INFORMATION: Synthetic: 2H2 VL CDR2

<400> SEQUENCE: 141

Gly Ala Ser Ser Arg Ala Thr
1 5

<210> SEQ ID NO 142
<211> LENGTH: 8
<212> TYPE: PRT
<213> ORGANISM: Artificial Sequence
<220> FEATURE:
<223> OTHER INFORMATION: Synthetic: 2H2 VL CDR3

<400> SEQUENCE: 142

Gln Gln Tyr Gly Ser Ser Tyr Thr
1 5

<210> SEQ ID NO 143
<211> LENGTH: 5
<212> TYPE: PRT
<213> ORGANISM: Artificial Sequence
<220> FEATURE:
<223> OTHER INFORMATION: Synthetic: 2E5 VH CDR1

<400> SEQUENCE: 143

Asn Tyr Gly Met His
1 5

<210> SEQ ID NO 144
<211> LENGTH: 17
<212> TYPE: PRT
<213> ORGANISM: Artificial Sequence
<220> FEATURE:
<223> OTHER INFORMATION: Synthetic: 2E5 VH CDR2

<400> SEQUENCE: 144

Val Ile Trp Tyr Asp Gly Ser Asn Glu Tyr Tyr Ala Glu Ser Val Lys
1 5 10 15

Gly

<210> SEQ ID NO 145
<211> LENGTH: 12
<212> TYPE: PRT
<213> ORGANISM: Artificial Sequence
<220> FEATURE:
<223> OTHER INFORMATION: Synthetic: 2E5 VH CDR3

<400> SEQUENCE: 145

Asp Pro Phe Tyr Gly Ser Gly Asn Tyr Phe Asp Tyr
1 5 10

<210> SEQ ID NO 146
<211> LENGTH: 11
<212> TYPE: PRT
<213> ORGANISM: Artificial Sequence
<220> FEATURE:
<223> OTHER INFORMATION: Synthetic: 2E5 VL CDR1

<400> SEQUENCE: 146

Arg Ala Ser Gln Ser Val Ser Ser Tyr Leu Ala
1 5 10

<210> SEQ ID NO 147
<211> LENGTH: 7
<212> TYPE: PRT
<213> ORGANISM: Artificial Sequence
<220> FEATURE:
<223> OTHER INFORMATION: Synthetic: 2E5 VL CDR2

<400> SEQUENCE: 147

Asp Ala Ser Asn Arg Ala Thr
1 5

<210> SEQ ID NO 148
<211> LENGTH: 10
<212> TYPE: PRT
<213> ORGANISM: Artificial Sequence
<220> FEATURE:
<223> OTHER INFORMATION: Synthetic: 2E5 VL CDR3

<400> SEQUENCE: 148

Gln Gln Arg Ser Asn Trp Pro Pro Trp Thr
1 5 10

<210> SEQ ID NO 149
<211> LENGTH: 5
<212> TYPE: PRT
<213> ORGANISM: Artificial Sequence
<220> FEATURE:
<223> OTHER INFORMATION: Synthetic: 24E5 VH CDR1

<400> SEQUENCE: 149

Ser Tyr Val Met Ser
1 5

<210> SEQ ID NO 150
<211> LENGTH: 17
<212> TYPE: PRT
<213> ORGANISM: Artificial Sequence
<220> FEATURE:
<223> OTHER INFORMATION: Synthetic: 24E5 VH CDR2

<400> SEQUENCE: 150

Gly Ile Ser Gly Ser Gly Gly Ser Thr Tyr Tyr Ala Asp Ser Val Lys
1 5 10 15

Gly

<210> SEQ ID NO 151
<211> LENGTH: 12
<212> TYPE: PRT
<213> ORGANISM: Artificial Sequence
<220> FEATURE:
<223> OTHER INFORMATION: Synthetic: 24E5 VH CDR3

<400> SEQUENCE: 151

Asp Gln Asp Ile Ile Ala Ala Tyr Tyr Phe Val Tyr
1 5 10

<210> SEQ ID NO 152
<211> LENGTH: 11
<212> TYPE: PRT
<213> ORGANISM: Artificial Sequence
<220> FEATURE:
<223> OTHER INFORMATION: Synthetic: 24E5 VL CDR1

<400> SEQUENCE: 152

Arg Ala Ser Gln Gly Ile Ser Ser Trp Leu Ala
1 5 10

<210> SEQ ID NO 153
<211> LENGTH: 7
<212> TYPE: PRT
<213> ORGANISM: Artificial Sequence
<220> FEATURE:
<223> OTHER INFORMATION: Synthetic: 24E5 VL CDR2

<400> SEQUENCE: 153

Ala Ala Ser Ser Leu Gln Ser
1 5

<210> SEQ ID NO 154
<211> LENGTH: 9
<212> TYPE: PRT
<213> ORGANISM: Artificial Sequence
<220> FEATURE:
<223> OTHER INFORMATION: Synthetic: 24E5 VL CDR3

<400> SEQUENCE: 154

Gln Gln Tyr Asn Ser Tyr Pro Leu Thr
1 5

<210> SEQ ID NO 155
<211> LENGTH: 5
<212> TYPE: PRT
<213> ORGANISM: Artificial Sequence
<220> FEATURE:
<223> OTHER INFORMATION: Synthetic: 21D9 VH CDR1

<400> SEQUENCE: 155

Asn Tyr Ala Met Asn
1 5

<210> SEQ ID NO 156
<211> LENGTH: 17
<212> TYPE: PRT
<213> ORGANISM: Artificial Sequence
<220> FEATURE:
<223> OTHER INFORMATION: Synthetic: 21D9 VH CDR2

<400> SEQUENCE: 156

Val Ile Ser Val Ser Gly Gly Ser Thr Tyr Tyr Ala Asp Ser Val Lys
1 5 10 15

Gly

<210> SEQ ID NO 157
<211> LENGTH: 16
<212> TYPE: PRT
<213> ORGANISM: Artificial Sequence
<220> FEATURE:
<223> OTHER INFORMATION: Synthetic: 21D9 VH CDR3

<400> SEQUENCE: 157

Asp Tyr Tyr Tyr Asp Ser Gly Ser Tyr Tyr Asp Ser Phe Phe Asp Tyr
1 5 10 15

<210> SEQ ID NO 158
<211> LENGTH: 12
<212> TYPE: PRT
<213> ORGANISM: Artificial Sequence
<220> FEATURE:
<223> OTHER INFORMATION: Synthetic: 21D9 VL CDR1

<400> SEQUENCE: 158

Arg Ala Ser Gln Ser Val Ser Ser Ser Tyr Leu Ala
1 5 10

<210> SEQ ID NO 159
<211> LENGTH: 7
<212> TYPE: PRT
<213> ORGANISM: Artificial Sequence
<220> FEATURE:
<223> OTHER INFORMATION: Synthetic: 21D9 VL CDR2

<400> SEQUENCE: 159

Gly Ala Ser Ser Arg Ala Thr
1 5

<210> SEQ ID NO 160
<211> LENGTH: 9
<212> TYPE: PRT
<213> ORGANISM: Artificial Sequence
<220> FEATURE:
<223> OTHER INFORMATION: Synthetic: 21D9 VL CDR3

<400> SEQUENCE: 160

Gln Gln Tyr Gly Ser Ser Pro Leu Thr
1 5

<210> SEQ ID NO 161
<211> LENGTH: 5
<212> TYPE: PRT
<213> ORGANISM: Artificial Sequence
<220> FEATURE:

<223> OTHER INFORMATION: Synthetic: 21A5 VH CDR1

<400> SEQUENCE: 161

Asp Tyr Tyr Leu His
1 5

<210> SEQ ID NO 162
<211> LENGTH: 17
<212> TYPE: PRT
<213> ORGANISM: Artificial Sequence
<220> FEATURE:
<223> OTHER INFORMATION: Synthetic: 21A5 VH CDR2

<400> SEQUENCE: 162

Ile Phe His Pro Ser Gly Asp Ile Thr Ser Ser Ala Gln Asn Phe Gln
1 5 10 15

Gly

<210> SEQ ID NO 163
<211> LENGTH: 15
<212> TYPE: PRT
<213> ORGANISM: Artificial Sequence
<220> FEATURE:
<223> OTHER INFORMATION: Synthetic: 21A5 VH CDR3

<400> SEQUENCE: 163

Gly Gly Val Leu Arg Tyr Leu Asp Trp Ser His Ala Phe Asp Ile
1 5 10 15

<210> SEQ ID NO 164
<211> LENGTH: 12
<212> TYPE: PRT
<213> ORGANISM: Artificial Sequence
<220> FEATURE:
<223> OTHER INFORMATION: Synthetic: 21A5 VL CDR1

<400> SEQUENCE: 164

Arg Ala Ser Gln Ser Val Ser Ser Ser Tyr Leu Ala
1 5 10

<210> SEQ ID NO 165
<211> LENGTH: 7
<212> TYPE: PRT
<213> ORGANISM: Artificial Sequence
<220> FEATURE:
<223> OTHER INFORMATION: Synthetic: 21A5 VL CDR2

<400> SEQUENCE: 165

Gly Ala Ser Ser Arg Ala Thr
1 5

<210> SEQ ID NO 166
<211> LENGTH: 6
<212> TYPE: PRT
<213> ORGANISM: Artificial Sequence
<220> FEATURE:
<223> OTHER INFORMATION: Synthetic: 21A5 VL CDR3

<400> SEQUENCE: 166

Gln Gln Tyr Gly Ser Thr
1 5

<210> SEQ ID NO 167
<211> LENGTH: 5
<212> TYPE: PRT
<213> ORGANISM: Artificial Sequence
<220> FEATURE:
<223> OTHER INFORMATION: Synthetic: 10F10 VH CDR1

<400> SEQUENCE: 167

Ser Tyr Ala Met His
1 5

<210> SEQ ID NO 168
<211> LENGTH: 17
<212> TYPE: PRT
<213> ORGANISM: Artificial Sequence
<220> FEATURE:
<223> OTHER INFORMATION: Synthetic: 10F10 VH CDR2

<400> SEQUENCE: 168

Ile Ile Ser Tyr Asp Glu Tyr Asn Lys Tyr Tyr Ala Asp Ser Val Lys
1 5 10 15

Gly

<210> SEQ ID NO 169
<211> LENGTH: 7
<212> TYPE: PRT
<213> ORGANISM: Artificial Sequence
<220> FEATURE:
<223> OTHER INFORMATION: Synthetic: 10F10 VH CDR3

<400> SEQUENCE: 169

Glu Trp Val Gly Ile Arg Tyr
1 5

<210> SEQ ID NO 170
<211> LENGTH: 11
<212> TYPE: PRT
<213> ORGANISM: Artificial Sequence
<220> FEATURE:
<223> OTHER INFORMATION: Synthetic: 10F10 VL CDR1

<400> SEQUENCE: 170

Arg Ala Ser Gln Gly Ile Ser Ser Ala Leu Ala
1 5 10

<210> SEQ ID NO 171
<211> LENGTH: 7
<212> TYPE: PRT
<213> ORGANISM: Artificial Sequence
<220> FEATURE:
<223> OTHER INFORMATION: Synthetic: 10F10 VL CDR2

<400> SEQUENCE: 171

Asp Ala Ser Ser Leu Glu Ser
1 5

<210> SEQ ID NO 172
<211> LENGTH: 9
<212> TYPE: PRT
<213> ORGANISM: Artificial Sequence
<220> FEATURE:
<223> OTHER INFORMATION: Synthetic: 10F10 VL CDR3

<400> SEQUENCE: 172

Gln Gln Phe Asn Ser Tyr Pro Ile Thr
1 5

<210> SEQ ID NO 173
<211> LENGTH: 16
<212> TYPE: PRT

<213> ORGANISM: Artificial Sequence
<220> FEATURE:
<223> OTHER INFORMATION: Synthetic: Residues 127-142 of hILT4

<400> SEQUENCE: 173

Ser Ala Gln Pro Ser Pro Val Val Thr Ser Gly Gly Arg Val Thr Leu
1               5                   10                  15

<210> SEQ ID NO 174
<211> LENGTH: 32
<212> TYPE: PRT
<213> ORGANISM: Artificial Sequence
<220> FEATURE:
<223> OTHER INFORMATION: Synthetic: Residues 182-213 of hILT4

<400> SEQUENCE: 174

Ser Val Gly Pro Val Ser Pro Asn Arg Arg Trp Ser His Arg Cys Tyr
1               5                   10                  15

Gly Tyr Asp Leu Asn Ser Pro Tyr Val Trp Ser Ser Pro Ser Asp Leu
            20                  25                  30

<210> SEQ ID NO 175
<211> LENGTH: 15
<212> TYPE: PRT
<213> ORGANISM: Artificial Sequence
<220> FEATURE:
<223> OTHER INFORMATION: Synthetic: Residues 378-392 of hILT4

<400> SEQUENCE: 175

Gln Ala Glu Phe Pro Met Ser Pro Val Thr Ser Ala His Ala Gly
1               5                   10                  15

<210> SEQ ID NO 176
<211> LENGTH: 454
<212> TYPE: PRT
<213> ORGANISM: Artificial Sequence
<220> FEATURE:
<223> OTHER INFORMATION: Synthetic: 21D9.e,IgG1f (Same Fc as SEQ ID NO:
      98 w/o C-term. K)

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Val Ile Ser Val Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Tyr Tyr Asp Ser Gly Ser Tyr Tyr Asp Ser Phe Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Arg Val Glu
210 215 220

Pro Lys Ser Cys Asp Lys Thr His Thr Cys Pro Pro Cys Pro Ala Pro
225 230 235 240

Glu Leu Leu Gly Gly Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr
290 295 300

Asn Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Ala Leu
325 330 335

Pro Ala Pro Ile Glu Lys Thr Ile Ser Lys Ala Lys Gly Gln Pro Arg
340 345 350

Glu Pro Gln Val Tyr Thr Leu Pro Pro Ser Arg Glu Glu Met Thr Lys
355 360 365

Asn Gln Val Ser Leu Thr Cys Leu Val Lys Gly Phe Tyr Pro Ser Asp
370 375 380

Ile Ala Val Glu Trp Glu Ser Asn Gly Gln Pro Glu Asn Asn Tyr Lys
385 390 395 400

Thr Thr Pro Pro Val Leu Asp Ser Asp Gly Ser Phe Phe Leu Tyr Ser
405 410 415

Lys Leu Thr Val Asp Lys Ser Arg Trp Gln Gln Gly Asn Val Phe Ser
420 425 430

Cys Ser Val Met His Glu Ala Leu His Asn His Tyr Thr Gln Lys Ser
435 440 445

Leu Ser Leu Ser Pro Gly
450

<210> SEQ ID NO 177
<211> LENGTH: 454
<212> TYPE: PRT
<213> ORGANISM: Artificial Sequence
<220> FEATURE:
<223> OTHER INFORMATION: Synthetic: 21D9.e.IgG1.1f (Fc is the same as SEQ ID NO: 103)

<400> SEQUENCE: 177

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Asn Trp Val Arg Gln Ala Pro Gly Lys Gly Leu Glu Trp Val
35 40 45

Ser Val Ile Ser Val Ser Gly Gly Ser Thr Tyr Tyr Ala Asp Ser Val
50 55 60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Tyr Tyr Asp Ser Gly Ser Tyr Tyr Asp Ser Phe Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Ala Glu Gly Ala Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly
    450
```

<210> SEQ ID NO 178
<211> LENGTH: 449

<212> TYPE: PRT
<213> ORGANISM: Artificial Sequence
<220> FEATURE:
<223> OTHER INFORMATION: Synthetic: 21D9.e.IgG4_S228P

<400> SEQUENCE: 178

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Val Ile Ser Val Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Tyr Tyr Asp Ser Gly Ser Tyr Tyr Asp Ser Phe Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380
```

Glu Trp Glu Ser Asn Gly Gln Pro Glu Asn Asn Tyr Lys Thr Thr Pro
385 390 395 400

Pro Val Leu Asp Ser Asp Gly Ser Phe Phe Leu Tyr Ser Arg Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser

<210> SEQ ID NO 179
<211> LENGTH: 324
<212> TYPE: PRT
<213> ORGANISM: Artificial Sequence
<220> FEATURE:
<223> OTHER INFORMATION: Synthetic: hIgG4 S228P (Fc of SEQ ID NO: 178)

<400> SEQUENCE: 179

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Pro Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Gln Gly Asn Val Phe Ser

```
    290                 295                 300

Cys Ser Val Met His Glu Ala Leu His Asn His Tyr Thr Gln Lys Ser
305                 310                 315                 320

Leu Ser Leu Ser


<210> SEQ ID NO 180
<211> LENGTH: 116
<212> TYPE: PRT
<213> ORGANISM: Artificial Sequence
<220> FEATURE:
<223> OTHER INFORMATION: Synthetic: 9G4 VH amino acid

<400> SEQUENCE: 180

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Asn Trp Ile Arg Gln Pro Pro Gly Lys Gly Leu Glu Trp Leu
        35                  40                  45

Gly Tyr Ile Tyr Tyr Ser Gly Ser Thr Lys Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ser Gly Trp Tyr Tyr Phe Asp Tyr Trp Gly Gln Gly Thr Leu Val
            100                 105                 110

Thr Val Ser Ser
        115


<210> SEQ ID NO 181
<211> LENGTH: 348
<212> TYPE: DNA
<213> ORGANISM: Artificial Sequence
<220> FEATURE:
<223> OTHER INFORMATION: Synthetic: 9G4 VH DNA

<400> SEQUENCE: 181

caggtgcagc tgcaggagtc gggcccagga ctggtgaagc cttcggagac cctgtccctc      60

acctgcactg tctctggtgg ctccatcagt agttactact ggaactggat ccggcagccc     120

ccagggaagg gactggagtg gcttgggtac atctattaca gtgggagtac caagtacaac     180

ccctccctca agagtcgagt caccatatca gtagacacgt ccaagaacca gttctccctg     240

aagctgagct ctgtgaccgc tgcggacacg gccgtgtatt attgtgccag cagtggctgg     300

tactactttg actattgggg ccagggaacc ctggtcaccg tctcctca                  348


<210> SEQ ID NO 182
<211> LENGTH: 107
<212> TYPE: PRT
<213> ORGANISM: Artificial Sequence
<220> FEATURE:
<223> OTHER INFORMATION: Synthetic: 9G4 VL amino acid

<400> SEQUENCE: 182

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Gly Tyr Tyr Cys Gln Gln Arg Ser Tyr Trp Pro Trp
85 90 95

Thr Phe Gly Gln Gly Thr Lys Val Glu Ile Lys
100 105

<210> SEQ ID NO 183
<211> LENGTH: 321
<212> TYPE: DNA
<213> ORGANISM: Artificial Sequence
<220> FEATURE:
<223> OTHER INFORMATION: Synthetic: 9G4 VL DNA

<400> SEQUENCE: 183
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat gcgtccaaca gggccactgg catcccagcc 180
aggttcagtg gcagtgggtc tgggacagac ttcactctca ccatcagcag cctagagcct 240
gaagattttg caggttatta ctgtcagcag cgtagctact ggccgtggac gttcggccaa 300
gggaccaagg tggaaatcaa a 321

<210> SEQ ID NO 184
<211> LENGTH: 98
<212> TYPE: PRT
<213> ORGANISM: Artificial Sequence
<220> FEATURE:
<223> OTHER INFORMATION: Synthetic: Germline hIGHV3-23*01

<400> SEQUENCE: 184

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys

<210> SEQ ID NO 185
<211> LENGTH: 11
<212> TYPE: PRT
<213> ORGANISM: Artificial Sequence
<220> FEATURE:
<223> OTHER INFORMATION: Synthetic: Germline J Gene IGHJ4

<400> SEQUENCE: 185

Trp Gly Gln Gly Thr Leu Val Thr Val Ser Ser
1 5 10

<210> SEQ ID NO 186
<211> LENGTH: 96
<212> TYPE: PRT
<213> ORGANISM: Artificial Sequence
<220> FEATURE:
<223> OTHER INFORMATION: Synthetic: Germline hIGKV3-20*01

<400> SEQUENCE: 186

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

<210> SEQ ID NO 187
<211> LENGTH: 10
<212> TYPE: PRT
<213> ORGANISM: Artificial Sequence
<220> FEATURE:
<223> OTHER INFORMATION: Synthetic: Germline J Gene IGKJ4

<400> SEQUENCE: 187

```
Phe Gly Gly Gly Thr Lys Val Glu Ile Lys
1               5                   10
```

<210> SEQ ID NO 188
<211> LENGTH: 98
<212> TYPE: PRT
<213> ORGANISM: Artificial Sequence
<220> FEATURE:
<223> OTHER INFORMATION: Synthetic: Germline hIGHV1-46*01

<400> SEQUENCE: 188

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 189
<211> LENGTH: 11
<212> TYPE: PRT
<213> ORGANISM: Artificial Sequence
<220> FEATURE:
<223> OTHER INFORMATION: Synthetic: Germline J Gene IGHJ3

<400> SEQUENCE: 189

Trp Gly Gln Gly Thr Met Val Thr Val Ser Ser
1 5 10

<210> SEQ ID NO 190
<211> LENGTH: 98
<212> TYPE: PRT
<213> ORGANISM: Artificial Sequence
<220> FEATURE:
<223> OTHER INFORMATION: Synthetic: Germline hIGHV3-30*01

<400> SEQUENCE: 190

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Ala Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg

<210> SEQ ID NO 191
<211> LENGTH: 11
<212> TYPE: PRT
<213> ORGANISM: Artificial Sequence
<220> FEATURE:
<223> OTHER INFORMATION: Synthetic: Germline J Gene IGHJ4

<400> SEQUENCE: 191

Trp Gly Gln Gly Thr Leu Val Thr Val Ser Ser
1 5 10

<210> SEQ ID NO 192
<211> LENGTH: 95
<212> TYPE: PRT
<213> ORGANISM: Artificial Sequence
<220> FEATURE:
<223> OTHER INFORMATION: Synthetic: Germline hIGKV1-13*02

<400> SEQUENCE: 192

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Tyr Gln Gln Lys Pro Gly Lys Ala Pro Lys Leu Leu Ile
35 40 45

Tyr Asp Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro
85 90 95

<210> SEQ ID NO 193

-continued

```
<211> LENGTH: 10
<212> TYPE: PRT
<213> ORGANISM: Artificial Sequence
<220> FEATURE:
<223> OTHER INFORMATION: Synthetic: Germline J Gene IGKJ5

<400> SEQUENCE: 193

Phe Gly Gln Gly Thr Arg Leu Glu Ile Lys
1               5                   10
```